US008034940B2

(12) United States Patent
Weinstein et al.

(10) Patent No.: US 8,034,940 B2
(45) Date of Patent: Oct. 11, 2011

(54) MODULATORS OF GLUCOCORTICOID RECEPTOR, AP-1, AND/OR NF-κB ACTIVITY AND USE THEREOF

(75) Inventors: David S. Weinstein, East Windsor, NJ (US); Ping Chen, Belle Mead, NJ (US); T. G. Murali Dhar, Newtown, PA (US); Jingwu Duan, Yardley, PA (US); Hua Gong, King of Prussia, PA (US); Bin Jiang, Norristown, PA (US); Bingwei Vera Yang, Belle Mead, NJ (US); Arthur M. Doweyko, Long Valley, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1098 days.

(21) Appl. No.: 11/835,438

(22) Filed: Aug. 8, 2007

(65) Prior Publication Data

US 2009/0075995 A1 Mar. 19, 2009

Related U.S. Application Data

(60) Provisional application No. 60/836,496, filed on Aug. 9, 2006.

(51) Int. Cl.
*C07D 491/052* (2006.01)
*A61K 31/436* (2006.01)

(52) U.S. Cl. .............................. 546/80; 546/89; 514/291

(58) Field of Classification Search ................... 546/80, 546/89; 514/291
See application file for complete search history.

(56) References Cited

U.S. PATENT DOCUMENTS

| | | | |
|---|---|---|---|
| 5,453,421 | A | 9/1995 | Atwal et al. |
| 5,563,169 | A | 10/1996 | Yoshida et al. |
| 5,776,932 | A | 7/1998 | Schindler et al. |

FOREIGN PATENT DOCUMENTS

| | | |
|---|---|---|
| DE | 196 10 882 | 9/1997 |
| EP | 0 301 729 | 2/1989 |
| EP | 0 345 428 | 12/1989 |
| EP | 0 438 869 | 7/1991 |
| JP | 440225787 | 10/1969 |
| JP | 2007-169270 | 7/2007 |
| WO | WO 93/06096 | 4/1993 |
| WO | WO 96/08475 | 3/1996 |
| WO | WO 98/15546 | 4/1998 |
| WO | WO 98/35944 | 8/1998 |
| WO | WO 99/33786 | 7/1999 |
| WO | WO 00/69810 | 11/2000 |
| WO | WO 03/049702 | 6/2003 |
| WO | WO 2004/056744 | 7/2004 |
| WO | WO 2005/066153 | 7/2005 |
| WO | WO 2005/066161 | 7/2005 |
| WO | WO 2005/115977 | 12/2005 |
| WO | WO 2006/053342 | 5/2006 |
| WO | WO 2006/076509 | 7/2006 |
| WO | WO2008/057856 | 5/2008 |
| WO | WO2008/057857 | 5/2008 |
| WO | WO2008/057859 | 5/2008 |
| WO | WO2008/057862 | 5/2008 |

OTHER PUBLICATIONS

Dorwald F. A. Side Reactions in Organic Synthesis, 2005, Wiley: VCH, Weinheim p. IX of Preface.* Database Caplus [Online] Chemical Abstracts Service, Columbus, Ohio, US; Jul. 5, 2007, XP002470068 retrieved from STN Database Accession No. 2007:726515 abstract.
Database Caplus [Online] Chemical Abstracts Service, Columbus, Ohio, US; Feb. 20, 2002, XP002470069 retrieved from STN Database Accession No. 2002:130851 abstract.
Database Caplus [Online] Chemical Abstracts Service, Columbus, Ohio, US; May 12, 1984, XP002470070 retrieved from STN Database Accession No. 1978:62329 abstract.
Database Caplus [Online] Chemical Abstracts Service, Columbus, Ohio, US; May 12, 1984, XP002470071 retrieved from STN Database Accession No. 1970:109347 abstract.

(Continued)

*Primary Examiner* — Rita Desai
(74) *Attorney, Agent, or Firm* — Burton Rodney

(57) ABSTRACT

Novel non-steroidal compounds are provided which are useful in treating diseases associated with modulation of the glucocorticoid receptor, AP-1, and/or NF-κB activity, including inflammatory and immune diseases, having the structure of formula (I):

an enantiomer, diastereomer, or tautomer thereof, or a prodrug ester thereof, or a pharmaceutically-acceptable salt thereof, in which:
Z is heterocyclo or heteroaryl;
A is a 5- to 8-membered carbocyclic ring or a 5- to 8-membered heterocyclic ring;
B is a cycloalkyl, cycloalkenyl, aryl, heterocyclo, or heteroaryl ring, wherein each ring is fused to the A ring on adjacent atoms and optionally substituted by one to four groups which are the same or different and are independently selected from $R_5$, $R_6$, $R_7$, and $R_8$;
$J_1$, $J_2$, and $J_3$ are at each occurrence the same or different and are independently -$A_1QA_2$-; Q is a bond, O, S, S(O), or $S(O)_2$; $A_1$ and $A_2$ are the same or different and are at each occurrence independently selected from a bond, $C_{1-3}$alkylene, substituted $C_{1-3}$alkylene, $C_{2-4}$alkenylene, and substituted $C_{2-4}$alkenylene, provided that $A_1$ and $A_2$ are chosen so that ring A is a 5- to 8-membered carbocyclic or heterocyclic ring;
$R_1$ to $R_{11}$ are as defined herein.
Also provided are pharmaceutical compositions and methods of treating inflammatory- or immune-associated diseases and obesity and diabetes employing said compounds.

11 Claims, No Drawings

OTHER PUBLICATIONS

Khan, M.A.J.A. et al., "Synthesis of Some New Tetrahydrocarbazole Derivatives as Possible Antibacterial Agents", Indian Journal of Heterocyclic Chemistry, vol. 11, pp. 111-114 (2001).

Latif, N. et al., "Cyano Esters and Malononitriles, IV. Cyano(fluorenyl)acetohydrazides and Fluorenylpyrazolones", Aust. J. Chem., vol. 30, pp. 2255-2262 (1977).

Lewis, A. et al., "Semisynthetic Cephalosporins. II. Structure-Activity Studies in 7-Acylaminocephalosporanic Acids Derived from Dicarboxylic Acids", Antimicrobial Agents and Chemotherapy, pp. 109-114 (1969).

Database Caplus [Online] Chemical Abstracts Service, Columbus, Ohio, US; May 12, 1984, XP002470072 retrieved from STN Database Accession No. 1970:12746 abstract.

CAS Reg. No. 18435-91-1.
CAS Reg. No. 18435-92-2.
CAS Reg. No. 18435-93-3.
CAS Reg. No. 18435-94-4.
CAS Reg. No. 18435-95-5.
CAS Reg. No. 26133-54-0.
CAS Reg. No. 150330-13-5.
CAS Reg. No. 150330-14-6.
CAS Reg. No. 172729-90-7.
CAS Reg. No. 312522-39-7.
CAS Reg. No. 339283-73-7.
CAS Reg. No. 341936-31-0.
CAS Reg. No. 345990-49-0.
CAS Reg. No. 360572-06-1.
CAS Reg. No. 606096-43-9.
CAS Reg. No. 606096-44-0.
CAS Reg. No. 606096-45-1.
CAS Reg. No. 690647-57-5.
CAS Reg. No. 696604-11-2.
CAS Reg. No. 863437-19-8.

Baldwin, Jr., A.S., "The transcription factor NF-κB and human disease", The Journal of Clinical Investigation, vol. 107, No. 1, pp. 3-6 (2001).

Burke, J.R., "Targeting IκB kinase for the treatment of inflammatory and other disorders", Current Opinion in Drug Discovery & Development, vol. 6, No. 5, pp. 720-728 (2003).

Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).

Chakravarti, D. et al., "Role of CBP/P300 in nuclear receptor signalling", Nature, vol. 383, pp. 99-103 (1996).

Diamond, M.I. et al., "Transcription Factor Interactions: Selectors of Positive or Negative Regulation from a Single DNA Element", Science, vol. 249, pp. 1266-1272 (1990).

Evdokimoff, V. et al., "9-Substituted xanthene derivatives", Annali di Chimica (Rome, Italy), vol. 57, No. 12, pp. 1520-1532 (1967).

Firestein, G.S. et al., "Signal Transduction and Transcription Factors in Rheumatic Disease", Arthritis & Rheumatism, vol. 42, No. 4, pp. 609-621 (1999).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Manning, A.M., et al., "Targeting JNK for Therapeutic Benefit: from Junk to Gold?", Nature, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Peitz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-*erb-A* oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

\* cited by examiner

MODULATORS OF GLUCOCORTICOID RECEPTOR, AP-1, AND/OR NF-κB ACTIVITY AND USE THEREOF

This application claims a benefit of priority from U.S. Provisional Application No. 60/836,496, filed Aug. 9, 2006, the entire disclosure of which is incorporated herein by reference.

FIELD OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107, 3 (2001); Firestein, G. S., and Manning, A. M., *Arthritis and Rheumatism*, 42, 609 (1999); and Peltz, G., *Curr. Opin. in Biotech.*, 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228, 740-742 (1985); Weinberger et al., *Nature*, 318, 670-672 (1986) and for results in rats see Miesfeld, R., *Nature*, 312, 779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62, 1189 (1990); Yang-Yen, H. F. et al, *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of co-activators by GR have also been proposed. See Kamei, Y. et al., *Cell*, 85, 403 (1996); and Chakravarti, D. et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93, 531 (1998) and Reichardt, H. M., *EMBO J.*, 20, 7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents. However their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and/or obesity and diabetes, and to a method for using such compounds to treat these and related diseases.

In accordance with one aspect of the invention, compounds are provided having the structure of formula I

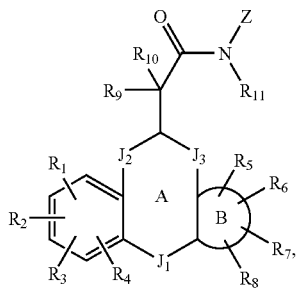

an enantiomer, diastereomer, tautomer, or a pharmaceutically-acceptable salt thereof, wherein:

Z is selected from heterocyclo, heteroaryl and cyano;

A is selected from a 5- to 8-membered carbocyclic ring and a 5- to 8-membered heterocyclic ring;

the B ring is selected from a cycloalkyl, cycloalkenyl, aryl, heterocyclo ring, and heteroaryl ring, wherein the B ring is fused to the A ring, and the B ring is optionally substituted by one to four groups which are the same or different and are independently selected from $R_5$, $R_6$, $R_7$, and $R_8$;

$J_1$, $J_2$, and $J_3$ are the same or different and at each occurrence are independently $-A_1QA_2-$;

Q is independently at each occurrence selected from a bond, O, S, S(O), and S(O)$_2$;

$A_1$ and $A_2$ are the same or different and at each occurrence are independently selected from a bond, $C_{1-3}$alkylene, substituted $C_{1-3}$alkylene, $C_{2-4}$alkenylene, and substituted $C_{2-4}$alkenylene, provided that $A_1$ and $A_2$ are chosen so that ring A is a 5- to 8-membered carbocyclic ring or a 5- to 8-membered heterocyclic ring;

$R_1$, $R_2$, $R_3$, $R_4$, $R_5$, $R_6$, $R_7$, and $R_8$ are the same or different and at each occurrence are independently selected from (i) hydrogen, halogen, alkyl, substituted alkyl, alkenyl, substituted alkenyl, alkynyl, substituted alkynyl, alkoxy, substituted alkoxy, nitro, cyano, $OR_{12}$, $-NR_{12}R_{13}$, $-C(=O)R_{12}$, $-CO_2R_{12}$, $-C(=O)NR_{12}R_{13}$, $-OC(=O)NR_{12}R_{13}$,

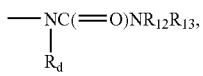

$-OC(=O)R_{12}$, $-NR_{12}C(=O)R_{13}$, $-NR_{12}C(=O)OR_{13}$, $-NR_{12}C(S)OR_{13}$, $S(O)_pR_{16}$, $NR_{12}SO_2R_{16}$, dialkylaminoalkoxy, alkoxyalkyloxyalkyloxy, $SO_2NR_{12}R_{13}$, cycloalkyl, cycloalkenyl, cycloalkynyl, heterocyclo, aryl, and heteroaryl; and/or (ii) where possible, each one of $R_1$-$R_8$ is taken together with any one of $R_1$-$R_8$ located on an adjacent atom to form a fused ring; and/or (iii) where possible any one of $R_1$-$R_8$ is taken together with any one of $R_1$-$R_8$ located on the same atom to form an oxo, alkenyl, substituted alkenyl, cycloalkyl, cycloalkenyl, or heterocyclo group;

$R_9$ and $R_{10}$ are the same or different and at each occurrence are independently selected from (i) hydrogen, halogen, alkyl, substituted alkyl, alkenyl, substituted alkenyl, alkynyl, substituted alkynyl, nitro, cyano, $OR_{14}$, $NR_{14}R_{15}$, $C(=O)R_{14}$, $CO_2R_{14}$, $C(=O)NR_{14}R_{15}$, $-O-C(=O)R_{14}$, $NR_{14}C(=O)R_{15}$, $NR_{14}C(=O)OR_{15}$, $NR_{14}C(=S)OR_{15}$, $S(O)_pR_{17}$, $NR_{14}SO_2R_{17}$, $SO_2NR_{14}R_{15}$, cycloalkyl, cycloalkenyl, heterocyclo, aryl, and heteroaryl; or (ii) together with the atom to which the are attached, $R_9$ and $R_{10}$ are taken together to form a carbonyl, alkenyl, substituted alkenyl, cycloalkyl, cycloalkenyl, or heterocyclo group;

$R_{11}$ is selected from hydrogen, alkyl, substituted alkyl, $C(=O)$alkyl, $CO_2$(alkyl), $SO_2$alkyl, alkoxy, amino, substituted amino, aryl, heteroaryl, heterocyclo, and cycloalkyl;

$R_{12}$, $R_{13}$, $R_{14}$, and $R_{15}$, are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R_{12}$ is taken together with $R_{13}$, and/or where possible $R_{14}$ is taken together with $R_{15}$ to form a heteroaryl or heterocyclo ring;

$R_{16}$ and $R_{17}$, are the same or different and at each occurrence are independently selected from alkyl, substituted alkyl, alkenyl, substituted alkenyl, alkynyl, substituted alkynyl, cycloalkyl, cycloalkenyl, aryl, heteroaryl, and heterocyclo;

$R_d$ is H, alkyl or aryl; and p is 0, 1 or 2, provided that (1) where the tricyclic moiety in the formula I compound is

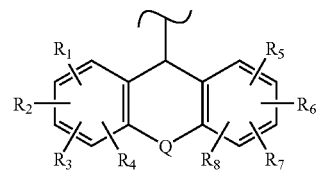

where Q is O and $R_1$ to $R_8$ are each H, then (a) Z is other than

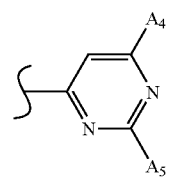

where $A_4$ and $A_5$ are the same or different and are independently H or $C_1$-$C_2$alkyl-; or (b) Z is other than

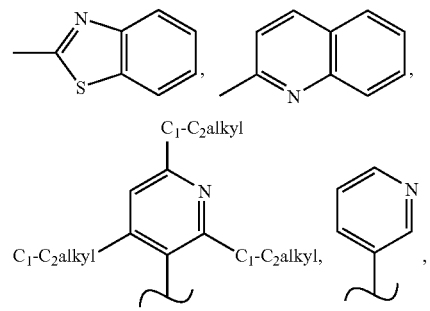

-continued

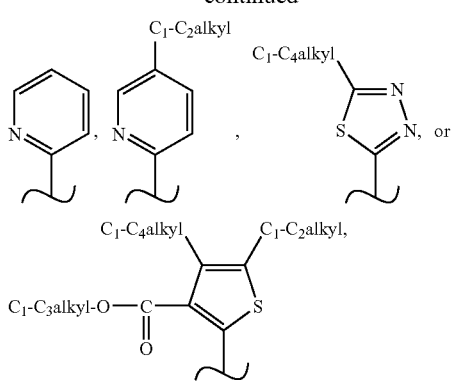

(2) where the tricyclic moiety is

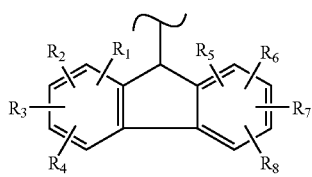

where $R_1$ to $R_8$ are each H,
then
(a) Z is other than

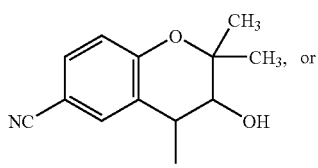

(b) where Z is

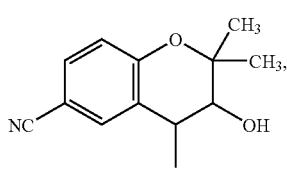

then $R_{11}$ is other than a substituted $C_1$-$C_2$-alkylene;
(3) where the tricyclic moiety is

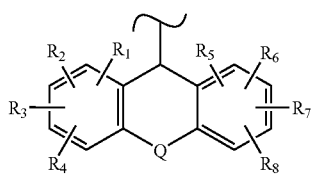

where Q is S or $SO_2$, and $R_1$ to $R_8$ are each H,
then Z is other than

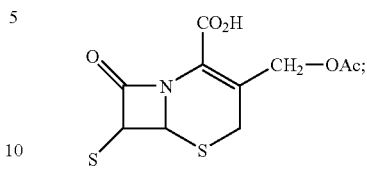

(4) where the tricyclic moiety is

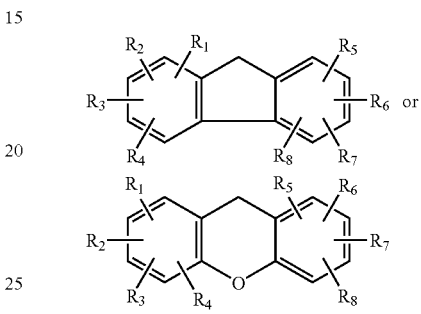

where $R_1$ to $R_8$ are each H,
then Z is other than

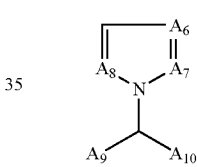

where $A_6$, $A_7$ and $A_8$ are independently N or CH,
$A_9$ is —$(CH_2)_d$-$A_{11}$ where d is 0 to 4;
$A_{11}$ is OH, $CO_2H$, 5-tetrazolyl, —COO($C_1$-$C_4$alkyl)$_{n_a}$ or CN—;
$n_a$ is 0 to 4; and
$A_{10}$ is $C_4$-$C_7$ straight chain alkyl;
(5) where the tricyclic moiety is

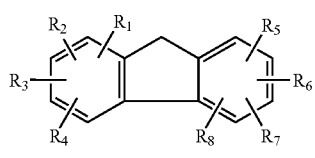

then Z is other than

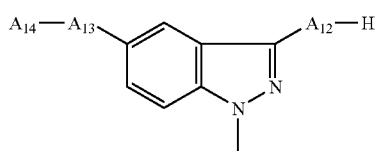

where $A_{12}$ is O or S; and
$A_{13}$ is O or an NH,

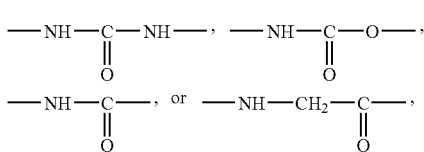

wherein the last 3 groups are joined to the aromatic ring through the N-atom;
$A_{14}$ is H,
alkyl,
$C_3$-$C_7$ cycloalkyl,
phenyl, naphthyl, anthranyl or fluorenyl optionally substituted, or a quinolin-2-ylmethoxy or pyridin-ylmethoxy; or
Z is other than

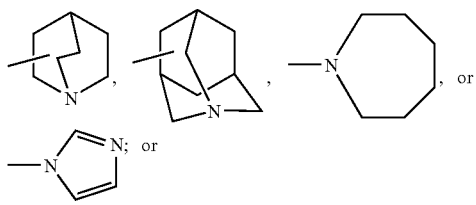

Z is other than

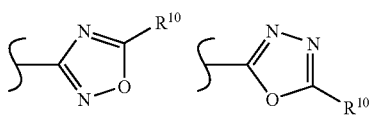

where $R^{10}$ is a non-aromatic azacyclic or non-aromatic azabicyclic ring system;
(6) where the tricyclic moiety is

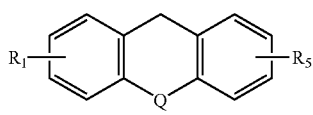

Q is —O—, —S—, —C($R^3R^4$)—, —CH$_2$CH$_2$—, —CH=CH—CH$_2$—, —CH$_2$—CH=CH—, —CH$_2$—(C=O)—, —(C=O)—CH$_2$—, CH$_2$CH$_2$CH$_2$—, —CH=CH—, —O—CH$_2$—, —CH$_2$—O—, —O—CH$_2$—O—, —CH$_2$—O—CH$_2$—, —S—CH$_2$—, —CH$_2$—S—, —CH($R^5$)CH$_2$—, —CH$_2$CH($R^5$)—, —(C=O)—, or —(S=O)— wherein $R^3$ and $R^4$ independently are hydrogen or $C_{1-7}$-alkyl; and wherein $R^5$ is $C_{1-7}$-alkyl or phenyl;
then Z is other than

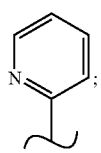

(7) where the tricyclic moiety is

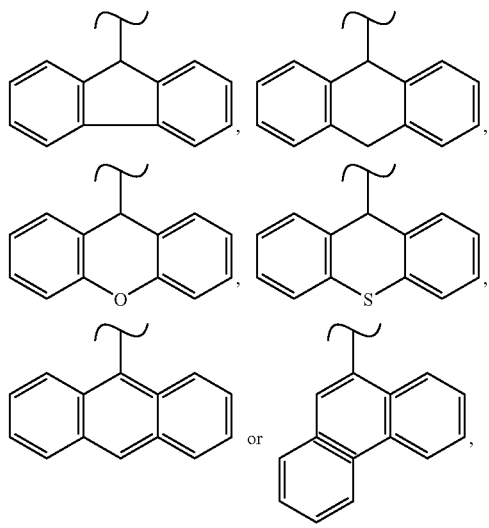

then Z is other than

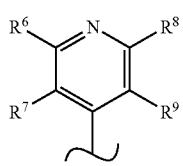

wherein:
$R^6$ and $R^7$ are each independently selected from $C_1$-$C_6$alkyl, halo-$C_1$-$C_6$alkyl containing 1 to 5 halogen atoms, $C_1$-$C_2$alkoxy-$C_1$-$C_6$alkyl, nitro-$C_1$-$C_6$alkyl, cyano-$C_1$-$C_6$alkyl, $C_1$-$C_2$alkanoyl-$C_1$-$C_6$alkyl, $C_1$-$C_2$alkoxycarbonyl-$C_1$-$C_6$alkyl, $C_1$-$C_2$alkylthio-$C_1$-$C_6$alkyl, $C_1$-$C_2$alkanesulfinyl-$C_1$-$C_6$alkyl, $C_1$-$C_2$alkanesulfonyl-$C_1$-$C_6$alkyl, $C_2$-$C_6$alkenyl, halo-$C_2$-$C_6$alkenyl containing 1-5 halogen atoms, $C_2$-$C_6$alkynyl, halo-$C_2$-$C_6$alkynyl containing 1-5 halogen atoms, $C_3$-$C_7$cycloalkyl and halogen; or
$R^6$ and $R^7$, taken together, form a saturated or unsaturated 5- to 7-membered carbocyclic or heterocyclic ring which may contain one or two hetero atoms selected from O and S; and
$R^8$ and $R^9$ are each independently selected from hydrogen, $C_1$-$C_6$alkyl and halogen;
(8) where the tricyclic moiety is

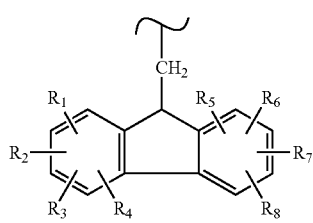

then
  a) Z is other than

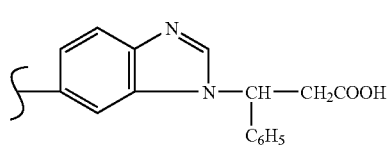

or a homolog thereof,
  b) if Z is

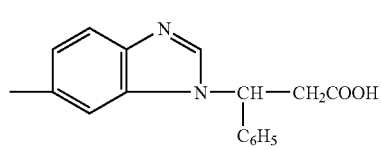

or a homolog thereof, then $R_{11}$ is other than H; or
  (9) where the tricyclic moiety is

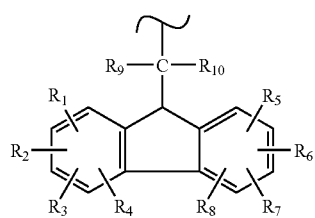

then

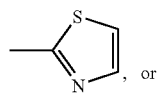, or a) Z is other than substituted or unsubstituted

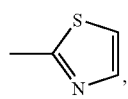, b) where Z is substituted or unsubstituted then at least one or $R_9$ and $R_{10}$ is other than H and/or $R_{11}$ is other than H;
  (10) where the tricyclic moiety is

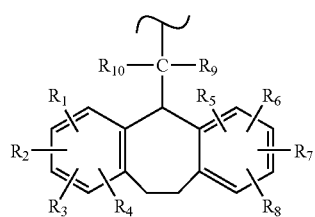

then

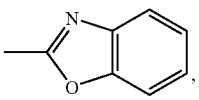, a) Z is other than

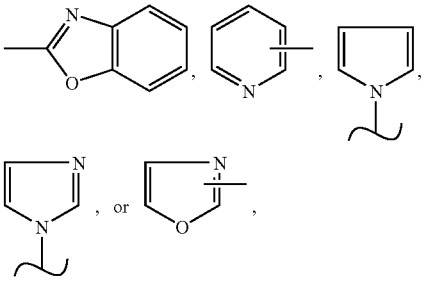

b) where Z is
    then $R_{11}$ is other than H and/or at least one of $R_9$ and $R_{10}$ is other than H;
  (11) where the tricyclic moiety is

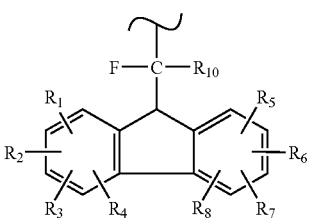

then
  a) Z is other than heteroaryl, or
  b) where Z is heteroaryl, then $R_{11}$ is other than H and/or $R_{10}$ is other than H; or
  (12) where the tricyclic moiety is

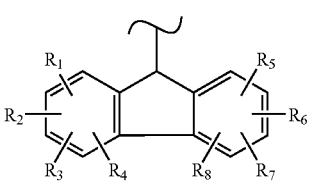

then $R_1$, $R_2$, $R_3$, $R_4$, $R_5$, $R_6$, $R_7$ and $R_8$ is other than

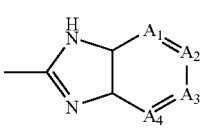

wherein $A_1$, $A_2$, $A_3$ and $A_4$ are selected from $CR_a$ or N, where $R_a$ is H or a substituent; or

(13) where the tricyclic moiety is

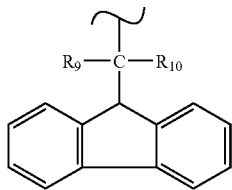

then Z is other than

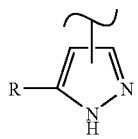

where R is $C_3$-$C_6$cycloalkyl optionally substituted by $C_1$-$C_6$alkyl or arylalkyl or a homolog thereof;

(14) where the tricyclic moiety is

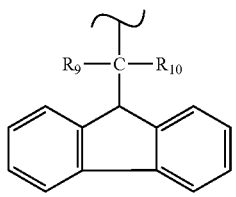

and Z is heteroaryl containing or heterocyclyl containing an N atom in the ring, then the Z heteroaryl or heterocyclyl cannot be substituted with an R'A group where R' is optionally substituted heterocyclic or phenyl and A is $(CH_2)_{0-2}(O)_{0\ or\ 1}$ or $(CR^3R^4)_{0\ or\ 1}NR^5(CO)_{0\ or\ 1}$ where $R^3$, $R^4$=H or $R^3+R^4$-imino and $R^5$<H or alkyl;

(15) where the tricyclic moiety is

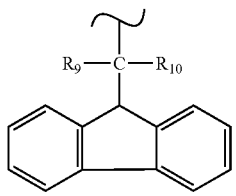

and Z is other than a 5-7 membered heterocyclic ring containing an N, O and/or S which heterocyclic ring is substituted by

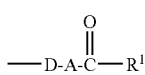

where D is $^{1-4}$Calkylene, O or S,

A is a 3 to 7 carbocyclic ring or a 5- to 7-membered heterocyclic ring containing N, O and/or S, and $R^1$ is OH, alkoxy, or $NR^{10}R^{11}$ where $R^{10}$ and $R^{11}$ can be H or alkyl which Z and/or also may be optionally substituted by 1-3 group which can be $C_{1-4}$alkyl, $C_{1-4}$alkoxy, halo, trihalomethyl, CN, or $NO_2$; or

(16) where the tricyclic moiety is

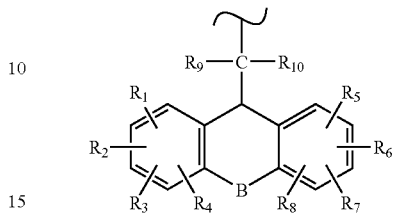

where B is O or S, then a) Z is other than optionally substituted dihydrofuryl or optionally substituted dihydrothienyl, b) or if Z is optionally substituted dihydrofuryl or optionally substituted dihydrothienyl, then 1) at least one of $R_9$ and/or $R_{10}$ is other than H, or 2) $R_{11}$ is other than H or lower alkyl.

The tricyclic moiety

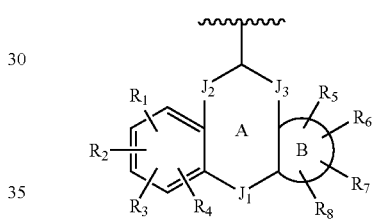

as used herein includes the moieties

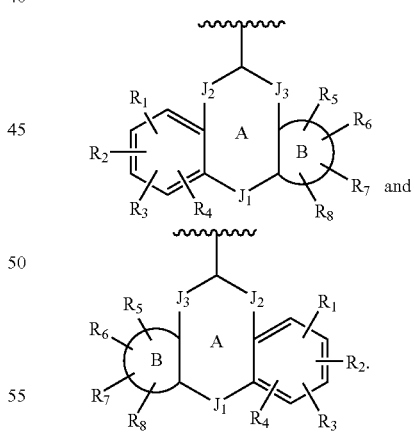

Preferred B moieties are aryl and heteroaryl and includes phenyl, pyridinyl and pyrazinyl.

In the above moieties, it is preferred that

B is a phenyl, pyridinyl or pyrazinyl ring;

$J_1$ is O, S, SO, $SO_2$, a bond, $CH_2$, or $CH_2CH_2$; and $J_2$ and $J_3$ are each a bond.

More preferably $J_1$, is O, S, SO, $SO_2$, or a bond, especially O, S, SO, or $SO_2$.

More preferably B is pyridinyl substituted with aryl or substituted aryl.

More preferably $R_1$, $R_2$, $R_3$ are each hydrogen, and $R_4$ is hydrogen, $CF_3$, $CH_3O$, $N(CH_3)_2CH_2CH_2O$—, OH,

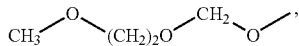

$R_5$, $R_6$, and $R_7$ are each hydrogen and $R_8$ is hydrogen, hydroxyl, $CF_3$, alkoxy, halogen, dialkylaminoalkoxy, alkyloxyalkyloxyalkyloxy, alkylamino, heterocyclo, pyridyl, arylalkylamino, alkoxyarylalkylamino, dialkylamino,

alkoxyaryl, aryl, trifluoromethoxylaryl, carboxyaryl, haloalkyl, dialkylaminoaryl, naphthyl, alkylphenyl, $CF_3$aryl, alkylcarbonylaminoaryl, dialkylaryl, hydroxyaryl, alkoxycarbonylaryl, alkylcarbonylaminoaryl, alkylsulfonylaminoaryl, arylaryl, alkylsulfonylaryl, aminoaryl, arylalkyloxyarylcyanoaryl, or alkylaryl.

More preferably $R_5$, $R_6$, and $R_7$ are each hydrogen; and $R_8$ is selected from hydrogen, Cl, $(CH_3)_2N(CH_2)_2O$—, $CH_3OCH_2CH_2OCH_2O$—, benzylamino, methoxybenzylamino, $N(CH_3)_2CH_2CH_2O$—, OH, $CF_3$, $CH_3O$—, dimethylamino, methoxyphenyl, phenyl, $CF_3OC_6H_4$—, $CO_2H$—$C_6H_4$, $CN$—$C_6H_4$, s-$C_4H_9$—$C_6H_4$—$C_2H_5O$—$C_6H_4$, s-$C_4H_9$—$C_6H_4$—, —$C_3H_7$—$C_6H_4$—, n-$C_4H_9$—$O$—$C_6H_4$—, $C_2H_5$—$C_6H_4$—, t-$C_4H_9$—$C_6H_4$—, $CH_3COC_6H_4$—, $C_6H_5CH_2OC_6H_4$—, $C_6H_5$—$C_6H_4$—, $C_6H_5$—$O$—$C_6H_4$—, $CH_3SC_6H_4$—, $NH_2C_6H_4$—, $CH_3$—$SO_2$—$NHC_6H_4$—, F—$C_6H_4$, $C_6H_5$—, $ClC_6H_4$, -di$CH_3$-amino, naphthyl, $CH_3C_6H_4$, $CF_3C_6H_4$—, $CH_3CONHC_6H_4$—, $CH_3OC_6H_4$,

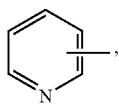

di-$CH_3C_6H_3$—, $HOC_6H_4$—, $CH_3OCOC_6H_4$—,

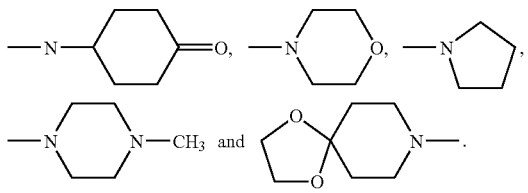

It is preferred that in the compounds of formula I of the invention where Z is heteroaryl or heterocyclo and the heteroaryl and/or heterocyclo is fused to an aryl group, the point of attachment of the fused group to the N atom of the

will be with the heteroaryl or heterocyclo portion and not the aryl portion.

In preferred embodiments, the moiety

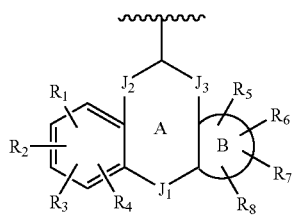

(also referred to as the tricyclic moiety) is

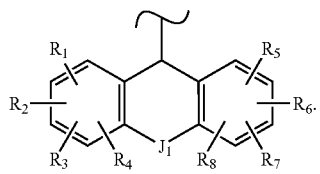

More preferred embodiments are those where $J_1$ is O, S, SO, $SO_2$, a bond, $CH_2$, or $CH_2CH_2$;

$R_1$ is selected from hydrogen, $CF_3$, alkoxy, halogen, hydroxyl and dialkylaminoalkoxy; and $R_5$ is selected from hydrogen, $CF_3$, alkoxy, halogen, amino, dialkylamino, heterocyclo, aryl, carboxyaryl, alkoxyaryl, alkylaryl, heterocyclocarbonylaryl, alkoxy(halo)aryl, carboxy(halo)aryl, dialkylaminocarbonylaryl, alkylamino, hydroxyl, dialkylaminoalkoxy, arylalkylamino, alkoxyarylalkylamino, alkylheterocyclo, arylalkyl, heterocycloalkoxy, arylheterocyclo, arylalkyl(alkyl)amino, haloaryl, dialkylaminoaryl, haloaryl, alkoxyalkoxyalkoxyl, alkylcarbonylamino, heteroaryl, dialkylaryl, hydroxyaryl, alkoxycarbonylaryl, alkylcarbonylaminoaryl, alkylsulfonylaminoaryl, aryloxyaryl, alkylthioaryl, aminoaryl, alkylcarbonylaryl, arylalkoxyaryl, and cyanoaryl.

Also preferred are compounds of formula I (1) where the tricyclic moiety is exclusive of

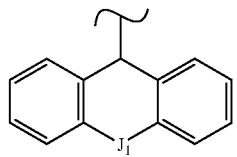

where $J_1$ is other than a bond, —$CH_2CH_2$—, or —CH═CH—; and (2) where the tricyclic moiety ring B includes one, two or three hetero atoms selected from N, O, and S, preferably N.

Preferred compounds of the invention within the scope of formula I are those, including all enantiomers and diastereomers, or prodrug ester or pharmaceutically acceptable salts or hydrates, thereof, in which Z is a 5- to 6-membered heteroaryl or heterocyclo group, each group substituted with one, two or three groups which are the same or different and are independently selected from hydrogen, halogen, alkyl, substituted alkyl, alkenyl, substituted alkenyl, alkynyl, substituted alkynyl, nitro, cyano, $OR^c$, $NR^aR^b$, $C(=O)R^a$, $CO_2R^a$, $C(=O)NR^aR^b$, $-O-C(=O)R^a$, $NR^aC(=O)R^b$, $NR^aC(=O)OR^b$, $NR^aC(=S)OR^b$, $S(O)_pR^c$, $NR^aSO_2R^c$, $SO_2NR^aR^b$, cycloalkyl, cycloalkenyl, heterocyclo, aryl, and heteroaryl;

$R^a$ and $R^b$ are the same or different and at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible together with the atoms to which they are attached $R^a$ is taken together with $R^b$ to form a heteroaryl or heterocyclo ring; and $R^c$ at each occurrence is independently selected from alkyl, substituted alkyl, alkenyl, substituted alkenyl, alkynyl, substituted alkynyl, cycloalkyl, cycloalkenyl, aryl, heteroaryl, and heterocyclo.

More preferably, Z is selected from
Z is selected from:

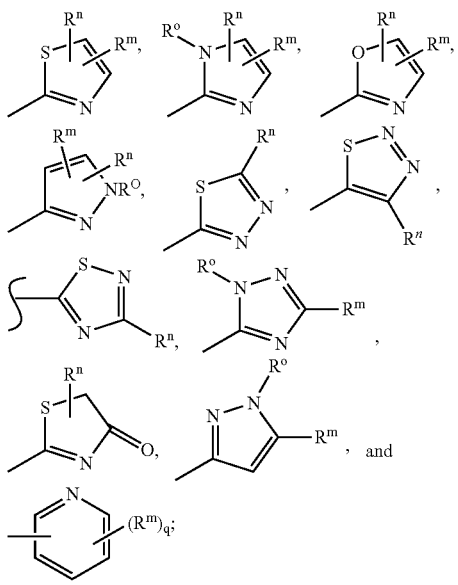

$R^m$ and $R^n$ are the same or different and at each occurrence are independently selected from any of the heteroaryl substituents for Z set out above and are preferably selected from hydrogen, halogen, alkoxy, $-COR_1^a$, $-CO_2R_1^a$, $-C(O)N(R_1^a)(R_1^b)$, $C_{1-6}$alkyl, $CF_3$, substituted alkyl, aryl-NHC(O)-aryl, aryl, arylalkyl, $CH_2OH$, $-SR_1^a$, $S(O)_{1-2}R_1^c$, $N(R_1^a)(R_1^b)$, $CH_2F$, cyano, $C_{3-6}$cycloalkyl, and a 5 to-7-membered heteroaryl with a heteroatom selected from N, O or S;

$R^o$ is hydrogen or $C_{1-6}$alkyl;

$R_1^a$ and $R_1^b$ are the same or different and at each occurrence are independently selected from hydrogen, alkyl, substituted alkyl, $C(=O)$alkyl, $CO_2$(alkyl), $SO_2$alkyl, alkenyl, substituted alkenyl, alkoxy, amino, substituted amino, aryl, heteroaryl, heterocyclo, and cycloalkyl, provided $R_1^a$ and $R_1^b$ are not both alkoxy, amino, or substituted amino;

or $R_1^a$ and $R_1^b$, where possible can be taken together with the nitrogen to which they are attached to form a 5-, 6- or 7-membered heteroaryl or cycloheteroalkyl ring which contains 1, 2 or 3 hetero atoms which can be N, O, or S;

$R_1^c$ is selected from alkyl, substituted alkyl, alkenyl, substituted alkenyl, alkynyl, substituted alkynyl, alkoxy, amino, substituted amino, heteroaryl, heterocyclo, cycloalkyl, and aryl; and q is 1 or 2.

$R_1^c$ is selected from hydrogen, alkyl, substituted alkyl, alkenyl, substituted alkenyl, alkynyl, substituted alkynyl, alkoxy, amino, substituted amino, heteroaryl, heterocyclo, cycloalkyl, and aryl;

$R^o$ is hydrogen or alkyl; and q is 1 or 2.

Still, more preferably, Z is selected from

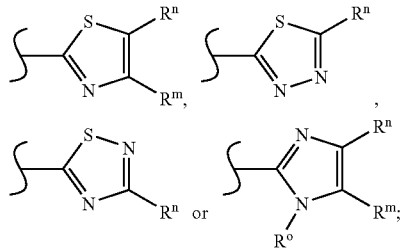

$R^m$ and $R^n$ are the same or different and at each occurrence are independently selected from hydrogen, $-C(O)N(R_1^a)(R_1^b)$, $C_{1-6}$alkyl, $CF_3$, $CH_2OH$, $-SR_1^a$, $N(R_1^a)(R_1^b)$, $CH_2F$, cyano, and $C_{3-6}$cycloalkyl;

$R^o$ is hydrogen or $C_{1-6}$alkyl; and $R_1^a$ and $R_1^b$ are the same or different and at each occurrence are independently selected from hydrogen, $C_{1-6}$alkyl, and $C_{3-6}$cycloalkyl.

In other preferred embodiments $R^m$ is selected from hydrogen, $C_1$-$C_4$alkyl, phenyl, $CO_2$alkyl, naphthyl, quinolinyl, and $-C(R^{18})(R^{19})$-T wherein the naphthyl or quinolinyl group is substituted by one or more substituents selected from the group consisting of hydrogen, amino, hydroxy, $C_{1-4}$alkyl, $C_{1-4}$alkoxy, perfluoro substituted $C_{1-4}$alkyl (for example $CF_3$), cyano, nitro, $-C(O)NHR^{22}$ (where $R^{22}$ is phenyl which may optionally be substituted), and halogen;

$R^n$ is selected from hydrogen, bromo, chloro, and $CH_3$;

T is selected from a cycloalkyl, cycloalkenyl, heterocyclo, aryl, and heteroaryl ring where each ring is substituted by 0-4 $R^{20}$ and 0-1 $R^{21}$;

$R^{18}$ and $R^{19}$ are the same or different and are independently at each occurrence selected from hydrogen, halogen, hydroxy, alkyl, alkenyl, alkynyl, alkoxy, cyano, nitro, $NR^aK^b$, and CHO; or $R^{18}$ and $R^{19}$ combine to form $=O$ or a double bond, wherein a carbon linked to the double bond is substituted by hydrogen, alkyl, substituted alkyl, alkenyl, substituted alkenyl, alkynyl, substituted alkynyl, alkoxy, amino, substituted amino, heteroaryl, heterocyclo, cycloalkyl, or aryl; and $R^{20}$ and $R^{21}$ are the same or different and at each occurrence are independently selected from hydrogen, halogen, hydroxy, alkyl, substituted alkyl, alkenyl, substituted alkenyl, alkynyl, substituted alkynyl, alkoxy, aryloxy, aryl, cycloalkyl, heteroaryl, heterocyclo, cyano, heteroarylaminocarboyl, heterocyclocarbonyl, cyanoalkyl, alkylaminoalkyl, hydroxyalkyl, hydroxyaryl, aryloxyalkyl, alkoxyalkyl, nitro, oxo, $NR_1^aR_1^b$, CHO, $CO_2$alkyl, $CONR_1^aR_1^b$, $CH_2NR_1^aR_1^b$, $CO_2H$, $CH_2OH$, $CH_2NHC(O)R_1^c$, $NHCOR_1^c$, NHCONR$_1{}^a$R$_1{}^b$, NHSO$_p$R$_1{}^c$, —SO$_2$NR$_1{}^a$R$_1{}^b$, NR$^a$SO$_2$NR$_1{}^a$R$_1{}^b$, and NR$^a$SO$_p$R$_1{}^c$; or R$^7$ and R$^8$ located on adjacent atoms can be taken together to form an optionally substituted cycloalkyl, aryl, heteroaryl, or heterocyclo ring.

In a more preferred embodiment,

R$^n$ is H;

R$^m$ is

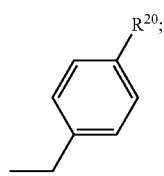

R$^{18}$ and R$^{19}$ are the same or different and at each occurrence are independently selected from hydrogen, halogen, and hydroxy; or R$^{18}$ and R$^{19}$ combine to form =O; and R$^{20}$ is selected from C$_{1-4}$alkoxy, halogen, pyrimidine, isoxazole, pyrazole, and pyridine, where the C$_{1-4}$alkoxy, pyrimidine, isoxazole, pyrazole, or pyridine groups are substituted by hydrogen, morpholinyl, C$_{1-4}$alkoxy, and C$_{1-4}$alkyl;

or R$^m$ is selected from

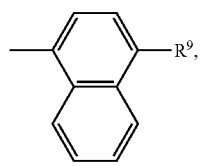

and CO$_2$C$_{1-4}$alkyl; and

R$^9$ is selected from methyl, CF$_3$, fluoro, chloro, and bromo.

In still more preferred embodiments,

Z is 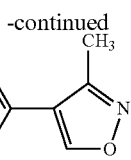, where R$^m$ is

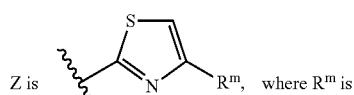

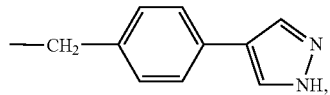

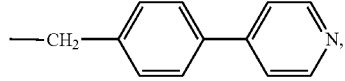

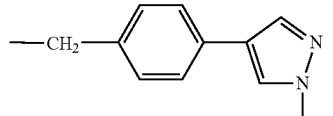

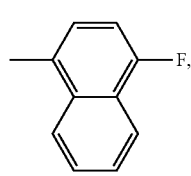

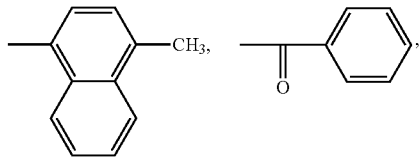

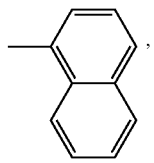

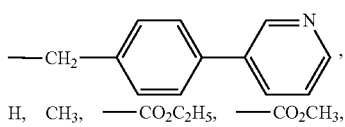

H, CH$_3$, —CO$_2$C$_2$H$_5$, —CO$_2$CH$_3$,

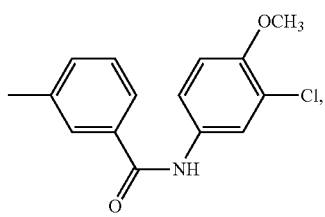

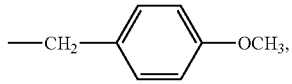

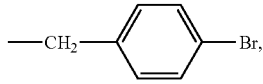

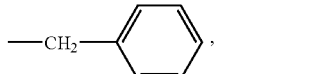

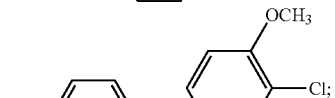

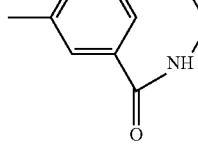

Z is

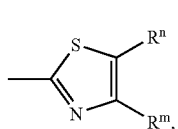

where R$^n$ is CH$_3$, R$^m$ is CH$_3$;

Z is

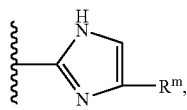

where $R^m$ is 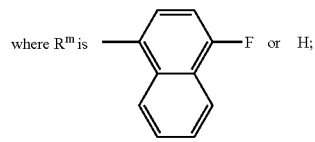

Z is

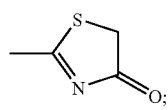

Z is

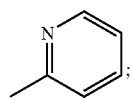

Z is

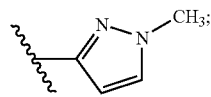

Z is

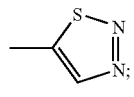

Z is

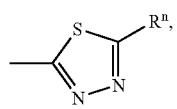

where $R^n$ is $CH_3$, H, $CF_3$, C(O)OEt, C(O)$NH_2$, C(O)NH(cyclopropyl), C(O)$NHCH_3$, C(O)NHEt, $CH_2OH$, S(methyl), N(methyl)$_2$, $CH_2F$, cyano, ethyl, or cyclopropyl; or Z is

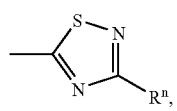

where $R''$ is $CH_3$ or H.

Also preferred are compounds having the structure

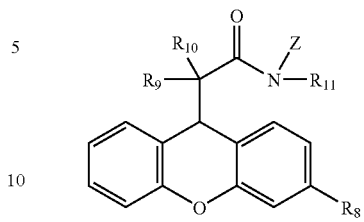

or an enantiomer, diastereomer, tautomer or a pharmaceutically acceptable salt thereof, wherein:

$R_8$ is hydroxy, cyano, —C(=O)$NR_{14}R_{15}$, —$CO_2R_{14}$, —C($NH_2$)=NOH, —$NR_{14}$C(=O)$OR_{15}$, —OC(O)$NR_{14}R_{15}$, —NHC(O)$NR_{14}R_{15}$, or —NHC(O)$R_{15}$;

$R_9$ and $R_{10}$ are the same or different and at each occurrence are independently selected from (i) hydrogen, halogen, alkyl, substituted alkyl, alkenyl, substituted alkenyl, alkynyl, substituted alkynyl, nitro, cyano, —$OR_{14}$, —$NR_{14}R_{15}$, —C(=O)$R_{14}$, —$CO_2R_{14}$, —C(=O)$NR_{14}R_{15}$, —O—C(=O)$R_{14}$, —$NR_{14}$C(=O)$R_{15}$, —$NR_{14}$C(=O)$OR_{15}$, —$NR_{14}$C(=S)$OR_{15}$, —S(O)$_pR_{17}$, —$NR_{14}SO_2R_{17}$, —$SO_2NR_{14}R_{15}$, cycloalkyl, cycloalkenyl, heterocyclo, aryl, and heteroaryl; or (ii) together with the atom to which the are attached, $R_9$ and $R_{10}$ are taken together to form a carbonyl, alkenyl, substituted alkenyl, cycloalkyl, cycloalkenyl, or heterocyclo group;

$R_{11}$ is selected from hydrogen, alkyl, substituted alkyl, C(=O)alkyl, $CO_2$(alkyl), $SO_2$alkyl, alkoxy, amino, substituted amino, aryl, heteroaryl, heterocyclo, and cycloalkyl; and Z is a heteroaryl ring which is linked via a carbon atom to the N atom where Z is preferably

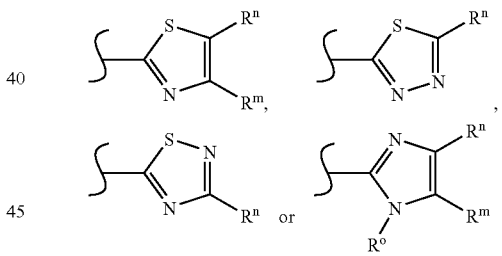

and $R^n$, $R^m$, and $R^o$ are as defined above.

In addition, preferred are compounds of the structure

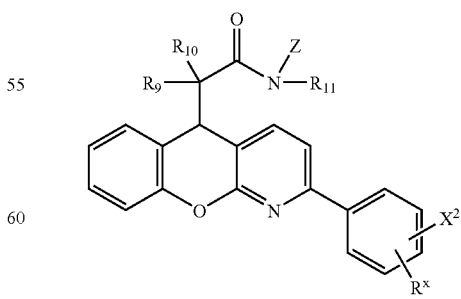

or an enantiomer, diastereomer, or tautomer thereof, or a prodrug ester thereof, or a pharmaceutically acceptable salt thereof, wherein:

$X^2$ is halogen, alkoxy, H, or alkyl;

$R^x$ is H, C(O)NR$_2^a$R$_2^b$, OR$_2$, R$_2^a$, COOH, CF$_3$,

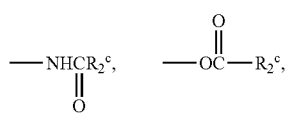

—NHSO$_2$R$_2^c$, aryl, aryloxy, alkylthio, amino, acyl or cyano;

R$_2^a$ and R$_2^b$ are the same or different and at each occurrence are independently selected from hydrogen, alkyl, substituted alkyl, C(=O)alkyl, CO$_2$(alkyl), SO$_2$alkyl, hydrogen, alkenyl, substituted alkenyl, alkoxy, amino, substituted amino, aryl, heteroaryl, heterocyclo, and cycloalkyl;

or R$_2^a$ and R$_2^b$ where possible can be taken together with the nitrogen to which they are attached to form a 5-, 6- or 7-membered heteroaryl or cycloheteroalkyl ring which contains 1, 2 or 3 hetero atoms which can be N, O, or S;

R$_2^c$ is selected from hydrogen, alkyl, substituted alkyl, alkenyl, substituted alkenyl, alkynyl, substituted alkynyl, alkoxy, amino, substituted amino, heteroaryl, heterocyclo, cycloalkyl, and aryl;

R$_9$ and R$_{10}$ are the same or different and at each occurrence are independently selected from (i) hydrogen, halogen, alkyl, substituted alkyl, alkenyl, substituted alkenyl, alkynyl, substituted alkynyl, nitro, cyano, OR$_{14}$, NR$_{14}$R$_{15}$, C(=O)R$_{14}$, CO$_2$R$_{14}$, C(=O)NR$_{14}$R$_{15}$, —O—C(=O)R$_{14}$, NR$_{14}$C(=O)R$_{15}$, NR$_{14}$C(=O)OR$_{15}$, NR$_{14}$C(=S)OR$_{15}$, S(O)$_p$R$_{17}$, NR$_{14}$SO$_2$R$_{17}$, SO$_2$NR$_{14}$R$_{15}$, cycloalkyl, cycloalkenyl, heterocyclo, aryl, and heteroaryl; or (ii) together with the atom to which they are attached, R$_9$ and R$_{10}$ are taken together to form a carbonyl, alkenyl, substituted alkenyl, cycloalkyl, cycloalkenyl, or heterocyclo group; and R$_{11}$ is selected from hydrogen, alkyl, substituted alkyl, C(=O)alkyl, CO$_2$(alkyl), SO$_2$alkyl, alkoxy, amino, substituted amino, aryl, heteroaryl, heterocyclo, and cycloalkyl.

In a more preferred embodiment, Z is a heteroaryl ring which is linked via a carbon atom to the N atom, where Z is preferably

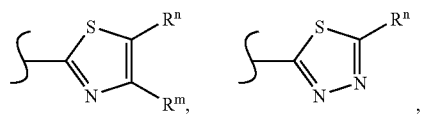

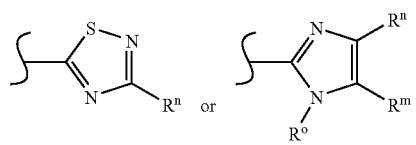

and R$^n$, R$^m$, and R$^o$ are as defined above.

Also preferred are (1) compounds of formula I where

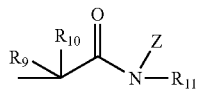

is

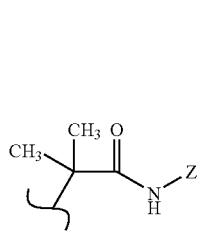

where

Z is

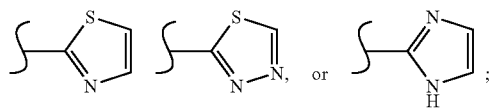

and the tricyclic moiety is

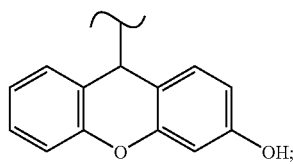

and (2) compounds of formula I wherein

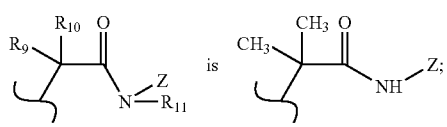

Z is

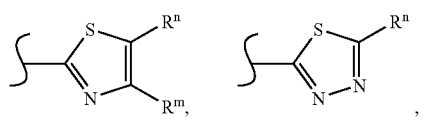

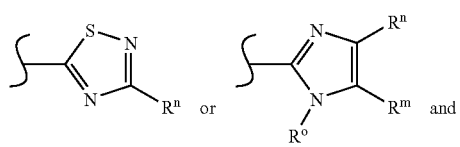

R″, R‴, and Rᵒ are as defined above;
the tricyclic moiety is

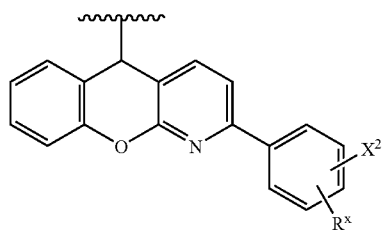

$X^2$ is halogen, alkoxy, H, or alkyl; and
$R^x$ is H, $C(O)NR_2^a R_2^b$, $OR_2^c$, $R_2^a$, COOH, $CF_3$,

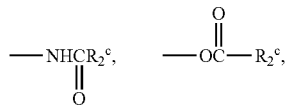

—$NHSO_2R_2^c$, aryl, aryloxy, alkylthio, amino, acyl or cyano;
(where $R_2^a$, $R_2^b$ and $R_2^c$ are as defined hereinafter).
In other preferred embodiments,

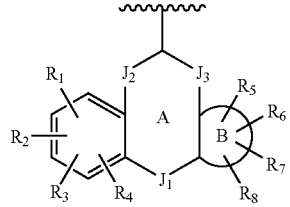

is

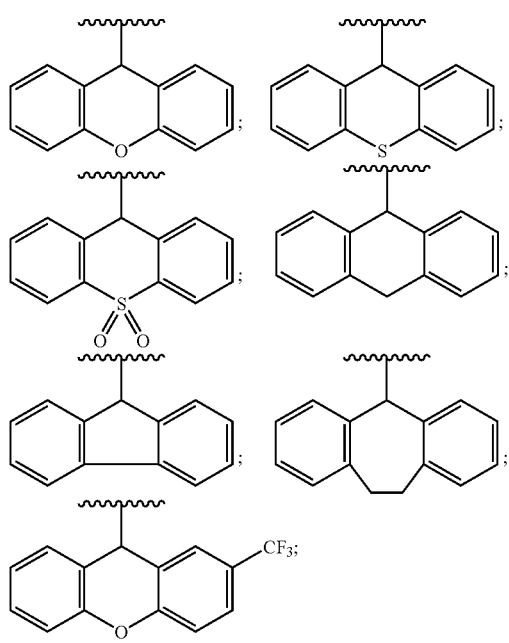

-continued

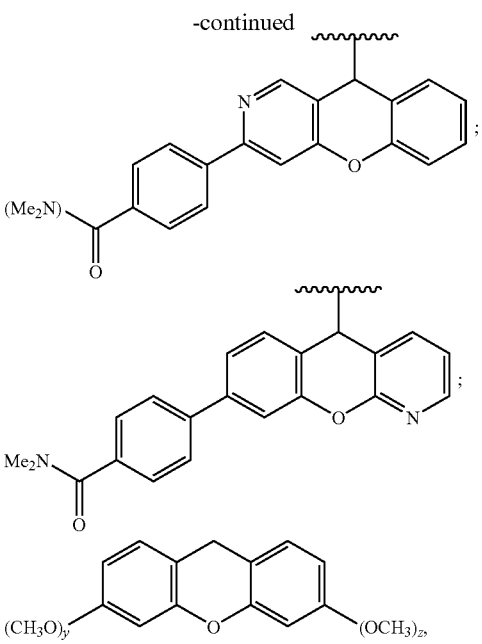

where z is 0 or 1 and y is 0 or 1;

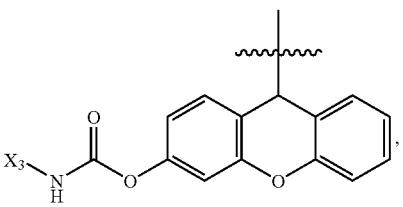

where $X_3$ is benzyl, $(CH_2)_3CH_3$, Ethyl, $CH_2$(2-furyl), cyclohexyl, $(CH_2)_7CH_3$, $(CH_2)_2$(phenyl), $CH_2$(2-thienyl), $CH_2$(4-fluorophenyl), tert-butyl, $CH(CH_3)$ethyl, $(CH_2)_2$(4-methoxyphenyl), 4-methoxyphenyl, or $CH_2$(cyclohexyl);

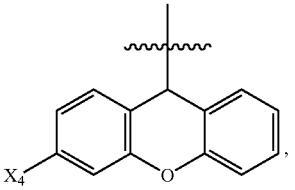

where $X_4$ is NHC(O)O(cyclohexyl), NHC(O)O(methyl), —C≡C—$(CH_2)_2CH_3$, $C(O)NHCH_2$(phenyl), $C(O)CH_3$, —NHC(O)NH$(CH_2)(O)N(Me)_2$, —NHC(O)NH$(CH_2)$(N-pyrollidinyl),

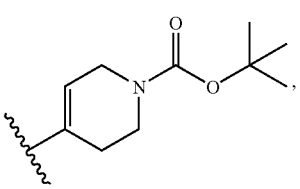

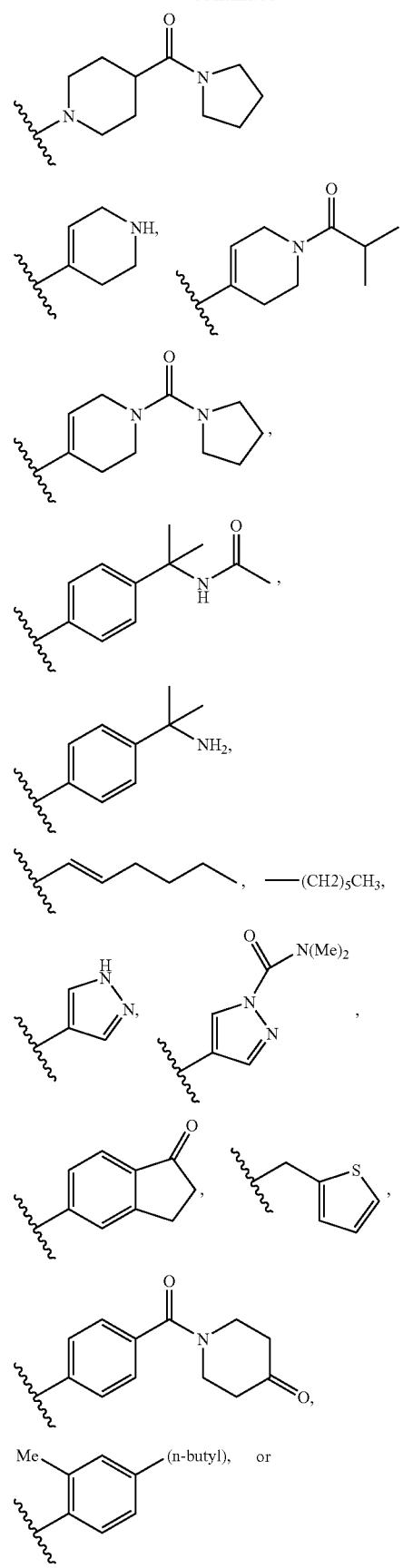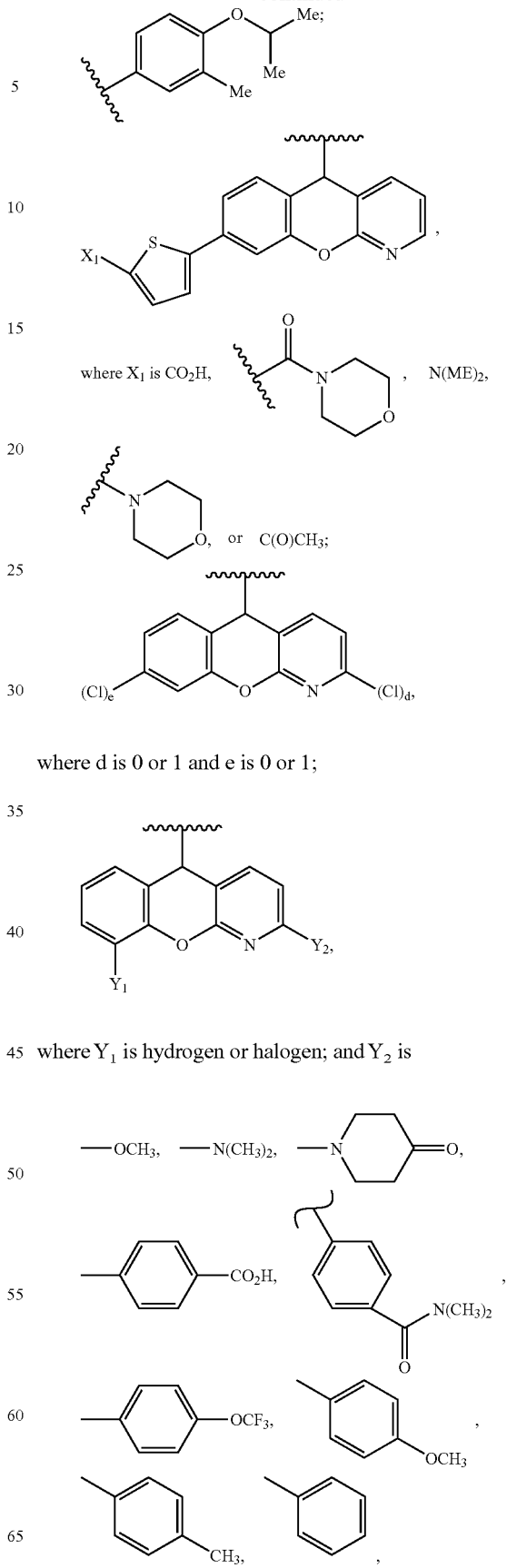
where d is 0 or 1 and e is 0 or 1;
where $Y_1$ is hydrogen or halogen; and $Y_2$ is -continued

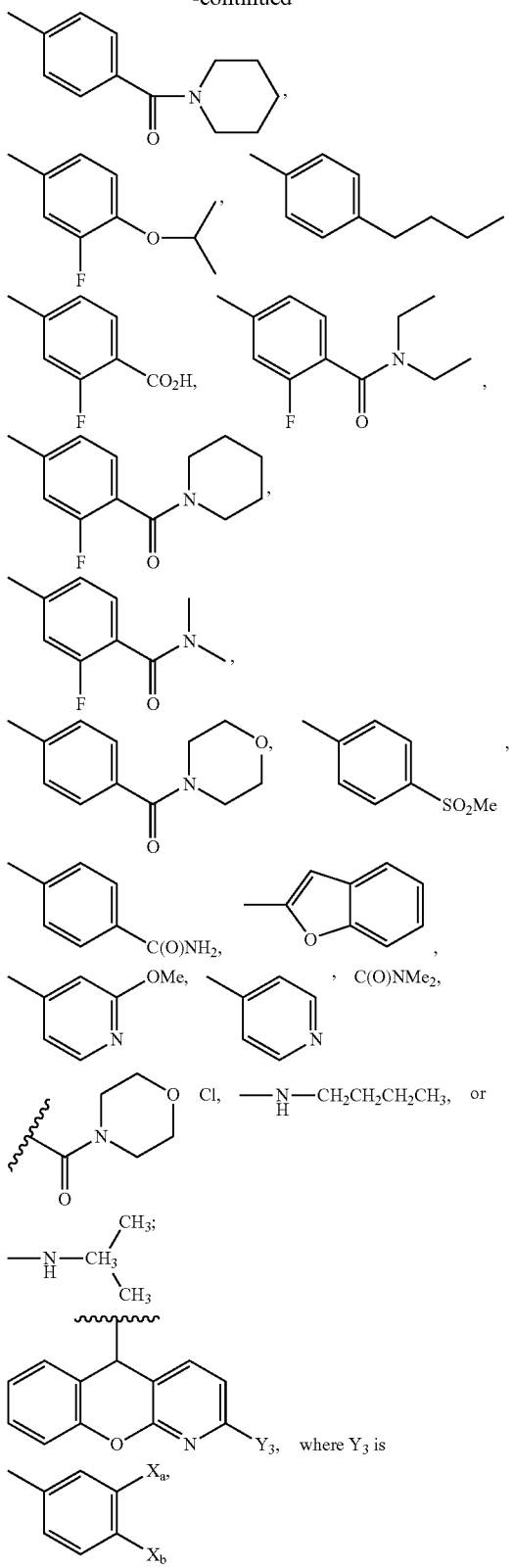

$X_a$ is hydrogen or fluoro, and $X_b$ is selected from cyclohexyl, —O(isopropyl), hydroxyl, hydrogen, —S(ethyl), $SO_2$(ethyl), $SO_2$(isopropyl), $C(O)CH_3$, —O(n-propyl), $CH_2CO_2H$, $SO_2N(CH_3)_2$, $SO_2$(N-morpholinyl), $C(OH)Me_2$, $SO_2NHCH_2CH_3$, $SO_2NH$(cyclopropyl), $SO_2NH$(isopropyl), $CH_2CO_2CH_3$, $CH(OH)CH_3$, $CH(OH)$(Isopropyl), $S(O)CH_3$,

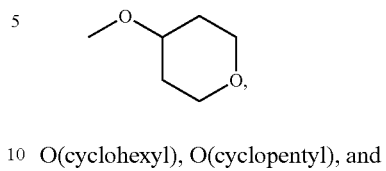

O(cyclohexyl), O(cyclopentyl), and

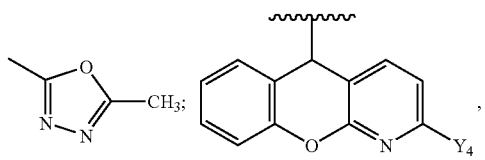

where $Y_4$ is $NR_aR_b$, $NEt_2$, piperidine, $NMe_2$, NMeEt, pyrrolidine, NHMe, NMe(n-Pr), NME(Bn),

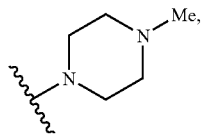

morpholine, NMe(i-Pr), $NEt_2$, $NMe_2$, piperidine, $NMe(CH_2)_2 CN$, 4-Me-, piperidine, 4-OH-piperidine, $NMe(CH_2)_2 CH(CH_3)_2$,

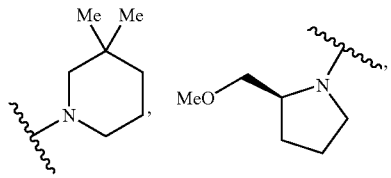

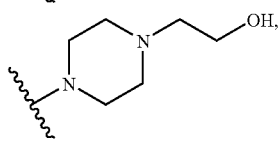

$N(Me)(CH_2)_2Ph$,

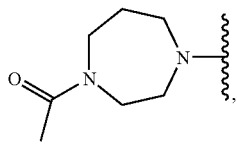

4-Bn-piperidine,
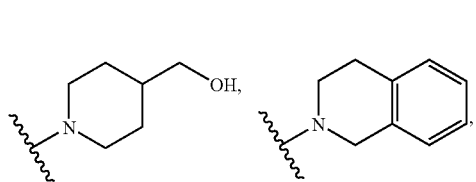
4-Ph-piperidine,
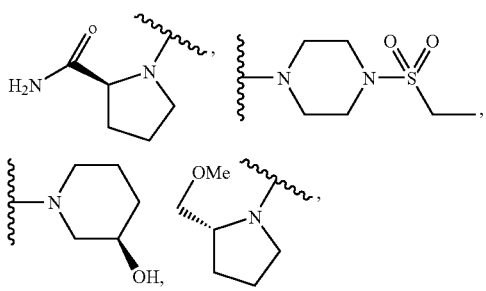
NMe(CH₂)₂SO₂Me,
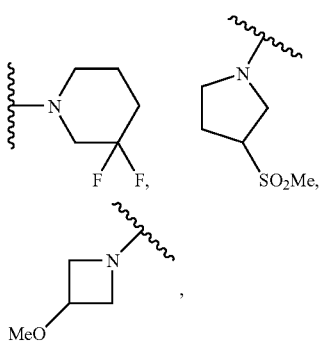
4-(CF₃)-piperidine,
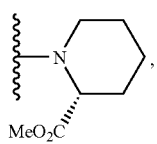
NMe(n-Bu), NMeCH₂CO₂Me, NMe(CH₂)₂OH, NMe(CH₂)₂OMe,
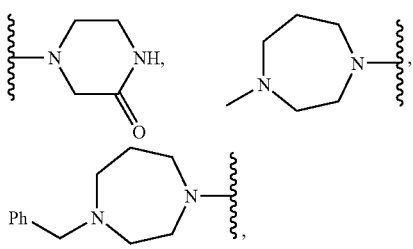
-continued
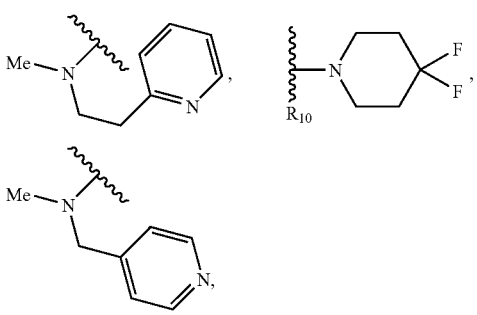
NMe(CH₂)₂O(t-Bu),
N((CH₂)₂OH)₂,
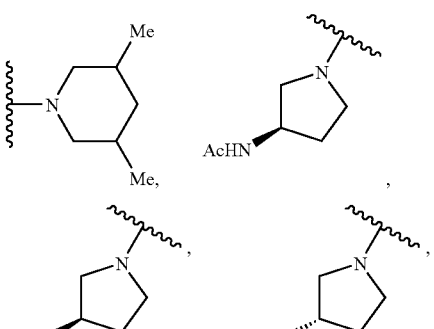
4-OMe-piperidine,
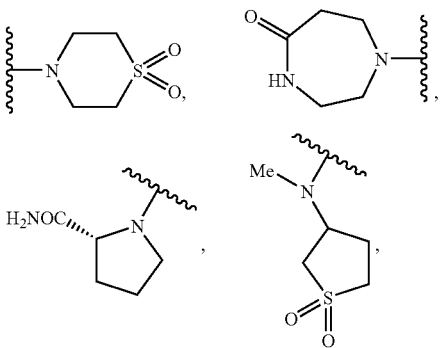
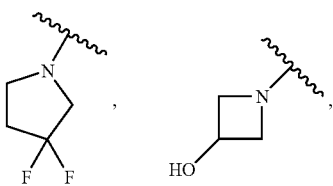

-continued
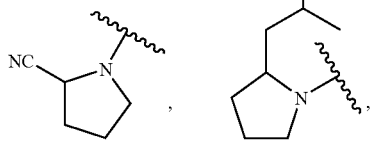
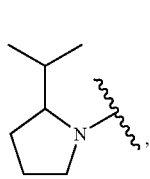 , 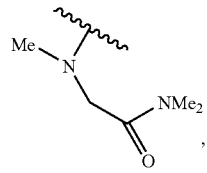 ,
NEt(CH$_2$)$_2$OH,
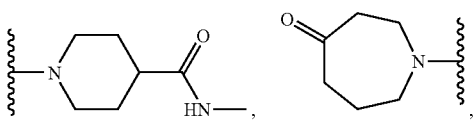
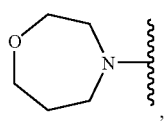
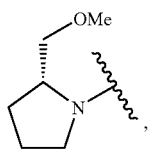
NMe(CH$_2$)$_2$CN, morpholinyl, NMe(-Pr),
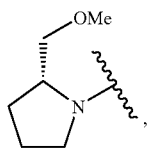 , 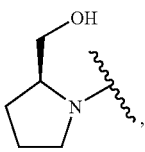 ,
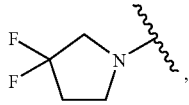
NEtMe,
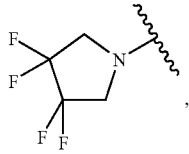
NMe(CH$_2$)CO$_2$H,
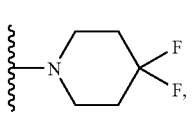 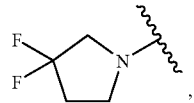
pyrrolidine,
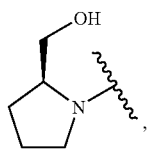
NMe(n-Pr),
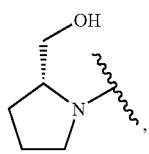
NMeEt, NMe(n-Pr), NMe$_2$, NHMe, NHBn,
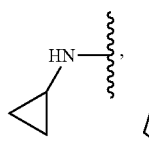 , 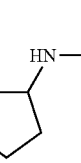 , 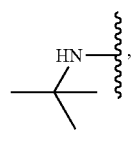 ,
NHiPr, NH(CH$_2$)$_2$Ph, NH(CH$_2$)$_2$Ome, NH(CH$_2$)$_2$C(CH$_3$)$_3$, NH(CH$_2$)$_2$OH, NH(n-Pr), NH(CH$_2$)$_3$OH,
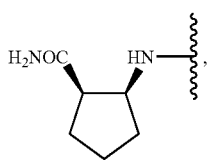
or NHMe;
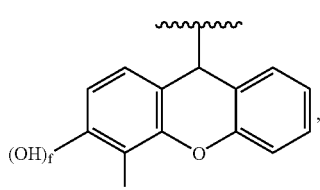
where e is 0 or 1 and f is 0 or 1, provided that only one of e and f can be 1;

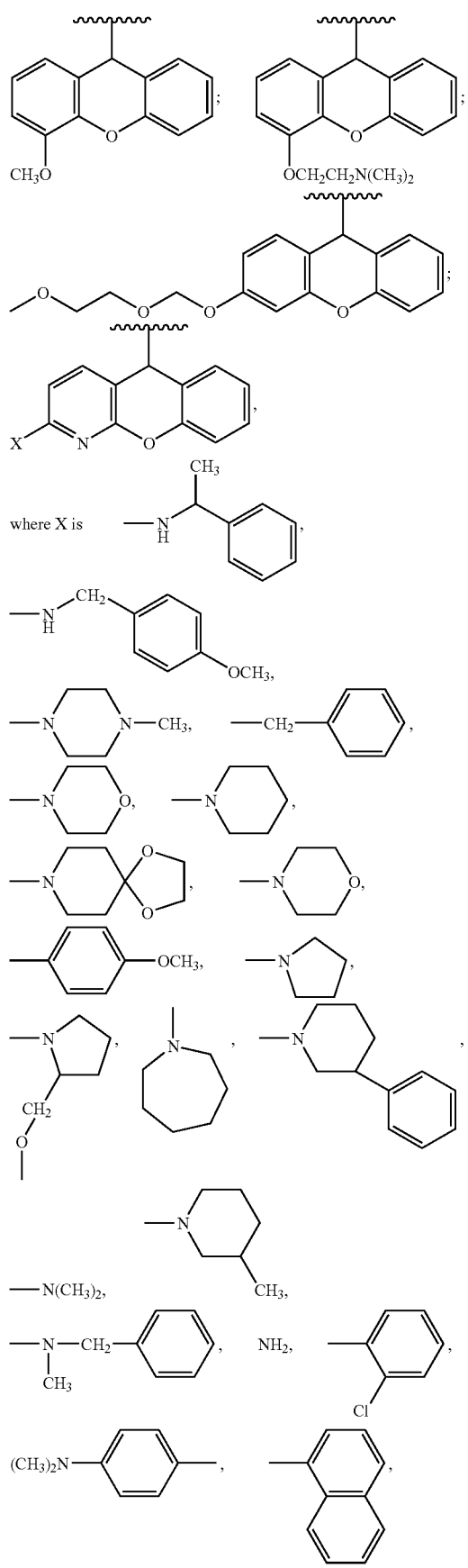

-continued
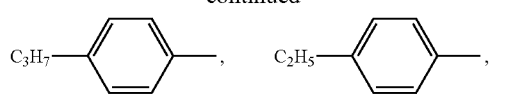
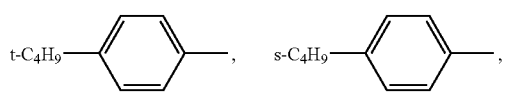
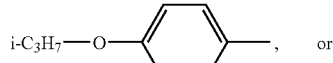, or
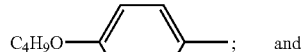; and
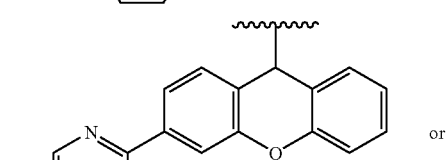 or
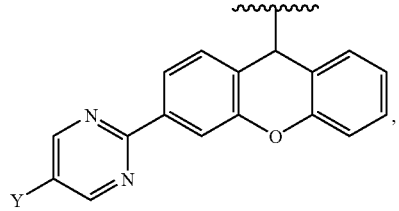,
where Y is $C_{1-6}$alkyl, $C(O)N(C_{1-6}alkyl)_2$, COOH, and $OC_{1-6}$ alkyl.
Most preferred are compounds of the structure
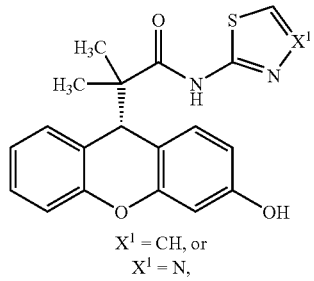
$X^1$ = CH, or $X^1$ = N,
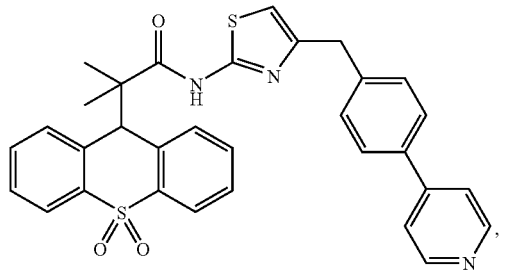,
-continued
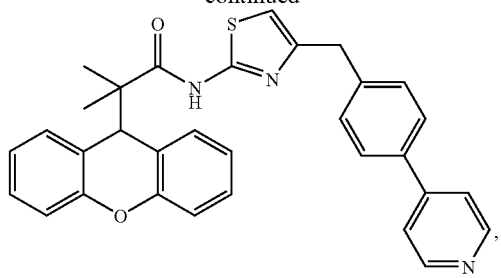,
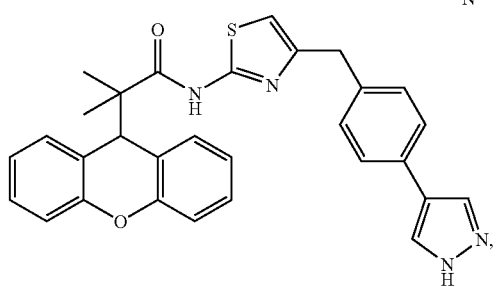,
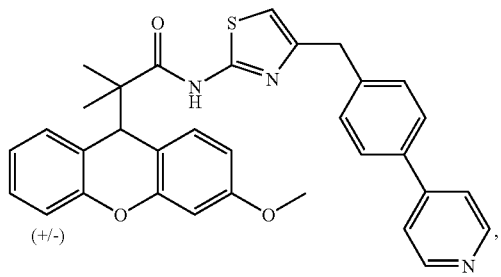
(+/−)
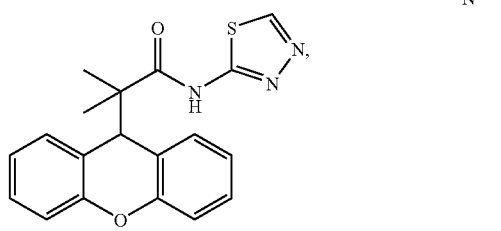
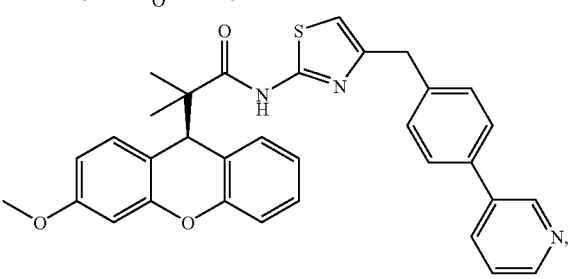
and compounds of the structure
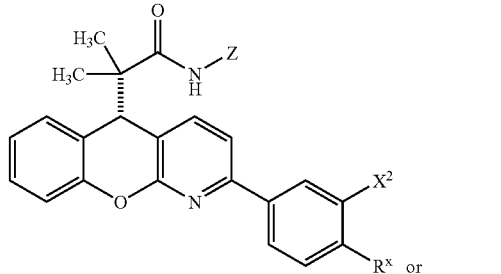 or
IC -continued

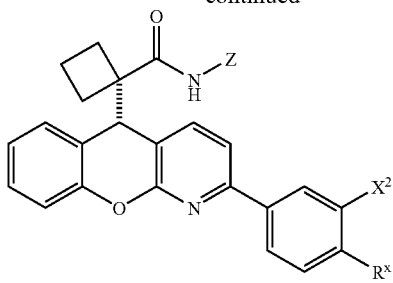

wherein:
$X^2$ is H, halogen, or alkyl;
$R^x$ is H, $C(O)NR_2{}^a R_2{}^b$, $OR_2{}^a$, $R_2{}^a$, COOH, $CF_3$,

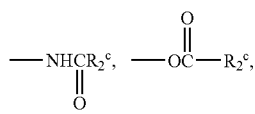

—$NHSO_2R_2{}^c$, aryl, aryloxy, alkylthio, amino, acyl or cyano;
$R_2{}^a$ is selected from hydrogen, alkyl, substituted alkyl, C(=O)alkyl, $CO_2$(alkyl), $SO_2$alkyl, hydrogen, alkenyl, substituted alkenyl, alkoxy, amino, substituted amino, aryl, heteroaryl, heterocyclo, and cycloalkyl;
$R_2{}^b$ is selected from alkyl, substituted alkyl, C(=O)alkyl, $CO_2$(alkyl), $SO_2$alkyl, hydrogen, alkenyl, substituted alkenyl, alkoxy, amino, substituted amino, aryl, heteroaryl, heterocyclo, and cycloalkyl;
or $R_2{}^a$ and $R_2{}^b$ are taken together with the nitrogen to which they are attached to form a 5-, 6- or 7-membered heteroaryl or cycloheteroalkyl ring which contains 1, 2 or 3 hetero atoms which can be N, O, or S; and
$R_2{}^c$ is selected from alkyl, substituted alkyl, alkenyl, substituted alkenyl, alkynyl, substituted alkynyl, alkoxy, amino, substituted amino, heteroaryl, heterocyclo, cycloalkyl, and aryl.
wherein $R^a$, $R^b$ and $R^cC$ are as defined hereinafter, preferably $C(O)NR^aR^b$, alkoxy or alkyl.
Still, more preferably, Z is selected from

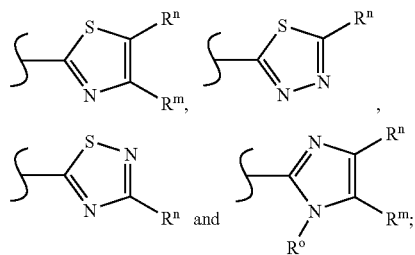

$R^m$ and $R^n$ are the same or different and at each occurrence are independently selected from hydrogen, —$C(O)N(R_1{}^a)(R_1{}^b)$, $C_{1-6}$alkyl, $CF_3$, $CH_2OH$, —$SR_1$, $N(R_1{}^a)(R_1{}^b)$, $CH_2F$, cyano, and $C_{3-6}$cycloalkyl;
$R^o$ is hydrogen or $C_{1-6}$alkyl; and
$R_1{}^a$ and $R_1{}^b$ are the same or different and at each occurrence are independently selected from hydrogen, $C_{1-6}$alkyl, and $C_{3-6}$cycloalkyl.
Most preferred is the S-enantiomer over the R-enantiomer.
Most preferred $R^x$ is at the 4-position and $R^x$ is tertiary amide (i.e., $R^x\uparrow C(O)NR^aR^b$), alkoxy, or alkyl.

More preferred is $X^2$=F.
More preferred is where Z is

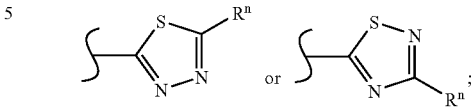

and $R^n$ is $CH_3$, H, $CF_3$, C(O)OEt, $C(O)NH_2$, C(O)NH(cyclopropyl), $C(O)NHCH_3$, C(O)NHEt, $CH_2OH$, S(methyl), N(methyl)$_2$, $CH_2F$, cyano, ethyl, or cyclopropyl.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which including a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, immune disease, metabolic disease (diabetes and/or obesity), and neoplastic disease. A disease associated with the expression product of a gene whose transcription is stimulated or repressed by glucocorticoid receptors, or a disease associated with AP-1- and/or NF-κB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger, et al., Science, 228:740-742 (1985), and in Weinberger, et al., Nature, 318:670-672 (1986); rat glucocorticoid receptor as disclosed in Miesfeld, R., Nature, 312:779-781 (1985); mouse glucocortoid receptor as disclosed in Danielson, M. et al., EMBO J., 5:2513; sheep glucocorticoid receptor as disclosed in Yang, K. et al., J. Mol. Endocrinol., 8:173-180 (1992); marmoset glucocortoid receptor as disclosed in Brandon, D. D. et al., J. Mol. Endocrinol. 7:89-96 (1991); and human GR-beta as disclosed in Hollenberg, S. M. et al., Nature, 318:635 (1985); Bamberger, C. M. et al., J. Clin Invest., 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhea, pulmonary inflammation, eye uveitis, hepatitis, Graves' disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, asthma, inflammatory bowel disease, systemic lupus erythematosis, psoriasis and chronic pulmonary disease.

Accordingly, one embodiment of the present invention is a method of treating a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which comprise administering to a patient in need of treatment, a therapeutically effective amount of a compound as defined in Claim 1.

In a preferable embodiment the disease or disorder is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia greata, autoimmune alopecia, autoimmune hypopituatarism, Guillain-Barre syndrome, and alveolitis; contact hypersensitivity, delayed-type hypersensitivity, contact dermatitis, uticaria, skin allergies, respiratory allergies, hayfever, allergic rhinitis and gluten-sensitive enteropathy, osteoarthritis, acute pancreatis, chronic pancreatitis, acute respiratory distress syndrome, Sezary's syndrome, restenosis, stenosis and artherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, psoriasis, seborrheic dermatitis, seasonal or perennial allergic rhinitis, bronchial asthma, contact dermatitis, atopic dermatitis, drug hypersensitivity reactions, allergic conjuncivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, Crohn's disease, Sjogren's syndrome, autoimmune vasculitis, multiple sclerosis, myasthenia gravis, sepsis, and chronic obstructive pulmonary disease.

In an even more preferable embodiment, the disease or disorder is selected from transplant rejection, rheumatoid arthritis, psoriatic arthritis, multiple sclerosis, asthma, inflammatory bowel disease, systemic lupus, erythematosis, and psoriasis.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

In still another embodiment, pharmaceutical combinations are contemplated comprising a compound as defined in Claim 1, an enantiomer, diastereomer, or tautomer thereof, or a prodrug ester thereof, or a pharmaceutically-acceptable salt thereof, and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or α-adrenergic blocker.

More preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid_lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of Homochiral Examples May be Carried Out by Techniques Known to One skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

SCHEME 1

Condensation of carboxylic acid II with amine III to form product I

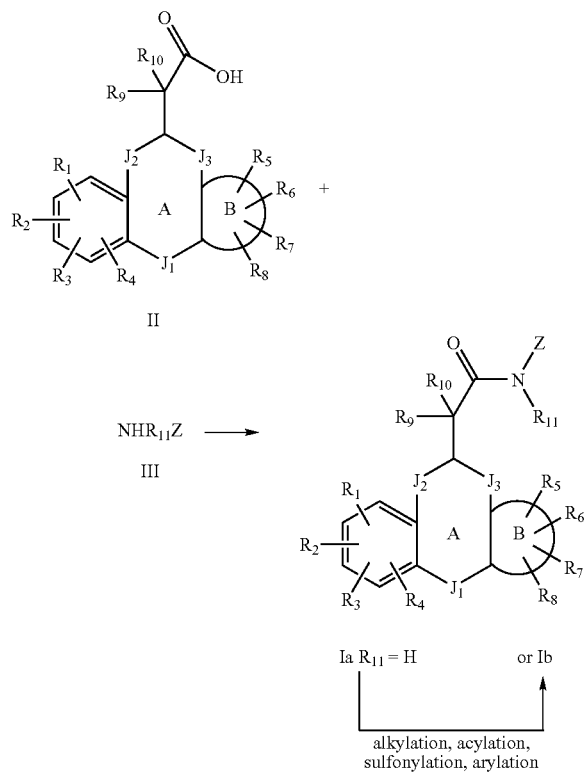

Scheme 1 illustrates the preparation of title compounds of the invention (I) from intermediate carboxylic acids II. The amides I may be prepared from II by many of the myriad ways known to prepare carboxamides by the dehydrative condensation of carboxylic acids and amines. For example, condensation of acid II with amine ($NR_{11}Z$, III, where $R_{11}$=H, alkyl, cycloalkyl, alkoxy, dialkylamino, aryl or heteroaryl) may be effected by treatment of II with an activating reagent, such as a water-soluble carbodiimide (EDC), in the presence of an N-hydroxy triazole (HOAt or HOBt, or the like) and amine in the presence of base (preferably triethylamine, diisopropylethylamine, or the like) in an appropriate polar aprotic solvent (N,N-dimethylformamide, acetonitrile, dichloromethane, or the like). The carboxylic acid II may also be converted to an acid chloride by treatment with an appropriate chlorinating agent (thionyl chloride, oxalyl chloride, or the like). Similarly, II may be converted to an acyl fluoride upon exposure to a fluorinating agent (such as cyanuric fluoride). Condensation of the acyl halide (chloride or fluoride) with the amine III (typically carried out in the presence of a base such as pyridine or triethylamine in an aprotic solvent) may then provide the amide Ia. In cases where $R_{11}$=H (i.e., III=$NH_2Z$), the immediate product of condensation of II and III (Ia, $R_{11}$=H) may be converted to Ib ($R_{11}$=alkyl) by treatment of Ia with an alkylating agent (alkyl halide, alkyl sulfonate, or the like) in the presence of a base (cesium carbonate, sodium hydride, or the like). Ia ($R_{11}$=H) may be converted to Ib ($R_{11}$=C(O)alkyl, $CO_2$alkyl) by treatment with a strong base (sodium hydride, lithium diisopropyl amide, or the like) followed by acylation with an appropriate acylating reagent (an acid chloride, chloroformate, or the like). Similarly, sulfonylation may be effected by treatment with a base and sulfonyl halide to provide Ib ($R_{11}$=$SO_2$aryl or $SO_2$alkyl). Arylation of Ia to give Ib ($R_{11}$=aryl) may also be effected by palladium-catalyzed N-arylation of amides (see, for example, Yin, J.; Buchwald S. *Org. Lett.* 2000, 2, 1101-1104 and references cited therein) or the copper-promoted arylation of amides with aryl boronic acids or arylsiloxanes (see, for example, Lam, P. et al. *Synlett* 2000, 674-676).

Scheme 2 illustrates various methods for the preparation of the intermediate carboxylic acid II. The intermediate ketone IV may be reduced to alcohol V by treatment with a reducing agent (typically a metal hydride such as sodium borohydride in methanol or lithium aluminum hydride in diethyl ether or THF). In one mode of preparation, the alcohol may be condensed with malonic acid to give, after decarboxylation of a putative intermediate dicarboxylic acid, the desired intermediate II (Jones et al. *J. Am. Chem. Soc.* 1948, 70, 2843; Beylin et al. *Tetrahedron Lett.* 1993, 34, 953-956.). The alcohol V may also be treated with a silyl ketene acetal, represented by VI. In cases where $R_9$=$R_{10}$=$R_{50}$=$R_{51}$=Me, VI may be obtained from commercial sources. The condensation of V ($J_2$=$J_3$=bond) with VI to give ester VII generally requires the presence of a Lewis acid, such as boron trifluoride etherate, titanium tetrachloride, or the like and is best carried out in a polar, aprotic solvent such as dichloromethane. Saponification of ester VII to II may be carried out with sodium hydroxide or potassium hydroxide in water in the presence of co-solvents such as methanol, THF, and/or DMSO. In cases where $R_9$=$R_{10}$=alkyl, the hydrolysis of ester VII is best carried out at elevated temperature (generally 80° C.) for prolonged times (>5h).

SCHEME 2 Preparation of carboxylic acids II from ketones IV

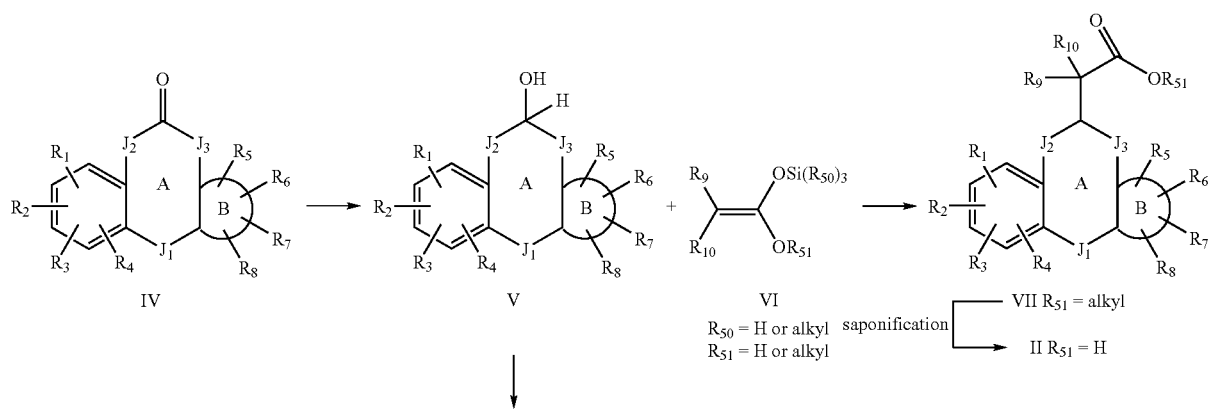

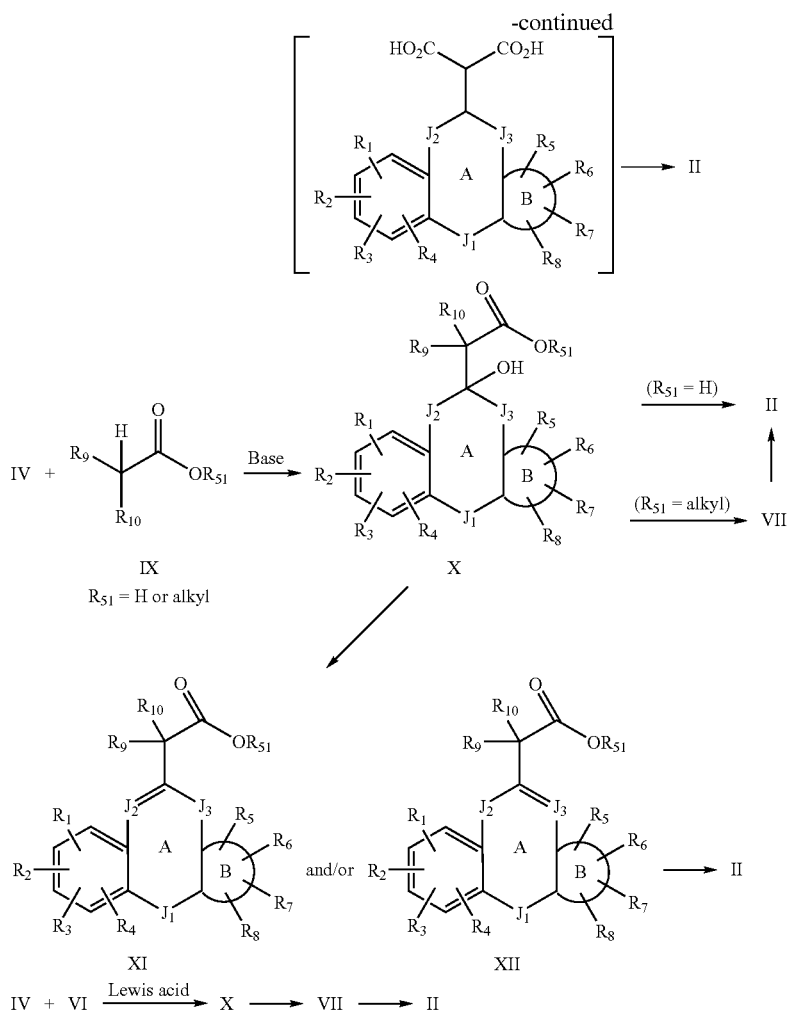

The ketone IV may also be condensed with an enolate derived from ester IX ($R_{51}$=alkyl), prepared by treatment of IX with an appropriate base (lithium diisopropyl amide, lithium or potassium hexamethyldisilizane or the like) at low temperature (−78° C. to 0° C.), to give ester X. An intermediate carboxylic acid X ($R_{51}$=H) may also be prepared by first treating a carboxylic acid IX ($R_{50}$=H) with at least two equivalents of a strong base (preferably lithium diisopropyl amide or lithium diethyl amide) to generate an enediolate dianion. Generation of the enediolate is preferably carried out at 0° C. to 55° C. Condensation of the in situ prepared enediolate with ketone IV may then give the hydroxy acid X ($R_{51}$=H). In cases where one or both of $J_2$, $J_3$=alkylene, the intermediate alcohol X may readily dehydrate to give the unsaturated intermediates XI and/or XII. The dehydration may occur spontaneously by exposure of X ($J_2$, $J_3$=alkylene) to acidic conditions, such as aqueous acid or Lewis acid (boron trifluoride, titanium tetrachloride, or the like). The intermediate olefins XI and XII may be reduced to give ester VII ($R_{51}$=alkyl) under catalytic hydrogenation (typically palladium on carbon in the presence of hydrogen gas), which may be saponified as described above to prepare carboxylic acid II. Alternatively, in cases where olefins XI and XII are carboxylic acids ($R_{51}$=H), catalytic hydrogenation (typically palladium on carbon in the presence of hydrogen gas) may directly provide the carboxylic acid II. In cases where dehydration of alcohol X to XI and/or XII does not spontaneously occur, X ($R_{51}$=H) may be reduced to II. The reaction is preferably carried out with a silane (typically triethylsilane) in the presence of a protic acid (typically trifluoroacetic acid). The ester X ($R_{51}$=alkyl) may also be reduced to ester VII under the same conditions employed for conversion of X to II. Ester VII may be hydrolyzed to acid II under conditions described above.

The ketone IV may also be treated with silyl ketene acetal VI to provide the hydroxy ester X ($R_{51}$=alkyl). The condensation is best carried out in the presence of a Lewis acid (boron trifluoride etherate, or the like) in dichloromethane at 0° C. Hydroxy ester X may be isolated, or, alternatively, in situ reduction to ester VII may be carried out. In cases where any one or more of $R_1$-$R_4$=OH, addition of triethylsilane to the reaction mixture containing the unisolated hydroxy ester X may give the ester VII. Alternatively, addition of a strong protic acid (typically trifluoroacetic acid) and triethylsilane to the reaction mixture containing unisolated hydroxy ester X may provide ester VII. Conversion of ester VII to carboxylic acid II may then be carried out as described above.

The synthesis of hydroxylated xanthene-based examples and derivatives is described in Scheme 3. 3-Hydroxy-9H-xanthen-9-one XIII ("Sieber linker", Sieber P. *Tetrahedron Lett.*, 1987, 28, 6147-6150) may be converted to ester XIV by treatment with a silyl ketene acetal (e.g., (1-methoxy-2-methylprop-1-enyloxy)trimethylsilane, where $R_9=R_{10}=Me$) in the presence of an appropriate Lewis acid (preferably boron trifluoride etherate) in dichloromethane at 0° C. Subsequent addition of a reducing agent (preferably triethylsilane) may give the methyl ester XIV. The phenolic hydroxyl group of XIV may be derivatized by a number of different means. Treatment of XIV with a triflating reagent (triflic anhydride, PhNTf$_2$, or the like) in the presence of a suitable base (triethylamine, pyridine, or the like) may give an aryl triflate XV which may undergo metal-mediated cross-coupling reactions. For example, Suzuki coupling may be effected by treatment of XV with an aryl boronic acid or aryl boronate ester in the presence of a palladium catalyst (tetrakis triphenylphosphine palladium, or the like) and an aqueous base (potassium carbonate, sodium carbonate, potassium phosphate or the like) in an appropriate solvent or solvent combination (DMF, toluene/ethanol, 1,4-dioxane or the like) at elevated temperature (typically 100° C.) may provide an arylated intermediate methyl ester XVI. (R1=aryl). The triflate may also undergo a variety of other metal-mediated cross-coupling reactions known to one skilled in the art (See, for example, de Meijere, A., & Diederich, F. (2004). *Metal-Catalyzed Cross-Coupling Reactions*. ($2^{nd}$ ed.): John Wiley & Sons). Saponification of the ester XVI under conditions described above for the preparation of II from VII, followed by condensation under the conditions described above for the preparation of Ia from II may give xanthene products XVII. The phenol ester XIV may also be hydrolyzed to carboxylic acid XVIII under conditions described above for the preparation of VII from II. Amide XIX may then be prepared as described above for the preparation of Ia from II. The amide XVII may also be prepared from amide XIX by conversion to a triflate derivative as described above for the preparation of XV from XIV followed by palladium-catalyzed cross-coupling as described above for the preparation of XVI from XV.

SCHEME 3 Preparation of phenolic xanthenes and their derivatives

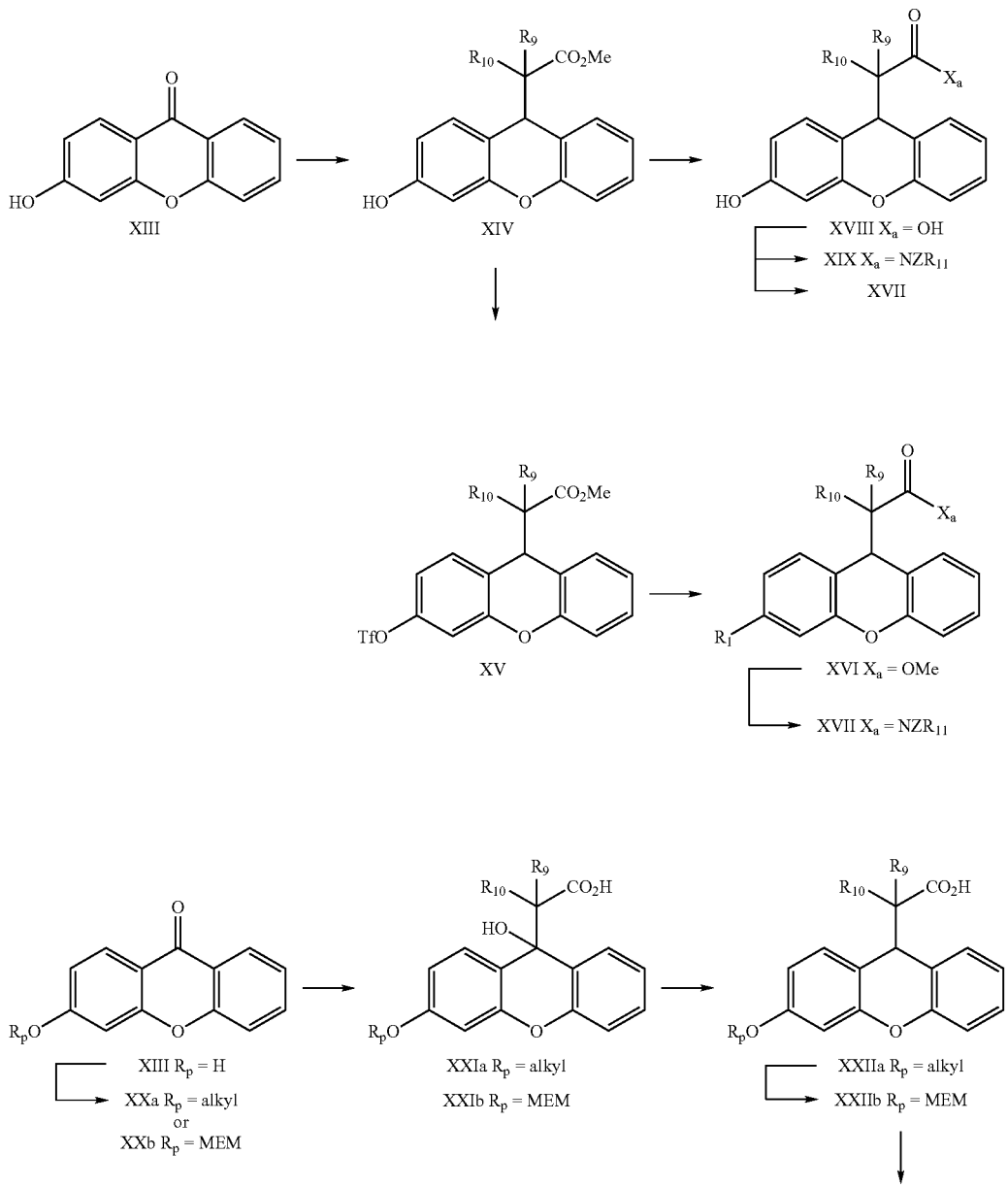

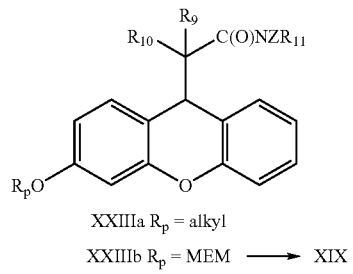

XXIIIa $R_p$ = alkyl

XXIIIb $R_p$ = MEM $\longrightarrow$ XIX

3-Hydroxy-9H-xanthen-9-one ("Sieber linker") (XIII) may be converted to the corresponding alkyl ether XXa or (2-methoxyethoxy)methyl (MEM) ether XXb by treatment with an appropriate base (typically sodium hydride) in a polar aprotic solvent (typically DMF) in the presence of an alkyl halide (typically a primary halide such as iodomethane) or MEM-Cl. The hydroxy acids XXIa and XXIb may be prepared as described above for the preparation of X ($R_{51}$=H).

Reduction as described above for the preparation of II directly from X may then give XXIIa or XXIIb, which may be converted to XXIIIa or XXIIIb under the conditions described above for the preparation of 1a from II. XXIIIa may be converted to phenol XIX by treatment with thiophenol or 2-aminothiophenol in the presence of a stoichiometric quantity of potassium carbonate in N-methyl-pyrrolidinone at high temperature (typically 200° C.-205° C. in a microwave reactor) (see Chakraborti, et al. *J. Org. Chem.* 2002, 67, 6406-6414).

SCHEME 4 Preparation of substituted non-phenolic xanthene derivatives

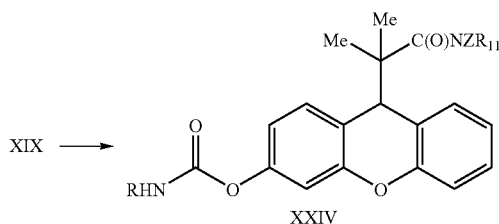

XIX $\longrightarrow$

XXIV

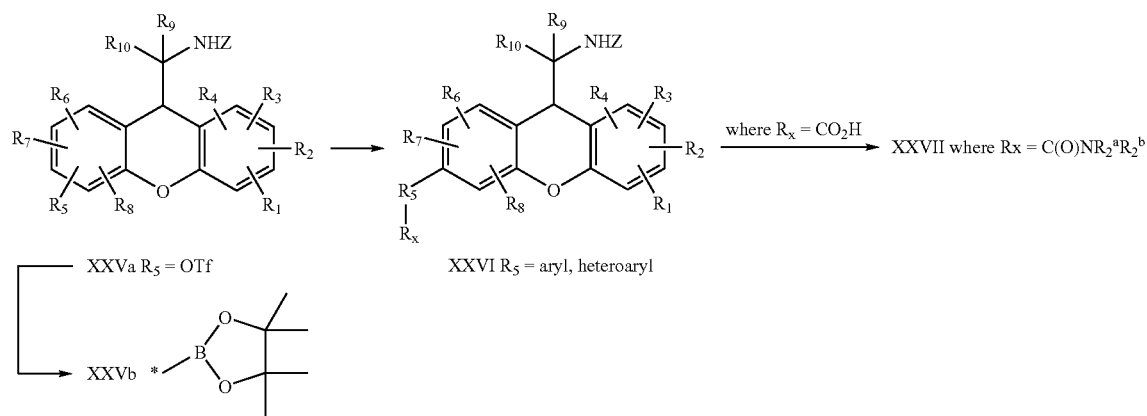

where $R_x$ = $CO_2H$

XXVII where $Rx$ = $C(O)NR_2^aR_2^b$

XXVa $R_5$ = OTf

XXVb * = [pinacol boronate]

XXVI $R_5$ = aryl, heteroaryl

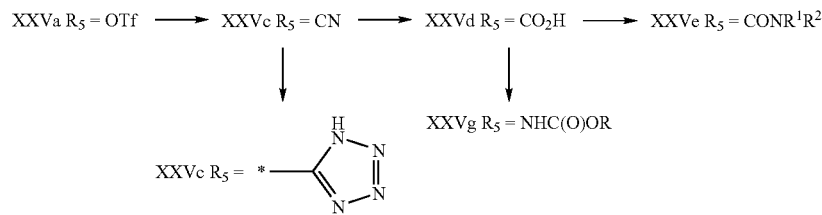

XXVa $R_5$ = OTf $\longrightarrow$ XXVc $R_5$ = CN $\longrightarrow$ XXVd $R_5$ = $CO_2H$ $\longrightarrow$ XXVe $R_5$ = $CONR^1R^2$ XXVg $R_5$ = NHC(O)OR XXVc $R_5$ = *—[tetrazole]

In one embodiment, example compounds represented by XIX may be converted to example compounds represented by XXIV (Scheme 4). Thus, treatment of XIX with an alkyl or aryl isocyanate in the presence of a non-nucleophilic base (preferably N,N-diisopropylethyl amine) in a polar, aprotic solvent (preferably 1,4-dioxane), preferably at ambient temperature may provide XXIV. Intermediate XXV, where $R_5$ is triflate or nonoflate (ONf) may be converted to arylated xanthene XXVI by Suzuki coupling with an appropriate aryl boronate. For example, treatment of XXV with any aryl boronic acid, aryl trifluoroborate salt, or aryl boronate (e.g., aryl pinacol boronate) in the presence of a palladium (0) catalyst (preferably tetrakistriphenylphosphine palladium (0)), and base (preferably, aqueous sodium carbonate, potassium carbonate, potassium phosphate, or the like) in a solvent system typically employed for Suzuki coupling reactions (such as toluene/ethanol, water/DMF, or the like) may provide XXVI. Alternatively, XXV may be converted to a boronate ester (for example, pinacol boronate XXVb) by treatment with a palladium catalyst (typically 1,1'-bis(diphenylphosphino)ferrocene-palladium (II) dichloride) in the presence of a boron source (preferably bis(pinacolato)diboron) in the presence of a base (preferably potassium acetate). Conversion of XXVb to XXVI may be carried out by cross-coupling with an aryl or heteroaryl halide under Suzuki conditions as described above for the conversion of XXV to XXVI. Where XXVI is appended with a carboxylic acid group, conversion to a carboxamide (XXVII) may be effected under any number of the typical conditions for dehydrative condensation of amines and carboxylic acids, for example as described for the conversion of II to Ia. The triflate (or nonflate) XXVa may also be converted to nitriles XXVc by methods for palladium-catalyzed cyanation of aryl halides (Sundmeier, M. et al, Eur. J. Inorg. Chem. 2003, 3513). For example, treatment of XXVa with a cyanide source (typically zinc cyanide) in the presence of a palladium catalyst (typically tetrakis triphenylphosphine palladium (0)) in a polar solvent (typically DMF) at elevated temperature (typically 120° C.) provides nitriles XXVc. The nitriles XXVc may be hydrolyzed to provide carboxylic acids XXVd by treatment with sodium peroxide in water. Condensation of acids XXVd with primary or secondary amines (as described for conversion of II to Ia) may provide carboxamides XXVe. The nitriles XXVc may be converted to tetrazoles XXVf by condensation with a source of azide (preferably sodium azide) in the presence of an acid (preferably ammonium chloride or trimethylsilyl azide or tributyl tin oxide). The carboxylic acids XXVd may also be converted to carbamates XXVg by Curtius rearrangement. Thus, conversion of XXVd to an acyl azide (typically effected by exposure to diphenylphosphoryl azide), in the presence of a tertiary amine (typically triethylamine), with heating, followed by quenching with an alcohol, may give carbamates XXVg.

Azaxanthene-based examples may be prepared as illustrated in Scheme 5. 5H-Chromeno[2,3-b]pyridin-5-one XXVIII (commercially available or prepared in the manner described by Villani et al., J. Med. Chem. 1975, 18, 1) may be reduced to the corresponding alcohol XXIX upon treatment with sodium borohydride in anhydrous methanol as described by Bristol, et al. (J. Med. Chem., 1981, 24, 1010-1013). Treatment of XXIX with the trimethyl silyl ketene acetal of methyl isobutyrate as described above for the preparation of V from V may give the ester XXX. Hydrolysis of the ester as described above for the preparation of II from VII, followed by amidation as described for the preparation of Ia from II and III may provide the azaxanthene amides XXXI. Alternatively, oxidation of XXX may be effected under conditions for the preparation of pyridine N-oxides (preferably mCPBA in dichloromethane) to give the N-oxide XXXII, which may then be treated with an appropriate chlorinating reagent (preferably phosphorous oxychloride, $POCl_3$, in the absence of a co-solvent) to give the chloroazaxanthene XXXIII. Saponification of XXXIII to carboxylic acid XXXIV may be effected under conditions described above for the preparation of VII from II, preferably in the absence of DMSO. Condensation of XXXIV with an amine ($NHR_{12}R_{13}$) at elevated temperature (typically 130° C.) may provide XXXVa (Scheme 6, $R_5=NR_{12}R_{13}$)— Alternatively, Suzuki coupling of XXXIV with a suitable aryl boronic acid or aryl boronate as described above for the preparation of XVI from XV may provide XXXVb. XXXVa and XXXVb may be converted to XXXVIa or XXXVIb, respectively, following the conditions described above for the preparation of Ia from II and III. The carboxylic acid XXXIV may also be converted to amide XXXVII as described above for the preparation of Ia from II and III. Arylation as described above for the preparation of XVI from XV may provide XXXVIb. Any of the racemic intermediates XXX-XXXVII or example compounds may be separated into purified, single enantiomers by any of the various methods known to one skilled in the art.

SCHEME 5 Preparation of 5H-chromeno[2,3-b]pyridines

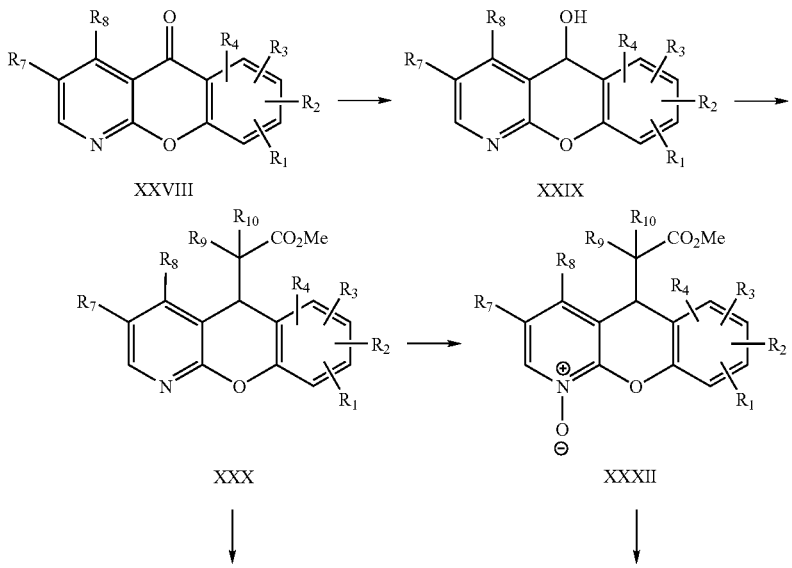

-continued

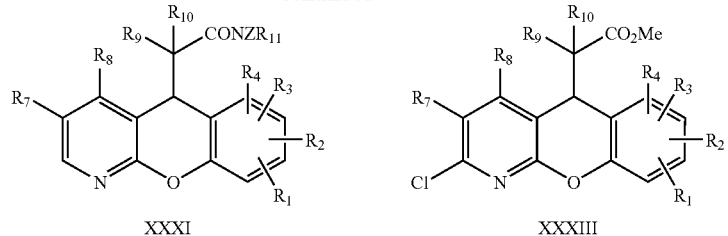

XXXI

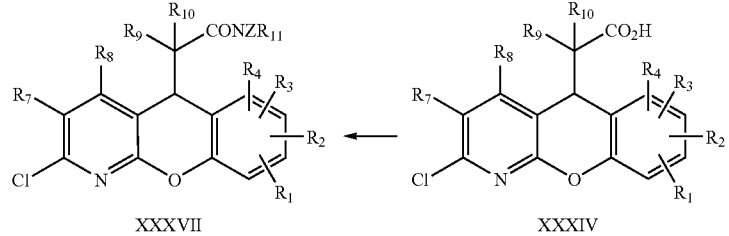

XXXIII

XXXIV

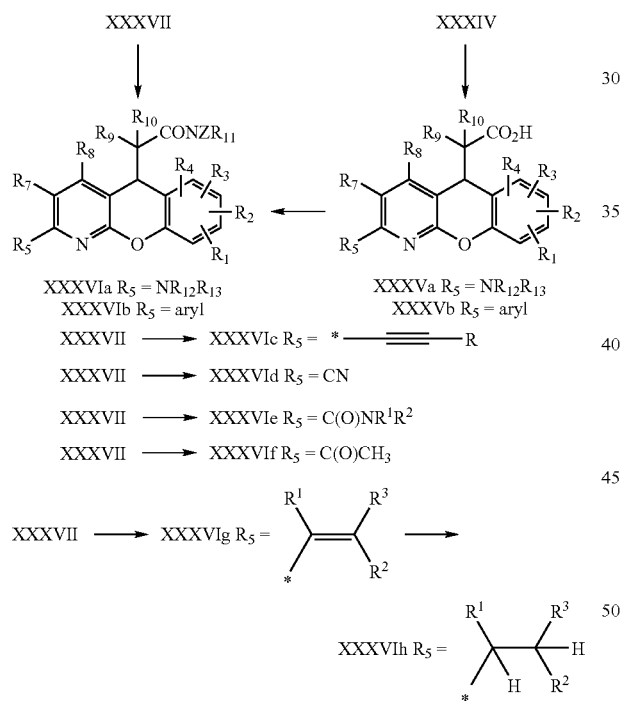

SCHEME 6 Elaboration of 2-chloro-5H-chromeno[2,3-b]pyridines

XXXVIa $R_5 = NR_{12}R_{13}$
XXXVIb $R_5 = $ aryl

XXXVa $R_5 = NR_{12}R_{13}$
XXXVb $R_5 = $ aryl

XXXVII ⟶ XXXVIc $R_5 = $ *—≡—R

XXXVII ⟶ XXXVId $R_5 = $ CN

XXXVII ⟶ XXXVIe $R_5 = $ C(O)NR$^1$R$^2$

XXXVII ⟶ XXXVIf $R_5 = $ C(O)CH$_3$

XXXVII ⟶ XXXVIg $R_5 = $

XXXVIh $R_5 = $

The chloride XXXVII (Scheme 6) may also undergo Sonagashira or Stevens-Castro cross-couplings with alkynes in the presence of a palladium catalyst (preferably bis(triphenylphosphine)-palladium (II(chloride) with catalytic cuprous iodide in the presence of a hindered secondary amine base (preferably diisopropylamine) to give alkynes XXXVIc. XXXVII may also be converted to nitrites XXXVId, as described for the preparation of XXVc from XXVa. XXXVII may also be converted to amides XXXVIe in a two-step procedure involving initial hydrolysis by hydroxide (typically potassium hydroxide) to give a carboxylic acid ($R_5$=$CO_2H$) which may then be condensed with primary or secondary amines as described for the preparation of Ia from II to give carboxamides XXVIe. XXXVII may also be converted to ketones XXXVIf as described by Jean-Yves Legros et al (*Tetrahedron* 2001, 57, 2507). Treatment of XXXVII with alkenyl boronates (or trifluoroborate salts) under conditions described for the preparation of XXXVIb from XXXVII may afford alkenyl example compounds (XXXVIg). Hydrogenation of XXXVIg may be effected with a palladium catalyst (preferably palladium on charcoal) under an atmosphere of hydrogen to afford corresponding alkyl compounds XXXVIh.

SCHEME 7 Preparation of amino-, urea-, and carbamoyl- substituted 5H-chromeno[2,3-b]pyridines

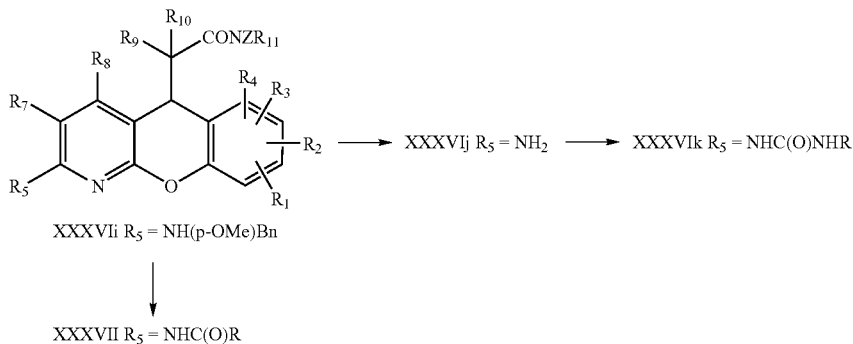

XXXVIi R$_5$ = NH(p-OMe)Bn

Amino-, urea-, and carbamoyl-substituted 5H-chromeno [2,3-b]pyridines may be prepared as shown in Scheme 7. Thus, heating a solution of p-methoxy benzylamino-substituted XXXVIi (prepared as described above for the preparation of XXXVIa) in trifluoroacetic acid (preferably at 50° C.) may provide amines XXXVIj. The amines XXXVIj may be converted to ureas XXXVIk by first treating with a carbonylating reagent (such as phenyl chloroformate) in the presence of a base (preferably pyridine) to afford carbamoylated intermediates (R5=NHC(O)OPh) which, without isolation, may then be condensed with amines, with heating (typically at 100° C.). The amines XXXVIi may also be converted to amides XXXVII by acylation with an appropriate acylating reagent (acid halide, or other suitably activated carboxylic acid as described for the preparation of Ia from II), followed by cleavage of the p-methoxybenzyl group as described for the preparation of XXXVIj from XXXVIi.

2-(Para-substituted phenyl)-5H-chromeno[2,3-b]pyridines may be further elaborated as depicted in Scheme 8. Phenols XXXVIm (R$_x$<OH) may be alkylated under Mitsunobu conditions (*Synthesis* 1, 1981). Thus treatment of XXXVIm with an alcohol (R$_y$OH) in the presence of a phosphine (preferably, triphenylphosphine) and an alkyl diazodicarboxylate (preferably diisopropyl azodicarboxylate or diethylazodicarboxylate) in tetrahydrofuran may provide ethers XXXVIn. Thioethers (for example, XXXVIo, R$_x$=SMe) may be oxidized to sulfoxides or sulfones (XXXVIp) by treatment with any of a number of oxidants, including m-chloroperbenzoic acid. Carboxylic acids (XXXVIq) may be converted to benzamides (XXXVIr) using many of the myriad methods for the conversion of benzoic acids to benzamides. Preferably, treatment of XXVIq with activating reagent(s) (typically HOBt in the presence of a carbodiimide such as EDCI) in the presence of tertiary amine bases (typically triethylamine or diisopropylethylamine) and primary or secondary amines in a polar, aprotic solvent (typically acetonitrile or DMF) gives benzamides XXXVIr. Aldehyde XXXVIs may be converted to alcohol XXXVIt by reduction with an appropriate reducing agent (sodium borohydride, or the like) or by treatment with an organometallic nucleophile (alkyl or aryl lithium, Grignard reagent, or the like). Similarly, ketones XXXVIv may be condensed with organometallic nucleophiles to provide tertiary alcohols XXXVIv.

SCHEME 8 Elaboration of phenyl-substituted 5H-chromeno[2,3-b]pyridines

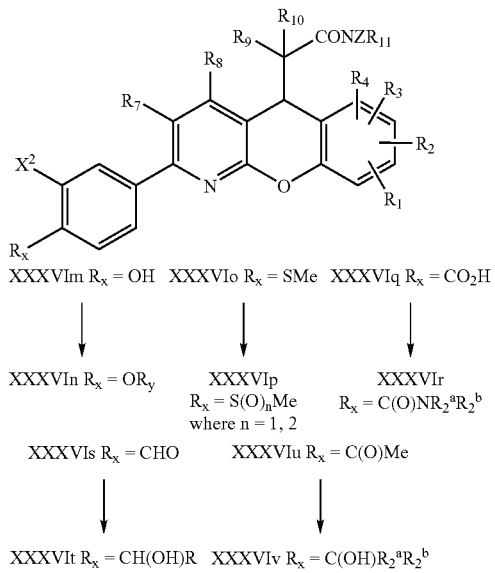

Scheme 9 illustrates a number of classic methods for synthesizing reactive intermediates XXXVIII-XLIII which are then used to form heterocycles XLIV and XLV (NHR$_{11}$Z). Scheme 5, reaction (1) shows typical conditions for brominating alpha to a ketone. In this specific case, bromination occurs first at the benzylic position and then at the desired R8-substituted position. Using the procedure of Chi et al (*Org. Lett.* 2003, 5, 411-414), dibromination followed by debromination with acetone yields the desired alpha-bromoketone XXXVIII.

Scheme 5, reaction (2) is the same transformation as reaction (1) but when the benzylic position is substituted with R$^4$ and R$^5$, bromination occurs selectively or exclusively at the desired position to give structure XXXIX.

Scheme 5, reaction (3) is a summary of the method of Takano (*Heterocycles* 1989, 29, 1861-1864; also see Zhao et al *Bioorg. Med. Chem. Lett.* 1998, 6, 2531-2539) which describes the use of cuprates to open epichlorohydrin to form chlorohydrins. It should be noted that Grignard reagents themselves open epoxides either in the presence or absence of copper salts (see, Mazzocchi et al *Synth Commun.* 1986, 309-312; *Eur. J. Med. Chem.* 1979, 14, 165-170). Oxidation of the chlorohydrin using Dess-Martin periodinane or other suitable oxidant yields the desired chloromethylketone XL.

Another method of forming chloromethylketones is shown in Scheme 5 reaction (4). Lithiation of activated methyl groups using butyllithium followed by reaction with chloroacetylchloride (or ethyl chloroacetate, *Khim. Geterot. Soed.* 1986, 6, 802-809) directly provides the chloromethylketone XLI intermediate.

Scheme 5, reaction (5) shows the method of Nugent et al (*J. Org. Chem.* 2004, 69, 1629-1633) which uses dimethylsulfoxonium methylide to nucleophilically add to esters forming reactive β-keto sulfur ylides XLII.

Lastly, a widely used acid homologation procedure shown in Scheme 5 reaction (6) involves the conversion of a carboxylic acid to a mixed anhydride (or acid chloride) followed by treatment with diazomethane and then HCl to form the chloromethylketone XLIII.

Reactive intermediates XXXVIII-XLIII can be treated with thiourea with or without added acid to yield the desired substituted 2-aminothiazoles XLIV. Synthesis of substituted 2-aminoimidazoles XLV is best accomplished using the procedure of Little and Webber (*J. Org. Chem.* 1994, 59, 7299-7305) using N-acetylguanidine as the nucleophile followed by acid hydrolysis of the acetyl group.

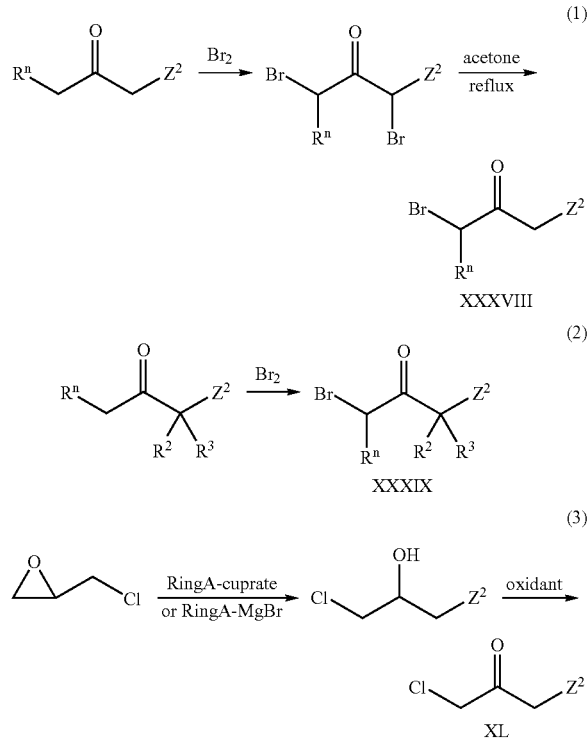

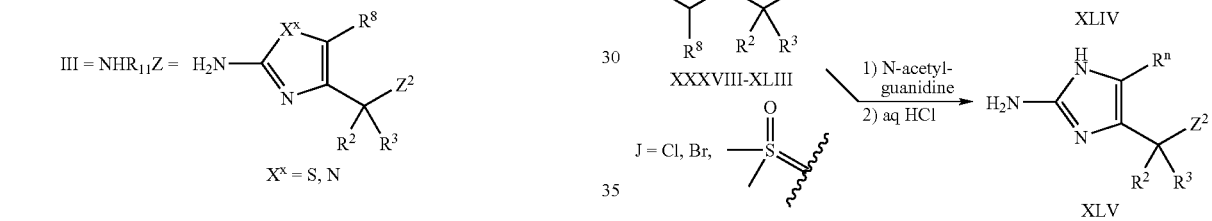

$Z^2$ is a cycloalkyl, cycloalkenyl, cycloheteroalkyl, aryl, or heteroaryl ring; $R_2$ and $R_3$ are independently at each occurrence hydrogen, halogen, hydroxy, alkyl, alkenyl, alkynyl, alkoxy, cyano, nitro, $NR^eR^f$, or CHO;

or $R^2$ and $R^3$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl;

$R^e$ and $R^f$ are independently at each occurrence selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, provided $R^e$ and $R^f$ are not both alkoxy or amino; or $R^e$ and $R^f$ at each occurrence can be taken together with the nitrogen to which they are attached to form a 5-, 6- or 7-membered heteroaryl or cycloheteroalkyl ring which contains 1, 2 or 3 hetero atoms which can be N, O or S.

Two other syntheses of 2-aminoimidazoles are listed in Scheme 10 below. In Scheme 10, reaction (1), an aminomethylketone is condensed with cyanamide to form an intermediate guanidinomethylketone which undergoes dehydration upon treatment with HCl (see, Lancini and Lazzari, *J. Het. Chem.* 1966, 3, 152-154) to form compound XLVI. Aminomethyl ketones can be synthesized from the reactive intermediates XXXVIII-XLIII (Scheme 5) using standard procedures known to one skilled in the art.

SCHEME 10 Additional Syntheses of 2-aminoimidazoles

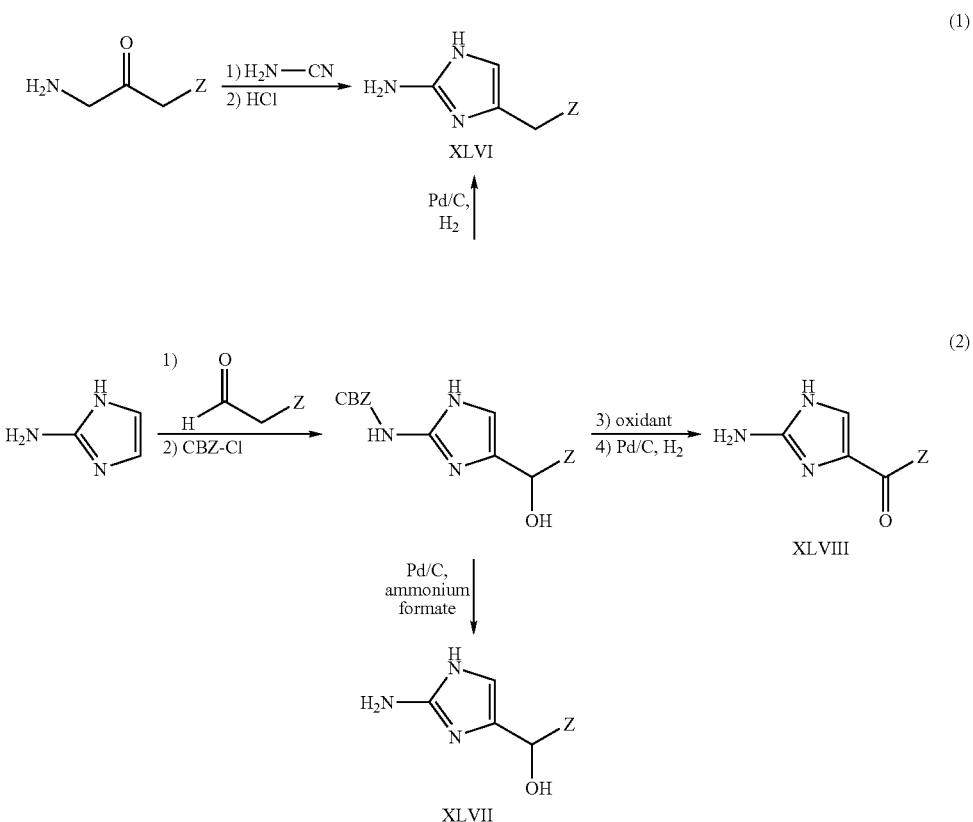

Scheme 10 (above) details the procedure of Horne et al (*Tetrahedron. Lett.* 1993, 34, 6981-6984) to make substituted 2-aminoimidazoles. Commercially available 2-aminoimidazole reacts with aldehydes to form hydroxyalkylaminoimidazoles which are conveniently protected in situ with a CBZ group in situ to facilitate purification. Catalytic hydrogenation of this intermediate under mild conditions first reduces the CBZ group to give the hydroxyalkylaminoimidazoles XLVIII. Prolonged hydrogenation under stronger conditions reduces the benzylic hydroxyl group to give compound XLVI. If the intermediate hydroxyalkylaminoimidazole is first oxidized (using Dess-Martin periodinane for example) and then treated with under mild hydrogenation conditions, the 2-amino-4-ketoimidazole compound XLVIII is formed.

Scheme 11 illustrates several other synthetic transformations to make substituted 2-aminothiazoles. Starting from commercially available 2-aminothiazole-4-carboxylic ester, the amino group was protected using Boc anhydride and the ester reduced with RedAl. Oxidation of the alcohol with Dess-Martin periodinane gives the aldehyde which can undergo reactions with organometallic reagents such as Grignard reagents to give compound XLIX. TFA deprotection of XLIX gives L which is ready for coupling to different cores to make compounds of Formula I. Alternatively, oxidation of intermediate XLIX gives the keto compound LI that can be deprotected to give compound LII, fluoridated using (diethylamino) sulfur trifluoride (DAST) and deprotected to give compound LIII, or homologated using a Horner-Wadsworth-Emmons procedure to give the α,β-unsaturated ester LIV. Ester LIV can be deprotected with TFA to give compound LV, the ester converted using standard procedures to amide LVI, and lastly reduced to amide LVII.

SCHEME 11 Additional Syntheses of 2-aminothiazoles

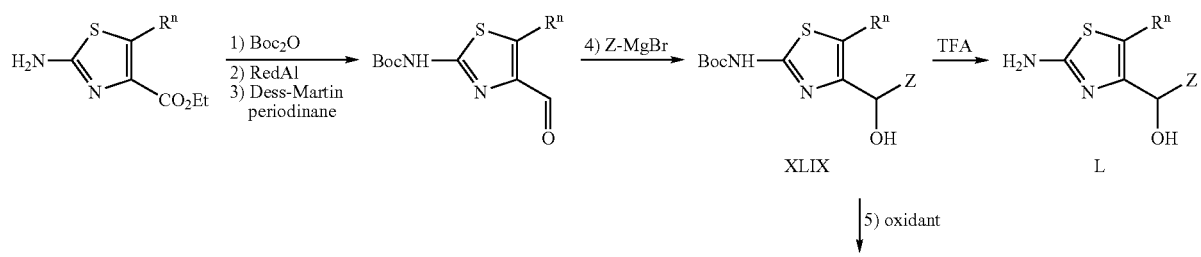

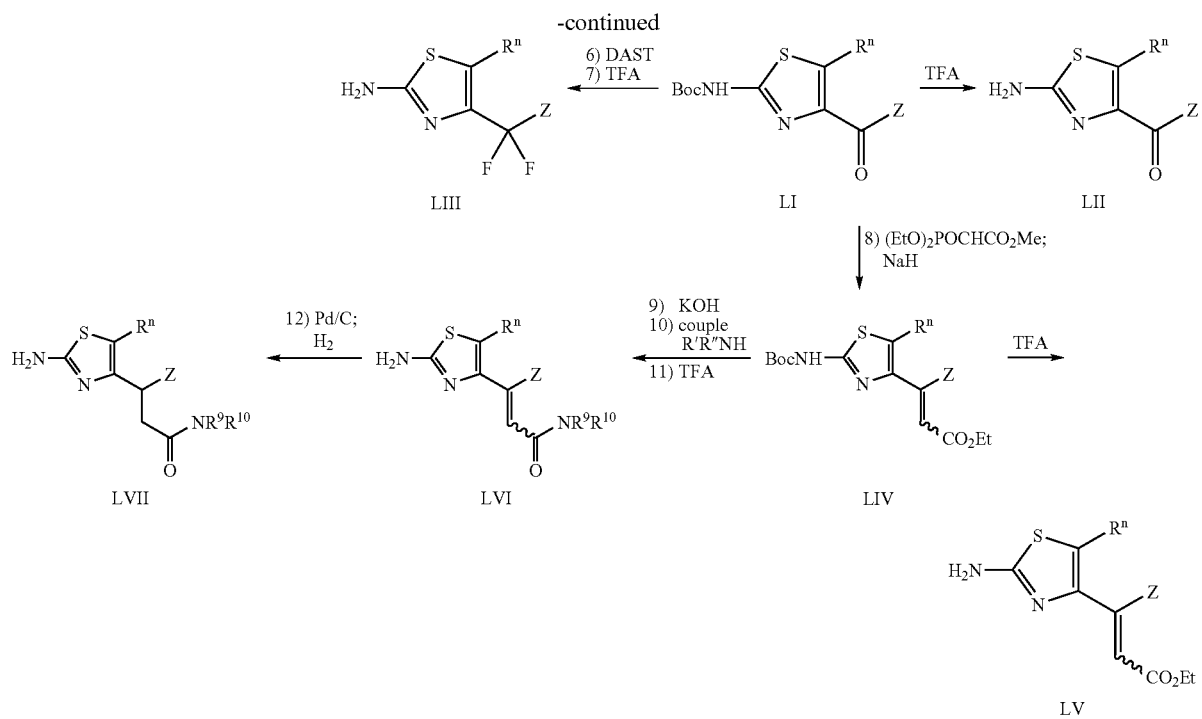

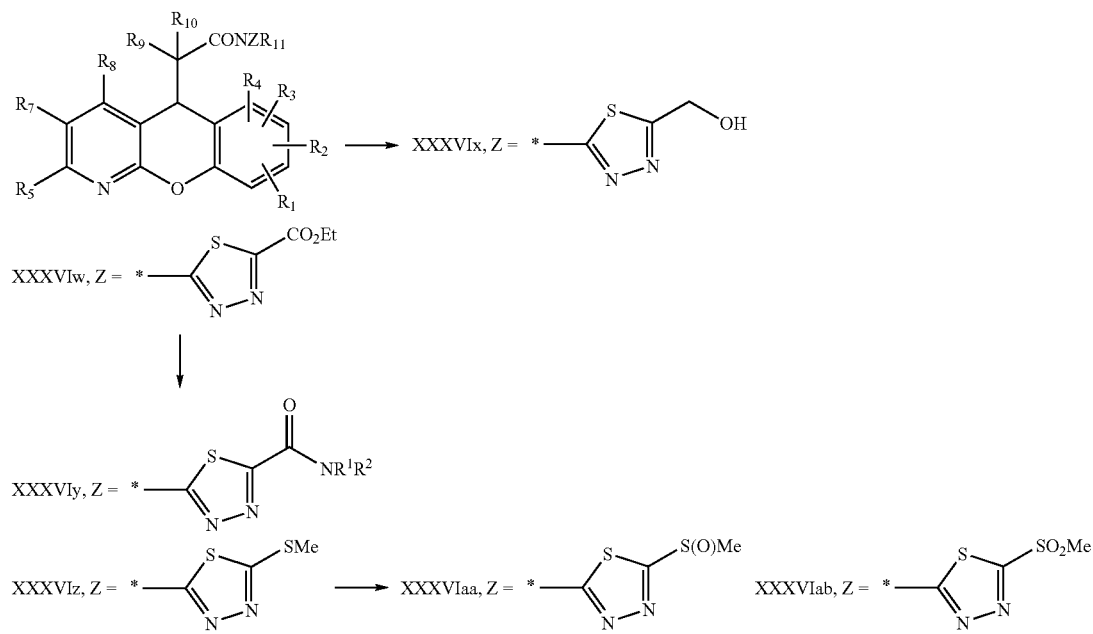

Scheme 12 illustrates the preparation of some example compounds where group Z is a 5-substituted-1,3,4-thiadiazole. Thus, the ester XXXVIw may be reduced by the action of any number of reducing agents, such as sodium borohydride, to give alcohol XXXVIx. Alternatively, ester XXXVIw may be hydrolyzed to a carboxylic acid (typically employing aqueous sodium hydroxide in methanol) which may then undergo condensation with primary or secondary amines under standard conditions (such as described for the preparation of Ia from II) to provide carboxamides XXXVIy. Example compounds containing 5-alkylthio-1,3,4-thiadiazoles (XXXVIz) may be oxidized to sulfoxides (XXXVIaa) and/or sulfones (XXVIab) under the action of an appropriate oxidant, such as m-CPBA.

Scheme 13 illustrates just several syntheses of ketones IV which have been described in the literature. Scheme 13, reaction (1) shows the method of Zhao and Larock (Organic Letters 2005, 7, 4273-4275) for the one-pot synthesis of xanthones and thioxanthones by the tandem coupling-cyclization of arynes and salicylates. Scheme 13, reaction sequence (2) illustrates the preparation of xanthones LVIII by the Ullman condensation of o-halobenzoic acids and phenols followed by polyphosphoric acid-induced cyclization, as described by Galt et al. (J. Med. Chem. 1989, 32, 2357-2362). A variety of related methyl-, nitro-, carboxy-, and nitro-substituted xanthones may be prepared by a similar method (Pickert et al. Arch. Pharm. Pharm. Med. Chem. 1998, 331, 177-192). Similar chemistry may be utilized for the preparation of variably substituted 9-oxo-9H-xanthene-4-acetic acids as per the procedures of Rewcastle et al. (J. Med. Chem. 1991, 34, 217-222 and J. Med. Chem. 1989, 32, 793). 4-Methoxyxanthone may be prepared by the two-step procedure described by Coelho et al. (Helv. Chim. Act. 2001, 84, 117-123). 1-Hydroxyxanthone may be prepared by the condensation of salicylic acid and resorcinol in the presence of zinc chloride (ibid). 2-Hydroxy and 3-hydroxyxanthone may be prepared following the methods described by Lin et al. (J. Pharm. Sci. 1993, 82, 11) and Quillinan et al. (J. Pharm. Sci. 1965, 54, 633). Scheme 13, reaction sequence (3) shows the synthesis of 5H-[1]benzopyrano[2,3-b]-1,2,3,4-tetrahydropyridin-5-ones LIX by the two step sequence reported by Pasutto et al. (Heterocycles 1985, 2293-2297). The starting benzopyranopyridin-5-ones LX may be obtained by the method of Villani et al. (J. Med. Chem. 1975, 18, 1-8). Scheme 13, reaction sequence (4) illustrates the method of Sato et al. (Chem. Pharm. Bull. 1990, 38, 1266-1277) which may be employed for the preparation of 3-methoxy and 3-hydroxy xanthones (LXI and LXII, respectively) by the Friedel-Crafts acylation of resorcinol dimethyl ethers with o-fluoro benzoyl chlorides followed by base-induced cyclization. 5H-[1]benzopyrano[2,3-b]pyridine-5-ones LXIII (Scheme 13, reaction sequence (5)) may also be prepared from 4-oxo-4H-1-benzopyran-3-carbonitriles following the procedures described by Nohara et al. (J. Med. Chem. 1985, 28, 559-567). The benzopyranopyridines LXIV, LXV and LXVI (isomers of benzopyranopyridin-5-ones LX) may be prepared by the methods of Villani et al. (J. Med. Chem. 1975, 18, 1-8, Scheme 8, reaction sequences (6-8)). Benzopyranopyridine LXVI may also be prepared from (4-fluoro-3-pyridyl)-2-methoxyphenylmethanone by the method of Marsais, et al. (J. Heterocycl. Chem. 1988, 25, 81-87) or from N,N-diethyl-2-(pyridine-4-yloxy) benzamide by the method of Familoni et al. (Syn. Lett. 1997, 9, 1081-1083). 10-Oxo-10H-[1]benzopyrano[2,3-b]pyrazines LXVII (Scheme 13, reaction sequence (9)) may be prepared by the sequence of reactions described by Turck et al. (Synthesis 1988, 11, 881-884 and J. Organometallic Chem. 1991, 412, 301-310). 4-Azaxanthone LXVIII may also be prepared as shown in Scheme 8, reaction (10) (Trecourt, et al., J. Chem. Soc. Perkin Trans. 1990, 2409-2415).

SCHEME 13 Preparation of ketones IV

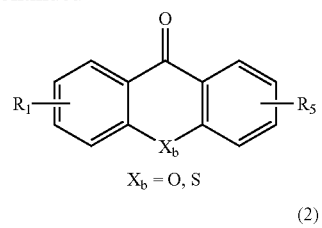

(2)

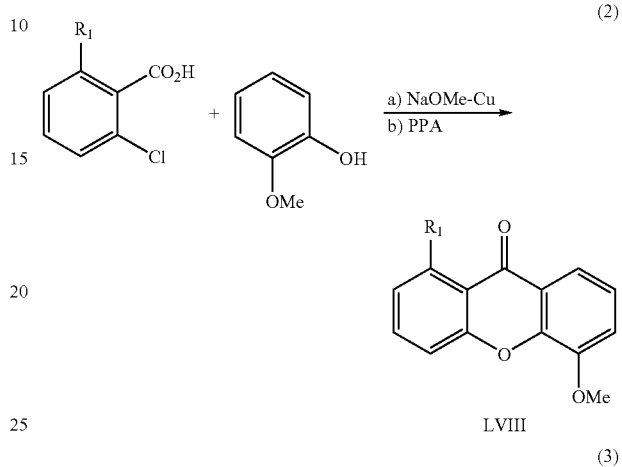

(3)

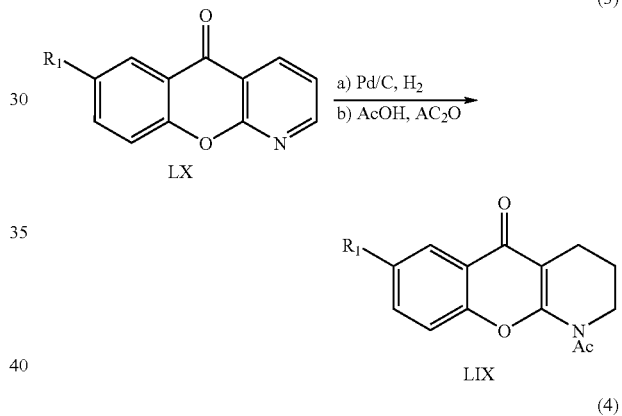

(4)

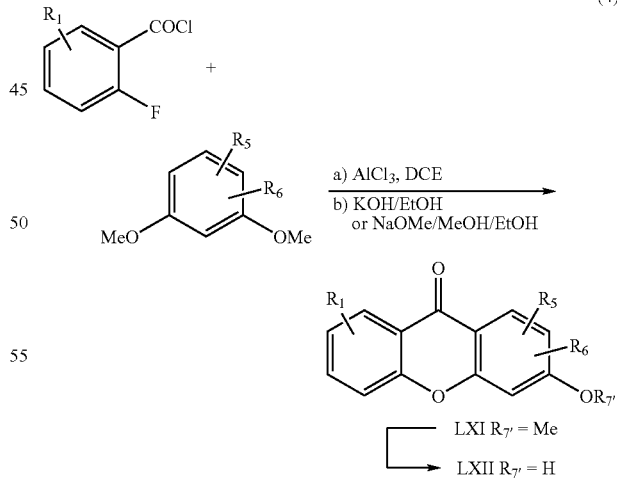

(5)

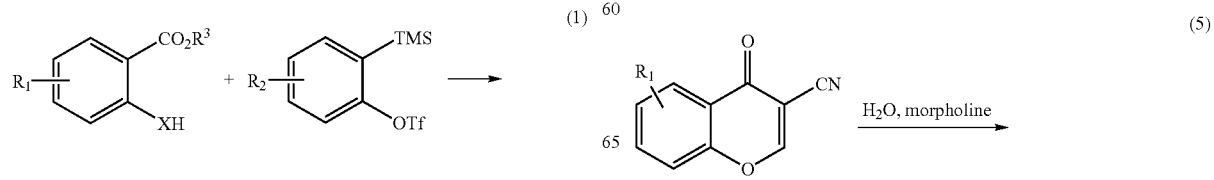

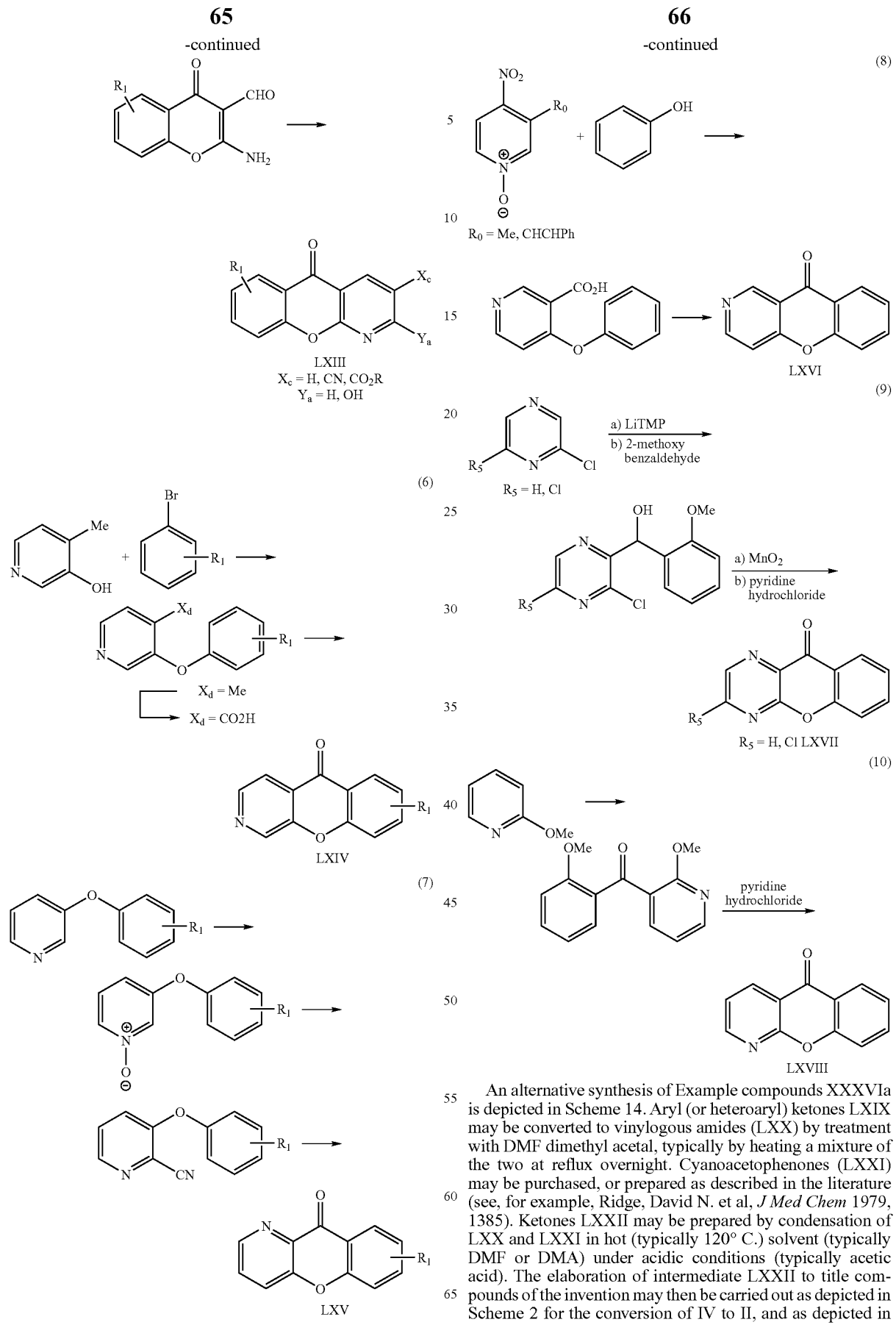

An alternative synthesis of Example compounds XXXVIa is depicted in Scheme 14. Aryl (or heteroaryl) ketones LXIX may be converted to vinylogous amides (LXX) by treatment with DMF dimethyl acetal, typically by heating a mixture of the two at reflux overnight. Cyanoacetophenones (LXXI) may be purchased, or prepared as described in the literature (see, for example, Ridge, David N. et al, *J Med Chem* 1979, 1385). Ketones LXXII may be prepared by condensation of LXX and LXXI in hot (typically 120° C.) solvent (typically DMF or DMA) under acidic conditions (typically acetic acid). The elaboration of intermediate LXXII to title compounds of the invention may then be carried out as depicted in Scheme 2 for the conversion of IV to II, and as depicted in Scheme 1, for the conversion of II to Ia.

SCHEME 14 Preparation and Elaboration of 2-aryl-5H-chromeno[2,3-b]pyridine-5-ones

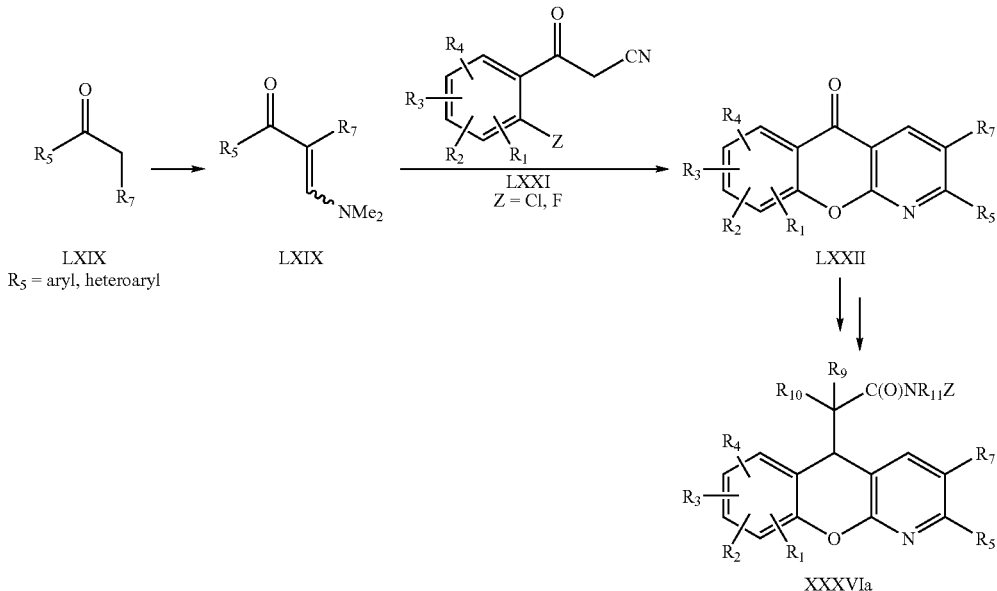

Another synthesis of compounds of the invention (LXXIII) is depicted in Scheme 15. Para-chloro-cyanoacetophenones LXXIV may be prepared as described for the preparation of LXXI. Alternatively, LXXIV may be prepared by treatment of alkyl-p-chlorobenzoates (LXXV) with the anion derived from treatment of acetonitrile with a strong base (preferably LDA). Condensation of LXXIV with (E)-3-dimethylamino acrylaldehyde may be carried out as described for the conversion of LXX to LXXII (Scheme 14) to provide ketones LXXVI. LXXVI may be elaborated to amides LXXVII as described for the conversion of IV to II (Scheme 2) and II to Ia (Scheme 1). Conversion of LXXVII to LXXIII may be then carried out as described for the preparation of XXXVb from XXXIV, employing a palladium catalyst/ligand useful for the cross-coupling arylation of aryl chlorides (see, for example, Littke, A. F.; *Angew. Chem. IEE* 2002, 4176). The aryl chlorides LXXVII may also be converted to LXXIII by way of a boronate ester, as described for the conversion of XXVa to XXVI via XXVb (Scheme 4).

SCHEME 15 Preparation and Elaboration of 8-chloro-5H-chromeno[2,3]b-pyridine-5-ones

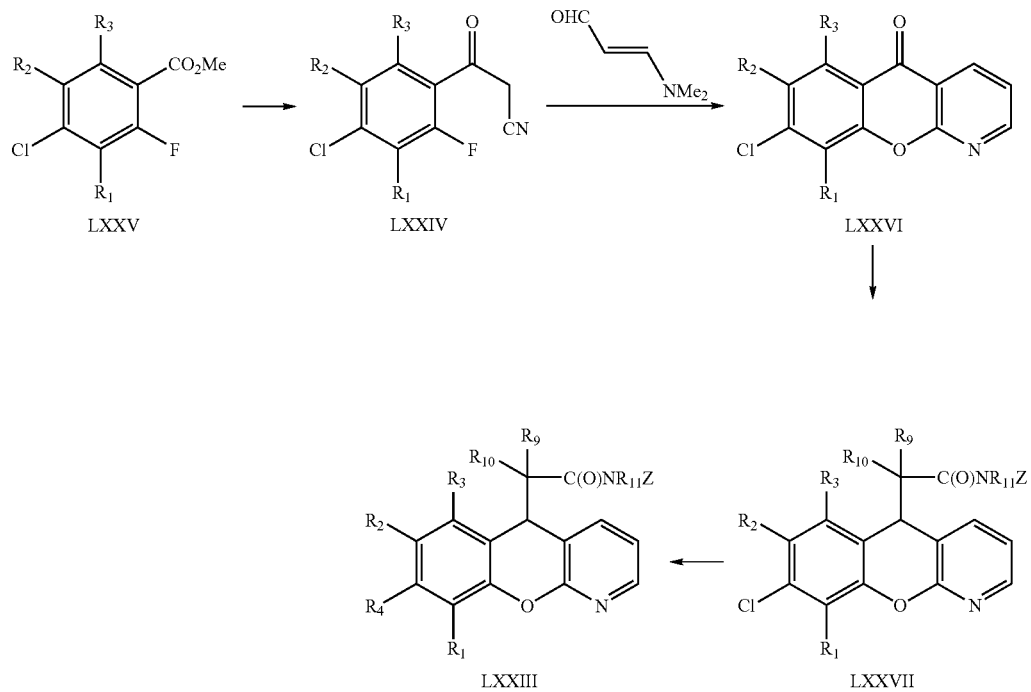

DEFINITIONS

The following are definitions of terms used in this specification and appended claims. The initial definition provided for a group or term herein applies to that group or term throughout the specification and claims, individually or as part of another group, unless otherwise indicated.

The term "alkyl" alone or as part of another group refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

"Alkyl" includes "unsubstituted" and "substituted alkyl" where the alkyl may be substituted with any of the substituents for substituted alkyl set out below.

The term "substituted alkyl" refers to an alkyl group as defined above having one, two, or three substituents independently selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R^a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$, group optionally has up to three further substituents attached at any available carbon or nitrogen atom of $R_a$, $R_b$, and/or $R_c$, said substituent(s) being the same or different and are independently selected from the group consisting of ($C_{1-6}$)alkyl, ($C_{2-6}$)alkenyl, hydroxy, halogen, cyano, nitro, $CF_3$, $O(C_{1-6}$ alkyl), $OCF_3$, $C(=O)H$, $C(=O)(C_{1-6}$alkyl), $CO_2H$, $CO_2$ ($C_{1-6}$ alkyl), $NHCO_2(C_{1-6}$alkyl), —$S(C_{1-6}$alkyl), —$NH_2$, $NH(C_{1-6}$ alkyl), $N(C_{1-6}$alkyl$)_2$, $N(CH_3)_3^+$, $SO_2(C_{1-6}$alkyl), —$NHC(=O)$alkyl, $C(=O)(C_{1-4}$alkylene)$NH_2$, $C(=O)(C_{1-4}$ alkylene)$NH$(alkyl), $C(=O)(C_{1-4}$alkylene)$N(C_{1-4}$ alkyl$)_2$, $C_{3-7}$cycloalkyl, phenyl, benzyl, phenylethyl, phenyloxy, benzyloxy, naphthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below and/or as defined for substituted alkyl.

One skilled in the field will understand that, when the designation "$CO_2$" is used herein, this is intended to refer to the group

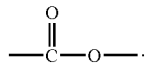

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" (which includes unsubstituted or substituted alkenyl) alone or as part of another group refers to straight or branched chain hydrocarbon groups having 2 to 12 carbon atoms and at least one double bond. Alkenyl groups of 2 to 6 carbon atoms and having one double bond are most preferred.

The term "alkynyl" (which includes unsubstituted or substituted alkynyl) alone or as part of another group refers to straight or branched chain hydrocarbon groups having 2 to 12 carbon atoms and at least one triple bond. Alkynyl groups of 2 to 6 carbon atoms and having one triple bond are most preferred.

The term "alkylene" (which includes unsubstituted or substituted alkylene) alone or as part of another group refers to bivalent straight or branched chain hydrocarbon groups having 1 to 12 carbon atoms, preferably 1 to 8 carbon atoms, e.g., $\{$—$CH_2$—$\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" (which includes unsubstituted and "substituted heteroalkylene") alone or as part of another group is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g. as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen.

Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; $A_2$ is a bond, $C_{1-3}$alkylene, $C_{2-3}$alkenylene, —$C_{1-4}$alkylene-NR$_d$—, —$C_{1-4}$alkylene-NR$_d$C(=O)—, —$C_{1-4}$alkylene-S—, —$C_{1-4}$alkylene-SO$_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "carbonyl" is intended to designate the group —C(O)—.

It should be understood that the selections for alkoxy, thioalkyl, and aminoalkyl will be made by one skilled in the field to provide stable compounds. Thus, for example, in compounds of formula I, when $R_5$, $R_6$, $R_7$ or $R_8$ is attached to a nitrogen atom (N*) of ring B and is selected from an alkoxy or alkylthio group, the alkoxy and alkylthio groups will have at least one carbon atom bonded directly to ring B (at N*), with the oxygen or sulfur atoms being at least one atom away from said nitrogen atom.

The term "acyl" alone or as part of another group refers to a carbonyl group linked to an organic radical, more particularly, the group C(=O)R$_e$, as well as the bivalent groups —C(=O)— or —C(=O)R$_e$—, which are linked to organic radicals or a ring in compounds of formula I. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula I, when it is recited that $R_1$ to $R_8$ can be "acyl," this is intended to encompass a selection for $R_1$ to $R_8$ of —C(=O)— and also the groups —C(=O)R$_e$— or —R$_e$C(=O)—, wherein in this instance, the group R$_e$ will be selected from bivalent groups, e.g. alkylene, alkenylene, alkynylene, bivalent aminoalkyl, substituted alkylene, substituted alkenylene, or substituted alkynylene.

The term "alkoxycarbonyl" alone or as part of another group refers to a carboxy group

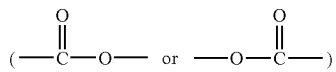

linked to an organic radical (CO$_2$R$_e$), as well as the bivalent groups —CO$_2$—, —CO$_2$R$_e$— which are linked to organic radicals in compounds of formula I, wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.). Accordingly, "alkoxycarbonyl," is intended to encompass the groups —CO$_2$R$_e$— or —R$_e$CO$_2$—, wherein in this instance, the group R$_e$ will be selected from bivalent groups, e.g. alkylene, alkenylene, alkynylene, bivalent aminoalkyl, substituted alkylene, substituted alkenylene, or substituted alkynylene.

The term "amide" or "amidyl" alone or as part of another group refers to the group C(=O)NR$_a$R$_b$ (or other R groups other than R$_a$ or R$_b$ linked to an N atom), wherein the groups R$_a$ and R$_b$ are defined as recited above in the definition for substituted alkyl groups.

The term "sulfonyl" alone or as part of another group refers to a sulphoxide group linked to an organic radical in compounds of formula I, more particularly, the monovalent group S(O)$_{1-2}$—R$_e$, or the bivalent group —S(O)$_{1-2}$— linked to organic radicals in compounds of formula I. Accordingly, in compounds of formula I, "sulfonyl," is intended to encompass —S(=O)— or —SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" alone or as part of another group refers to the group —S(O)$_2$NR$_a$R$_b$ (or other R groups other than R$_a$ or R$_b$ linked to an N atom), wherein R$_a$ and R$_b$ are as defined above for substituted alkyl groups. Additionally, the sulfonamidyl group may be bivalent, in which case one of the groups R$_a$ and R$_b$ will be a bond. Thus, in compounds of formula I, sulfonamidyl is intended to mean the group —S(O)$_2$ NR$_a$—.

The term "cycloalkyl" alone or as part of another group refers to fully saturated and partially unsaturated hydrocarbon rings of 3 to 9, preferably 3 to 6 carbon atoms. Accordingly, the term "cycloalkyl" is intended to include a cycloalkenyl (e.g. cyclohexenyl) ring. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, $SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_e$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

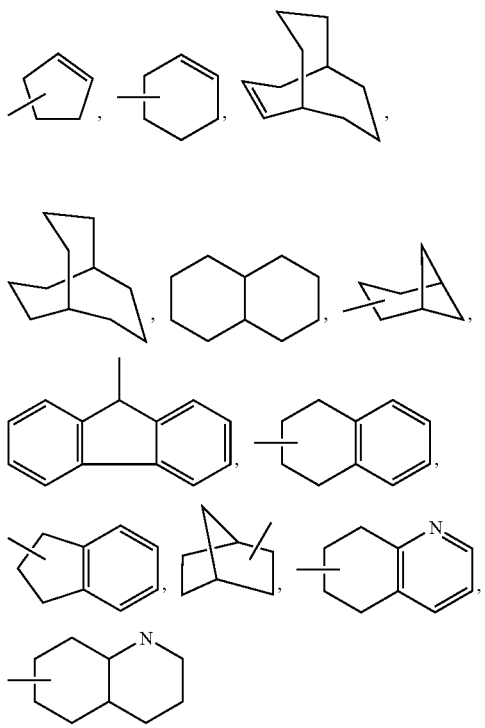

and the like, which optionally may be substituted at any available atoms of the ring(s). Preferred cycloalkyl groups include cyclopropyl, cyclobutyl, cyclopentyl, cyclohexyl,

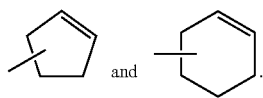

The term "halo" or "halogen" alone or as part of another group refers to chloro, bromo, fluoro and iodo.

The term "haloalkyl" alone or as part of another group means a substituted alkyl having one or more halo substituents. For example, "haloalkyl" includes mono, bi, and trifluoromethyl.

The term "haloalkoxy" alone or as part of another group means an alkoxy group having one or more halo substituents. For example, "haloalkoxy" includes $OCF_3$.

The term "aryl" alone or as part of another group refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$ —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above, or any of the substituents for alkyl set out hereinbefore. Additionally, two substituents attached to an aryl, particularly a phenyl group, may join to form a further ring such as a fused or spiro-ring, e.g. cyclopentyl or cyclohexyl, or fused heterocyclo or heteroaryl. When an aryl is substituted with a further ring (or has a second ring fused thereto), said ring in turn is optionally substituted with one to four, preferably one or two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $C(=O)NH_2$, $SO_2(C_{1-4}alkyl)$, $C(=O)(C_{1-4} alkylene)NH_2$, $C(=O)(C_{1-4}alkylene)NH(alkyl)$, and/or $C(=O)(C_{1-4}alkylene)N(C_{1-4}alkyl)_2$.

Thus, examples of aryl groups include:

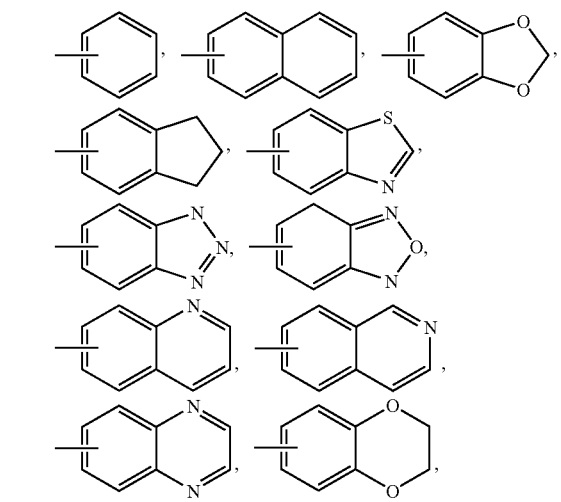

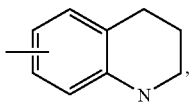

and the like, which optionally may be substituted at any available carbon or nitrogen atom. A preferred aryl group is optionally-substituted phenyl.

The terms "heterocyclo" or "heterocyclic" or "cycloheteroalkyl" alone or as part of another group refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$—$SO_2NR_aR_b$, $-SO_2NR_aC$(=O)$R_b$, $SO_3H$, $-PO(OH)_2$, $-C$(=O)$R_a$, $-CO_2R_a$, $-C$(=O)$NR_aR_b$, $-C$(=O)($C_{1-4}$alkylene)$NR_aR_b$, $-C$(=O)$NR_a(SO_2)R_b$, $-CO_2(C_{1-4}$alkylene)$NR_aR_b$, $-NR_aC$(=O)$R_b$, $-NR_aCO_2R_b$, $-NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of ($C_{1-4}$)alkyl, ($C_{2-4}$)alkenyl, halogen, hydroxy, cyano, nitro, $CF_3$, $O(C_{1-4}$alkyl), $OCF_3$, $C$(=O)H, $C$(=O)($C_{1-4}$alkyl), $CO_2H$, $CO_2(C_{1-4}$alkyl), $NHCO_2(C_{1-4}$alkyl), $-S(C_{1-4}$alkyl), $-NH_2$, $NH(C_{1-4}$alkyl), $N(C_{1-4}$alkyl)$_2$, $N(C_{1-4}$alkyl)$_3^+$, $SO_2(C_{1-4}$alkyl), $C$(=O)($C_{1-4}$alkylene)$NH_2$, $C$(=O)($C_{1-4}$alkylene)$NH$(alkyl), and/or $C$(=O)($C_{1-4}$alkylene)$N(C_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

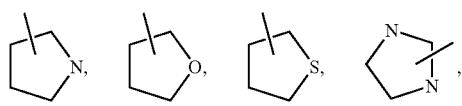

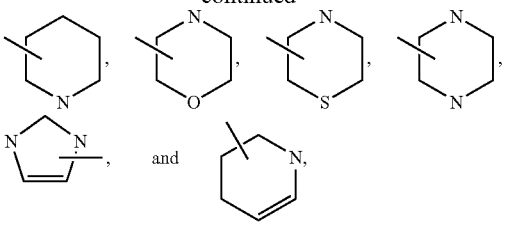

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC$(=O)$R_b$, $SO_3H$, $-PO(OH)_2$, $-C$(=O)$R_a$, $-CO_2R_a$, $-C$(=O)$NR_aR_b$, $-C$(=O)($C_{1-4}$alkylene)$NR_aR_b$, $-C$(=O)$NR_a(SO_2)R_b$, $-CO_2(C_{1-4}$alkylene)$NR_aR_b$, oxo(=O), $-NR_aC$(=O)$R_b$, $-NR_aCO_2R_b$, $-NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$)alkyl, ($C_{2-4}$)alkenyl, halogen, hydroxy, cyano, nitro, $CF_3$, $O(C_{1-4}$alkyl), $OCF_3$, $C$(=O)H, $C$(=O)($C_{1-4}$alkyl), $CO_2H$, $CO_2(C_{1-4}$alkyl), $NHCO_2(C_{1-4}$alkyl), $-S(C_{1-4}$alkyl), $-NH_2$, $NH(C_{1-4}$alkyl), $N(C_{1-4}$alkyl)$_2$, $N(C_{1-4}$alkyl)$_3^+$, $SO_2(C_{1-4}$alkyl), $C$(=O)($C_{1-4}$alkylene)$NH_2$, $C$(=O)($C_{1-4}$alkylene)$NH$(alkyl), and/or $C$(=O)($C_{1-4}$alkylene)$N(C_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

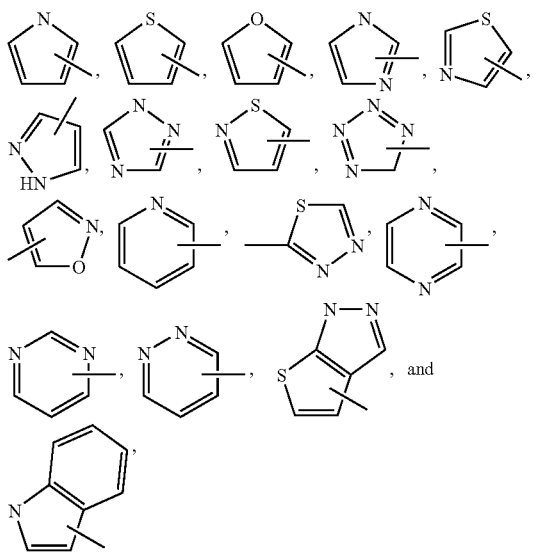

and the like, which optionally may be substituted at any available carbon or nitrogen atom.

Unless otherwise indicated, when reference is made to a specifically-named aryl (e.g., phenyl), cycloalkyl (e.g. cyclohexyl), heterocyclo (e.g. pyrrolidinyl) or heteroaryl (e.g. imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

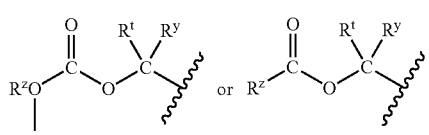

wherein $R^z$, $R^t$ and $R^y$ are H, alkyl, aryl or arylalkyl; however, $R^zO$ cannot be HO.

Examples of such prodrug esters include

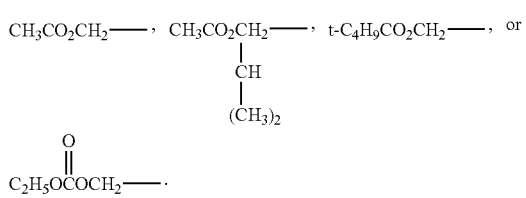

Other examples of suitable prodrug esters include

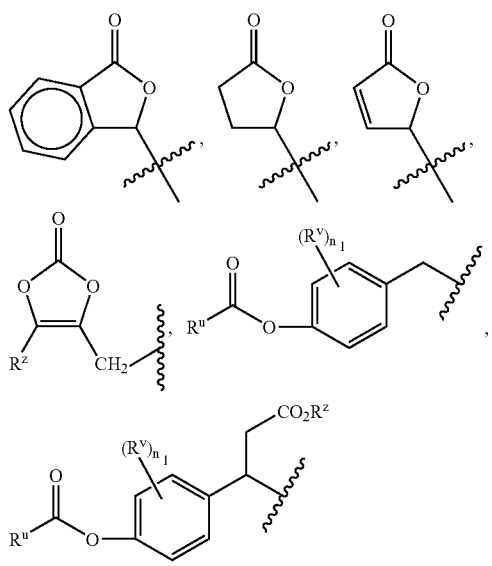

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4 Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

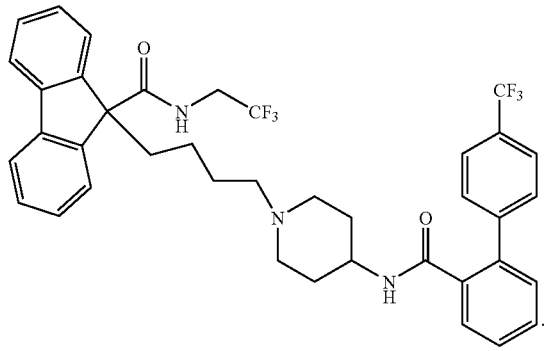

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, Vol. 31, No. 10, pp. 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, Vol. 2, pp. 1-40 (1996).

In addition, other squalene synthetase inhibitors suitable for use herein include the terpenoid pyrophosphates disclosed by P. Ortiz de Montellano et al., *J. Med. Chem.*, 1977, 20, 243-249, the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 1987, 109, 5544 (1987), and cyclopropanes reported by Capson, T. L., PhD dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24, 9-15 (1999), (Avasimibe); "The ACAT inhibitor, CI-1011 is effective in the prevention and regression of aortic fatty streak area in hamsters", Nicolosi et al., *Atherosclerosis* (Shannon, Irel). 137 (1), 77-85 (1998), "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.* (1998), 16(1), 16-30; "RP 73163: a bioavailable alkylsulfinyl-diphenylimidazole ACAT inhibitor", Smith, C., et al, *Bioorg. Med. Chem. Lett.* 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, *Chemtracts: Org. Chem.* 8(6), 359-62 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future*, 24, 425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J. Pharmacology* 120, 1199-1206 (1997), and Cornicelli et al, "15-Lipoxygenase and its Inhibition: A Novel Therapeutic Target for Vascular Disease", *Current Pharmaceutical Design,* 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the α-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594, 016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614, 492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2, 4-dioxo-5-thiazolidinyl)methyl]-2-methoxy-N-[[4-(trifluoromethyl)phenyl]methyl]- (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, (1999), TSL-225 (tryptophyl-1,2,3,4-tetrahydro-isoquinoline-3-carboxylic acid (disclosed by Yamada et al, Bioorg. & Med. Chem. Lett. 8 1537-1540 (1998), 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5):173 (1986); perindopril (Servier) disclosed in *Eur. J. Clin. Pharmacol.* 31:519 (1987); quinapril (Warner-Lambert) disclosed in U.S. Pat. No. 4,344,949 and CI925 (Warner-Lambert) ([3S-[2-[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of the examples are inhibitors of AP-1 activity and/or compete with known ligands of the glucorcorticoid receptor.

Identical and/or similar assays are described in copending provisional application No. 60/396,907, filed Jul. 18, 2002 which is incorporated in its entirety herein by reference.

Assays

GR Binding Assays
Glucocorticoid Receptor Binding Assay (I)[a]

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)[b]

In order to measure the binding of compounds on the glucocorticoid receptor a commercially available kit was used (Glucocorticoid receptor competitor assay kit, PanVera Co., Madison, W1, P2816). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Cellular Transrepressional Assay

To measure the ability of test molecules to inhibit AP-1 induced transcriptional activity we utilized an A549 cell which was stably transfected with a plasmid containing 7× AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity. In the absence of an EC50 the maximum % inhibition recorded is the inhibition of AP-1 at a compound concentration of 10 micromolar.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J. Biol. Chem., December* 29, 270(52):31315-20 (1995) may be used.

The cellular transrepressional assays described above may be used to measure transrepression by any NHR. One of skill in the art will understand that assays may require the addition of components, such as a stimulus (e.g. PMA, lipopolysaccharide, TNF-α, etc) which will induce transcription mediated by AP-1 or NF-κB.

Additionally, AR mediated transrepression may be measured by the assay described in Palvimo. J. J. et al., *J. Biol. Chem., September* 27, 271(39):24151-6 (1996), and PR mediated transrepression may be measured by the assay described in Kalkhoven E., et al. *J. Biol. Chem., March* 15, 271(11):6217-24 (1996).

Abbreviations

The following abbreviations are employed in the following Preparations and Examples:
Ph=phenyl
Bn=benzyl
t-Bu=tertiary butyl
Me=methyl
Et=ethyl
TMS=trimethylsilyl
TMSN$_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(t-rimethylsilyl)amide
Ph$_3$P=triphenylphosphine
Pd(OAc)$_2$=Palladium acetate
(Ph$_3$P)$_4$Pd$^\circ$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH—90% H$_2$O—0.1% TFA
Solvent B=90% MeOH—10% H$_2$O—0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLES

The following Examples illustrate embodiments of the inventive compounds and starting materials, and are not intended to limit the scope of the claims.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20×100, 20×250 or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:
Method A (Used in all Cases, Unless Otherwise Indicated):
  Linear gradient of 0 to 100% solvent B over 4 minutes ("min"), with 1 minute ("min") hold at 100% B.
  Ultraviolet ("UV") visualization at 220 nanometers ("nm")
  Column: YMC S5 ODS Ballistic 4.6×50 mm
  Flow rate: 4 milliliters ("mL")/min
  Solvent A: 0.2% phosphoric acid, 90% water, 10% methanol
  Solvent B: 0.2% phosphoric acid, 90% methanol, 10% water
Method B:

| Column: | Phenomenex Luna C18(2), 4.6 × 50 mm × 5 um |
|---|---|
| Mobile Phase: | (A) 10:90 methanol:water; (B) 90:10 methanol:water |
| Buffer: | 0.1% TFA |
| Gradient Range: | 0-100% B |
| Gradient Time: | 4 min |
| Flow Rate: | 4 mL/min |
| Analysis Time: | 5 min |
| Detection: | |
| Detector 1: | UV at 220 nm |
| Detector 2: | MS (ESI+) |
| Detector 3: | ELSD |

Method C:

| Column: | Waters SunFire C18, 4.6 × 50 mm × 5 um |
|---|---|
| Mobile Phase: | (A) 10:90 methanol:water; (B) 90:10 methanol:water |
| Buffer: | 0.1% TFA |
| Gradient Range: | 0-100% B |
| Gradient Time: | 4 min |
| Flow Rate: | 4 mL/min |
| Analysis Time: | 5 min |
| Detection: | |
| Detector 1: | UV at 220 nm |
| Detector 2: | MS (ESI+) |
| Detector 3: | ELSD |

Method D:
Linear gradient of 0 to 100% solvent B over 4 min, with 1 min hold at 100% B.
UV visualization at 220 nm
Column: YMC CombiScreen ODS-A S5 4.6×50 mm
Flow rate: 4 mL/min
Solvent A: 0.2% phosphoric acid, 90% water, 10% methanol
Solvent B: 0.2% phosphoric acid, 90% methanol, 10% water Method E:
Linear gradient of 0 to 100% solvent B over 2 min, with 1 min hold at 100% B.
UV visualization at 254 nm
Column: YMC S5 ODS Ballistic 4.6×50 mm
Flow rate: 4 mL/min
Solvent A: 0.2% phosphoric acid, 90% water, 10% methanol
Solvent B: 0.2% phosphoric acid, 90% methanol, 10% water Method F:
Linear gradient of 0 to 100% solvent B over 2 min, with 1 min hold at 100% B.
UV visualization at 254 nm
Column: Phenomenex Luna C18 4.6×30 mm
Flow rate: 5 mL/min
Solvent A: 0.1% TFA, 90% water, 10% methanol
Solvent B: 0.1% TFA, 90% methanol, 10% water Preparation 1

4-(4-Fluoro-naphthalen-1-yl)-thiazol-2-ylamine

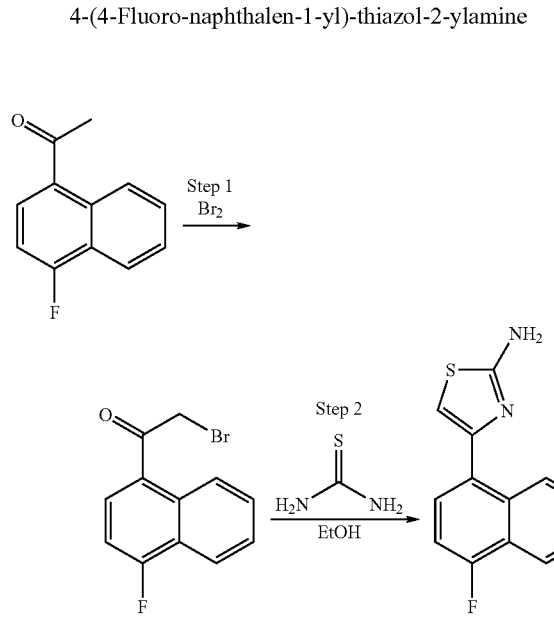

Step 1

To a solution of 4'-fluoro-1'-acetonaphthone (28.69 millimoles ("mmol"), 5.4 grams ("g")) in 1,4-dioxane (18.0 mL) at 0° C. was added bromine (35.13 mmol, 5.61 g). After 3 hours ("h" or "hr") at room temperature ("rt") the reaction mixture was concentrated in vacuo to give 7.66 g (Yield ("Y"): 100%) of the product of step 1.

Step 2

To a solution of the product of step 1 (28.69 mmol, 7.66 g) in ethyl alcohol ("EtOH") (20 mL) at room temperature was added thiourea (36.13 mmol, 2.75 g). After 1 hour at room temperature a precipitate formed. To the reaction mixture was added water (100 mL) and the solid was collected by vacuum filtration. The solid was then washed with water (3×100 mL) and dichloromethane (3×100 mL), then dried in vacuo to give 5.5 g (Y: 75%) of the title compound. Mass Spectrometry ("MS") (E+) m/z: 245 (MH+).

The following compounds were prepared in the same manner as the product of Preparation 1:

| Preparation No. | Structure |
| --- | --- |
| 2 | 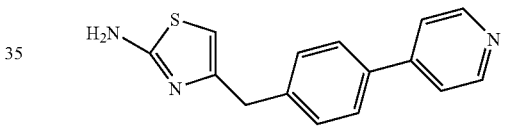 |
| 3 | 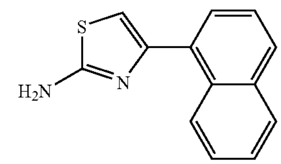 |

Preparation 4

$H_2N$—thiazole—$CH_2$—phenyl—pyridine structure (a) To a solution of commercially available 4-bromophenylacetone (25 g, 117 mmol) in 30 mL of acetic acid and 15 mL of 48% HBr was added a solution of bromine (40 g, 217 mmol) in 50 mL of acetic acid. After 4 hr, acetone (150 mL) was added and the reaction mixture was stirred for 3 d. The reaction was concentrated by rotary evaporator, diluted with brine, and extracted 2×DCM. The DCM extracts were dried over $MgSO_4$. The solution was filtered, concentrated by rotary evaporator, and chromatographed on $SiO_2$ using DCM to give 20.8 g (98%) of a dark oil 4a. $^1$H-NMR (400 MHz, $CDCl_3$): δ 7.49 (d, 2H), 7.12 (d, 2H), 3.94 (s, 2H), 3.92 (s, 2H).

(b) To a solution of 4a (116 mmol) in 200 mL of EtOH was added thiourea (9.0 g, 118 mmol) all at once. The reaction was heated at reflux for 4 hr. The reaction was concentrated by rotary evaporator and the crude residue was dissolved in EtOAc and extracted 3×1N HCl. The aqueous extracts were basified with 1N NaOH and then extracted 2×EtOAC. EtOAc extracts were dried over $MgSO_4$, and solid was triturated in 10% hexanes in EtOAc. Solid was collected and dried in vacuo to give 18 g (57%) of pure 6b. MS found: (M+H)+= 270.

(c) Charged a flask with 4b (8.07 g, 30 mmol), 4-pyridineboronic acid (6.1 g, 50 mmol), tetrakis(triphenylphosphine)palladium(0) (3.5 g, 3.0 mmol), 30 mL of 2M $K_2CO_3$, and 200 mL of DMF. The reaction mixture was degassed by bubbling nitrogen through for 15 min then heated at 100° C. overnight. The reaction mixture was diluted in EtOAc and extracted 3×1N HCl. The aqueous extracts were basified with 1N NaOH and then allowed to stand in refrigerator for 2 hr. Solid was collected and dried in vacuo to give 5.4 g (68%) of pure 4c. MS found: (M+H)+=268.

Preparation 5

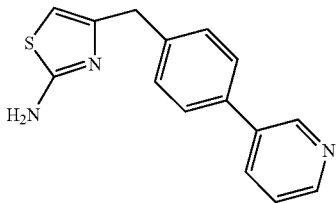

The title compound was prepared from intermediate bromide 4b in the same manner as 4c substituting 3-pyridylboronic acid for 4-pyridylboronic acid. MS (E-) m/z: 268 (M+H); $^1$H-NMR (400 MHz, CDCl$_3$): δ 8.80 (s, 1 H), 8.51 (dd, 1 H), 8.13 (dd, 1 H), 7.62 (d, 2 H), 7.53 (dd, 1 H), 7.40 (d, 2 H), 6.15 (s, 1 H), 3.89 (s, 2 H).

Preparation 6

(DMSO) δ 8.21 s (1H), 8.14 (dd, 1H), 7.72 (dd, 1H), 7.60 (app t, 1H), 7.27 (s, 1H), 7.19 (s, 2H).

Step 2

The product of Step 1 (6.73 g, 33.5 mmol) was suspended in 110 mL of conc HCl and refluxed while stirring for 4 hr. The homogeneous solution was cooled in an ice bath to form crystals which were filtered, washed with water and dried in vacuo to give 6.89 g of the desired product (94% yield). MS found: (M+H)+=221.

Step 3

To a solution of the product of Step 2 (6.89 g, 31.3 mmol) in DMF (100 mL) was added triethylamine (8.8 mL, 63 mmol), 1-hydroxy-7-azabenzotriazole ("HOAt") (4.26 g, 31.3 mmol), and 3-ethyl-3'-(dimethylamino)propyl-carbodiimide hydrochloride (or 1-(3-dimethylaminopropyl)-3-ethyl-carbodiimide hydrochloride) ("EDC") (6.0 g, 31.3 mmol). After stirring 25 min, a solution of 3-chloro-4-anisidine (5.92 g, 37.6 mmol) in 50 mL DMF and 8.8 mL triethylamine was added all at once at rt. After stirring for 24 h, the reaction was concentrated by rotary evaporator, extracted from a saturated sodium chloride solution ("brine") with EtOAc. The combined organics were dried over MgSO$_4$ to yield crude product. The crude product was concentrated in vacuo, dissolved in a minimum amount of EtOAc and triturated with hexane. The resulting solid was filtered and trituration was repeated twice to give a total of 5.7 g (51% yield) of pure product. MS found: (M+H)+=360. 1H-NMR (DMSO) δ 10.3 (s, 1H), 8.35

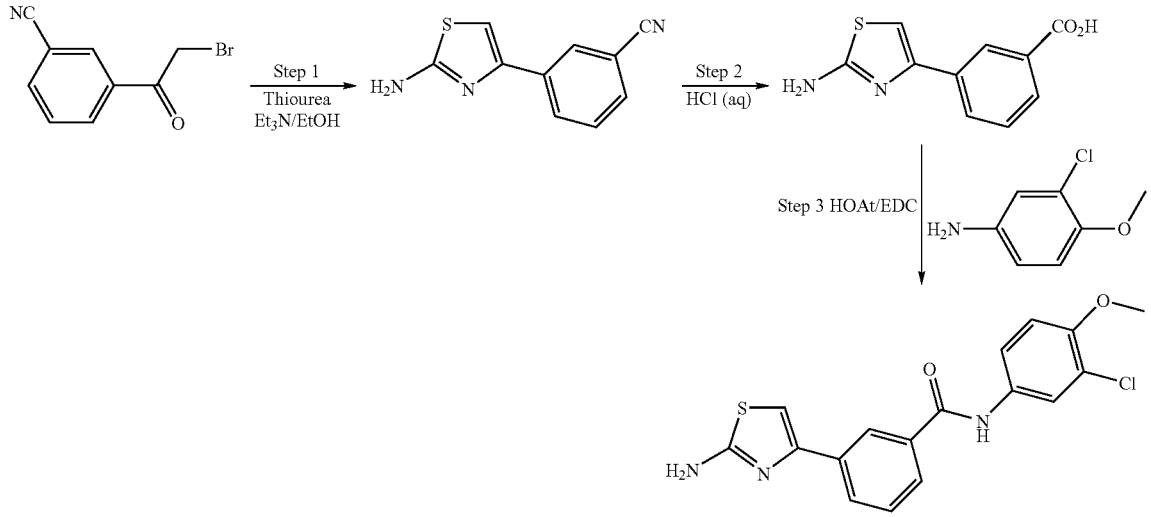

Step 1

To a solution of 3-(2-bromoacetyl)benzonitrile (15.0 g, 66.6 mmol) (prepared in the manner described in Tanaka et al., J. Med. Chem. 1998, 41, 2390-2410), in EtOH (220 mL) was added triethylamine ("TEA") (9.3 mL, 66.6 mmol) and thiourea (6.6 g, 86.6 mmol) and the reaction was stirred at rt overnight. After 20 h, the reaction was concentrated in vacuo and the residue partitioned between water and EtOAc. The aqueous layer was washed with EtOAc (3×). The combined organic extracts were washed with saturated ("sat.") sodium bicarbonate ("NaHCO$_3$"), dried over MgSO$_4$, filtered, and concentrated by rotary evaporator. The resulting solid was recrystallized from EtOAc and hexane to give 7.78 g of pale yellow solid in a first batch and 1.87 g of a second batch (72% yield combined). MS found: (M+H)+=202. $^1$H-NMR (s, 1H), 8.00 (d, 1H), 7.95 (d, 1H), 7.80 (d, 1H), 7.69 (d, 1H), 7.52 (t, 1H), 7.16 (m, 4H), 3.85 (s, 3H).

Preparation 7

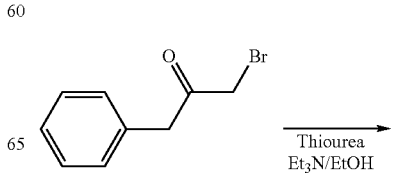

-continued

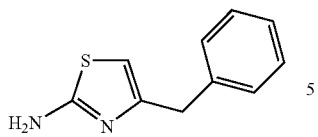

To a solution of 1-bromo-3-phenyl-2-propanone (2.2 g, 10 mmol) (prepared in the manner described in Choi et al., Org. Lett. 2003, vol. 5, no. 4, 411-414), in EtOH (100 mL) was added thiourea (1.0 g, 13 mmol) and the reaction was stirred at reflux overnight. After 20 h, the reaction was concentrated in vacuo and partitioned between water and ethyl acetate ("EtOAc"). The aqueous layer was washed with EtOAC (3×). The combined organic extracts were dried over magnesium sulfate ("MgSO$_4$"), filtered, and concentrated by rotary evaporator. The resulting solid was purified by silica gel chromatography using 10% MeOH/EtOAc as the eluent to give 2.1 g of pale yellow solid (95% yield). MS found: (M+H)+= 191. Proton nuclear magnetic resonance ("1H-NMR") in chloroform ("CDCl3") δ 7.2-7.35 m (5H), 6.01 (s, 1H), 4.8-5.3 (bs, 2H), 3.86 (s, 2H). NMR spectral data: s=singlet; d=doublet; m=multiplet; br=broad; t=triplet.

Preparation 8

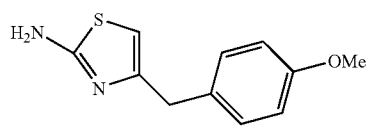

(a) Applying the method of Mazzocchi et al (Synth. Commun. 1986, 309-312) a cuprate was prepared from 4-methoxyphenylmagnesium bromide (20 mmol, 40 mL of 0.5 M THF solution) and CuBr (574 mg, 2.0 mmol) in 50 mL anhydrous ether. The cuprate was treated with epichlorohydrin (1.94 g, 21 mmol) and stirred at −40 C for 20 hr. The reaction was quenched with water, extracted 2×Et$_2$O, and the ethereal extracts were dried over MgSO$_4$. The solution was filtered, concentrated by rotary evaporator, and chromatographed on SiO$_2$ using 25% EtOAc in hexanes to give 888 mg (22%) of the chlorohydrin 5a as a yellow oil. $^1$H-NMR (400 MHz, CDCl$_3$): δ 7.18 (d, 2H), 6.88 (d, 2H), 4.0 (m, 1H), 3.82 (s, 3H), 3.65 (dd, 1H), 3.52 (dd, 1H), 2.83 (d, 2H).

(b) The intermediate alcohol 8a (888 mg, 4.44 mmol) was taken up in dichloromethane (40 mL) and treated with Dess-Martin periodinane (1.88 g, 4.44 mmol). The reaction was allowed to warm to rt and was complete by TLC monitoring after 4 hr. The reaction mixture was concentrated by rotary evaporation and the crude residue was purified on SiO$_2$ (dichloromethane as eluent) to give 762 mg (86% Y) of chloromethylketone 8b.

(c) This intermediate was taken up in 15 mL of EtOH and treated with a solution of thiourea (302 mg, 3.82 mmol) in 5 mL EtOH. The reaction was concentrated in vacuo and a solid formed on standing to give pure 8c, 208 mg (80%) as a yellow solid. MS found: (M+H)+=221.

Preparation 9

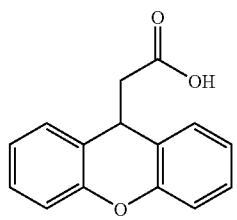

A mixture of 9-hydroxy xanthene (3.96 g, 20 mmol) and malonic acid (2.6 g, 25 mmol) in dry pyridine was stirred under nitrogen at 65° C., turning homogeneous after 20 min at that temperature. After heating 2 h at 65° C., the solution was warmed to 95° C., and heated at that temperature for an additional 4.5 h. The solution was then poured into 1N aqueous HCl, giving an oil which solidified over 1 h. The solid was collected and washed with water, then partitioned between 1N aqueous NaOH and dichloromethane. The aqueous layer was acidified with concentrated HCl, then washed with ethyl acetate. The organic layer was dried (sodium sulfate) and concentrated to give the product (2.48 g, Y=50%) as an off white/pale pink solid. MS (E-) m/z: 239 (M−H); LC retention time: 3.39 min.

Preparation 10

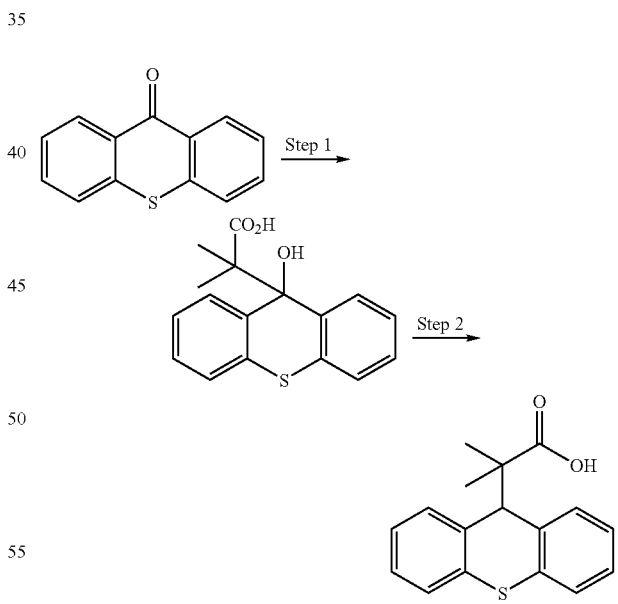

Step 1

To a solution of diisopropylamine (9.28 mL, 66.16 mmol) in dry THF (70 mL) at −30° C. was added n-butyl lithium (1.6 M in hexanes, 41.4 mL) dropwise. The resulting solution was warmed to 0° C. and a solution of isobutyric acid (3.06 mL, 33.1 mmol) in THF (10 mL) was then added dropwise. The mixture was heated at 55° C. for 1.5 h, then cooled to room temperature and added portionwise via canula to thioxanthen-9-one (5.0 g, 23.58 mmol) in THF (100 mL) at 0° C. The ice bath was removed and the reaction mixture stirred at room temperature for 2 h, then partitioned between ethyl acetate and 1N HCl. The organic layer was washed with 1N aqueous NaOH. The basic aqueous layer was then acidified to pH 2 with the dropwise addition of concentrated HCl, then washed with ethyl acetate. The organic layer was dried (sodium sulfate) and concentrated to give the crude product (3.5 g), which was used directly in the next step without further purification. MS (E+) m/z: 301 (M+H); LC retention time: 3.44 min.

Step 2

To a solution of the product of Step 1 (3.5 g, 11.7 mmol) in dichloromethane (40 mL) at 0° C. was added boron trifluoride etherate (2.6 mL, 20.4 mmol) followed by triethylsilane (3.4 mL, 21.3 mmol). The resulting solution was allowed to warm to room temperature over 1 h. After 2 h at room temperature, the reaction mixture was partitioned between dichloromethane and 1N aqueous NaOH. The aqueous layer was acidified to pH 2 with the dropwise addition of concentrated HCl, then washed with ethyl acetate. The organic layer was dried (sodium sulfate) and concentrated, then purified by flash column chromatography (silica, 1:1 ethyl acetate:hexanes, product Rf=0.6) to give the product (0.7 g) as a pale yellow solid. LC retention time: 3.83 min.

Preparation 11

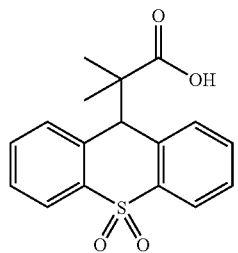

To a solution of the product of Preparation 9 (100 mg, 0.352 mmol) in glacial acetic acid (4 mL) at 0° C. was added hydrogen peroxide (4 mL). The solution was allowed to warm temperature, and stirred for 2 h. To the reaction mixture was added sodium tungstate dihydrate (30 mg, 0.10 mmol). After stirring another 12 h at ambient temperature, the reaction mixture was partitioned between ethyl acetate and water. The organic layer was washed sequentially with a saturated solution of aqueous sodium sulfite and water, then dried over sodium sulfate and concentrated to give the product (95 mg, 85% yield) as a white solid. LC retention time: 2.69 min.

Preparation 12

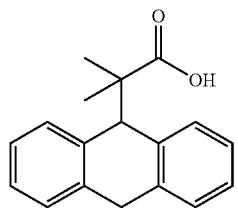

The title compound was prepared in the same manner as the title compound of Preparation 10, replacing thioxanthen-9-one with anthrone.

Preparation 13

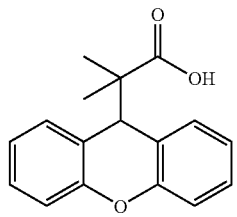

The title compound was prepared in the same manner as the title compound of Preparation 10, replacing thioxanthen-9-one with 9H-xanthen-9-one.

In alternative preparation of the title compound is as follows: To a solution of 9-hydroxy xanthene (250 mg, 1.26 mmol) in dichloromethane (11 mL) at ° C. under nitrogen was added titanium tetrachloride (1.0M in dichloromethane, 1.26 mL) dropwise to give a yellow, opaque mixture. After 5 min at 0° C., methyl trimethylsilyl dimethylketene acetal (MT-DKA) (0.64 mL, 3.15 mmol) was added dropwise, giving a brownish solution. After 30 min at 0° C., water (3 mL) was added and the mixture was stirred for 10 min, turning yellow with the formation of a precipitate. The mixture was filtered over Celite, and the organic layer separated, then washed with saturated aqueous sodium bicarbonate, dried over sodium sulfate, and concentrated. Purification of the residue by flash column chromatography (5% ethyl acetate in hexanes) provided the title compound (178 mg). LC retention time: 3.89 min.

Preparation 14

4-[1-(4-Fluoro)naphthyl]aminoimidazole

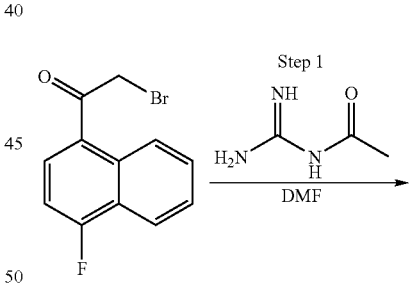

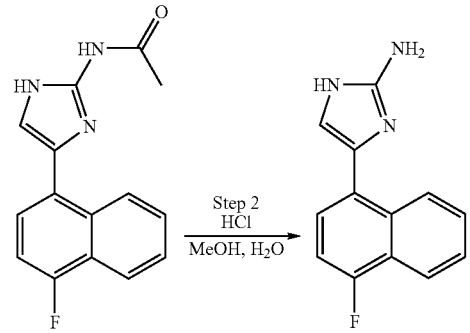

Step 1

To a solution of the product of Preparation 1, step 1 (18.73 mmol, 5.0 g) in DMF (15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo and the residue chromatographed on silica gel (eluted with 5% methanol in dichloromethane) to give 2.0 g (Y: 39%) of the product of step 1. MS (E+) m/z: 270 (MH+).

Step 2

To a solution of the product of Step 1 (7.43 mmol, 2.0 g) in methanol (17 mL) was added water (8.5 mL) and 12 N HCl (12.0 mL). After 1 hour at reflux the reaction mixture was concentrated in vacuo to approximately 15 mL. The resulting solution was then purified and neutralized by cation exchange SPE to give 1.66 g (Y: 99%) of the title compound 2a. MS (E+) m/z: 228 (MH+).

Preparation 15

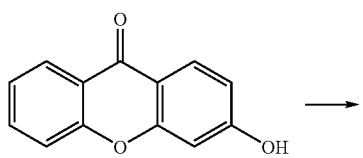

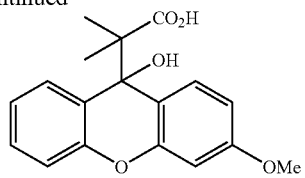

Step 1

To a solution of 3-hydroxy-9-H-xanthenone ("Sieber linker") (20.4 g, 96.2 mmol) in DMF (475 mL) was added methyl iodide (18.0 mL, 287 mmol) followed by NaH (60% w/w in mineral oil, 7.68 g, 192 mmol). The mixture was allowed to stir at rt for 2.5 h, then partitioned between ethyl acetate (750 mL) and 1N HCl (300 mL). The aqueous layer was extracted again with 2 portions of ethyl acetate. The combined organic layer was washed sequentially with water (500 mL), saturated sodium bicarbonate, and brine, then dried over sodium sulfate and concentrated. The crude solid was re-crystallized from EtOH and a second crop of crystals was obtained by re-crystallization of the mother liquor to give 20.21 g (93% yield) of 15a as needles. MS m/z: 227 (M+H); LC retention time: 3.38 min.

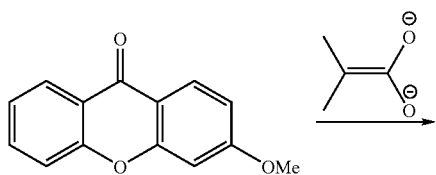

Step 2

To a solution of diisopropyl amine (6.63 mL, 47.25 mmol) in dry THF (35 mL) at −30° C. was added nBuLi (1.6 M/hexanes, 29.6 ml) dropwise. The solution was warmed to 0° C. A solution of isobutyric acid (2.19 mL, 23.63 mmol) in THF (10 mL) was then added dropwise. The solution was heated at 55° C. for 1.5 h, then cooled to room temperature and added portionwise via canula to the ketone 15a (3.56 g, 15.75 mmol) in THF (30 mL) at 0° C. The solution was allowed to warm slowly to room temperature. After 2 h, LC indicated 70% completion. The reaction mixture was partitioned between ethyl acetate and 1N aq HCl. The organic layer was washed with 1N aq NaOH. The basic aqueous layer was acidified at 0° C. with the dropwise addition of concentrated HCl until pH=2. The acidic aqueous layer was washed with ethyl acetate, and the organic layer dried over sodium sulfate and concentrated to give the product alcohol (4.45 g, 90% yield). MS m/z: 297 (M−OH); LC retention time: 3.22 min.

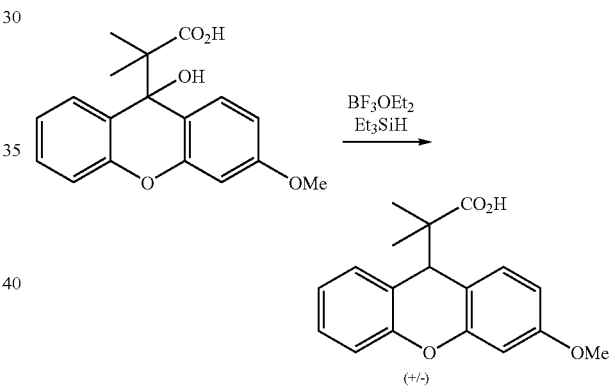

Step 3

To a solution of 15b (2.81 g, 8.95 mmol) in dichloromethane (35 mL) at 0° C. was added boron trifluoride diethyl etherate (2.27 mL, 17.9 mmol) followed by triethylsilane (2.86 mL, 17.9 mmol). The solution was allowed to warm to rt over 1 h. Reaction was complete after 2 h at rt as indicated by HPLC. Continuation of the reaction beyond 2 h led to a gradual increase in the production of a product derived from decarboxylation. The reaction mixture was partitioned between dichloromethane and 1N aq NaOH. The aqueous layer was acidified to pH 2 with the dropwise addition of conc. HCl, then washed with ethyl acetate. The organic layer was dried over sodium sulfate and concentrated to give the product as a solid (1.81 g, 68% yield). MS m/z: 321 (M+Na); LC retention time: 3.64 min

Preparation 16

The racemic carboxylic acid of Preparation 15 was resolved by chiral HPLC (Chiralpak AD, 1:1 ethanol:methanol, 0.05% TFA, isocratic) to provide the pure enantiomers 16a, 16b.

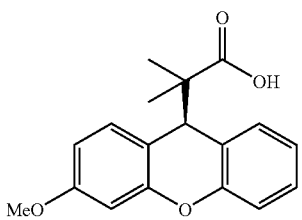

16a.

First to elute from preparative chiral HPLC. Analytical chiral HPLC (Chiralpak AD, 4.6×250 mm, 1:1 ethanol:methanol, isocratic, 0.5 mL/min) retention time=6.41 min, >99.9% ee.

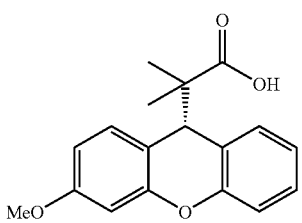

16b.

Second to elute from preparative chiral HPLC. Analytical chiral HPLC (Chiralpak AD, 4.6×250 mm, 1:1 ethanol:methanol, isocratic, 0.5 mL/min) retention time=10.3 min, >99% ee. X-ray crystallographic analysis of the salt derived from 16b and (R)(+)-alpha-methylbenzylamine proved 16b to be the R enantiomer.

Preparation 17

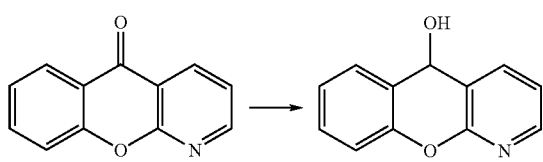

Step 1

To a suspension of 1-azaxanthone (purchased or prepared by the method of Villani et al., J. Med. Chem. 1975, 18, 1-8.) (18.5 g, 94 mmol) in MeOH (650 mL) at 0° C. was added sodium borohydride (4.26 g, 113 mmo) portionwise over 10 min. The reaction mixture was allowed to warm to room temperature, and stirred 15 h. HPLC analysis of the reaction mixture indicated two peaks, one corresponding to the alcohol, the other corresponding to 9-methoxy-1-azaxanthene which is presumably generated under the conditions of LC analysis. The pale yellow solution was then concentrated to one third volume and poured into cold brine (500 mL). This mixture was washed with choloroform (2×300 mL). The combined organic layers were dried over sodium sulfate and concentrated to give a yellowish solid 17a (17.80 g, 95% yield) which was used directly in the next step with no further purification. MS (E+) m/z: 200 (M+H); LC retention time: 2.01 min., 2.46 min.

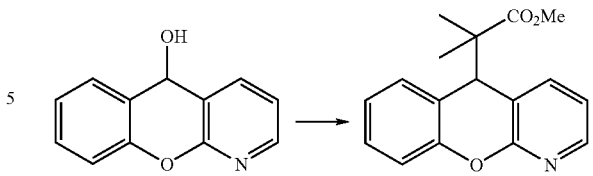

Step 2

To a suspension of 17a (17.80 g, 89 mmol) in dichloromethane (475 mL) at 0° C. was added titanium tetrachloride (1.0 M in dichloromethane, 89 mL) dropwise. The resulting tan-colored suspension stirred 10 min at 0 C (mechanical stirring recommended) before adding (1-methoxy-2-methyl-prop-1-enyloxy)trimethylsilane (36 mL, 173 mmol) to the mixture dropwise. The resulting dark, homogeneous solution was allowed to stir 1 h at 0° C., then quenched with the addition of saturated aqueous sodium bicarbonate, giving gas evolution and formation of a white precipitate. The mixture was filtered over celite, and the resulting organic layer of the filtrate separated, dried over sodium sulfate, and concentrated to give a solid (17b) (22.3 g, 89% yield) which was used directly in the next step with no further purification. MS (E+) m/z: 284 (M+H); LC retention time: 3.04 min.

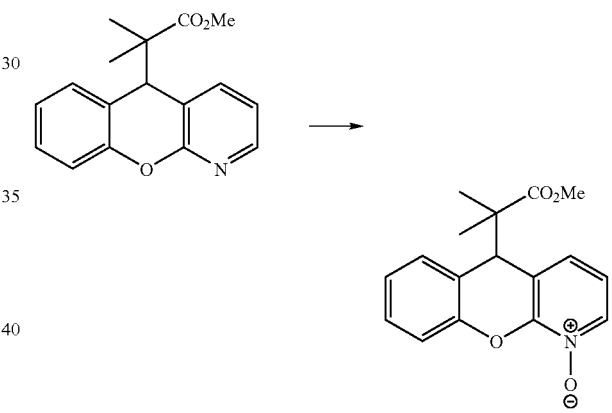

Step 3

To a solution of 17b (21.2 g, 74.9 mmol) in dichloromethane at room temperature was added mCPBA (containing 30% m-chlorobenzoic acid) (53 g). After 2 h, the reaction mixture was washed sequentially with 10% aqueous sodium sulfite (500 mL), 1N aqueous NaOH (200 mL), and water (200 mL). The organic layer was dried over sodium sulfate, and concentrated to provide the title compound (17c) as an amorphous solid (21.63 g, 97% yield) which was used directly in the next step with no further purification. MS (E+) m/z: 300 (M+H); LC retention time: 2.25 min.

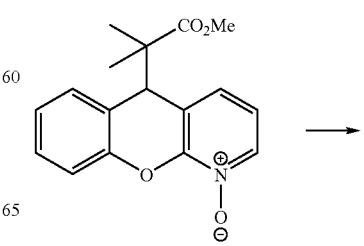

107

-continued

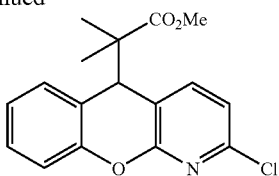

Step 4

A solution of 17c (21.15 g, 71.0 mmol) in phosphorous oxychloride (150 mL) was heated for 30 min at 90° C. The solvent was then removed by vacuum bulb-to-bulb distillation. The residual solid was dissolved in dichloromethane (250 mL) and transferred portionwise to a lL beaker containing ice (¾ full). Solid sodium carbonate was added portionwise with vigorous stirring (gas evolved) to the resulting slurry until it reached pH 6. The resulting emulsion was allowed to sit overnight in a separatory funnel. The organic layer was removed, dried (sodium sulfate), and concentrated to give the crude solid 17d 17.37 g (77% crude yield). This solid may be recrystallized to high purity from methanol or taken directly into the next step with no further purification. MS (E+) m/z: 318 (M+H); LC retention time: 3.37 min.

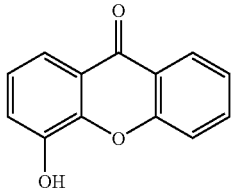

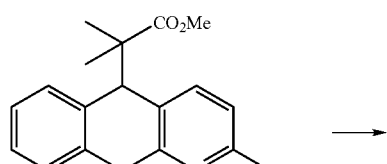

Step 5

To a solution of 17d (16.08 g, 50.7 mmol) in THF (240 mL) and methanol (400 mL) was added a solution of KOH (28.46 g, 507 mmol) in water (320 mL). The resulting solution was heated at reflux (65° C.) 10 h, then concentrated under reduced pressure to about ⅔ volume. The resulting solution was acidified to pH 5 with the dropwise addition of 12N HCl, then washed with ethyl acetate (2×300 mL). The combined organic layers were dried (sodium sulfate) and concentrated. The crude carboxylic acid (12.6 g) was dissolved in warm ethyl acetate (600 mL) and treated with benzylamine (9.2 mL, 48 mmol). The solution was allowed to gradually cool to room temperature, and allowed to sit for 3 h. The precipitate was collected and washed (diethyl ether), then partitioned between ethyl acetate (350 mL) and 1N aqueous HCl (200 mL). The organic layer was dried over magnesium sulfate and

108 concentrated to provide 17e as a solid (8.53 g, 43% yield for two steps). MS (E+) m/z: 304 (M+H); LC retention time: 3.19 min.

Preparation 18

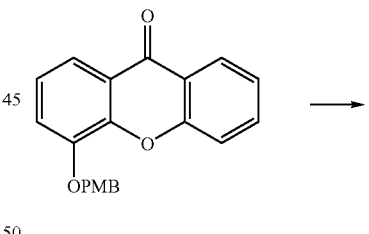

Step 1

To a solution of 4-hydroxy-9H-9-xanthenone (Maybridge) (512 mg, 2.42 mmol) and 4-methoxy benzyl chloride (0.393 mL, 2.90 mmol) in DMF (15 mL) was added sodium hydride (60 w % in mineral oil, 145 mg, 3.63 mmol), giving a dark red color and gas evolution. After 3 h at room temperature, the reaction mixture was partitioned between ethyl acetate and 1N aqueous HCl. The organic layer was washed sequentially with water, saturated aqueous sodium bicarbonate and brine, then dried over sodium sulfate and concentrated. The crude residue was purified by flash column chromatography (silica, 30% acetone in hexanes) to give the product 18a (420 mg). MS (E+) m/z: 333 (M+H).

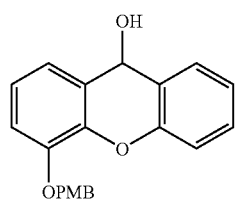

Step 2

A solution of 18a (197 mg, 0.59 mmol) in THF (6 mL) at 0° C. under nitrogen was treated with lithium aluminum hydride (1.0M in diethyl ether, 0.59 mL). After 30 min at 0° C., water (approx. 2 mL) was added dropwise to the mixture. After stirring for 5 min at 0° C., the mixture was filtered over a pad of Celite and sodium sulfate, then concentrated to give the 18b (183 mg, 93%). MS (E+) m/z: 317 (M−OH); LC retention time: 3.88 min.

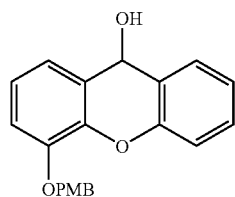 

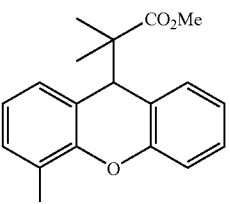 

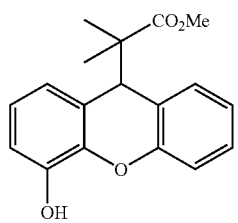

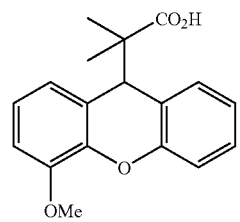

Step 3

To a solution of 18b (181 mg, 0.54 mmol) in dichloromethane (5 mL) at 0° C. was added titanium tetrachloride (1.0M in dichloromethane, 0.54 mL) dropwise to give a deep, dark red solution, which became opaque over the course of 10 min at 0° C. (1-methoxy-2-methylprop-1-enyloxy)trimethylsilane (0.219 mL, 1.08 mmol) was then added dropwise, giving a clear, dark red solution. After 20 min at 0° C., the reaction was quenched with the addition of water (1 mL), turning the mixture colorless, with the formation of a precipitate. The mixture was filtered over celite. The organic layer was separated and washed with saturated aqueous sodium bicarbonate, dried over sodium sulfate, and concentrated. The residue was purified by flash column chromatography (silica, 10-20% ethyl acetate in hexanes) to give the product 18c as the third eluting fraction (110 mg, 68%). MS (E-) m/z: 297 (M-H); LC retention time: 3.29 min.

Step 5

The intermediate 18e was obtained from 18d in the same manner described above for the preparation of the title compound of 17e from 17d. MS (ES-) m/z: 297 (M-H); LC retention time: 3.29 min.

Preparation 19

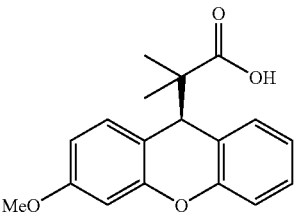

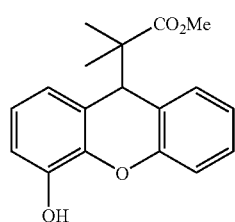 

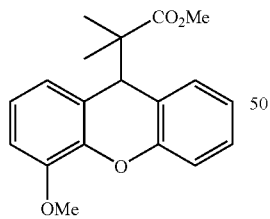

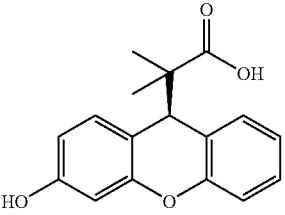

Step 4

A mixture of 18c (32 mg, 0.11 mmol), methyl iodide (0.014 mL, 0.22 mmol) and cesium carbonate (42 mg, 0.13 mmol) in DMF (1 mL) was heated at 60° C. for 6 h. The reaction mixture was then partitioned between ethyl acetate and water. The organic layer was washed sequentially with water, saturated aqueous sodium bicarbonate, and brine, then dried over sodium sulfate and concentrated. The intermediate 18d (28 mg, 82%) was used in the next step with no further purification. MS (ES+) m/z: 335 (M+Na); LC retention time: 3.57 min.

The product of Preparation 16a (600 mg, 2.01 mmol) was divided evenly into 3 microwave reaction vessels. To each reaction vessel was added 1-methyl-2-pyrrolidinone (4 mL), 2-aminothiophenol (92 mg, 0.74 mmol) and potassium carbonate (102 mg, 0.74 mmol). Each mixture was heated by microwave at 205° C. for 1.5 h. The reaction mixtures were combined and partitioned between ethyl acetate and water. The organic layer was extracted with 1N aqueous sodium hydroxide. The combined aqueous layers were acidified approximately to pH 2.0, then extracted with ethyl acetate (3×). The combined organic layers were washed with 1N aqueous HCl, then dried over sodium sulfate and concentrated. Purification of the residue by preparative HPLC provided the product as an amorphous solid (400 mg, 70%). MS (ES−) m/z: 283 (M−H); LC retention time: 3.16 min.

Preparation 20

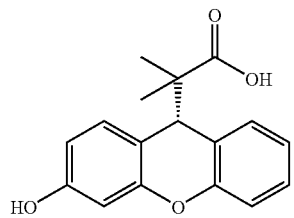

The title compound was prepared from the product of Preparation 16b following the procedure described above for the preparation of the title compound of Preparation 19. MS (ES−) m/z: 283 (M−H); LC retention time: 3.16 min.

Preparation 21

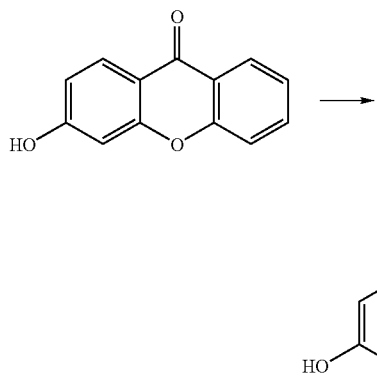

Step 1

To a suspension of 3-hydroxy-9-H-xanthenone ("Sieber linker") (1.0 g, 4.72 mmol) in dichloromethane (10 mL) at 0° C. under nitrogen was added boron trifluoride etherate (1.8 mL, 14.15 mmol) dropwise over 10 min. After stirring 10 min at 0° C., 1-methoxy-2-methylprop-1-enyloxy)trimethylsilane (2.88 mL, 14.15 mmol) was added dropwise to the suspension, giving a clear dark brown solution during the addition, which was stirred another 2 h at 0° C. Another portion of boron trifluoride etherate (1.8 mL, 14.15 mmol) was then added to the reaction mixture, followed by triethylsilane (2.26 mL, 14.15 mmol). The reaction mixture was allowed to warm slowly to room temperature, and stirred 15 h. A saturated aqueous solution of sodium bicarbonate was added to the reaction mixture, which was then extracted with dichloromethane. The organic phase was washed with another portion of saturated sodium bicarbonate, then dried over sodium sulfate and concentrated. The crude material was purified by passing through a short column of silica gel (30-50% ethyl acetate in hexanes) to give the product 21a (1.2 g, 85% yield) as a pale yellow solid. MS (ES−) m/z: 297 (M−H); LC retention time: 3.42 min.

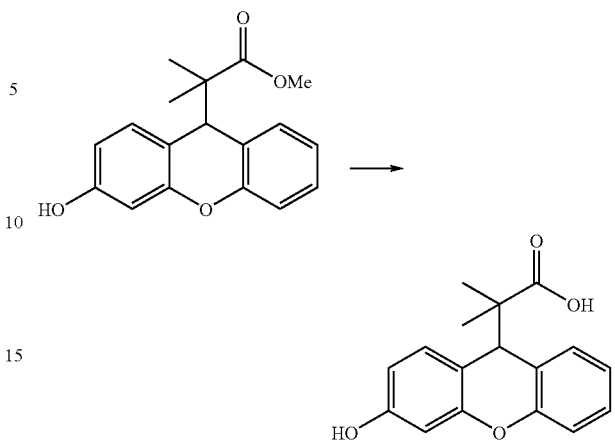

Step 2

A suspension of 21a (133 mg, 0.45 mmol) in methanol (1 mL), water (2 mL), DMSO (1 mL) and 4N aqueous KOH (1.13 mL) was heated at 100° C. for 3 h. The reaction mixture was then partitioned between ethyl acetate and 1N HCl. The organic layer was dried over sodium sulfate, and concentrated to give the product 21b (124 mg, 97% yield). LC retention time: 3.15 min.

Preparation 22

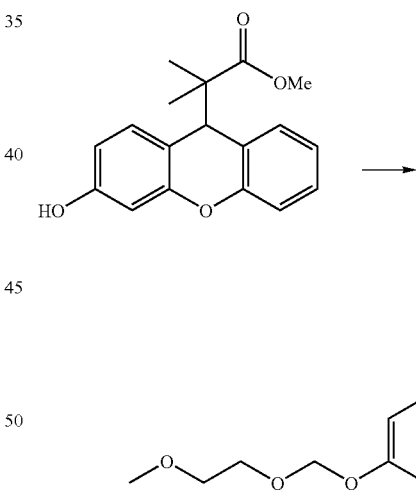

Step 1

To a solution of 21a (490 mg, 1.64 mmol) in THF (15 mL) at 0° C. was added 2-methoxyethoxymethyl (MEM) chloride (0.282 mL, 2.47 mmol), followed by sodium hydride (60% w/w in mineral oil, 85 mg). After 1.3 h, the reaction mixture was partitioned between ethyl acetate and 1N HCl. The organic layer was washed sequentially with saturated aqueous sodium bicarbonate and brine, then dried over sodium sulfate and concentrated to give 667 mg (ca. 99%) of the crude product 22a as an oil which was taken directly into the next step with no further purification. LC retention time: 3.83 min.

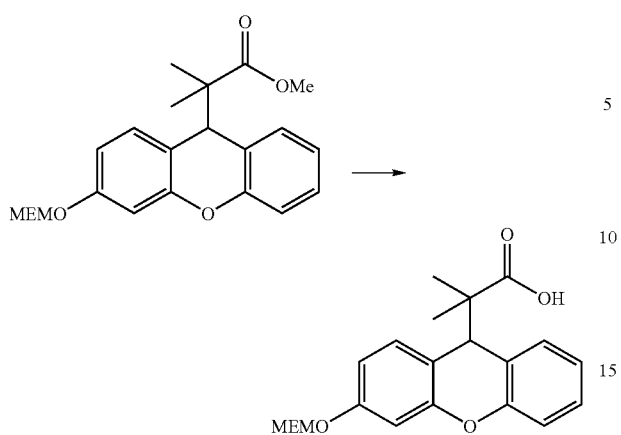

Step 2

A mixture of crude 22a (ca. 1.64 mmol) in methanol (4 mL), DMSO (3.5 mL), and 4N KOH (4.1 mL) was stirred at 100° C. for 3 h, then partitioned between ethyl acetate and 1N HCl. The organic layer was dried over sodium sulfate and concentrated. Flash column chromatography (silica, 50-60% ethyl acetate in hexanes) provided the product 22b (428 mg, 70% for two steps) as a pale yellow oil. LC retention time: 3.61 min.

Preparation 23

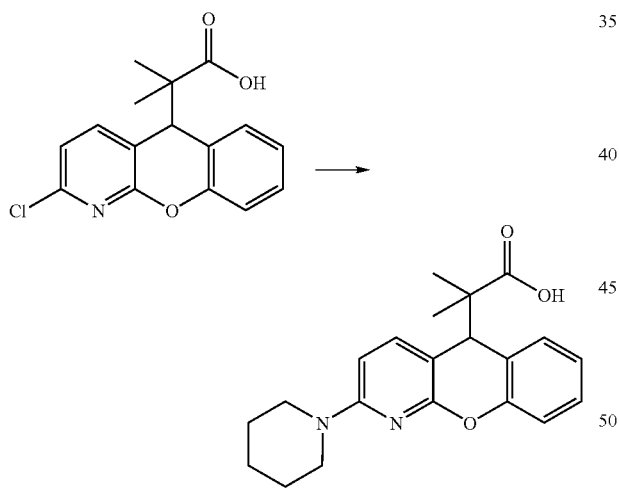

A solution of the product of Preparation 17e (1.0 g, 3.30 mmol) in piperidine (15 mL) in a sealed tube was hated at 150° C. for 4 h. Most of the piperidine was then removed in vacuo to obtain a solid, which was suspended in a 1:1 solution of diethyl ether in hexanes. This suspension was washed with a 1N sodium hydroxide solution. The aqueous layer was washed twice with 1:1 diethyl ether in hexanes, then acidified to pH 3.0 with the dropwise addition of concentrated HCl and extracted with ethyl acetate. The aqueous layer was washed twice with ethyl acetate. The combined ethyl acetate layers were dried over sodium sulfate and concentrated to give a yellow solid (1.10 g, 95% yield). MS (ES+) m/z: 353 (M+H); LC retention time: 3.71 min.

Preparations 24 to 29

The following compounds were prepared in the same manner as the product of Preparation 23.

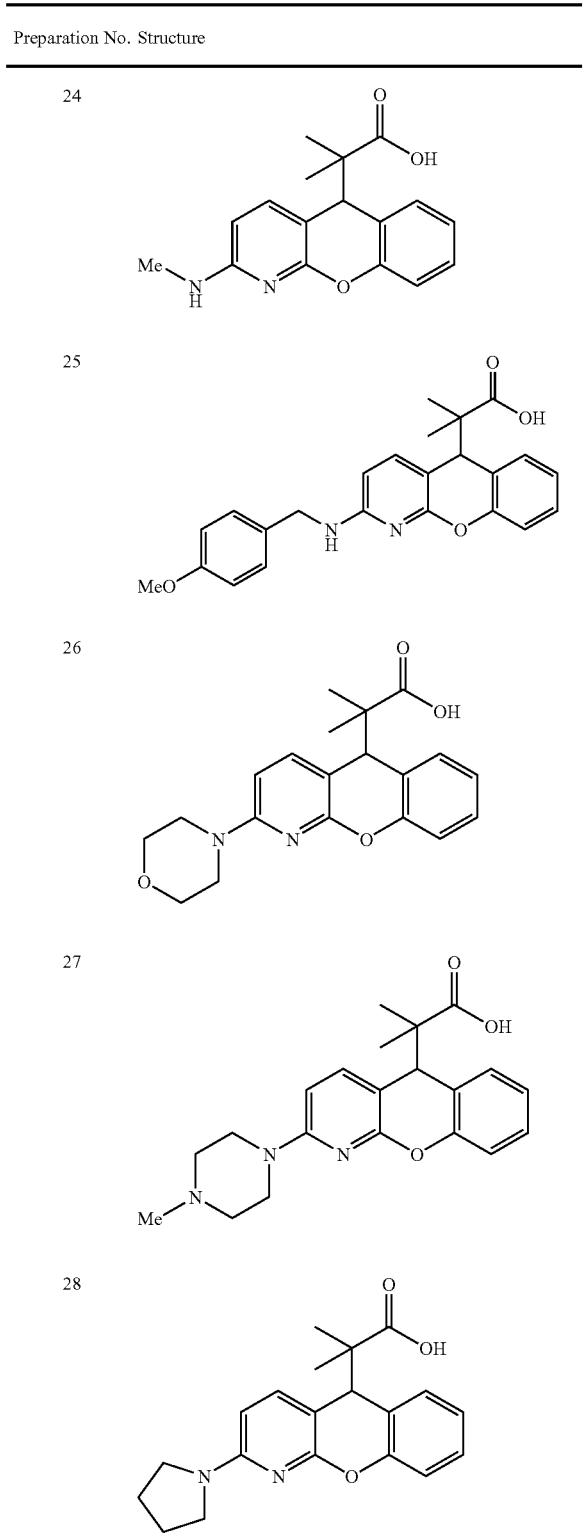

-continued

Preparation No. Structure

29

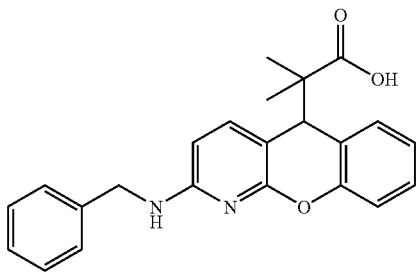

Preparation 30

The product of Preparation 17 (17e) was resolved into pure enantiomers by chiral supercritical fluid chromatography (SFC).

Preparative Conditions A:

| Column: | Chiralcel OJ 250 × 30 mm ID; 10 um |
|---|---|
| Temperature: | Ambient |
| Mobil Phase: | CO2/MeOH/TFA = 85:15:0.1 |
| Flow rate: | 65 mL/min |
| Injection volume: | 1.2 mL |
| UV Detection: | 220 nm |

Preparative Conditions B:

| Column: | Chiralpak AD-H (3 × 25 cm, 5 μm) |
|---|---|
| BPR Pressure: | 100 bars |
| Temperature: | 35° C. |
| Mobil Phase: | CO2/MeOH = 88:12 |
| Flow rate: | 150 mL/min |
| UV Detection: | 220 nm |
| Injection Program: | Stacked Injection (4.20 min/per cycle) |
| Injection Volume: | 2.20 mL |
| Sample Preparation: | 20,000 mg/450 mL MeOH = 46.7 mg/mL |

Analytical Conditions:

| Column: | Chiralpak OJ 250 × 4.6 mm ID; 10 um |
|---|---|
| Temperature: | Ambient |
| Mobil Phase: | Hex/IPA/TFA = 80:20:0.1 |
| Flow rate: | 1.0 mL/min |
| Injection volume: | 3~15 μl |
| UV Detection: | 290 nm |
| Retention Time (min): | $RT_1$: 5.349 RT2: 8.231 |

The first peak to elute under the preparative (SFC) conditions (Preparative Conditions A) described above also eluted first under the aforementioned analytical chiral LC conditions. A sample of the first-eluting material (30a) was co-crystallized with (R)-(+)-alpha-methylbenzylamine. An X-ray crystal structure determination of the crystalline material thus obtained proved 30a to be of the 'R' absolute stereochemistry. The second-eluting enantiomer (30b) of "Preparative Conditions A" was thus deduced to be of the 'S' absolute stereochemistry. The SFC separation conditions for 17e were further optimized as described above ("Preparative Conditions B"), in which case the 'S' enantiomer (30b) eluted first, while the 'R' enantiomer (30a) eluted second (confirmed by comparison of chromatographs of homochiral compounds obtained from both preparative methods (A and B) under the analytical conditions described above.

Preparations 31 to 34

The following compounds were prepared from 30a in the same manner described above for the preparation of the title compounds of Preparations 23 to 29.

| Preparation No. | Structure |
|---|---|
| 31 | 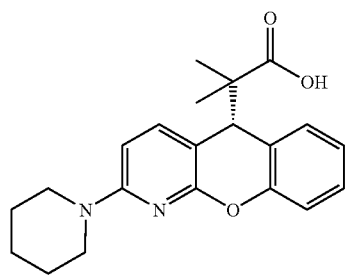 |
| 32 | 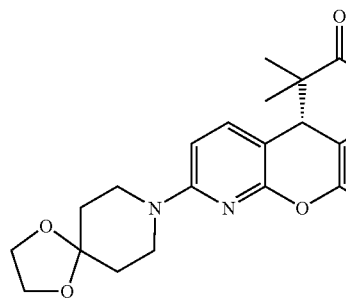 |
| 33 | 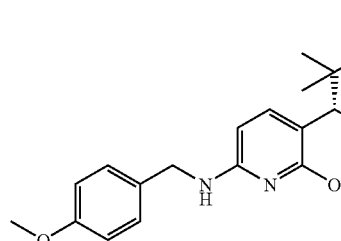 |
| 34 | 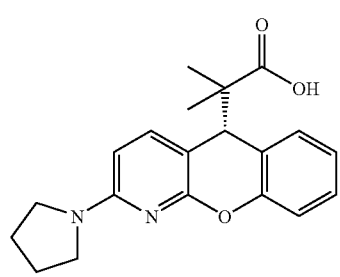 |

Preparations 35 to 47

The following compounds were prepared from 30b in the same manner described above for the preparation of the title compounds of Preparations 23 to 29.

| Preparation No. | Structure |
|---|---|
| 35 | 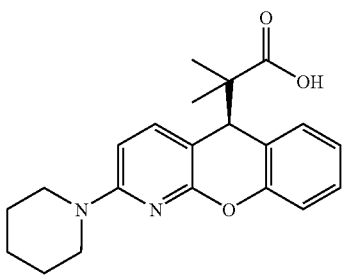 |
| 36 | 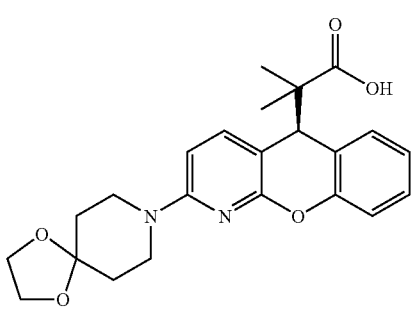 |
| 37 | 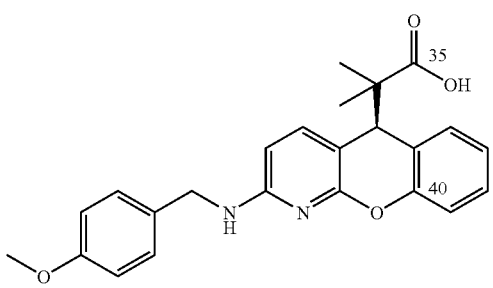 |
| 38 | 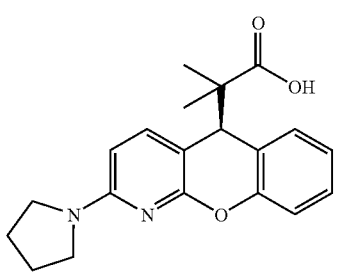 |
| 39 | 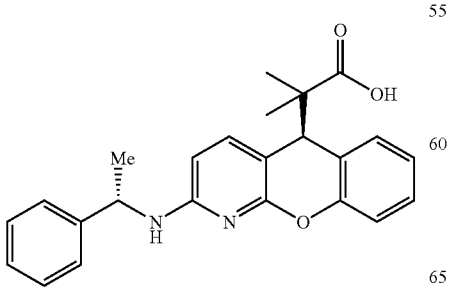 |
-continued
| Preparation No. | Structure |
|---|---|
| 40 | 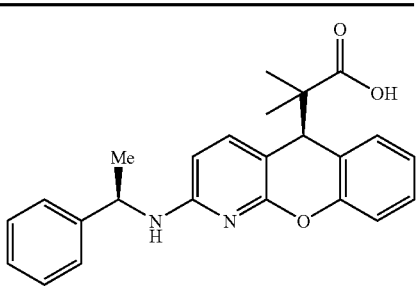 |
| 41 | 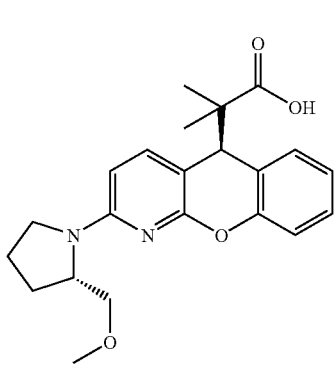 |
| 42 | 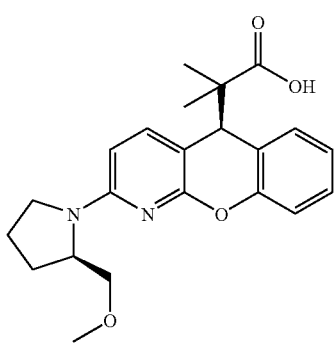 |
| 43 | 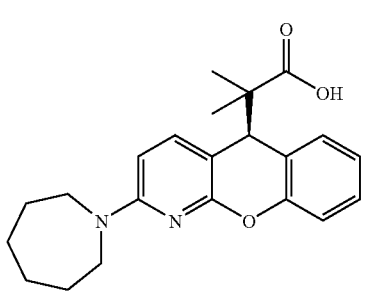 |

-continued

| Preparation No. | Structure |
|---|---|
| 44 | 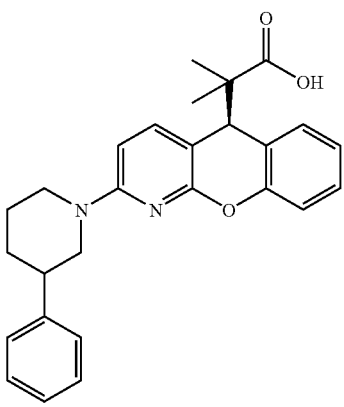 |
| 45 | 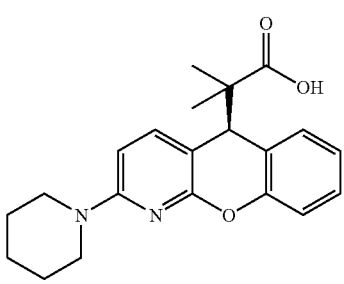 |
| 46 | 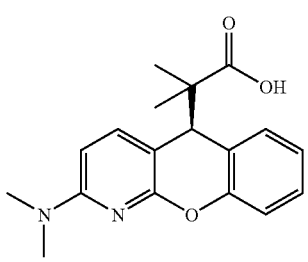 |
| 47 | 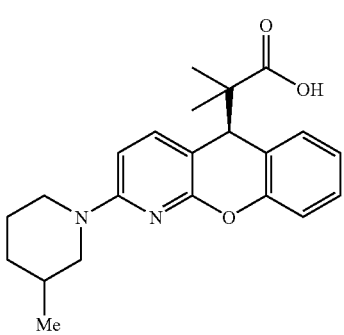 |

Preparation 48

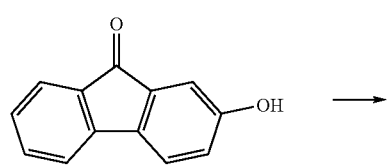

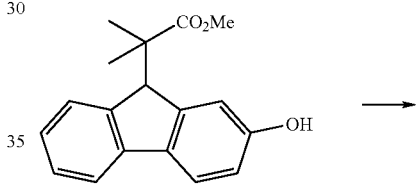

Step 1

To a rust-red colored suspension of 2-hydroxyfluorenone (303 mg, 1.54 mmol) in dichloromethane at 0° C. was added boron trifluoride etherate (0.392 mL, 3.09 mmol) dropwise, giving a brownish suspension. After 10 min at 0° C., 1-methoxy-2-methylprop-1-enyloxy)trimethylsilane (0.627 mL, 3.09 mmol) was added dropwise, giving a tan, clear solution. After 80 min at 0° C., trifluoroacetic acid (1.1 mL) was added, followed by triethylsilane (0.494 mL, 3.09 mmol). The reaction mixture was allowed to warm to room temperature and stirred overnight. Saturated aqueous sodium bicarbonate was added slowly to the reaction mixture with stirring. The organic layer was removed, dried over sodium sulfate, and concentrated to give 48a (452 mg, 99%) as a foam. The crude material was used directly in the next step with no further purification. MS (E+) m/z: 305 (M+Na); LC retention time: 3.55 min.

Step 2

The product (48b) was obtained in the manner described above for the preparation of 22b. MS (E+) m/z: 286 (M+H$_2$O); MS (E-) m/z: 267 (M-H); LC retention time: 3.32 min.

Preparations 49 to 51

The following compounds were prepared in the manner described for the preparation of the title compound of Preparation 10, replacing thioxanthen-9-one with either dibenzosuberone, 9-fluorenone, or 2-trifluoromethylxanthen-9-one.

| Preparation No. | Structure |
|---|---|
| 49 | 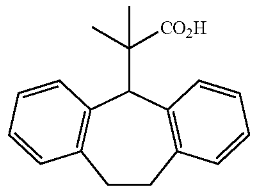 |
| 50 | 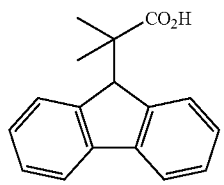 |
| 51 | 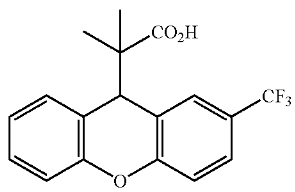 |

Preparation 52

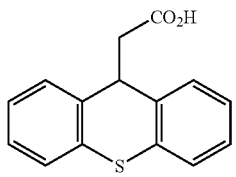

The title compound was prepared in the manner described above for the preparation of the title compound of Preparation 9, as described by Jones et al. (J. Am. Chem. Soc., 1948, 70, 2843).

Preparation 53

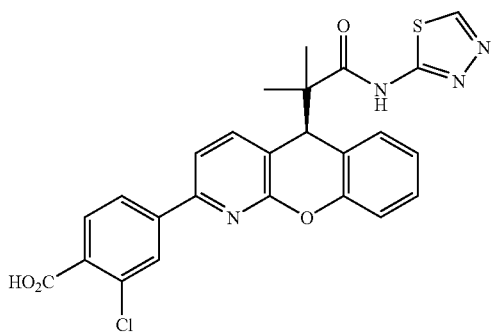

Step 1

To a soln. of (S)-2-(2-chloro-5H-chromeno[2,3-b]pyridin-5-yl)-2-methylpropanoic acid (30b, 10 g, 32.9 mmol) in acetonitrile (200 ml) was added triethylamine (22.94 ml, 165 mmol), O-(7-AZABENZOTRIAZOL-1-YL)-N,N,N',N'-TETRAMETHYLURONIUM PF6 (HATU) (16.27 g, 42.8 mmol) and 1,3,4-thiadiazol-2-amine (9.99 g, 99 mmol). The resulted mixture was heated at 80° C. for 12 h. The reaction mixture was then concentrated in vacuum and the residue was partitioned between EtOAc and 1N HCl. The obtained organic layer was washed with saturated NaHCO₃, brine, then dried (Na₂SO₄) and concentrated to give a solid. The solid was dissolved in EtOH (400 mL) with gentle warming. Added 1N HCl (~200 mL) portionwise. The solid was collected and washed with water, dried on vacuum pump overnight to give 10 g (79%) of (S)-2-(2-chloro-5H-chromeno[2,3-b]pyridin-5-yl)-2-methyl-N-(1,3,4-thiadiazol-2-yl)propanamide (53a). MS (E+) m/z: 387 (M+H); LC retention time: 3.12 min.

Step 2

To a soln. of (S)-2-(2-chloro-5H-chromeno[2,3-b]pyridin-5-yl)-2-methyl-N-(1,3,4-thiadiazol-2-yl)propanamide (53a) (1 g, 2.58 mmol) in DMF (40 mL) was added 4-borono-2-chlorobenzoic acid (1.036 g, 5.17 mmol) (crude from 68106-008) and Potassium Orthophosphate (5.17 mL, 10.34 mmol). Bubbled argon through for 10 min. and then palladium tetrakis-(triphenylphosphine) (0.209 g, 0.181 mmol) was added. Kept bubbling argon for another 5 min., The reaction vessel was sealed and heated to 90° C. for 4 h. Filtration, then washed with EtOAc. 1N HCl was added to pH ~2.0, and then extracted with EtOAc (3×). The combined organic layers were washed with base (1N NaOH, 3×), and then the base soln was acidified to Ph ~2.0, extracted with EtOAc (3×), dried (Na₂SO₄), concentrated.

Repurified by above same sequence, i.e. dissolved in EtOAc, washed with 1N NaOH, and then acidified to PH ~2.0, extracted with EtOAc, dried (Na₂SO₄), and concentrated. MS (E+) m/z: 507 (M+H); LC retention time: 3.51 min.

Preparation 54

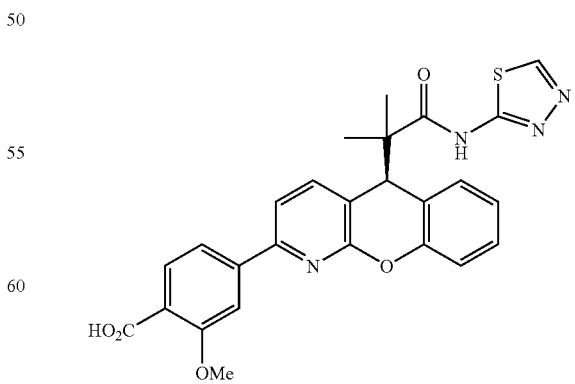

The title compound was prepared from the product of 53a in the same manner as described above for the preparation of the title compound of Preparation 53. MS (E+) m/z: 503.2 (M+H); LC retention time: 3.30 min.

Preparation 55

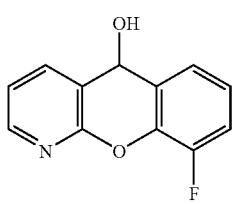

Step 1

The title compound (55a) was prepared from 9-fluoro-5H-chromeno[2,3-b]pyridine-5-one in the same manner as described above for the preparation of the title compound of Preparation 17a. 9-Fluoro-5H-chromeno[2,3-b]pyridine-5-one was prepared following the method of Villani et al. (J. Med. Chem. 1975, 18, 1-8), substituting phenol with 2-fluorophenol.

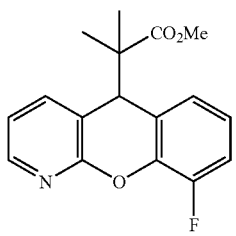

Step 2

The title compound (55b) was prepared from 55a in the same manner described above for the preparation of 17b from 17a. MS (E+) m/z: 302 (M+H); LC retention time: 2.96 min.

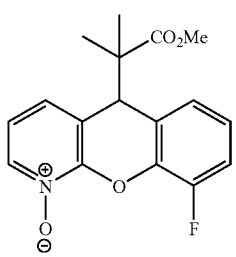

Step 3

The title compound (55c) was prepared from 55b in the same manner described above for the preparation of 17c from 17b. MS (E+) m/z: 318 (M+H); LC retention time: 2.13 min.

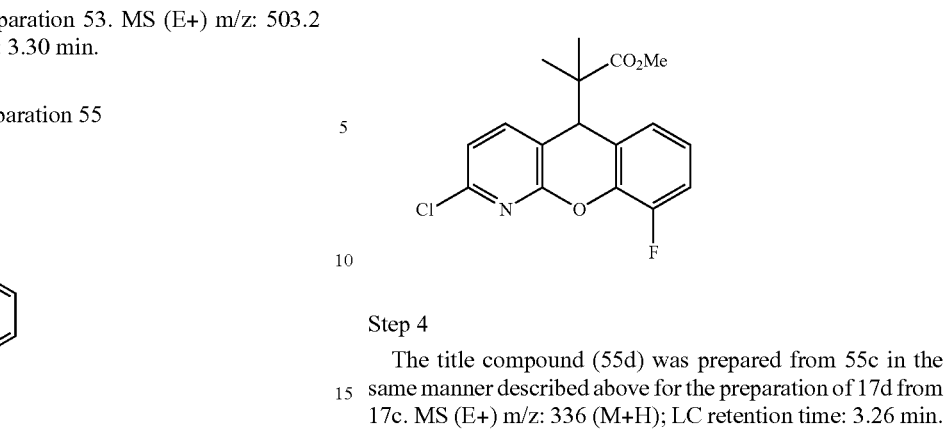

Step 4

The title compound (55d) was prepared from 55c in the same manner described above for the preparation of 17d from 17c. MS (E+) m/z: 336 (M+H); LC retention time: 3.26 min.

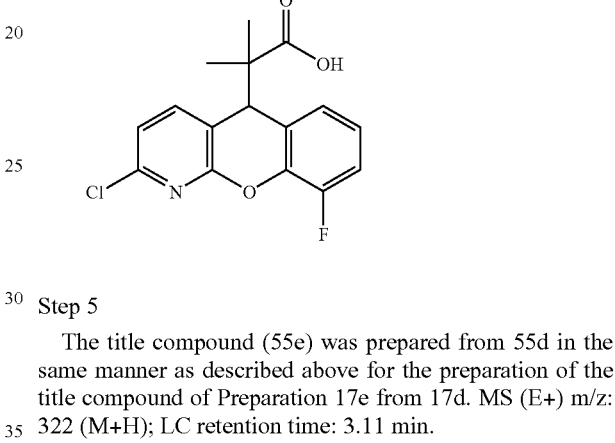

Step 5

The title compound (55e) was prepared from 55d in the same manner as described above for the preparation of the title compound of Preparation 17e from 17d. MS (E+) m/z: 322 (M+H); LC retention time: 3.11 min.

Preparation 56

The product of Preparation 55 (55e) was resolved into pure enantiomers (56a and 56b) by chiral supercritical fluid chromatography (SFC).

Preparative Conditions:

| | |
|---|---|
| Preparative Column: | Chiralcel OJ-H (3 × 25 cm, 5 μm) |
| BPR pressure: | 100 bars |
| Temperature: | 35° C. |
| Flow rate: | 70 mL/min |
| Mobile Phase: | $CO_2$/[IPA:ACN 1:1 w 0.1% TFA] (90/10) |
| Detector Wavelength: | 212 nm |
| Separation Program: | Sequence injection |
| Injection: | 0.25 mL/(100.0 mg/mL) with cycle time 7.5 minutes |
| Sample preparation: | 2 g/20 mL ACN/MeOH (1:1 v/v) |

Analytical Conditions:

| | |
|---|---|
| Analytical Column: | Chiralcel OJ-H (0.46 × 25 cm, 5 μm) |
| BPR pressure: | 100 bars |
| Temperature: | 35° C. |
| Flow rate: | 2.0 mL/min |
| Mobile Phase: | $CO_2$/[IPA:ACN 1:1 w 0.1% TFA] (90/10) |
| Detector Wavelength: | 212 nm |
| Retention Time (min): | $RT_1$: 7.43 RT2: 8.81 |

The first compound to elute under the preparative conditions (56a) also eluted with earlier retention time under the analytical conditions described above.

Preparation 57

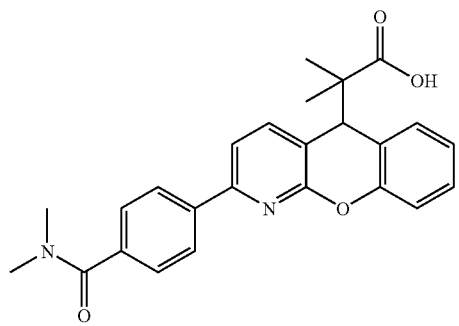

A DMF (50 mL) solution of 17e (10367, page 107, Preparation 17) (1.45 g, 4.77 mmol), 4-(N,N-dimethylaminocarbonyl)phenyl boronic acid (Combi-Blocks Inc., 1.35 g, 1.5 eq), Pd(Ph$_3$P)$_4$ (0.67 g, 0.12 eq) and a 2 M solution of K$_3$PO$_4$ (12 mL, 5 eq) was degassed by vacuum-N$_2$ refill cycle twice then heated at 100° C. under N$_2$ for 5 h. After cooling to room temperature, the crude material was poured into 1 N HCl and extracted with ethyl acetate. The ethyl acetate phase was washed with water and brine, dried over MgSO$_4$ and filtered. The filtrate was concentrated to give the expected product as a white needle crystal (1.59 g, 80% yield). MS (ES+) m/z: 417 (M+H); LC retention time: 3.79 min (Analytical HPLC Method D).

Preparation 58

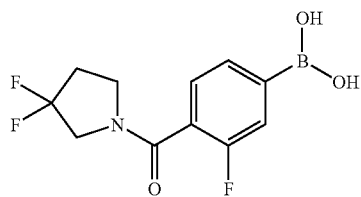

A DMF (6 mL) solution of 4-borono-2-fluorobenzoic acid (Combi-Bocks Inc., 1 g, 5.44 mmol), 3,3-difluoropyrrolidine hydrochloride salt (Matrix Scientific, 1 g, 1.3 eq), DIPEA (2.85 mL, 3 eq) and HATU (2.163 g, 1 eq) was stirred at room temperature for 1 h. The crude material was poured into 1 N HCl (16 mL) and extracted with ethyl acetate (40 mL). The aqueous phase was neutralized to pH 7 with solid NaOH then K$_2$CO$_3$, and extracted with ethyl acetate. The combined ethyl acetate extracts were dried over MgSO$_4$ and concentrated to give a thick brown oil. After addition of approximately equal volume of water, white needle crystals slowly precipitated out. The solid was collected by filtration and washed with small amount of ether to give the expected product (0.7811 g). The filtrate was purified by preparative reverse-phase HPLC (using Shimadzu 10A liquid chromatographs and Waters Sunfire S10 30×250 mm column) to give additional 0.5632 g of the expected product. Total yield was 1.3443 g (91%). MS (ES+) m/z: 274 (M+H); LC retention time: 2.68 min (Analytical HPLC Method D).

Preparations 59 to 63

Using procedure analogous to Preparation 58, the following intermediates were prepared by couplings between commercially available amines and boronic acids.

| Preparation No. | Structure |
|---|---|
| 59 | 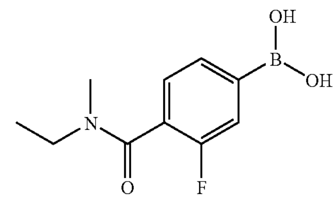 |
| 60 | 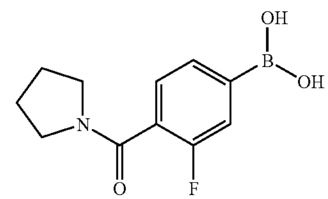 |
| 61 | 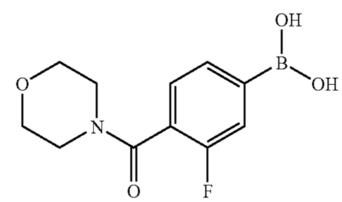 |
| 62 | 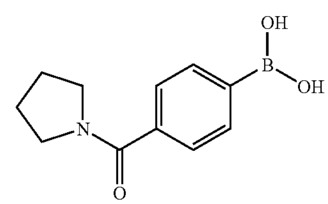 |
| 63 | 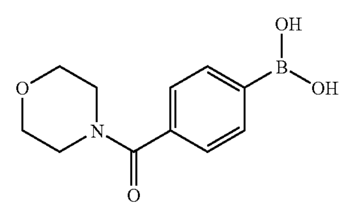 |

Preparation 64

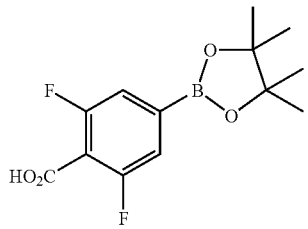

A dioxane (16.5 mL) solution of 4-bromo-2,6-difluorobenzoic acid (0.4 g, 1.6 mmol), 4,4,4',4',5,5,5',5'-octamethyl-2,2'-bi(1,3,2-dioxaborolane) (0.5 g, 2.0 mmol), PdCl$_2$(dppf) (0.12 g, 0.17 mmol) and potassium acetate (0.49 g, 4.9 mmol) was placed in a sealed vial and degassed by vacuum-N$_2$ refill cycle twice. The mixture was heated to 80° C. for 21 h, cooled to room temperature and filtered through a short bed of silica gel. The filtrate was concentrated and purified by flash column chromatography (ISCO 12 g silica gel cartridge, 20-100% ethyl acetate-hexanes) to give the expected product as a brown oil (0.11 g, 19%). MS (ES−) m/z: 283 (M−H); LC retention time: 1.48 min (Analytical HPLC Method D).

Preparations 65 to 73

Following procedure analogous to Preparation 57, the following intermediates were prepared by Suzuki couplings between boronic acids (commercially available or prepared in preparations 58-63 and 30b.

| Preparation No. | Structure |
|---|---|
| 65 | 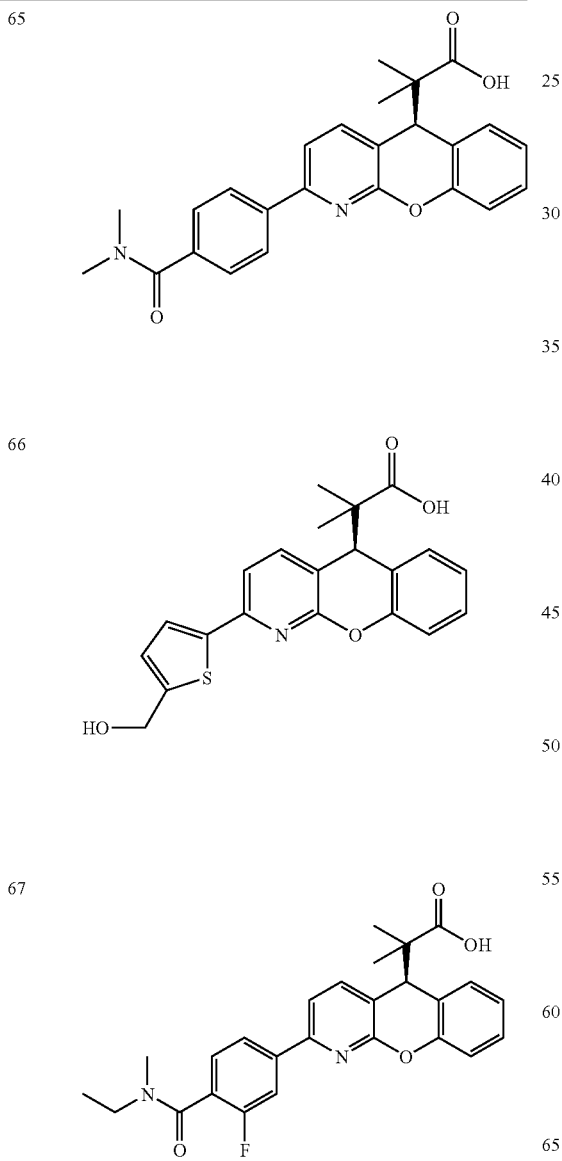 |
| 66 | 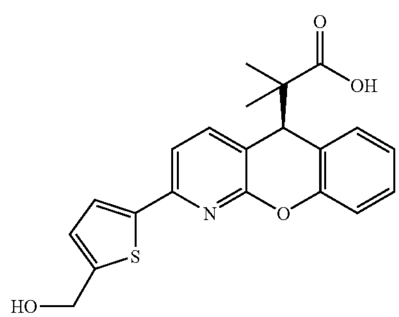 |
| 67 | 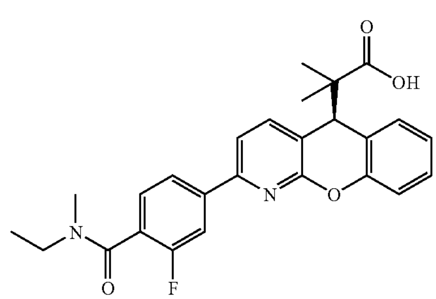 |

| Preparation No. | Structure |
|---|---|
| 68 | 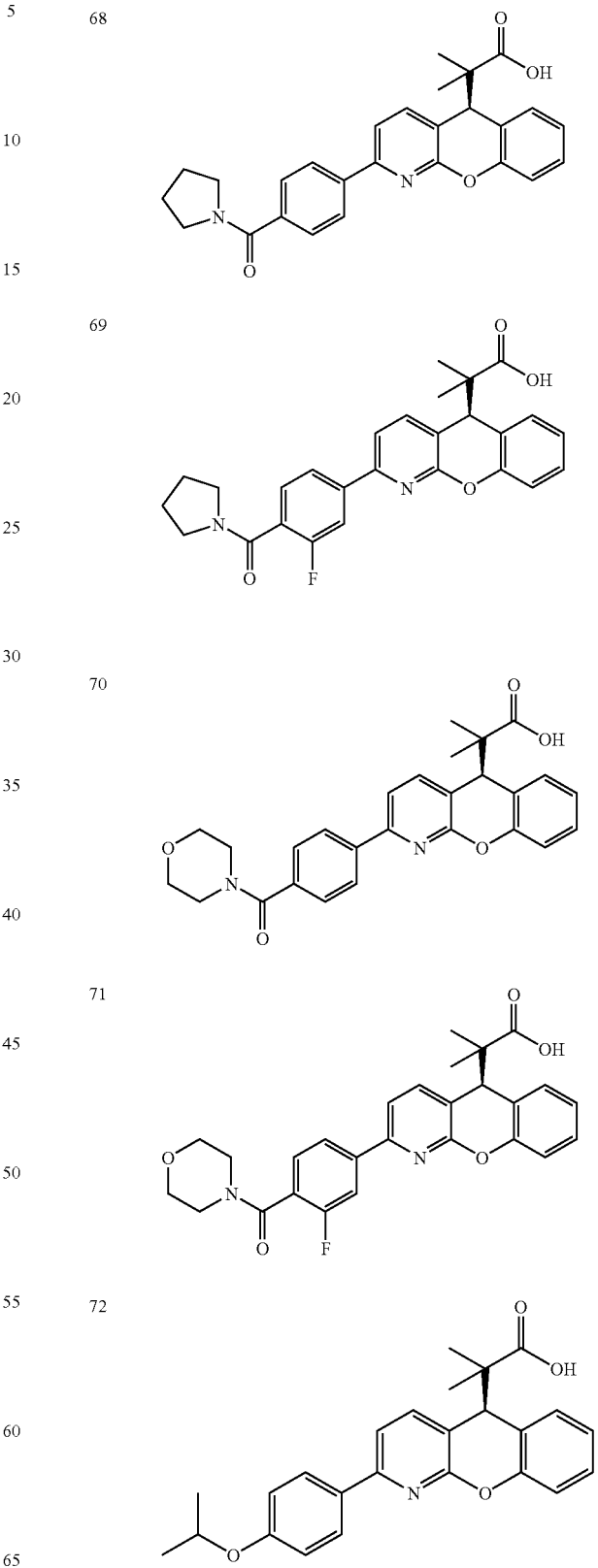 |
| 69 | 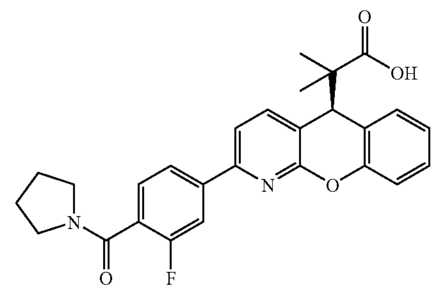 |
| 70 | 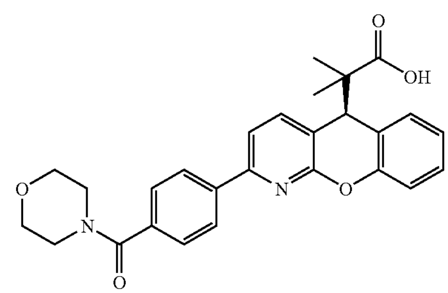 |
| 71 | 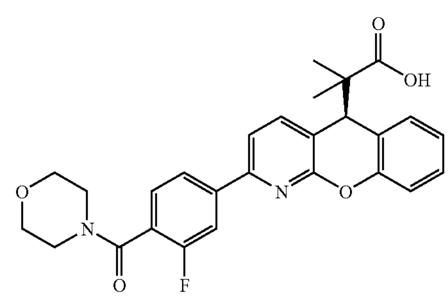 |
| 72 | 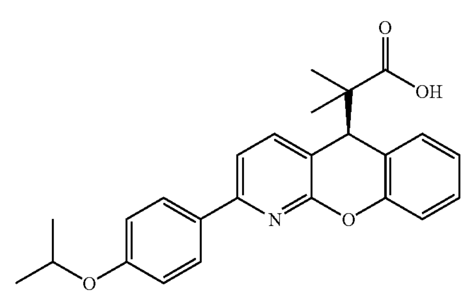 |

| Preparation No. | Structure |
|---|---|
| 73 | 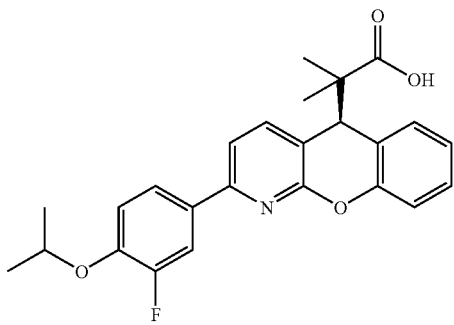 |

Preparations 74 to 76

Following procedures analagous to the product of the first step of Preparation 53 (53a), the following intermediates were prepared by reaction between commercially available amino azoles and the 'S' enantiomer of Preparation (30b).

| Preparation No. | Structure |
|---|---|
| 74 | 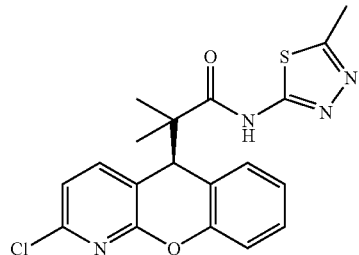 |
| 75 | 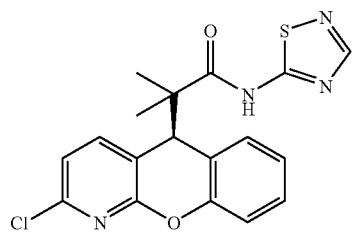 |
| 76 | 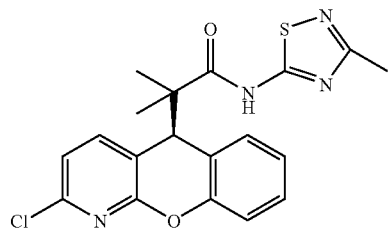 |

Preparations 77 to 81

Following procedure analogous to Preparation 57, the following intermediates were prepared by Suzuki couplings between boronic acids (commercially available or prepared in Preparations 58 to 64) and intermediates from Preparations 53a, 58 to 64.

| Preparation No. | Structure |
|---|---|
| 77 | 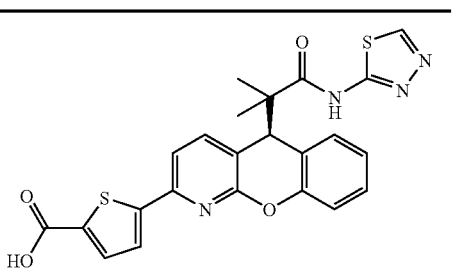 |
| 78 | 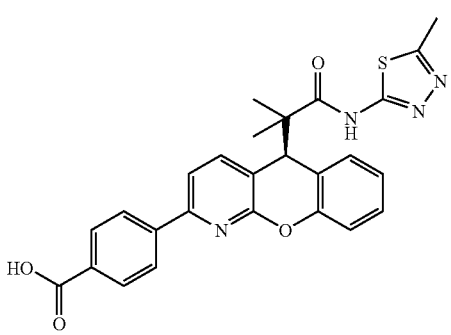 |
| 79 | 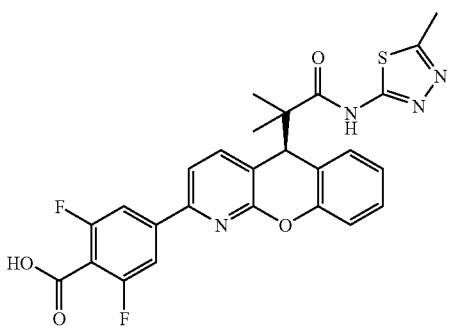 |
| 80 | 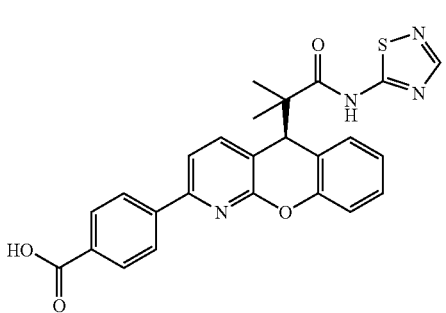 |
| 81 | 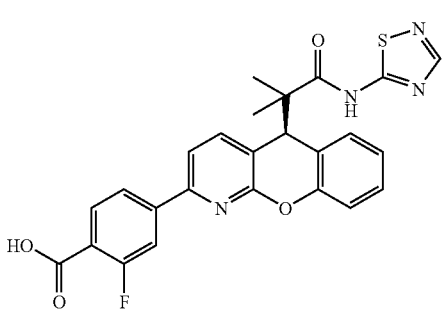 |

Preparation 82

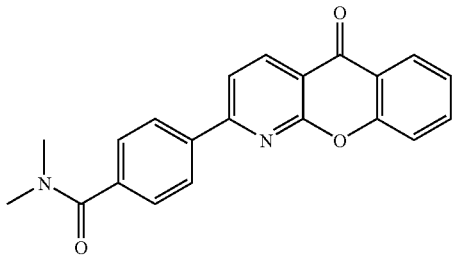

Step 1

A mixture of 4-acetylbenzoic acid (10.0 g, 60.9 mmol), 40% aqueous solution of dimethylamine (8.24 g, 73.1 mmol), EDC (14.0 g, 73.1 mmol), HOBT (11.2 g, 73.1 mmol) and DIEA (21.3 mL, 122 mmol) in CH₃CN (150 mL) was stirred at room temperature for 15 h and concentrated. The residue was dissolved in ethyl acetate (600 mL), washed with water (2×80 mL), brine (80 mL), dried (MgSO₄) and concentrated to provide 4-acetyl-N,N-dimethylbenzamide (9.80 g, 84%). MS (E+) m/z: 191 (M+H); HPLC retention time: 0.88 min (Analytical HPLC Method F).

Step 2

A mixture of 4-acetyl-N,N-dimethylbenzamide (9.80 g, 51.2 mmol) and DMF dimethyl acetal (60 mL) was heated to reflux for 15 h, cooled to room temperature and concentrated. The residue was recrystallized from ethyl acetate to give (E)-4-(3-(dimethylamino)acryloyl)-N,N-dimethylbenzamide as a brown solid (8.80 g, 70%). MS (E+) m/z: 247 (M+H).

Step 3

A mixture of (E)-4-(3-(dimethylamino)acryloyl)-N,N-dimethylbenzamide (4.0 g, 16.3 mmol), 3-(2-fluorophenyl)-3-oxopropanenitrile (3.44 g, 21.1 mmol) and acetic acid (4.65 mL, 81.0 mmol) in DMF (40 mL) was heated to 120° C. After 48 h at 120° C., the mixture was cooled to room temperature, diluted with ethyl acetate (600 mL), washed with saturated NaHCO₃ (80 mL), water (80 mL) and brine (80 mL), dried (MgSO₄) and concentrated. The residue was treated with MeOH and filtered to provide the expected product as brown solid (2.70 g, 48%). MS (E+) m/z: 345 (M+H); HPLC retention time: 1.67 min (Analytical HPLC Method F).

Preparation 83

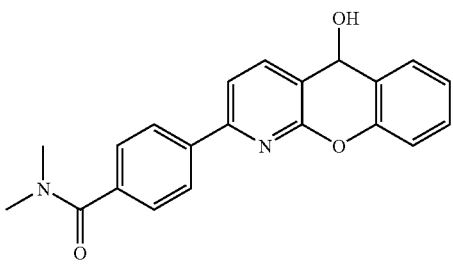

Sodium borohydride (1.48 g, 39.2 mmol) was added to a solution of the product from Preparation 82 (2.70 g, 7.84 mmol) in MeOH (160 mL) and dichloromethane (40 mL) at 0° C. After 2 h at this temperature, the mixture was quenched with saturated NaHCO₃ (40 mL). The organic solvents were evaporated in vacuo. The aqueous residue was extracted with dichloromethane (3×100 mL). The combined organic extracts were washed with water (30 mL), brine (30 mL), dried (MgSO₄) and concentrated to provide the expected product (1.80 g, 66%). MS (ES+) m/z: 347 (M+H).

Preparation 84

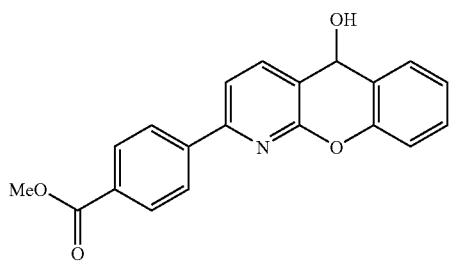

Following procedure of Steps 2 and 3 of Preparation 82, and Preparation 83, the title compound was prepared from methyl 4-acetylbenzoate. MS (ES+) m/z: 334 (M+H).

Example 1

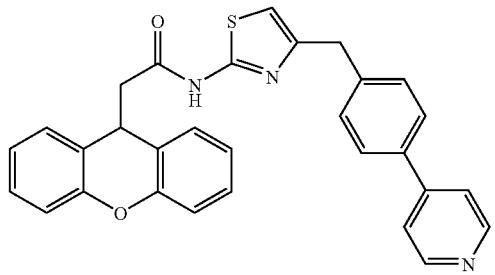

To a solution of the product of Preparation 9 (34 mg, 0.14 mmol) in DMF (1.2 mL) was sequentially added triethylamine (0.049 mL, 0.35 mmol), HOAt (23 mg, 0.17 mmol), EDC (33 mg, 0.17 mmol), and the product of Preparation 4 (42 mg, 0.16 mmol). The resulting mixture was heated at 85° C. for 16 h, filtered through a 0.45 micron syringe-tip filter, and purified by preparative HPLC. The product (30 mg, Y=35%) was obtained as a white solid, TFA salt. MS (E+) m/z: 490 (M+H); LC retention time: 3.24 min.

Examples 2 to 4

The following Examples 2 to 4 were prepared in the same manner as described for the preparation of the title compound of Example 1 using amines of Preparations 1 to 3.

| Example No. | Structure | Rt (min) | M/z (MH)+ |
|---|---|---|---|
| 2 | 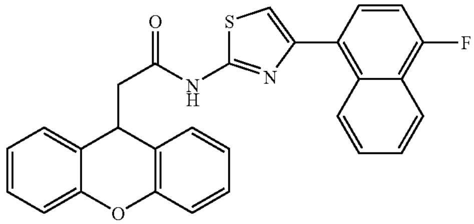 | 3.872 | 467 |
| 3 | 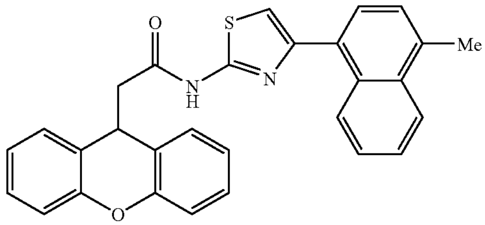 | 3.395 | 463 |
| 4 | 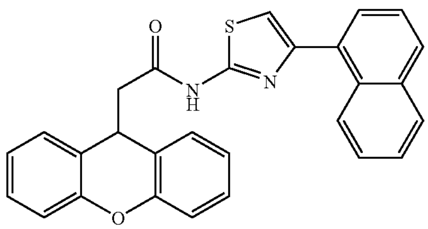 | 3.785 | 449.00 |

Examples 5 to 9

The following Examples 5 to 9 were prepared in the same manner as described for the preparation of the title compound of Example 1 using the carboxylic acid product of Preparation 10 and amines of Preparations 1 to 4 and 2-aminothiazole.

| Example No. | Structure | Rt (min) | M/z (MH)+ |
|---|---|---|---|
| 5 | 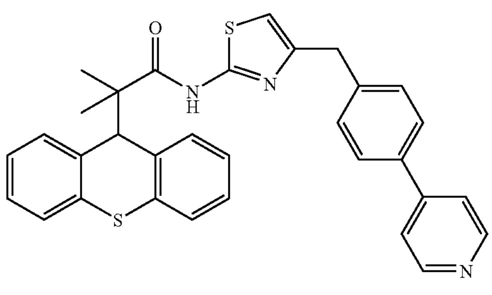 | 3.48 | 534 |
| 6 | 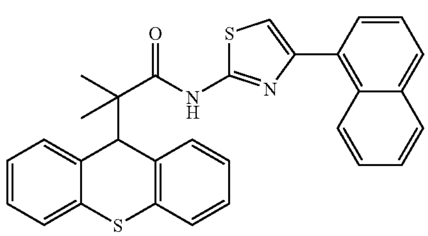 | 3.25 | 493 |

| Example No. | Structure | Rt (min) | M/z (MH)+ |
|---|---|---|---|
| 7 | 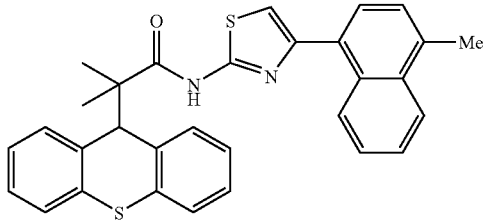 | 3.88 | 507 |
| 8 | 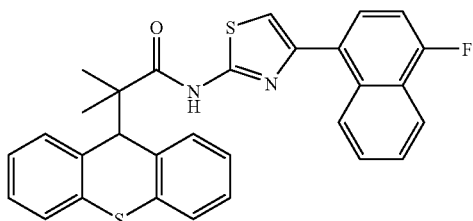 | 3.37 | 511 |
| 9 | 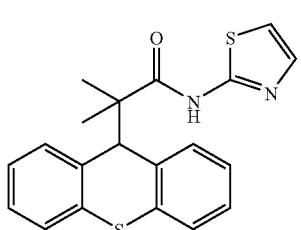 | 3.87 | 365 |

Example 10

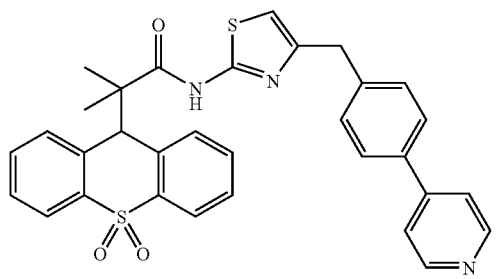

To a solution of the product of Preparation 11 (90 mg, 0.29 mmol) in acetonitrile (4 mL) were added HOAt (46 mg, 0.34 mmol) and EDC (66 mg, 0.34 mmol). The resulting solution was stirred at room temperature for 1 h, then treated with triethylamine (0.1 mL) and the product of Preparation 4 (84 mg, 0.31 mmol) and heated in a sealed pressure vessel at 140° C. for 1.5 h. The solution was then concentrated and purified by HPLC. The product thus obtained was lyophilized from water/acetonitrile to give the title compound (45 mg) as a white solid TFA salt. MS (E+) m/z: 566 (M+H); LC retention time: 2.89 min.

Examples 11 to 14

The following Examples 11 to 14 were prepared in the same manner as described for the preparation of the title compound of Example 10 using amines of Preparations 1 to 3 or 2-aminothiazole.

| Example No. | Structure | Rt (min) | M/z (MH)+ |
|---|---|---|---|
| 11 | 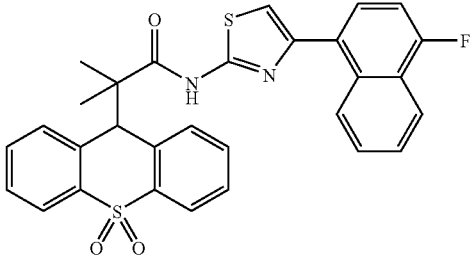 | 3.592 | 543 |

-continued

| Example No. | Structure | Rt (min) | M/z (MH)+ |
|---|---|---|---|
| 12 | 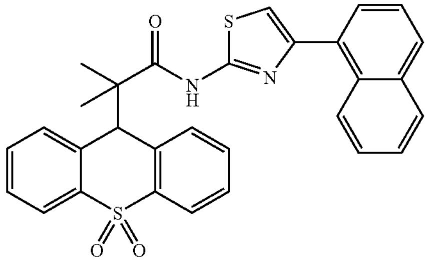 | 3.512 | 525 |
| 13 | 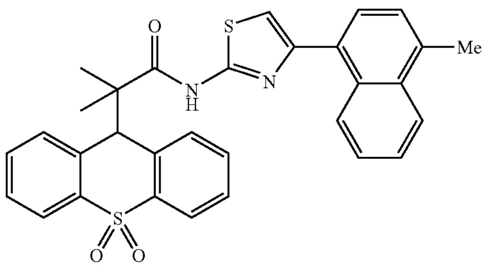 | 3.68 | 539 |
| 14 | 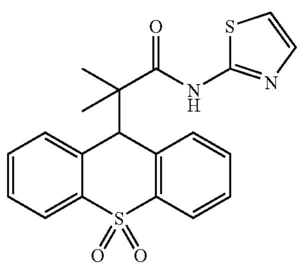 | 3.04 | 399 |

Examples 15 to 17

The following Examples 15 to 17 were prepared in the same manner as described for the preparation of the title compound of Example 10 using the product of Preparation 12 and amines of Preparations 1 to 3.

| Example No. | Structure | Rt (min) | M/z (MH)+ |
|---|---|---|---|
| 15 | 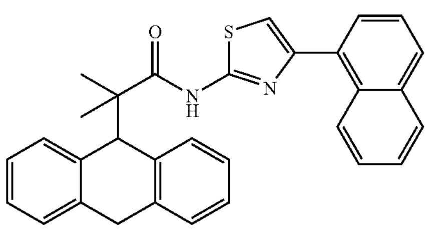 | 3.18 | 475 |
| 16 | 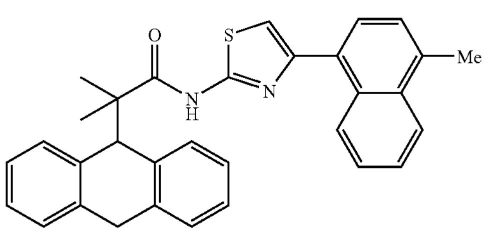 | 3.42 | 489 |

-continued
| Example No. | Structure | Rt (min) | M/z (MH)+ |
|---|---|---|---|
| 17 | 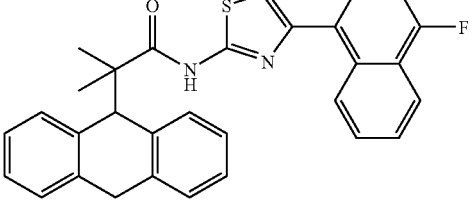 | 3.31 | 493 |
Examples 18 to 21
The following Examples 18 to 21 were prepared in the same manner as described for the preparation of the title compound of Example 18 using the product of Preparation 50 amines of Preparations 1 to 3 or 2-aminothiazole.
| Example No. | Structure | Rt (min) | M/z (MH)+ |
|---|---|---|---|
| 18 | 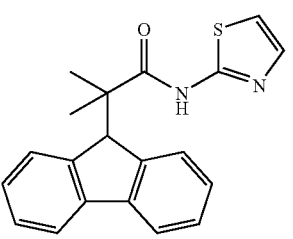 | 4.11 | 335 |
| 19 | 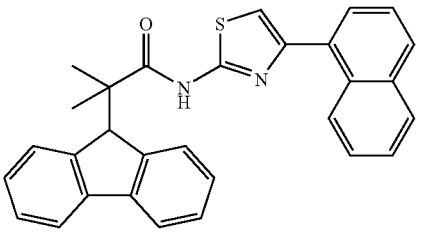 | 3.18 | 461 |
| 20 | 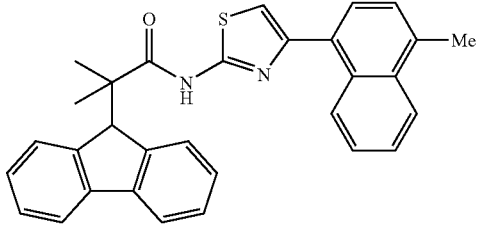 | 3.41 | 475 |
| 21 | 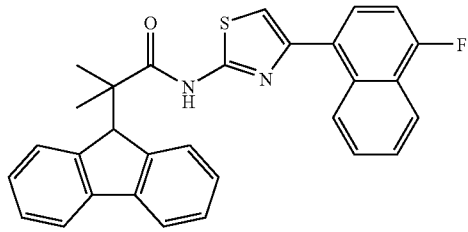 | 3.30 | 479 |

Example 22

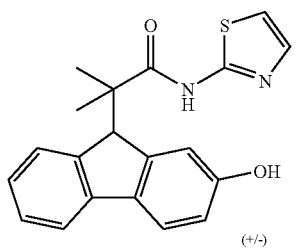

(+/-)

The title compound was prepared in the manner described for the preparation of the title compound of Example 10, using the product of Preparation 48b. MS (E+) m/z: 351 (M+H); LC retention time: 3.33 min.

Examples 23 to 25

The following Examples 23 to 25 were prepared in the same manner as described for the preparation of the title compound of Example 10 using the product of Preparation 49 and either the amine of Preparations 2 or 4, or 2-aminothiazole.

| Example No. | Structure | Rt (min) | M/z (MH)+ |
|---|---|---|---|
| 23 | 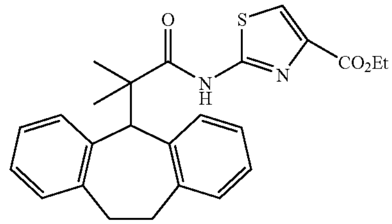 | 4.213 | 435.16 |
| 24 | 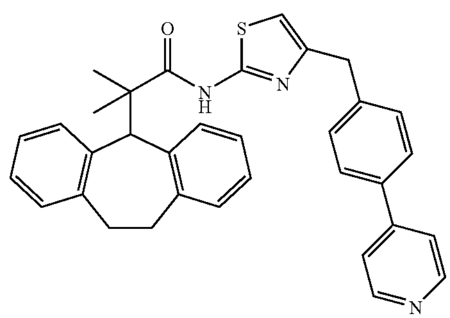 | 3.527 | 530.16 |
| 25 | 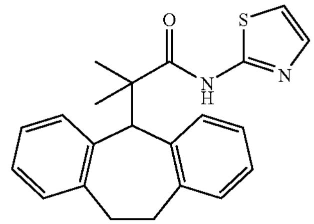 | 3.937 | 363.25 |

Examples 26 to 28

The following Examples 26 to 28 were prepared in the same manner as described for the preparation of the title compound of Example 10 using the product of Preparation 52 and amines of Preparations 1 to 3.

| Example No. | Structure | Rt (min) | M/z (MH)+ |
|---|---|---|---|
| 26 | 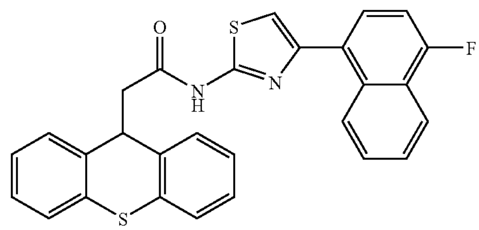 | 3.885 | 483 |
| 27 | 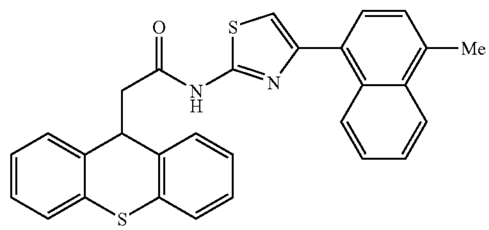 | 3.945 | 479 |
| 28 | 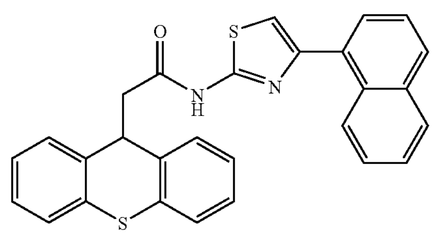 | 3.822 | 465 |

Examples 29 to 40

The following Examples 29 to 40 were prepared in the same manner as described for the preparation of the title compound of Example 10 using the carboxylic acids of Preparation 13 or Preparation 51 and either commercially available amines or amines of Preparations 1 to 7, 4b, or 14.

| Example No. | Structure | Rt (min) | M/z (MH)+ |
|---|---|---|---|
| 29 | 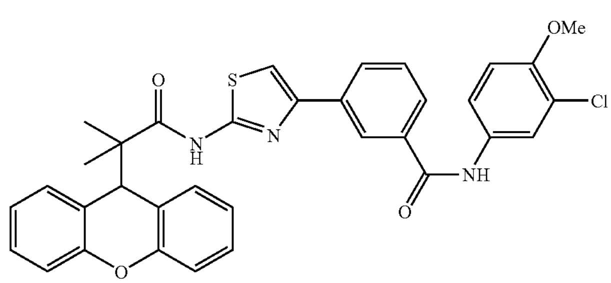 | 3.825 | 610.06 |

-continued

| Example No. | Structure | Rt (min) | M/z (MH)+ |
|---|---|---|---|
| 30 | 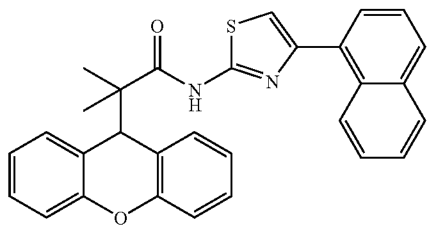 | 3.13 | 477 |
| 31 | 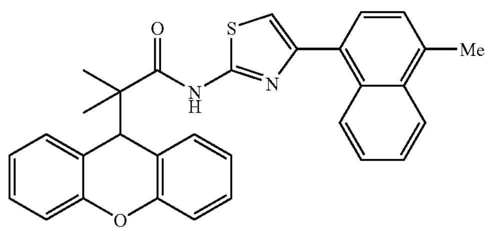 | 3.39 | 491 |
| 32 | 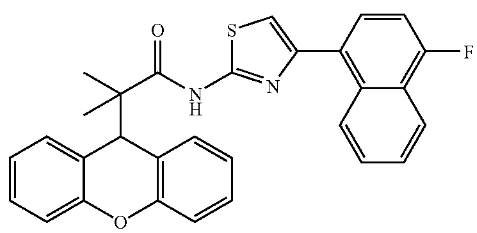 | 3.28 | 495 |
| 33 | 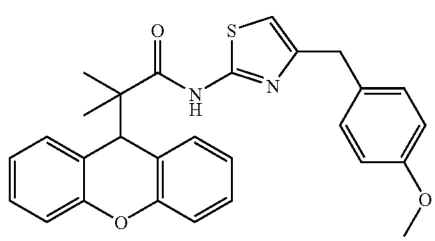 | 4.22 | 471 |
| 34 | 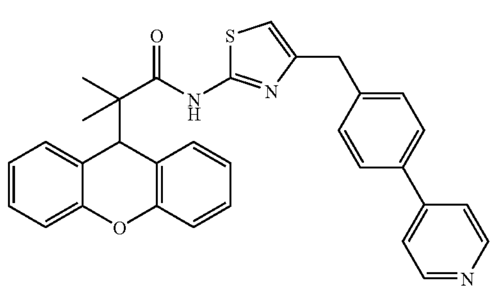 | 3.37 | 518 |
| 35 | 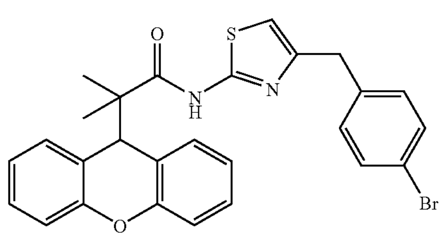 | 5.34 | 521 |

-continued
| Example No. | Structure | Rt (min) | M/z (MH)+ |
|---|---|---|---|
| 36 | 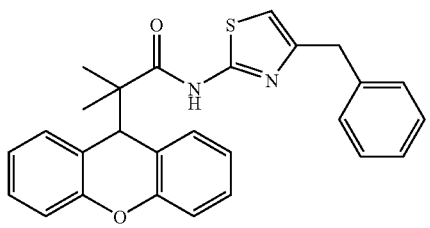 | 4.44 | 441 |
| 37 | 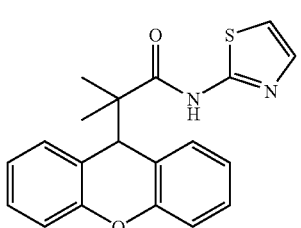 | 4.14 | 351 |
| 38 | 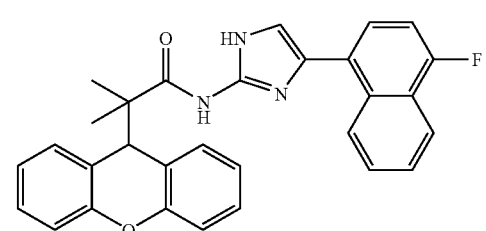 | 3.87 | 478 |
| 39 | 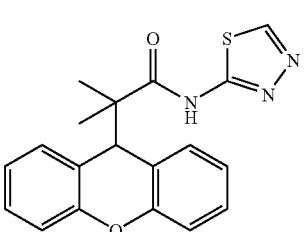 | 3.53 | * |
| 40 | 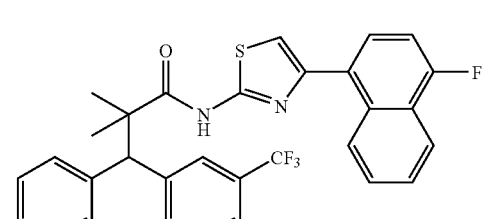 | 4.65 | 563 |
* observed m/e 350 (negative ion electrospray)

Example 41

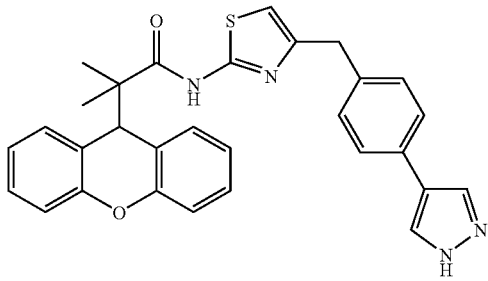

The title compound of Example 35 (25 mg, 0.048 mmol) and 4,4,5,5-tetramethyl-2-[1H-pyrazol-4-yl]-1,3,2-dioxaborolane (19 mg, 0.098 mmol) were dissolved in DMF (2 mL) in a microwave reaction vessel. Aqueous potassium phosphate (2.0M, 0.1 mL) was added and the mixture was purged with nitrogen gas for 5 min. Tetrakis (triphenylphosphine) palladium (21 mg, 0.018 mmol) was then added to the mixture which was heated in a Smith microwave reactor at 150° C. for 30 min. The reaction mixture was then filtered over Celite, washing with ethyl acetate. The filtrate was partitioned between ethyl acetate and water, and the organic layer removed, dried over sodium sulfate, and concentrated. Purification of the crude material by preparative HPLC provided the title compound (18 mg, 75% yield). MS (E+) m/z: 507 (M+H); LC retention time: 4.66 min.

Examples 42 to 43

The following Examples 42 and 43 were prepared in the same manner as the title compound of Example 41 using commercially available boronates or boronic acids.

| Example No. | Structure | Rt (min) | M/z (MH)+ |
|---|---|---|---|
| 42 | ![structure] | 4.80 | 521 |
| 43 | ![structure] | 4.68 | 536 |

Example 44

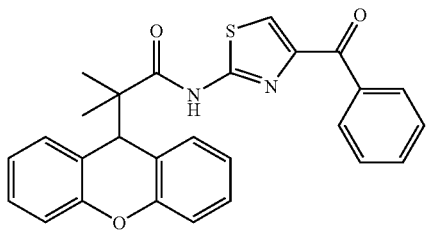

(a) To a solution of commercially available 1-phenyl-1,2-propanedione (3.3 g, 27.3 mmol) in 30 mL of was added a solution of bromine (34.7 g, 217 mmol) in 5 mL of CHCl₃ dropwise. The reaction was heated at reflux for 12 hr. The reaction was diluted with water and extracted 2×CHCl₃. The CHCl₃ extracts were dried over MgSO₄, filtered, and concentrated by rotary evaporator to give 5.0 g (100%) of a dark solid 45a. $^1$H-NMR (400 MHz, CDCl₃): δ 8.03 (d, 2H), 7.68 (t, 1H), 7.53 (dd, 2H), 4.4 (s, 2H).

(b) To a solution of 45a (1.5 g, 6.6 mmol) in 25 mL of EtOH was added thiourea (0.55 g, 7.2 mmol) all at once. The reaction was heated at reflux for 4 hr. The reaction was diluted with water and extracted 2×EtOAC. The EtOAc extracts were dried over MgSO₄, filtered, and concentrated by rotary evaporator to give 1.28 g (89%) of 46b. MS found: (M+H)+=205.

(c) The title compound was prepared in the same manner as described for the preparation of the title compound of Example 10 using the carboxylic acid of Preparation 12 and the amine of 45b. MS (E+) m/z: 455 (M+H); LC retention time: 4.79 min.

Examples 45 to 52

The following Examples 45 to 52 were prepared in the same manner as described for the preparation of the title compound of Example 10 using the carboxylic acid of Preparation 15 and either commercially available amines or amines of Preparations 1 to 4, 7, 8, or 4b.

| Example No. | Structure | Rt (min) | M/z (MH)+ |
|---|---|---|---|
| 45 | (structure, +/-) | 4.57 | 525 |
| 46 | (structure, +/-) | 4.70 | 521 |
| 47 | (structure, +/-) | 4.25 | 472 |
| 48 | (structure, +/-) | 4.02 | 453 |

-continued

| Example No. | Structure | Rt (min) | M/z (MH)+ |
|---|---|---|---|
| 49 | (+/-) | 4.22 | 501 |
| 50 | (+/-) | 4.59 | 549, 551 |
| 51 | (+/-) | 3.60 | 548 |
| 52 | (+/-) | 4.43 | 507 |

Examples 53 to 56

The following Examples 53 to 56 were prepared from the R-enantiomer carboxylic acid of Preparation 16 and 2-amino thiazole or amines of Preparations 8, 4, and 5 in the same manner as described for the preparation of the title compounds of Examples 45 to 52.

| Example No. | Structure | Rt (min) | M/z (MH)+ |
|---|---|---|---|
| 53 | 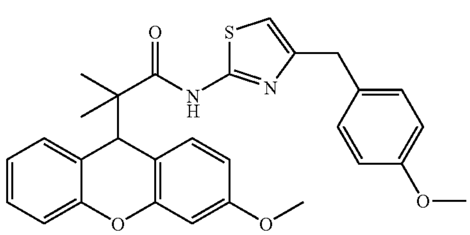 | 4.23 | 501 |

-continued

| Example No. | Structure | Rt (min) | M/z (MH)⁺ |
|---|---|---|---|
| 54 | 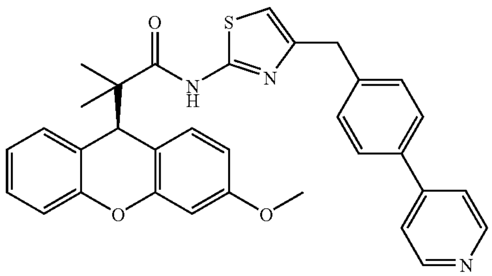 | 3.60 | 548 |
| 55 | 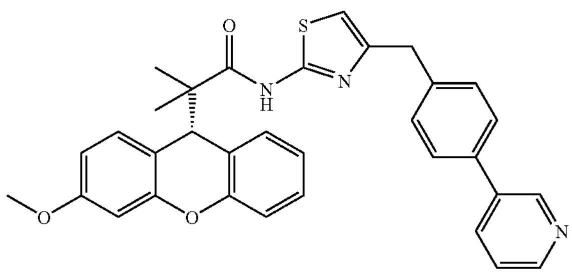 | 3.83 | 548.3 |
| 56 | 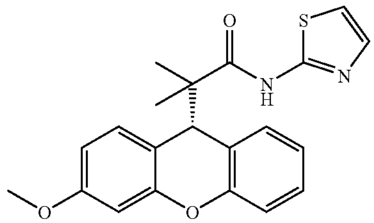 | 3.82 | 381 |

Examples 57 to 62

The following Examples 57 to 62 were prepared from the S-enantiomer carboxylic acid of Preparation 16 and amines of Preparations 4, 5, and 8 or commercially available amines in the same manner as described for the preparation of the title compounds of Examples 45 to 52.

| Example No. | Structure | Rt (min) | M/z (MH)⁺ |
|---|---|---|---|
| 57 | 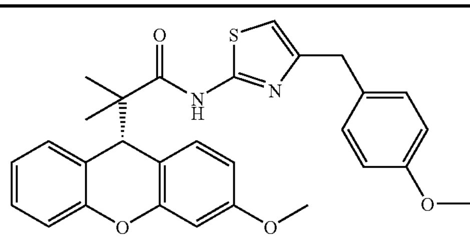 | 4.23 | 501 |
| 58 | 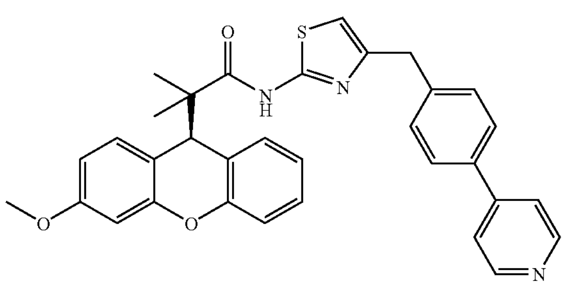 | 3.59 | 548 |

| Example No. | Structure | Rt (min) | M/z (MH)+ |
|---|---|---|---|
| 59 | 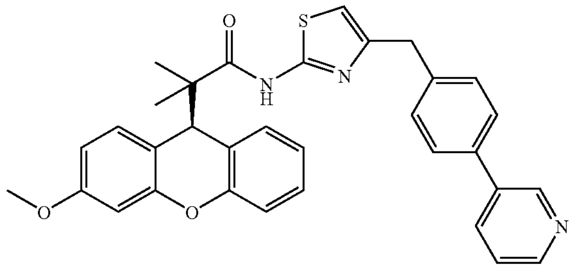 | 3.83 | 548 |
| 60 | 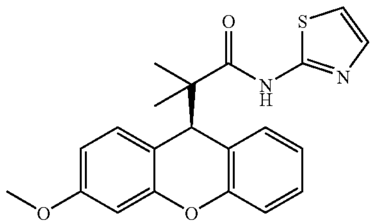 | 3.81 | 381 |
| 61 | 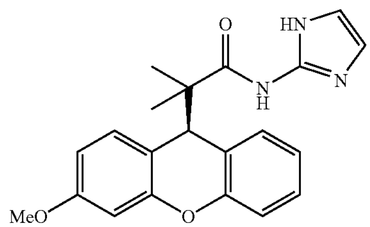 | 2.79 | 364 |
| 62 | 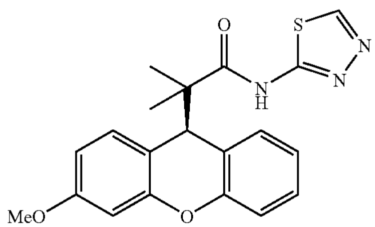 | 3.58 | 382 |

Example 63

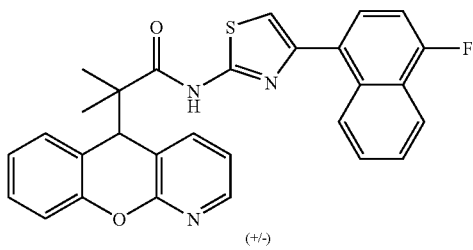

(+/-)

Step 1

To a solution of the product of Preparation 17b (1.0 g, 3.72 mmol) in methanol (30 mL) and THF (15 mL) was added a 4N aqueous solution of potassium hydroxide (9.3 mL). The resulting mixture was heated at 80° C. for 16 h, then acidified to about pH 2.0 with the dropwise addition of concentrated HCl. The mixture was extracted with ethyl acetate. The organic layer removed, dried over sodium sulfate, then concentrated to give the carboxylic acid 65a as a solid (990 mg, 99%). MS (E+) m/z: 270 (M+H); LC retention time: 2.84 min.

Step 2

A mixture of the product of Step 1 (20 mg, 0.052 mmol), triethylamine (0.022 mL, 0.16 mmol), HOBT hydrate (8.4 mg, 0.062 mmol) and EDC (12.0 mg, 0.062 mmol) in acetonitrile (0.6 mL) was heated for 4 h at 80° C. Purification by preparative HPLC provided the product, which was lypholized to give a colorless solid. MS (E+) m/z: 496 (M+H); LC retention time: 4.17 min.

Examples 64 to 71

The following Examples 64 to 71 were prepared either in the manner described above for the preparation of the title compound of Example 63 or in the manner described for the preparation of the title compounds of Examples 45 to 52 using the carboxylic acid of Example 63, Step 1, and either commercially available amines or amines prepared as described in the Preparations section.

| Example No. | Structure | Rt (min) | M/z (MH)+ |
|---|---|---|---|
| 64 | 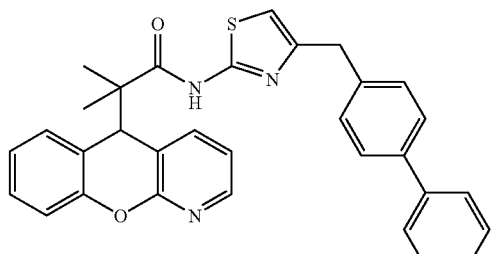 (+/-) | 2.99 | 519 |
| 65 | 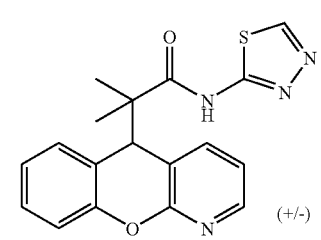 (+/-) | 2.81 | 353 |
| 66 | 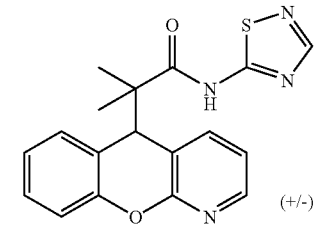 (+/-) | 3.07 | 353 |
| 67 | 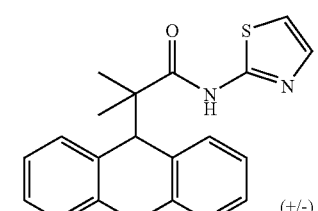 (+/-) | 3.11 | 352 |
| 68 | 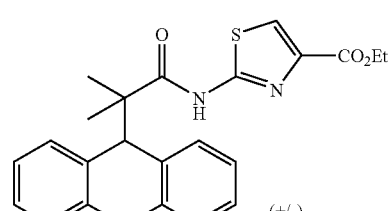 (+/-) | 3.50 | 424 |
| 69 | 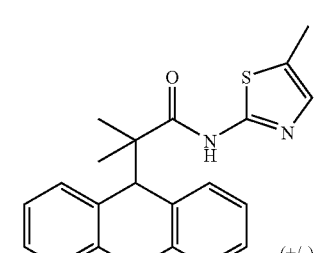 (+/-) | 3.30 | 366 |

| Example No. | Structure | Rt (min) | M/z (MH)+ |
|---|---|---|---|
| 70 | 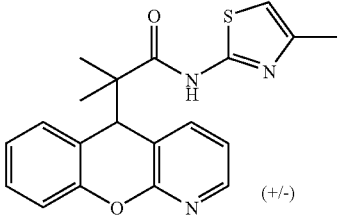 (+/-) | 3.26 | 366 |
| 71 | 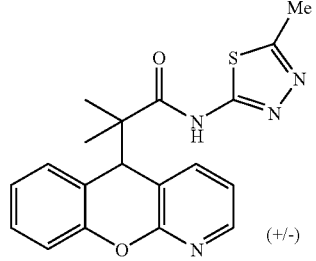 (+/-) | 3.02 | 367 |

Example 72

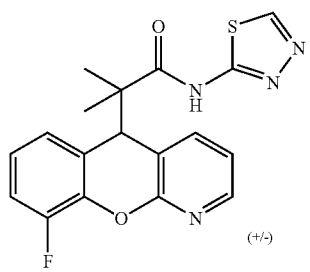

(+/-)

The title compound was prepared from the title compound of Preparation 55b in the same manner described above for the preparation of Examples 63 to 71. MS (E+) m/z: 371 (M+H); LC retention time: 2.51 min.

Examples 73 to 76

The following Examples 73 to 76 were prepared in the same manner described for the preparation of the title compounds of Examples 45 to 52 from the product of Preparation 17e and amines obtained from commercial sources or the preparations described above.

| Example No. | Structure | Rt (min) | M/z (MH)+ |
|---|---|---|---|
| 73 | 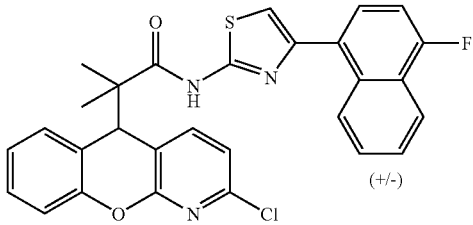 (+/-) | 4.31 | 530 |
| 74 | 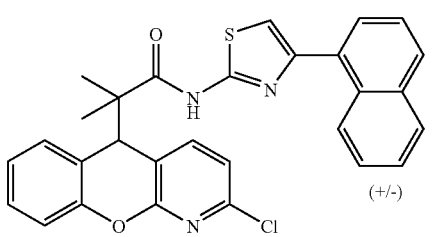 (+/-) | 4.23 | 512 |

| Example No. | Structure | Rt (min) | M/z (MH)+ |
|---|---|---|---|
| 75 | 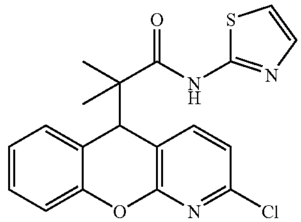 | 3.48 | 386 |
| 76 | (+/-) | 3.37 | 387 |

Example 77

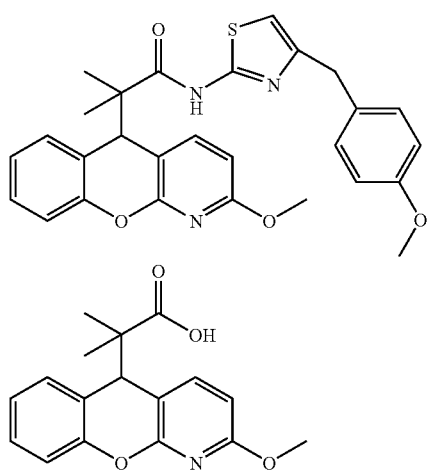

Step 1

A mixture of the title compound of Preparation 17e (150 mg, 0.50 mmol) in methanol (3 mL) and sodium methoxide in methanol (25% w/w, 1.23 mL) was heated by microwave at 140° C. for 40 min, then acidified with the addition of concentrated HCl. The resulting suspension was partitioned between dichloromethane and water, and the organic layer removed, dried over sodium sulfate, and concentrated to give the product of Step 1 (120 mg, 80%), which was used in the next step with no further purification. LC retention time: 3.23 min.

Step 2

The title compound was prepared from the product of Step 1 and the amine of Preparation 8 in the same manner described for the preparation of the title compounds of 47 to 54. MS (E+) m/z: 502 (M+H); LC retention time: 4.06 min.

Examples 78 to 80

The following Examples 78 to 80 were prepared in the manner described above for the preparation of the title compound of Example 77, replacing the amines of Preparation 1 and Preparation 4 for the amine of Preparation 8 or 2-amino-1,3,4-thiadiazole.

| Example No. | Structure | Rt (min) | M/z (MH)+ |
|---|---|---|---|
| 78 | (+/-) | 4.29 | 526 |

| Example No. | Structure | Rt (min) | M/z (MH)+ |
|---|---|---|---|
| 79 | 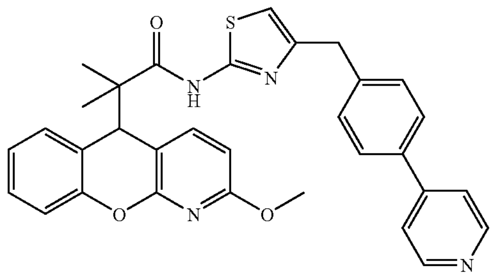 | 3.20 | 549 |
| 80 | 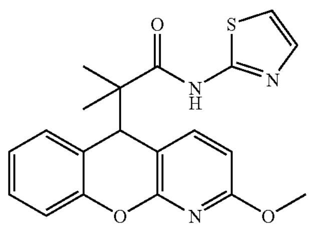 | 3.16 | 383 |

Example 81

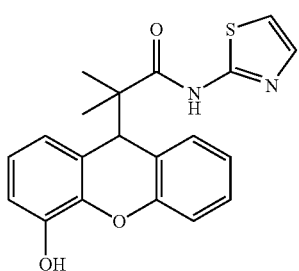

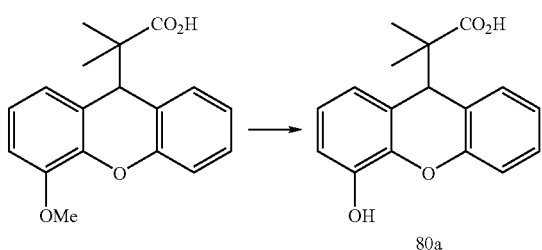

Step 1

A mixture of the acid 18e (50 mg, 0.17 mmol), thiophenol (0.019 mL, 0.18 mmol), and potassium carbonate (25 mg, 0.18 mmol) in 1-methyl-2-pyrrolidinone (NMP) (1.5 mL) was heated by microwave at 205° C. for 70 min. Another portion of thiophenol (0.01 mL) and potassium carbonate (12 mg) was added, and the mixture was heated by microwave another 30 min at 205° C. The reaction mixture was then partitioned between ethyl acetate and 0.5N HCl. The organic layer was removed and dried over sodium sulfate, concentrated, and purified by preparative HPLC to give the product of Step 1 (80a) as an amorphous solid (32 mg, 66%). MS (ES−) m/z: 283 (M−H); LC retention time: 3.02 min.

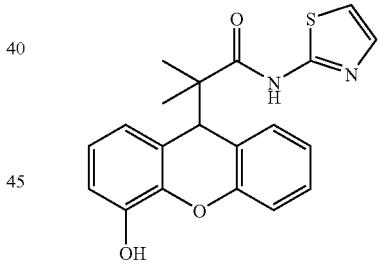

Step 2

A solution of the product of Step 1 (19 mg, 0.07 mmol), triethylamine (0.024 mL, 0.175 mmol), and HOAt (11 mg, 0.08 mmol) in acetonitrile (1 mL) was stirred at 65° C. for 35 min. 2-Aminothiazole (8 mg, 0.077 mmol) was then added to the reaction mixture, which was heated at 140° C. for 1 h. Purification of the reaction mixture by preparative HPLC gave the title compound (11 mg). MS (ES+) m/z: 367 (M+H); LC retention time: 3.26 min.

Examples 82 to 84

The following Examples 82 to 84 were prepared from 18e in the same manner described above for the preparations of the title compounds of Examples 76, 79 and 81.

| Example No. | Structure | Rt (min) | M/z (MH)+ |
|---|---|---|---|
| 82 | 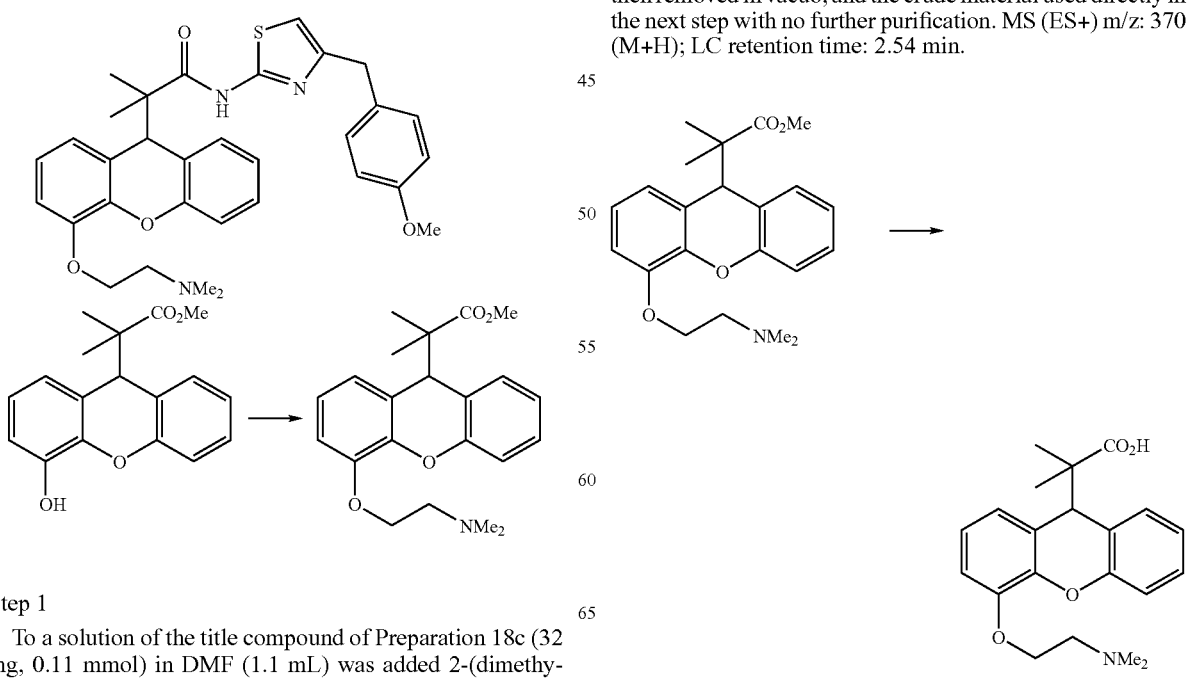 | 4.35 | 525 |
| 83 | 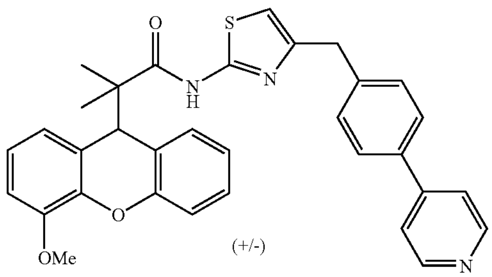 | 3.38 | 548 |
| 84 | 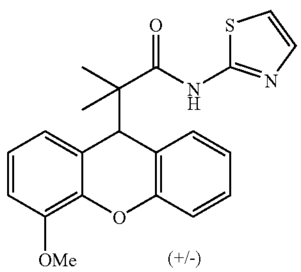 | 3.50 | NA |

Example 85

Step 1

To a solution of the title compound of Preparation 18c (32 mg, 0.11 mmol) in DMF (1.1 mL) was added 2-(dimethylamino)ethyl chloride hydrochloride (17 mg, 0.12 mmol), followed by sodium hydride (60% w/w in mineral oil, 9 mg). The mixture was heated at 80 C for 35 min. The solvent was then removed in vacuo, and the crude material used directly in the next step with no further purification. MS (ES+) m/z: 370 (M+H); LC retention time: 2.54 min.

Step 2

A mixture of the product of Step 1 (0.11 mmol), methanol (2 mL), THF (1 mL), and 4N aqueous KOH (1.1 mL) was heated at 80 C for 14 h. The reaction mixture was then acidified with concentrated HCl, then concentrated and purified by preparative HPLC to give the product of Step 2 (12 mg). MS (ES+) m/z: 356 (M+H); LC retention time: 2.33 min.

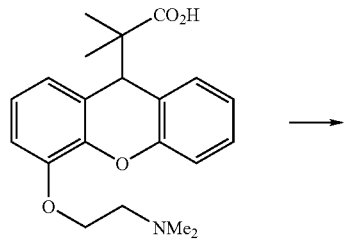

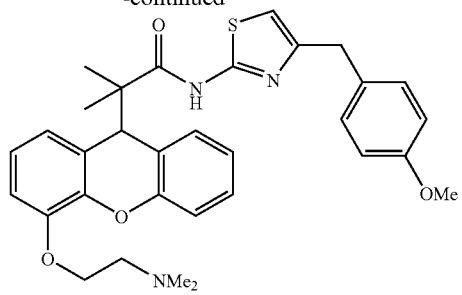

Step 3

The title compound was prepared from the product of Step 2 in the same manner as described for the preparation of the title compound of Example 57. MS (ES+) m/z: 558 (M+H); LC retention time: 3.27 min.

Examples 86 to 89

The following Examples 86 to 89 were prepared from the title compound of Preparation 19 and commercially available amines in the same manner as described above for the preparation of the title compound of Example 81.

| Example No. | Structure | Rt (min) | M/z (MH)+ |
|---|---|---|---|
| 86 | 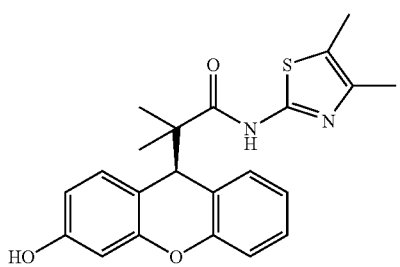 | 3.59 | 395 |
| 87 | 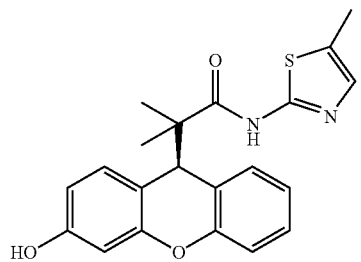 | 3.47 | 379 |
| 88 | 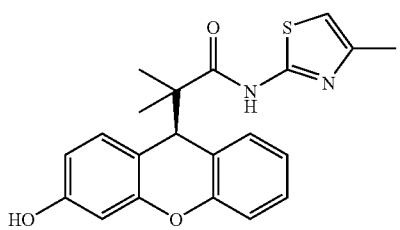 | 3.45 | 379 |

| Example No. | Structure | Rt (min) | M/z (MH)+ |
|---|---|---|---|
| 89 | 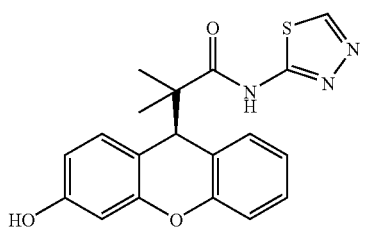 | 3.33 | 365 |

Example 90

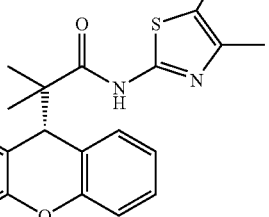

To a solution of the product of Preparation 19 (30 mg, 0.11 mmol) in dichloromethane (0.5 mL) were added sequentially pyridine (0.019 mL, 0.23 mmol), 4-dimethylaminopyridine (1 mg, catalytic), and chlorotrimethylsilane (0.029 mL, 0.23 mmol). After 4.5 h at room temperature, N,N-dimethylformamide (0.01 mL) followed by oxalyl chloride (0.01 mL, 0.11 mmol) were added to the reaction mixture. After an additional 1.5 h at room temperature, pyridine (0.044 mL, 0.55 mmol) was added to the reaction mixture, followed by 2-amino-1,3,4-thiadiazole (12 mg, 0.12 mmol). The reaction was allowed to sit at room temperature 10 min, then concentrated and purified by preparative thin layer chromatography (0.5 mm silica, 100 cm×200 cm, 7% methanol in dichloromethane) to give the title compound (15 mg, 37%) as a colorless solid. MS (ES+) m/z: 368 (M+H); LC retention time: 3.10 min.

Examples 91 to 94

The following Examples 90 to 93 were prepared from the title compound of Preparation 20 and commercially available amines in the same manner as described above for the preparation of the title compounds of Example 85 to 88.

| Example No. | Structure | Rt (min) | M/z (MH)+ |
|---|---|---|---|
| 91 | 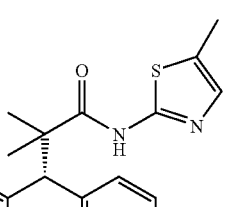 | 3.60 | 395 |
| 92 | 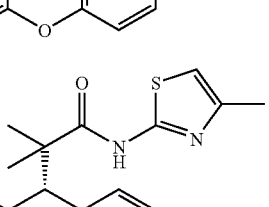 | 3.46 | 379 |
| 93 | 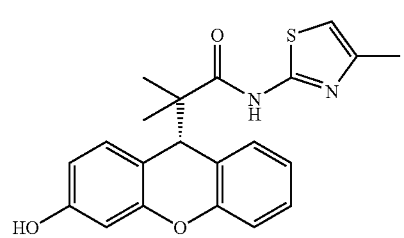 | 3.45 | 379 |

| Example No. | Structure | Rt (min) | M/z (MH)+ |
|---|---|---|---|
| 94 | 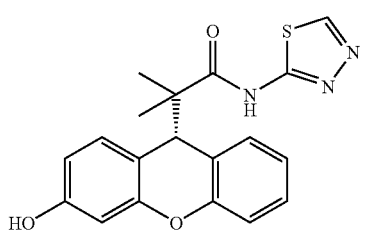 | 3.33 | 365 |

Example 95

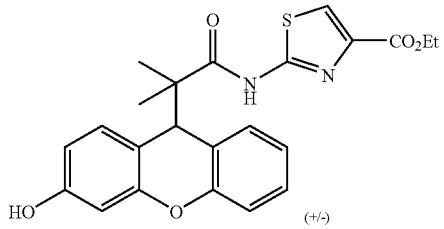

The title compound was prepared from the product of Preparation 20 in the same manner described above for the preparation of the title compound of Example 90. MS (ES+) m/z: 368 (M+H); LC retention time: 3.10 min.

Example 96

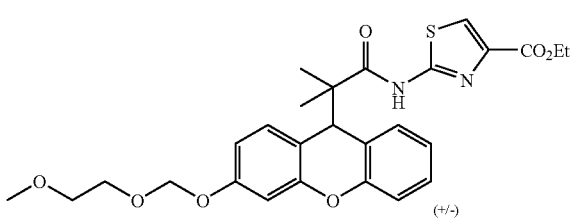

The title compound was prepared from the product of Preparation 21b in the same manner described above for the preparation of the title compound of Example 81, Step 1, substituting ethyl 2-aminothiazole-4-carboxylate for 2-aminothiazole. MS (ES+) m/z: 439 (M+H); LC retention time: 3.65 min.

Example 97

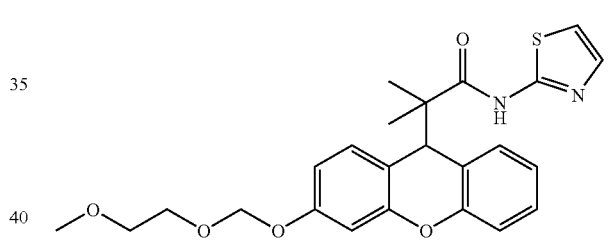

A mixture of the product of Preparation 22b (109 mg, 0.29 mmol), triethylamine (0.101 mL, 0.73 mmol), EDC (67 mg, 0.35 mmol), and HOAt (48 mg, 0.35 mmol) in acetonitrile (3.0 mL) stirred 12 h at room temperature. Ethyl 2-aminothiazole-4-carboxylate (55 mg, 0.32 mmol) was added to the mixture, which was heated in a sealed tube at 140° C. for 1.5 h. The reaction mixture was concentrated in vacuo and the residue partitioned between ethyl acetate (30 mL) and 1N HCl (20 mL). The organic layer was washed sequentially with saturated aqueous sodium bicarbonate and brine, then dried over sodium sulfate and concentrated. Flash column chromatography (silica, 50% ethyl acetate in hexanes) provided the title compound (94 mg, 62% yield) as a foam. MS (ES+) m/z: 527 (M+H); LC retention time: 4.00 min.

Example 98

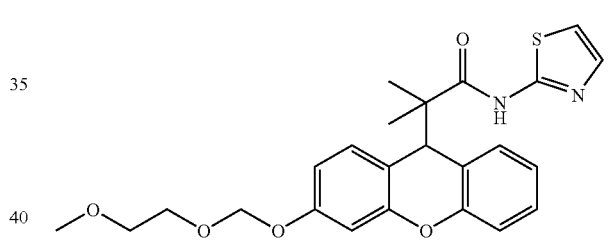

The title compound was prepared from the product of Preparation 22b in the same manner as described above for the preparation of the title compound of Example 97, substituting 2-amino thiazole for ethyl 2-aminothiazole-4-carboxylate. MS (ES+) m/z: 455 (M+H); LC retention time: 3.68 min.

Example 99

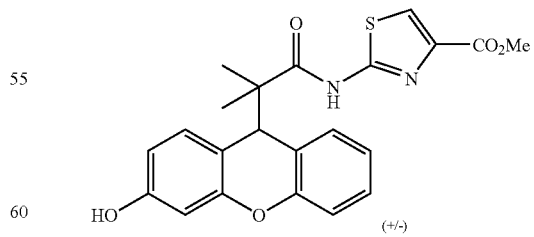

To a solution of the title compound of Example 97 (42 mg, 0.08 mmol) in dry methanol (0.8 mL) was added camphor sulfonic acid (5.5 mg, 0.024 mmol). The solution was heated at 70° C. for 24 h, then concentrated in vacuo. The residue was partitioned between ethyl acetate and saturated aqueous sodium bicarbonate. The organic layer was washed with brine, dried over sodium sulfate, then concentrated to give a sticky solid (22 mg, 65% yield). MS (ES+) m/z: 425 (M+H); LC retention time: 3.47 min.

Example 100

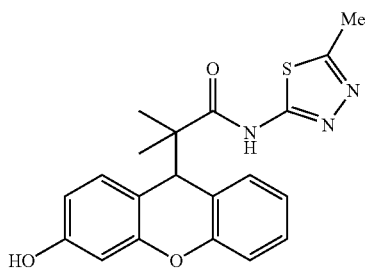

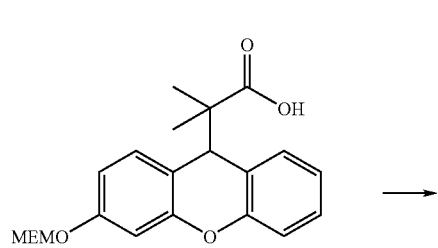

(MEMO = methoxyethoxymethoxy)

Step 1

The product 100a was prepared in the same manner as described above for the preparation of the title compound of Example 97, substituting 5-methyl-2-amino-1,3,4-thiadiazole for ethyl 2-aminothiazole-4-carboxylate. MS (ES+) m/z: 470 (M+H); LC retention time: 3.82 min.

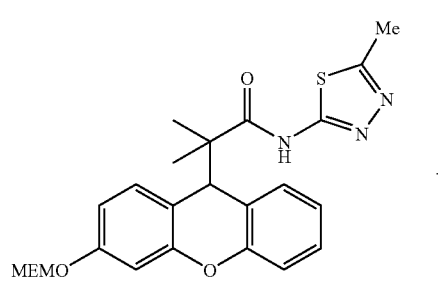

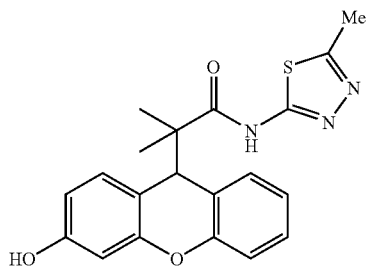

Step 2

The title compound was prepared in the same manner as described above for the preparation of the title compound of Example 99. MS (ES+) m/z: 382 (M+H); LC retention time: 3.32 min.

Example 101

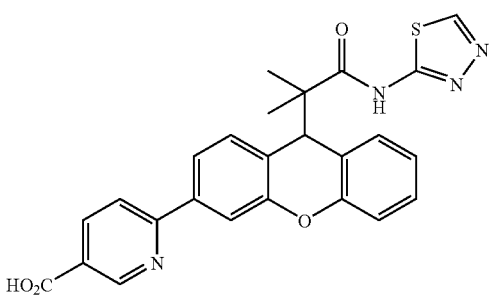

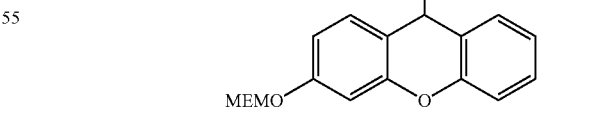

(MEMO = methoxyethoxymethoxy)

Step 1

The product of Step 1 was prepared in the manner described above for the preparation of the product of Step 1 of Example 100.

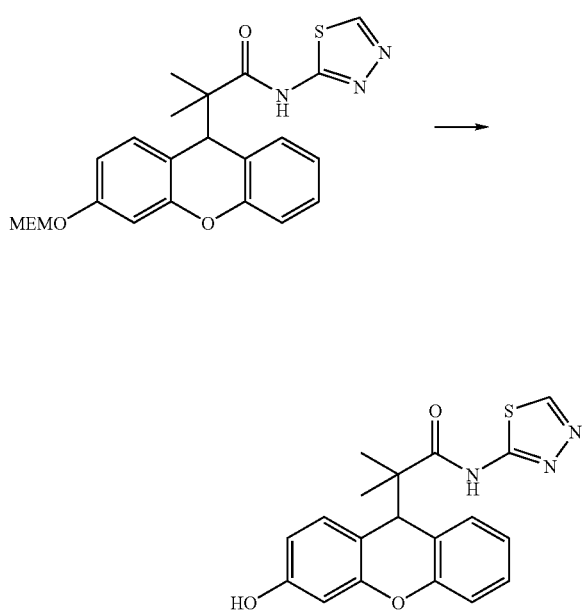

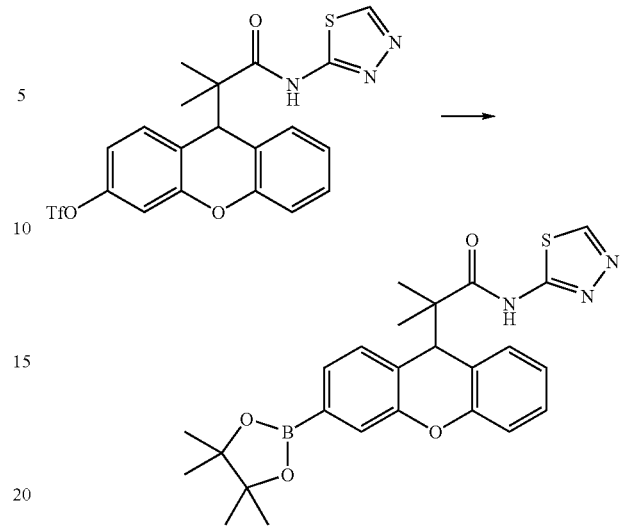

Step 2

The product of Step 2 was prepared in the manner described above for the preparation of the product of Step 2 of Example 100.

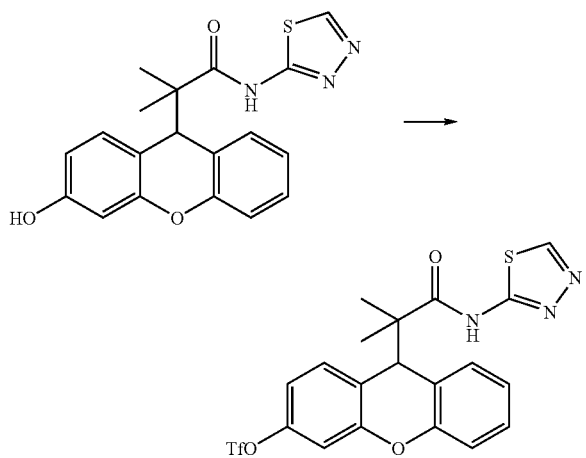

Step 3

To a solution of the product of Step 2 (200 mg, 0.545 mmol) in dichloromethane (5 mL) at 0° C. under nitrogen was added triethylamine (0.182 mL, 1.31 mmol) followed by 1,1,1-trifluoro-N-phenyl-N -(trifluoromethylsulfonyl)methanesulfonamide (292 mg, 0.817 mmol). The reaction mixture was allowed to stir at 0° C. for 2.5 h, then partitioned between dichloromethane and saturated aqueous sodium bicarbonate solution. The organic layer was dried over sodium sulfate and concentrated. Purification by flash column chromatography (40 g silica, 50% ethyl acetate in hexanes) afforded the product of Step 3 (150 mg, Y=55%) as a white solid. MS (ES+) m/z: 500 (M+H); LC retention time: 3.99 min.

Step 4

To a solution of the product of Step 3 (160 mg, 0.32 mmol) in 1,4-dioxane (3 mL) were sequentially added 1,1'-bis(diphenylphosphino)ferrocene-palladium(II)dichloride dichloromethane complex (24 mg, 0.03 mmol), bis(pinacolato)diboron (120 mg, 0.47 mmol), and potassium acetate (96 mg, 0.98 mmol). A stream of nitrogen gas was blown through the reaction mixture for 15 min, which was then heated at 80° C. for 5 h. The reaction mixture was concentrated in vacuo, and the residue purified by flash column chromatography (12 g silica, 20% to 50% ethyl acetate in hexanes) to provide the product of Step 4 (120 mg, Y=79%) as a yellow oil. MS (ES+) m/z: 478 (M+H); LC retention time: 4.07 min.

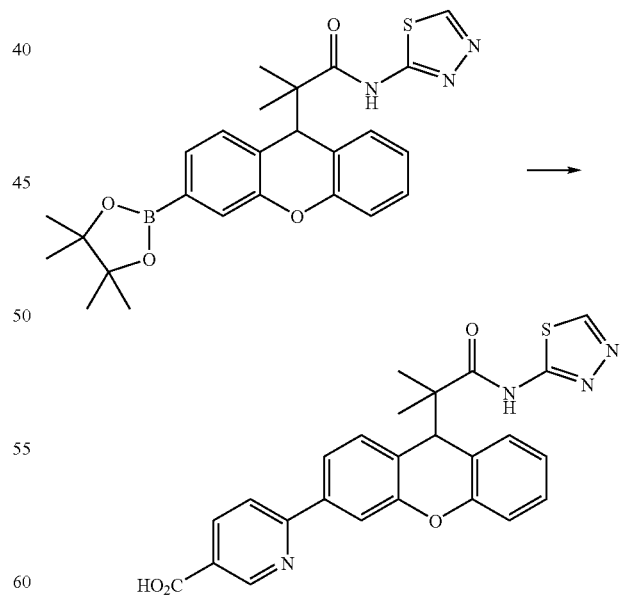

Step 5

To a solution of 6-chloronicotinic acid (7.4 mg, 0.047 mmol) in DMF (1 mL) was added the product of Step 4 (15 mg, 0.031 mmol), followed by aqueous potassium phosphate (2.0 M, 0.1 mL) and tetrakis(triphenylphosphine)palladium (0) (10 mg, 0.009 mmol). A stream of nitrogen gas was bubbled through the mixture for 15 min, which was then heated at 100° C. for 2 h. The reaction mixture was purified by preparative HPLC to give the title compound as a TFA salt which was lyophilized from acetonitrile/water to give a white powder (3.1 mg, Y=21%). MS (ES+) m/z: 473 (M+H); LC retention time: 3.55 min.

Example 102

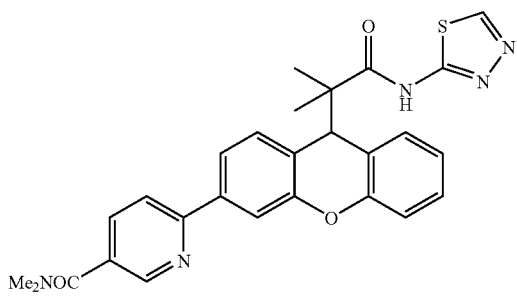

A mixture of the title compound of Example 101 (10 mg, 0.021 mmol), HOBT monohydrate (4.3 mg, 0.032 mmol), EDCI (6.12 mg, 0.032 mmol), triethylamine (0.1 mL) and dimethylamine hydrochloride (3.43 mg, 0.042 mmol) in acetonitrile (1 mL) was heated at 80° C. for 12 h. The reaction mixture was then purified by preparative HPLC to give the title compound, which was lyophilized from acetonitrile/water to give a white powder (4 mg, Y=38%). MS (ES+) m/z: 500 (M+H); LC retention time: 3.26 min.

Example 103

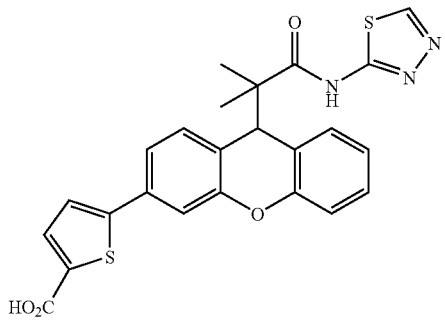

To a solution of the product of Example 101, Step 4 (45 mg, 0.094 mmol) and 5-bromothiophene-2-carboxylic acid (38 mg, 0.188 mmol) in DMF (9 mL) and water (0.1 mL) were added tetrakis(triphenylphosphine)palladium(0) (10 mg, 0.009 mmol) and barium hydroxide hexahydrate (89 mg, 0.28 mmol). Nitrogen gas was bubbled through the mixture for 10 min, which was then heated at 100° C. for 14 h. Purification by preparative HPLC provided the title compound (3 mg, Y=7%) as a white powder. MS (ES+) m/z: 478 (M+H); LC retention time: 3.75 min.

Example 104

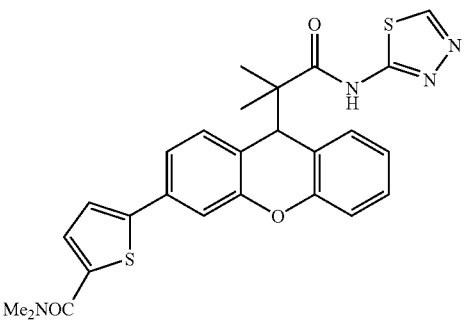

The title compound was prepared from the title compound of Example 103 in the manner described for the preparation of the title compound of Example 102 from Example 101. MS (ES+) m/z: 505 (M+H); LC retention time: 3.62 min.

Examples 105 to 108

The following Examples 105 to 108 were prepared in the same manner described above for the preparation of the title compound of Example 103 using the product of Example 101, step 4 or the title compound of Example 90 and commercially available halides in place of bromothiophene-2-carboxylic acid.

| Example No. | Structure | Rt (min) | M/z (MH)+ |
|---|---|---|---|
| 105 | (+/-) | 3.71 | 487 |

| Example No. | Structure | Rt (min) | M/z (MH)+ |
|---|---|---|---|
| 106 | (+/-) | 3.85 | 458 |
| 107 | 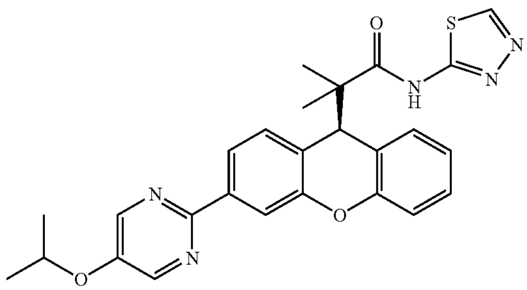 | 3.74 | 487 |
| 108 | (+/-) | 3.75 | 474 |

Example 109

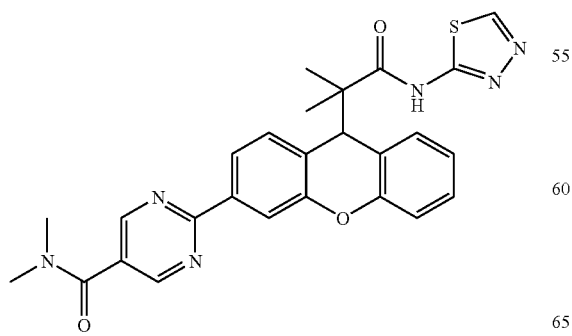

The title compound was prepared from the title compound of Example 108 in the same manner described above for the preparation of the title compound of Example 104 from the title compound of Example 103. MS (ES+) m/z: 501 (M+H); LC retention time: 3.42 min.

Examples 110 to 111

The following Examples 110 to 111 were prepared in the same manner described above for the preparation of the title compound of Example 106 using the title compounds of Example 95 and Example 90.

| Example No. | Structure | Rt (min) | M/z (MH)+ |
|---|---|---|---|
| 110 | 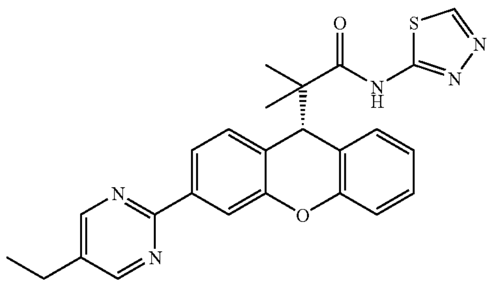 | 3.92 | 458 |
| 111 | 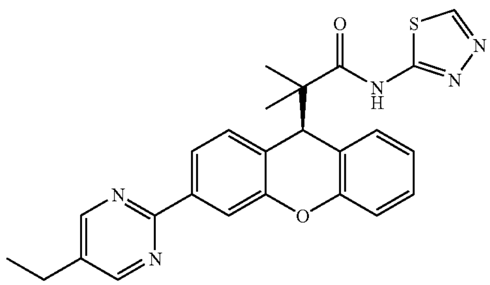 | 3.92 | 458 |

Example 112

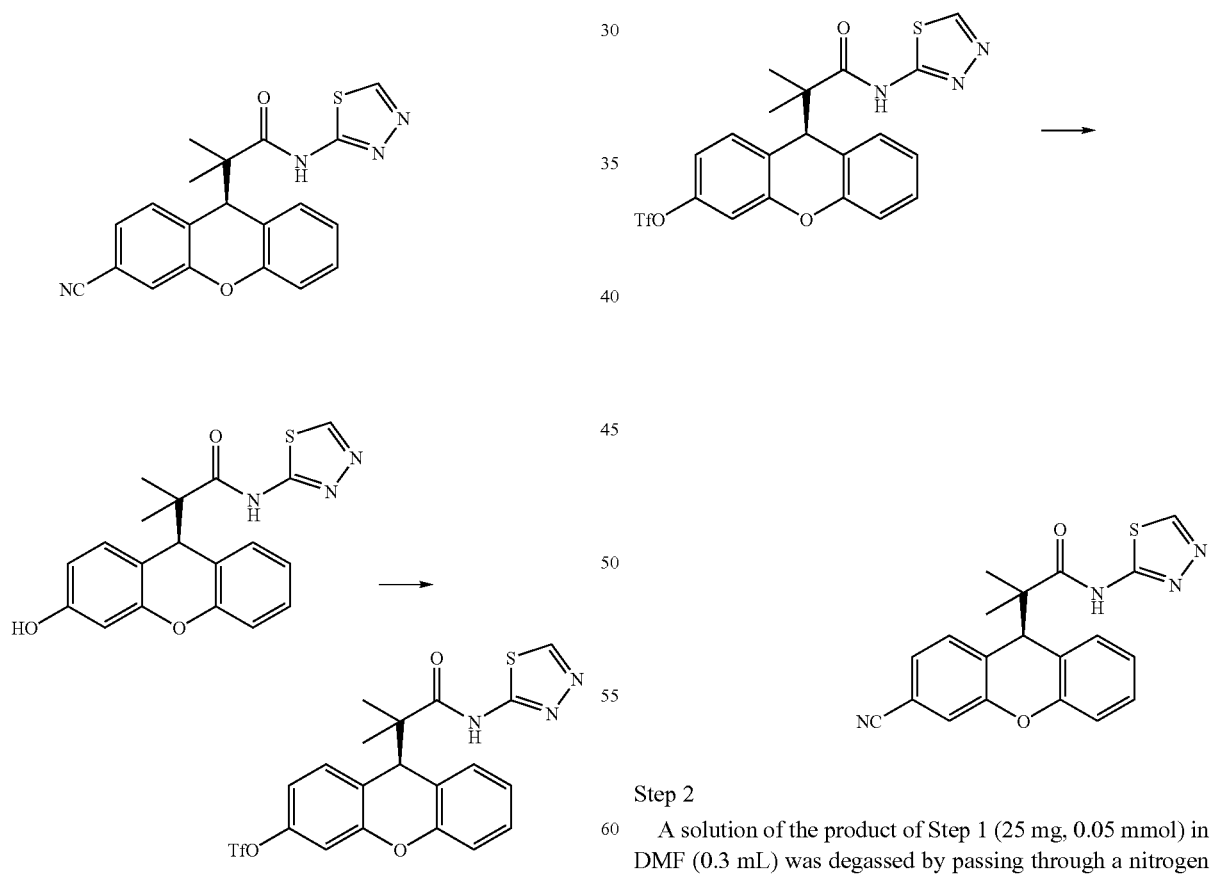

Step 1

The product of Step 1 was prepared from the title compound of Example 90 in the same manner as described above for the preparation of the product of Step 3 of Example 101.

Step 2

A solution of the product of Step 1 (25 mg, 0.05 mmol) in DMF (0.3 mL) was degassed by passing through a nitrogen stream for 5 min. Zinc cyanide (12 mg, 0.1 mmol) and tetrakis(triphenylphosphine)palladium(0) (12 mg, 0.05 mmol) were then added and the mixture was degassed for another 5 min, then heated at 120° C. for 2 h in a sealed vial. The mixture was filtered through a syringe-tip filter (0.45 micron, PTFE), then purified by preparative HPLC to give the product as a white solid. MS (ES+) m/z: 375; LC retention time: 3.40 min.

Example 113

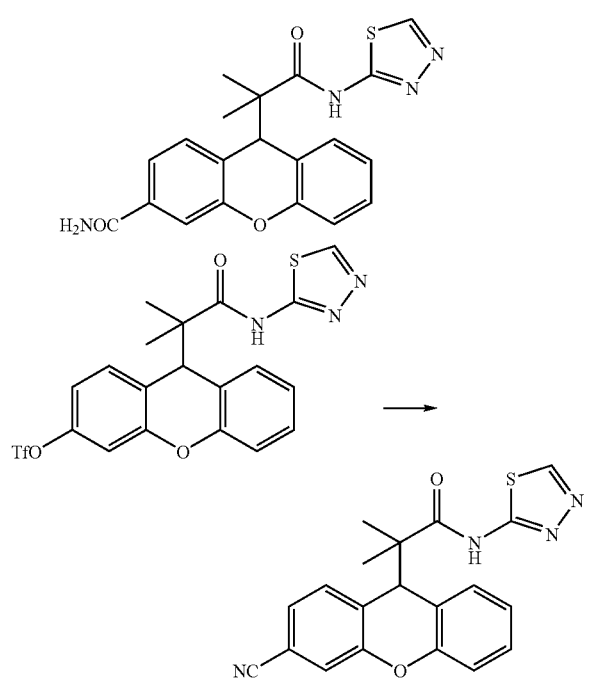

Step 1

The product of Step 1 was obtained from the product of Step 3 of Example 101 in the same manner described above for the preparation of the title compound of Example 112. MS (ES+) m/z: 375; LC retention time: 3.40 min.

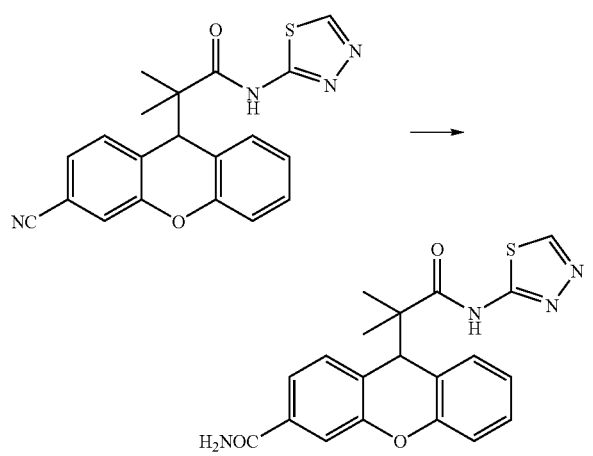

Step 2

To a suspension of the product of Step 1 (10 mg, 0.0266 mmol) in water (2 mL) was added sodium peroxide (12 mg, 0.16 mmol). The mixture was heated at 70° C. for 1 h, then acidified to pH ~5 with the dropwise addition of 6 N HCl and purified by preparative HPLC. The material thus obtained was lyophilized from acetonitrile/water to give the title compound as a white powder, TFA salt (4 mg, Y=29%). MS (ES+) m/z: 395 (M+H); LC retention time: 2.89 min.

Example 114

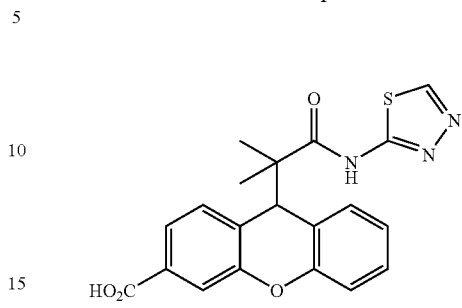

To a suspension of the product of Step 1 of Example 113 (10 mg, 0.027 mmol) in water (2 mL) was added sodium peroxide (30 mg, 0.38 mmol). The mixture was heated at 100° C. 16 h. Another portion of sodium peroxide (30 mg, 0.38 mmol) was then added and the mixture was heated at 100° C. for another 3 h, then purified by preparative HPLC to give the title compound as a white powder (3 mg, Y=28%). MS (ES+) m/z: 396 (M+H); LC retention time: 3.36 min.

Example 115

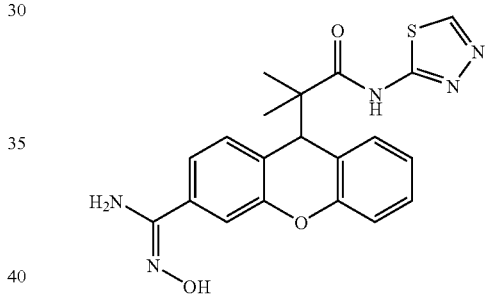

A mixture of the product of Example 113, step 1 (40 mg, 0.106 mmol), hydroxylamine hydrochloride (30 mg, 0.426 mmol) and potassium carbonate (59 mg, 0.426 mmol) in ethanol (5 mL) and water (1 mL) was heated to reflux overnight. Preparative HPLC afforded the product (28 mg, Y=65%). MS (ES+) m/z: 410 (M+H); LC retention time: 2.29 min.

Example 116

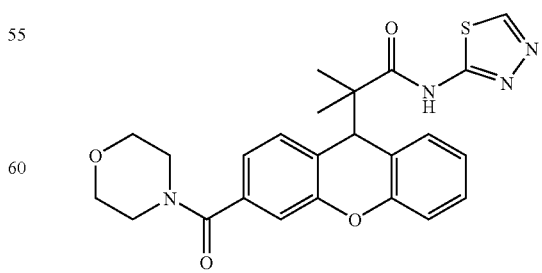

A solution of the title compound of Example 114 (5 mg, 0.013 mmol) in acetonitrile (2 mL) was treated with HOBT monohydrate (3 mg, 0.019 mmol), EDCI (4 mg, 0.019 mmol), pyridine (0.1 mL) and morpholine (0.003 mL, 0.025 mmol). The resulting solution was heated at 60° C. for 14 h, then purified by preparative HPLC to give the title compound (4.7 mg, Y=78%) as a white solid. MS (ES+) m/z: 465 (M+H); LC retention time: 3.07 min.

Examples 117 to 118

The following Examples 117 to 118 were prepared in the same manner described above for the preparation of the title compound of Example 116.

| Example No. | Structure | Rt (min) | M/z (MH)+ |
|---|---|---|---|
| 117 | 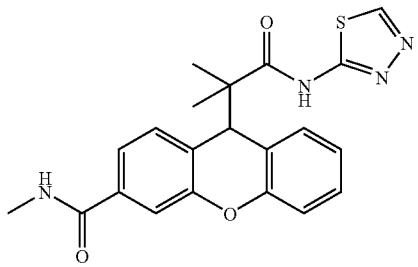 (+/-) | 2.96 | 409 |
| 118 | 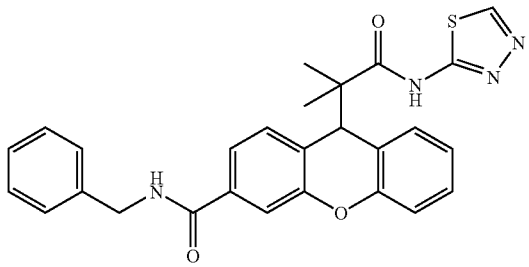 (+/-) | 3.49 | 485 |

Example 119

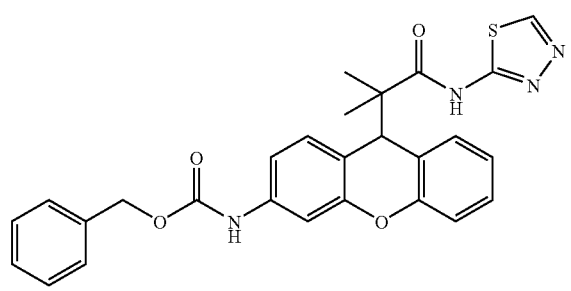

To a solution of the title compound of Example 114 (25 mg, 0.06 mmol) in toluene (3 mL) were added triethylamine (0.025 mL, 0.18 mmol) and diphenyl phosphoryl azide (0.026 mL, 0.12 mmol). The resulting solution was refluxed for 30 min, then cooled to room temperature. Benzyl alcohol (0.019 mL, 0.18 mmol) was then added to the reaction mixture, was refluxed for another 5 h. The solvent was removed in vacuo and the resulting residue purified by preparative HPLC to afford the product, which was lyophilized from acetonitrile/water to give the title compound (19 mg, Y=43%) as a white powder. MS (ES+) m/z: 501 (M+H); LC retention time: 3.79 min.

Examples 120 to 125

The following Examples 120 to 125 were prepared in the same manner described above for the preparation of the title compound of Example 119, substituting benzyl alcohol with commercially available alcohols and amines.

| Example No. | Structure | Rt (min) | M/z (MH)+ |
|---|---|---|---|
| 120 | (+/-) | 3.71 | 487 |
| 121 | (+/-) | 2.92 | 515 |
| 122 | (+/-) | 3.49 | 500 |
| 123 | (+/-) | 3.47 | 493 |

| Example No. | Structure | Rt (min) | M/z (MH)+ |
|---|---|---|---|
| 124 | 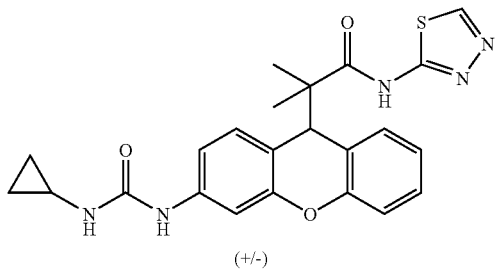 (+/-) | 3.17 | 450 |
| 125 | 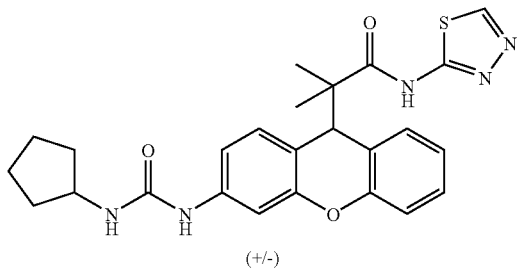 (+/-) | 3.51 | 478 |

Example 126

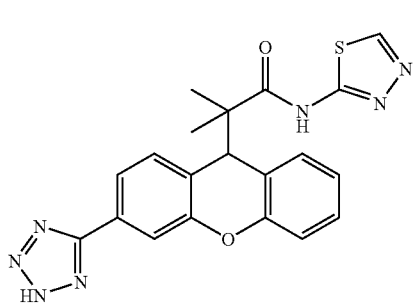

To a solution of the product of Example 113, step 1 (10 mg, 0.027 mmol) in DMF (1 mL) was added sodium azide (18 mg, 0.27 mmol) and ammonium chloride (53.5 mg, 0.27 mmol). The mixture was heated at 120° C. for 6 h. After cooling, the mixture was purified by preparative HPLC to give the product which was lyophilized from acetonitrile/water to afford the title compound (6 mg, Y=53%) as a white powder. MS (ES+) m/z: 420 (M+H); LC retention time: 3.14 min.

Example 127

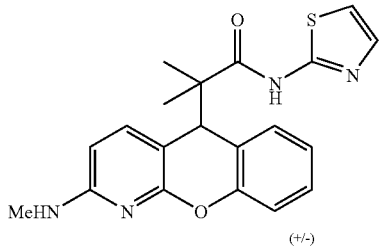
(+/-)

The title compound was prepared from the product of Preparation 24 in the same manner described above for the preparation of the title compound of Example 67. MS (ES+) m/z: 381 (M+H); LC retention time: 3.07 min.

Examples 128 to 129

The following Examples 128 to 129 were prepared in the same manner described above for the preparation of the title compound of Example 127 using compounds of Preparations 25 and 26 and 2-amino-1,3,4-thiadiazole in place of 2-aminothiazole.

| Example No. | Structure | Rt (min) | M/z (MH)+ |
|---|---|---|---|
| 128 | (+/−) | 3.55 | 488 |
| 129 | (+/−) | 3.19 | 438 |

Example 130

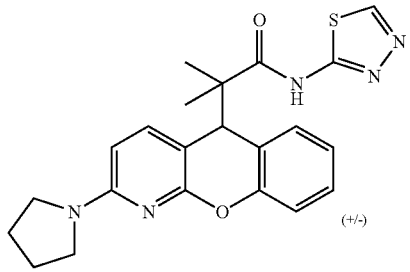

(+/−)

To a solution of the product of Preparation 28 (100 mg, 0.297 mmol) in acetonitrile (3.0 mL) was added O-(7-azabenzotriazol-1-yl)-N,N,N',N'-tetramethyluronium hexafluoro phosphate (HATU) (226 mg, 0.594 mmol), followed by triethylamine (0.2 mL) and 2-amino-1,3,4-thiadiazole (60 mg, 0.594 mmol). The solution was heated at 80° C. for 16 h, then concentrated in vacuo and purified by preparative HPLC to give the product as a solid (120 mg, 76%). MS (ES+) m/z: 422 (M+H); LC retention time: 3.38 min.

Example 131 to 133

The following Examples 131 to 133 were prepared from the compounds of Preparations 23, 27 and 29 in the manner described above for the preparation of the title compound of Example 130.

| Example No. | Structure | Rt (min) | M/z (MH)+ |
|---|---|---|---|
| 131 | (+/−) | 2.20 | 451 |

-continued

| Example No. | Structure | Rt (min) | M/z (MH)+ |
|---|---|---|---|
| 132 | (structure shown) (+/-) | 3.70 | 4.36 |
| 133 | (structure shown) (+/-) | 3.51 | 456 |

Examples 134 to 137

The following Examples 134 to 137 were prepared from the compounds of Preparations 31 to 34 in the manner described above for the preparation of the title compounds of Examples 130 to 133.

| Example No. | Structure | Rt (min) | M/z (MH)+ |
|---|---|---|---|
| 134 | (structure shown) | 3.70 | 436 |
| 135 | (structure shown) | 3.42 | 494 |

| Example No. | Structure | Rt (min) | M/z (MH)+ |
|---|---|---|---|
| 136 | (+/-) | 3.51 | 488 |
| 137 | 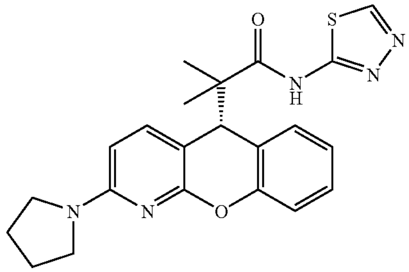 | 3.41 | 422 |

Examples 138 to 150

The following Examples 138 to 150 were prepared from the compounds of Preparations 35 to 47 in the manner described above for the preparation of the title compounds of Examples 130 to 137.

| Example No. | Structure | Rt (min) | M/z (MH)+ |
|---|---|---|---|
| 138 | 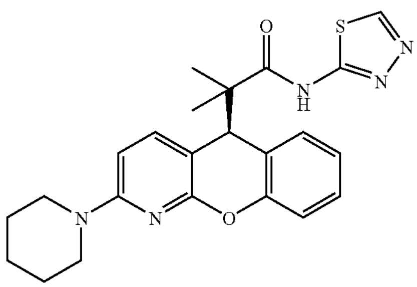 | 3.73 | 436 |
| 139 | 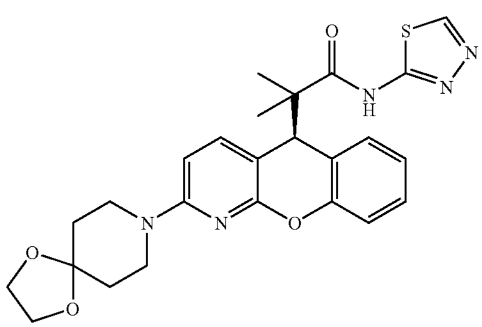 | 3.43 | 494 |

-continued
| Example No. | Structure | Rt (min) | M/z (MH)+ |
|---|---|---|---|
| 140 | 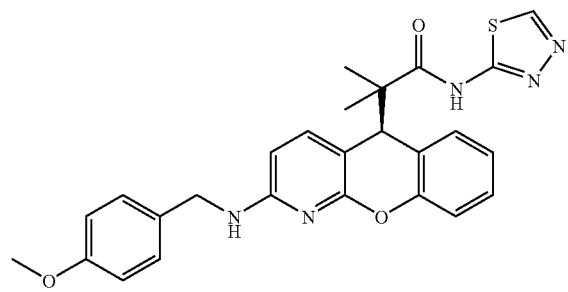 | 3.51 | 488 |
| 141 | 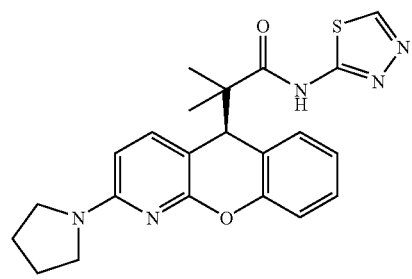 | 3.41 | 422 |
| 142 | 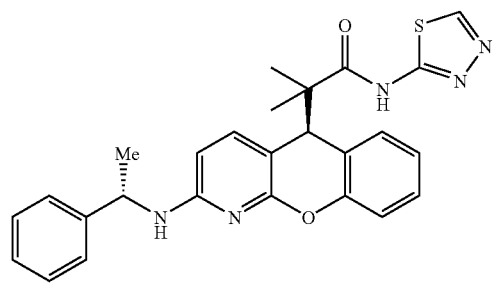 | 3.60 | 470 |
| 143 | 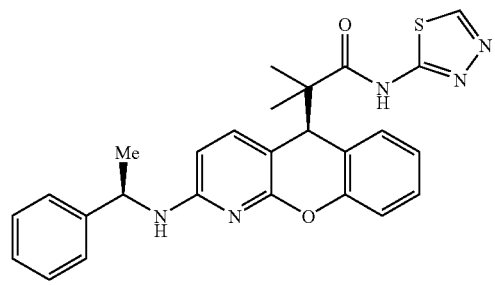 | 3.60 | 472 |
| 144 | 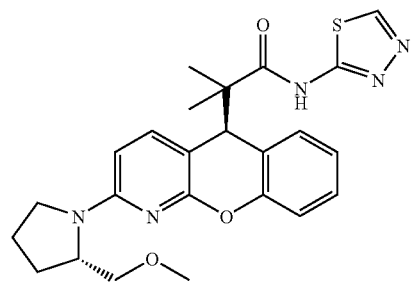 | 3.52 | 466 |

-continued
| Example No. | Structure | Rt (min) | M/z (MH)+ |
|---|---|---|---|
| 145 | 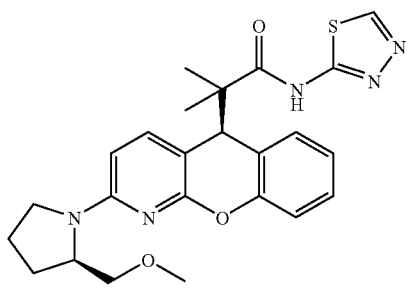 | 3.50 | 466 |
| 146 | 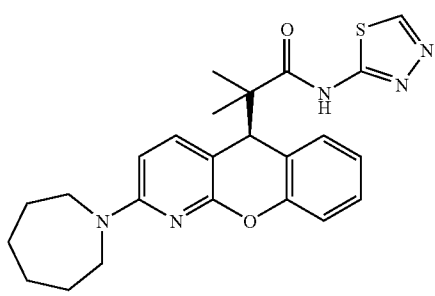 | 3.83 | 450, 448 |
| 147 | 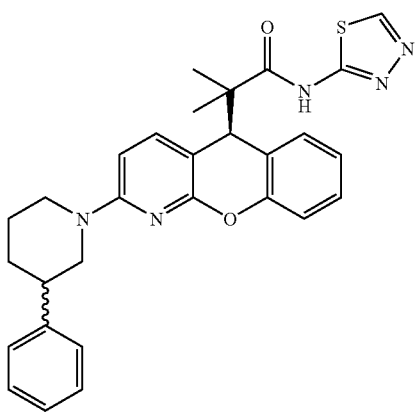 | 4.15 | 512 |
| 148 | 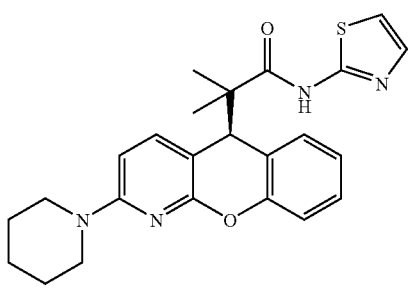 | 3.86 | 435, 433 |
| 149 | 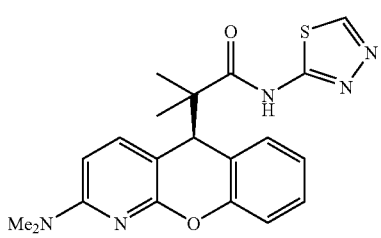 | 3.22 | 394, 396 |

| Example No. | Structure | Rt (min) | M/z (MH)+ |
|---|---|---|---|
| 150 | 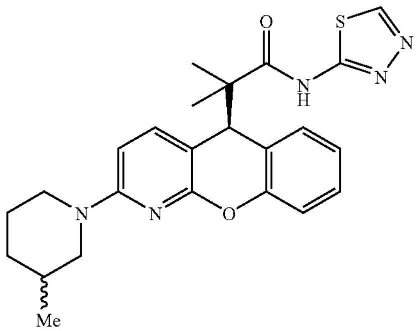 | 3.92 | 448, 450 |

Example 151

Step 1
To a solution of the title compound of Example 140 (20 mg, 0.04 mmol) in DMF (0.4 mL) were added triethylamine (0.028 mL, 0.2 mmol) and butyryl chloride (0.042 mL, 0.4 mmol), followed by N,N-dimethylaminopyridine (5 mg, 0.04 mmol). The mixture was heated at 80° C. for 30 min, then partitioned between ethyl acetate and 1N aqueous HCl. The organic layer was washed with saturated aqueous sodium bicarbonate and brine, then dried over sodium sulfate and concentrated. MS (ES+) m/z: 558 (M+H); LC retention time: 3.62 min. The crude material (140a) was used directly in the next step with no further purification.

Step 2
The product of Step 1 (140a) was dissolved in TFA (1 mL) and heated at 50° C. for 12 h. The solvent was removed in vacuo, and the residue purified by preparative HPLC to give the product (7 mg, 40% yield for two steps) as an off-white solid. MS (ES+) m/z: 438 (M+H); LC retention time: 3.24 min.

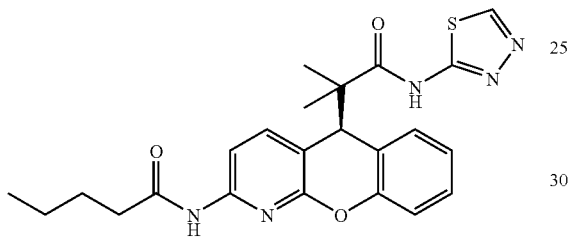

Example 152

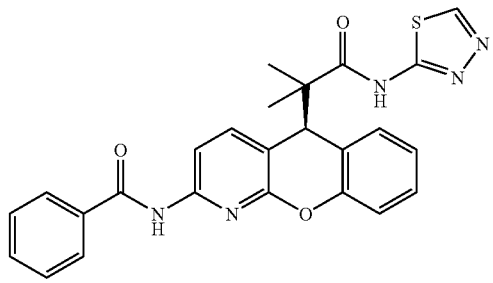

The title compound was prepared from the title compound of Example 140 in a similar manner as described above for the preparation of the title compound of Example 151. MS (ES+) m/z: 472 (M+H); LC retention time: 3.48 min.

Examples 153 to 157

The following Examples 153 to 157 were prepared in the same manner described above for the preparations of the title compounds of Preparations 23 to 29, using the title compound of Example 75 in place of the product of Preparation 17e.

| Example No. | Structure | Rt (min) | M/z (MH)+ |
|---|---|---|---|
| 153 | (+/-) | 3.70 | 487 |

| Example No. | Structure | Rt (min) | M/z (MH)+ |
|---|---|---|---|
| 154 | 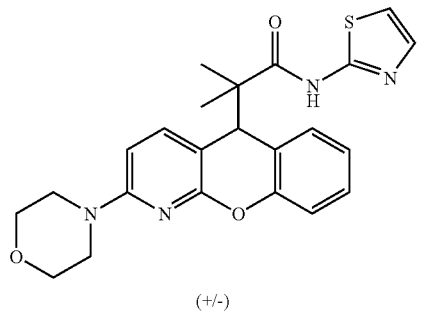<br>(+/-) | 3.39 | 435 |
| 155 | 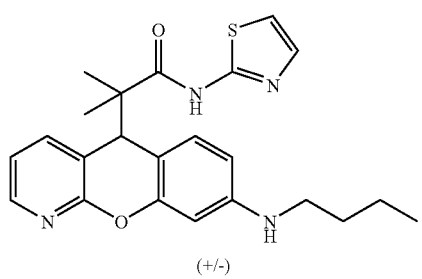<br>(+/-) | 4.00 | 423 |
| 156 | 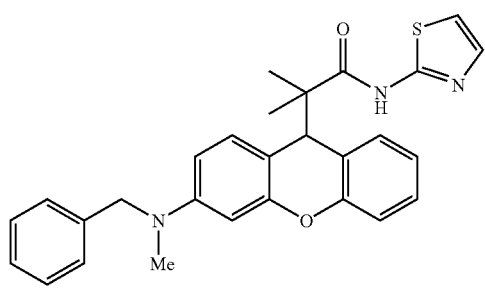<br>(+/-) | 4.39 | 471 |
| 157 | 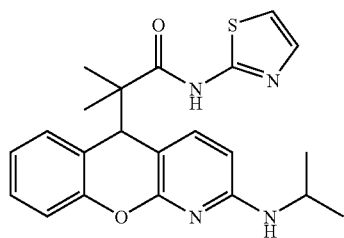<br>(+/-) | 3.47 | 409 |

Example 158

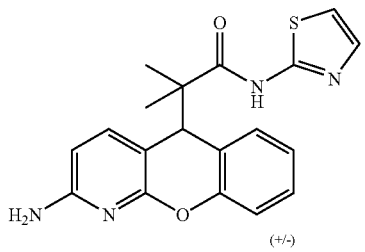

A solution of the title compound of Example 153 (10 mg, 0.021 mmol) in trifluoroacetic acid (1 mL) was heated at 50° C. for 0.5 h. The solvent was removed in vacuo and the residue purified by preparative HPLC to give the product (8.5 mg, 86%) as a solid. MS (ES+) m/z: 365; LC retention time: 2.79 min.

Example 159

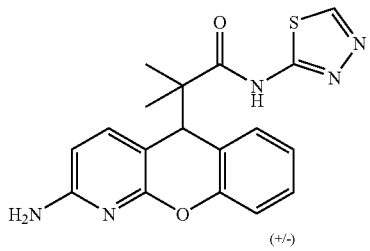

The title compound was prepared from the title compound of Example 128 in the manner described above for the preparation of the title compound of Example 158. MS (ES+) m/z: 368 (M+H); LC retention time: 2.50 min.

Example 160

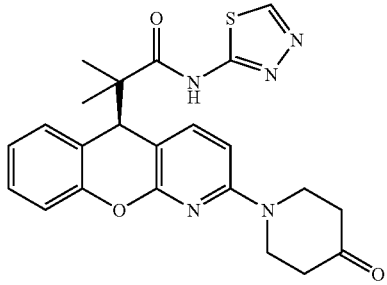

A solution of the title compound of Example 135 (11 mg, 0.022 mmol) in THF (0.6 mL) and 1N HCl (0.5 mL) was stirred at room temperature for 15 h. The product (2 mg, 20%) was isolated by preparative HPLC. MS (ES+) m/z: 464 (M+MeOH—OH); LC retention time: 3.10 min.

Example 161

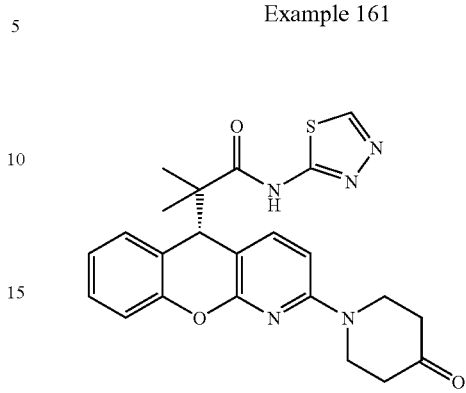

The title compound was prepared from the title compound of Example 139 in the manner described above for the preparation of the title compound of Example 160. MS (ES+) m/z: 464 (M+MeOH—OH); LC retention time: 3.10 min.

Example 162

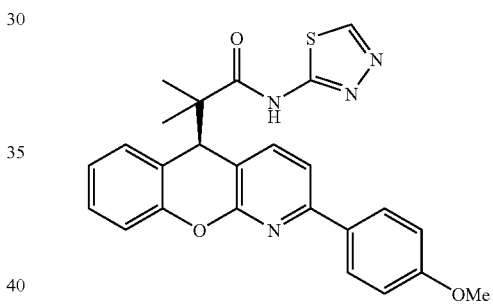

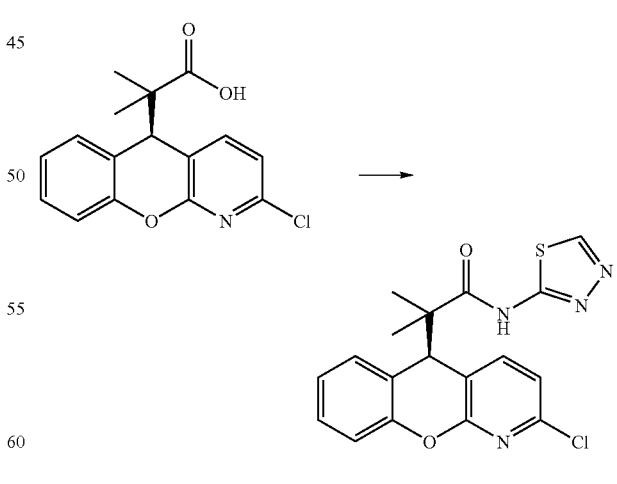

Step 1

The product of Step 1 (162a) was prepared from the R isomer of Preparation 30 (30a) in the same manner described above for the preparation of the title compound of Example 76.

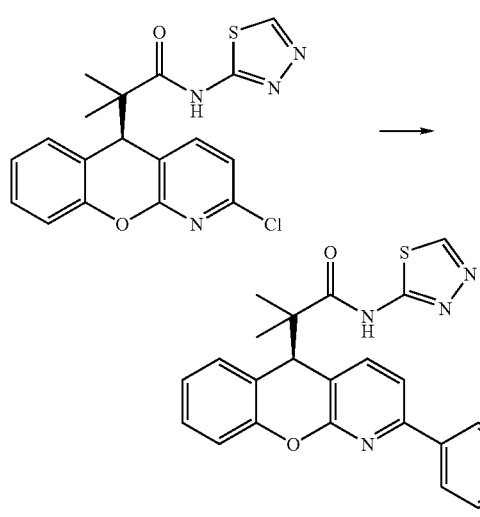

Step 2

4-Methoxyphenyl boronic acid (24 mg, 0.156 mmol) and 134a (30 mg, 0.078 mmol) were combined in a microwave reaction vessel and taken up in DMF (1 mL) and 2M aqueous potassium phosphate (0.2 mL). Nitrogen gas was bubbled through the solution for 5 min, at which point tetrakis(triphenylphosphine)palladium(0) (10 mg, 0.009 mmol) was added. The mixture was heated by microwave for 30 min at 100° C., then purified by preparative HPLC to give the title compound (21.2 mg, 60%) as a white solid. MS (ES+) m/z: 459 (M+H); LC retention time: 3.65 min.

Examples 163 to 167

The following Examples 163 to 167 were prepared from the title compound of Preparation 55e in the same manner as the preparation of the title compound of Example 162, using 2-amino-1,3,4-thiadiazole or 2-amino-5-methyl-1,3,4-thiadiazole in the first step and commercially available boronic acids in place of 4-methoxyphenyl boronic acid in the second step.

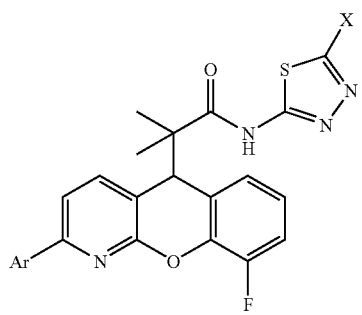

| Example No. | X | Ar | Rt (min) | M/z (MH)+ |
|---|---|---|---|---|
| 163 | H | *-C6H3(F)-O-iPr | 3.90 | 523 |
| 164 | H | *-C6H4-C(O)N(Me)2 | 3.20 | 518 |
| 165 | H | *-C6H3(F)-C(O)N(Me)2 | 3.25 | 536 |
| 166 | Me | *-C6H4-C(O)N(Me)2 | 3.31 | 532 |

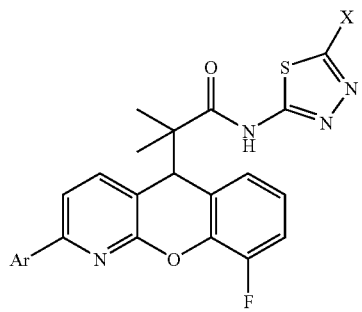

| Example No. | X | Ar | Rt (min) | M/z (MH)+ |
|---|---|---|---|---|
| 167 | Me | *-C6H3(F)-C(O)N(Me)2 | 3.40 | 550 |

Examples 163ᵃ to 166ᵃ

The following Examples 163a to 166a were prepared from the title compound of Preparation 56a in the same manner as the preparation of the title compound of Example 162, using 2-amino-1,3,4-thiadiazole or 2-amino-5-methyl-1,3,4-thiadiazole or 5-amino-3-methyl-1,2,4-thiadiazole in the first step and commercially available boronic acids in place of 4-methoxyphenyl boronic acid in the second step.

| Example No. | Structure | Rt (min) | M/z (MH)+ |
|---|---|---|---|
| 163ᵃ | 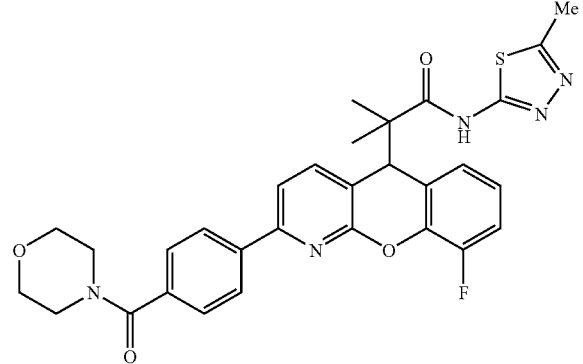 | 3.31 | 574 |
| 164ᵃ | 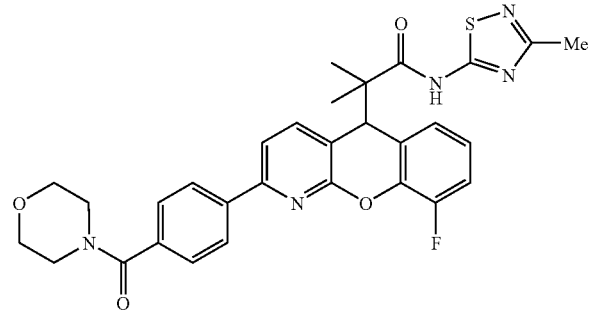 | 3.40 | 574 |

| Example No. | Structure | Rt (min) | M/z (MH)+ |
|---|---|---|---|
| 165a | | 3.38 | 550 |
| 166a | | 3.33 | 532 |

163a: ¹H NMR (400 MHz, CHLOROFORM-D) δ ppm 1.25 (d, J=13.85 Hz, 6 H) 2.77 (s, 3 H) 3.44-3.93 (m, 8 H) 4.65 (s, 1 H) 6.91 (d, J=7.81 Hz, 1 H) 7.00-7.07 (m, 1 H) 7.11-7.18 (m, 1 H) 7.53 (d, J=8.06 Hz, 2 H) 7.59 (d, J=7.81 Hz, 1 H) 7.70 (d, J=7.81 Hz, 1 H) 8.11 (d, J=8.31 Hz, 2 H)

164a: ¹H NMR (400 MHz, CHLOROFORM-D) δ ppm 1.24 (d, J=6.04 Hz, 6 H) 2.59 (s, 3 H) 3.42-3.93 (m, 8 H) 4.62 (s, 1 H) 6.89 (d, J=7.81 Hz, 1 H) 6.99-7.06 (m, 1 H) 7.12-7.18 (m, 1 H) 7.50-7.64 (m, 4 H) 8.11 (d, J=8.31 Hz, 2 H)

165a: ¹H NMR (400 MHz, CHLOROFORM-D) δ ppm 1.25 (d, J=12.59 Hz, 6 H) 2.78 (s, 3 H) 3.00 (d, J=1.26 Hz, 3 H) 3.19 (s, 3 H) 4.70 (s, 1 H) 6.94 (d, J=7.81 Hz, 1 H) 7.00-7.07 (m, 1 H) 7.11-7.18 (m, 1 H) 7.51 (t, J=7.30 Hz, 1 H) 7.57 (d, J=7.81 Hz, 1 H) 7.74 (d, J=7.81 Hz, 1 H) 7.88 (d, J=9.57 Hz, 2 H)

Example 168

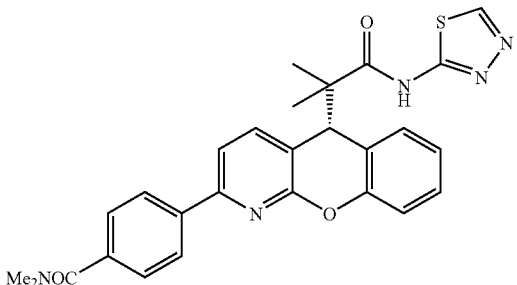

The title compound was prepared from the title compound of Example 162 Step 1 (162a) in the manner described above for the preparation of the title compounds of Example 162. MS (ES+) m/z: 500 (M+H); LC retention time: 3.22 min.

Examples 169 to 237

The following Examples 169 to 237 were prepared from the product of Preparation 53a in the manner described above for the preparation of the title compound of Example 162 from 162a, using commercially available boronic acids.

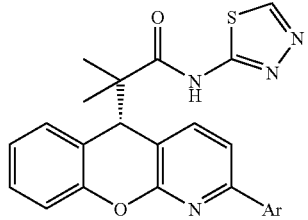
| Example No. | Ar | Rt (min) | Obs. MS Ion |
|---|---|---|---|
| 169 | *-C6H4-OMe | 3.65 | 459 |
| 170 | *-C6H4-Me | 3.81 | 443 |
| 171 | Ph | 3.06 | 429 |
| 172 | *-C6H4-C(O)NMe2 | 3.22 | 500 |
| 173 | *-C6H4-OCF3 | 4.03 | 513 |
| 174 | *-C6H4-CO2H | 3.42 | 473 |
| 175 | *-C6H4-Cl (ortho) | 3.65* | 463 |
| 176 | *-C6H4-NMe2 | 3.03* | 472 |
| 177 | 1-naphthyl | 3.84** | 479 |
| 178 | *-C6H4-Cl (para) | 3.96** | 463 |
| 179 | *-C6H4-Me (meta) | 3.84** | 443 |
| 180 | *-C6H4-Me (ortho) | 3.67** | 443 |

-continued
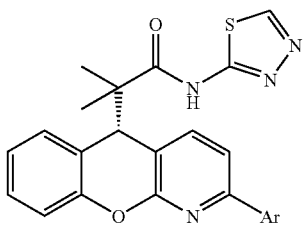
| Example No. | Ar | Rt (min) | Obs. MS Ion |
|---|---|---|---|
| 181 | *–C₆H₄–CF₃ (3-CF₃) | 4.02** | 497 |
| 182 | *–C₆H₄–CF₃ (4-CF₃) | 4.00** | 497 |
| 183 | *–C₆H₄–Cl (3-Cl) | 3.98** | 463 |
| 184 | *–C₆H₄–NHC(O)CH₃ (3-) | 3.33** | 486 |
| 185 | *–C₆H₄–OMe (2-) | 3.60** | 459 |
| 186 | 2-naphthyl | 4.02** | 479 |
| 187 | 3-pyridyl | 2.41** | 430 |
| 188 | *–C₆H₃–(Me)₂ (3,4-diMe) | 3.97** | 457 |
| 189 | *–C₆H₄–OH (2-) | 3.84** | 445 |
| 190 | *–C₆H₄–OH (2-) | 3.84** | 445 |
| 191 | *–C₆H₄–OH (4-) | 3.31** | 445 |

-continued
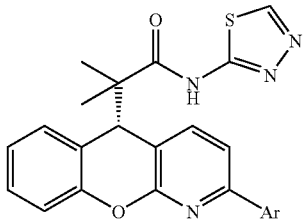
| Example No. | Ar | Rt (min) | Obs. MS Ion |
|---|---|---|---|
| 192 | *-C6H4-CO2Me (para) | 3.73** | 487 |
| 193 | *-C6H4-NHC(O)Me (para) | 3.30** | 486 |
| 194 | *-C6H4-NHSO2Me (para) | 3.23** | 522 |
| 195 | *-C6H4-NHSO2Me (meta) | 3.25** | 522 |
| 196 | *-C6H4-F (para) | 3.72** | 447 |
| 197 | *-C6H4-C6H5 (para, biphenyl) | 4.11** | 505 |
| 198 | *-C6H4-OPh (para) | 4.08** | 521 |
| 199 | *-C6H4-SMe (para) | 3.85** | 475 |
| 200 | *-C6H4-NH2 (para) | 2.69** | 444 |
| 201 | *-C6H4-COMe (para) | 3.51** | 471 |

-continued
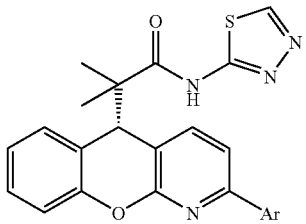
| Example No. | Ar | Rt (min) | Obs. MS Ion |
|---|---|---|---|
| 202 | 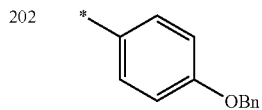 | 4.06** | 535 |
| 203 | 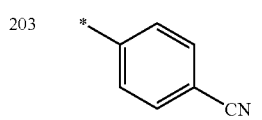 | 3.52** | 454 |
| 204 | 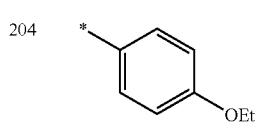 | 3.81** | 473 |
| 205 | 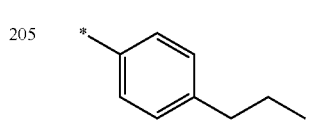 | 4.11** | 471 |
| 206 | 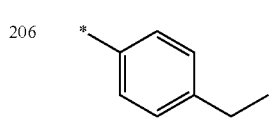 | 3.94** | 457 |
| 207 | 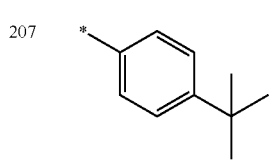 | 4.15** | 485 |
| 208 | 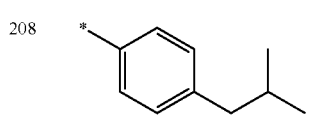 | 4.22** | 485 |
| 209 | 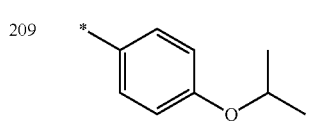 | 3.89** | 487 |
| 210 | 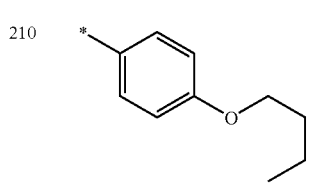 | 4.12** | 501 |
| 211 | 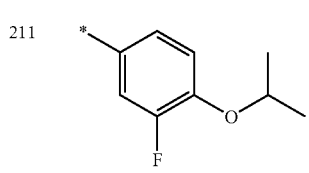 | 3.92 | 505 |

-continued
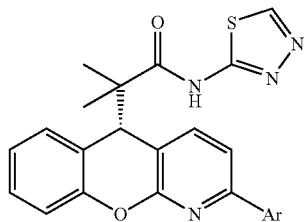
| Example No. | Ar | Rt (min) | Obs. MS Ion |
|---|---|---|---|
| 212 | 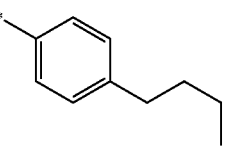 | 4.28 | 485 |
| 213 | 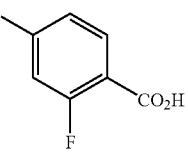 | 3.43 | 491 |
| 214 | 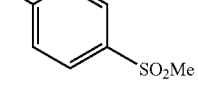 | 3.16 | 507 |
| 215 | 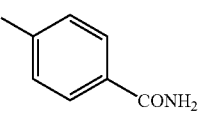 | 3.06 | 472 |
| 216 | 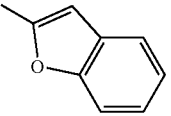 | 3.94 | 469 |
| 217 | 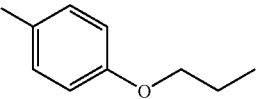 | 4.02 | 487 |
| 218 | 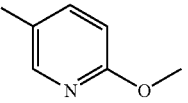 | 3.50 | 460 |
| 219 |  | 2.38 | 430 |
| 220 | 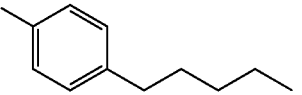 | 4.44 | 499 |

-continued
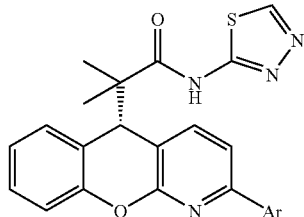
| Example No. | Ar | Rt (min) | Obs. MS Ion |
|---|---|---|---|
| 221 | *-C6H4-cyclohexyl (4-cyclohexylphenyl) | 4.47 | 511 |
| 222 | 2-Me-4-butylphenyl | 4.28 | 499 |
| 223 | 3-F-4-OH-phenyl | 3.35 | 463 |
| 224 | 3-Me-4-OiPr-phenyl | 4.12 | 501 |
| 225 | 3-F-phenyl | 3.72 | 447 |
| 226 | 4-SEt-phenyl | 4.01 | 489 |
| 227 | 4-SO2Et-phenyl | 3.26 | 521 |
| 228 | 4-SO2iPr-phenyl | 3.39 | 535 |
| 229 | 3-F-4-acetyl-phenyl | 3.63 | 489 |
| 230 | 3-F-4-OPr-phenyl | 4.01 | 505 |

-continued
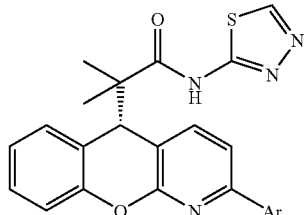
| Example No. | Ar | Rt (min) | Obs. MS Ion |
|---|---|---|---|
| 231 | 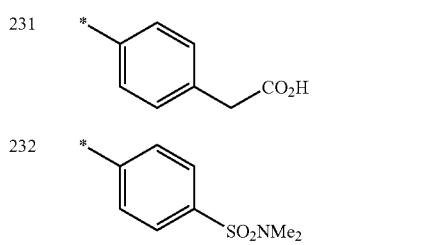 | 3.33 | 487 |
| 232 | 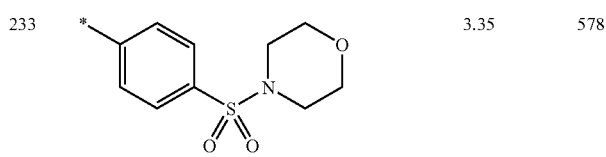 | 3.34 | 536 |
| 233 | 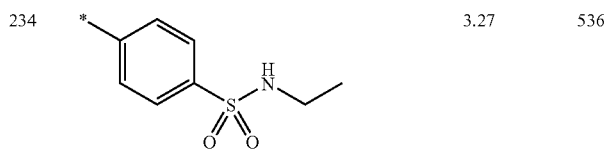 | 3.35 | 578 |
| 234 | 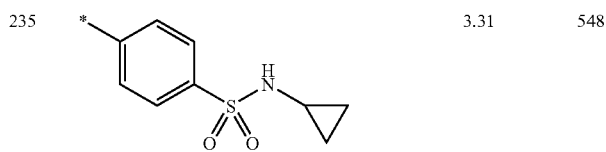 | 3.27 | 536 |
| 235 | 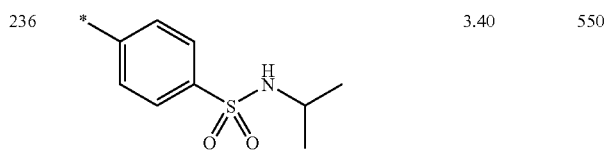 | 3.31 | 548 |
| 236 | 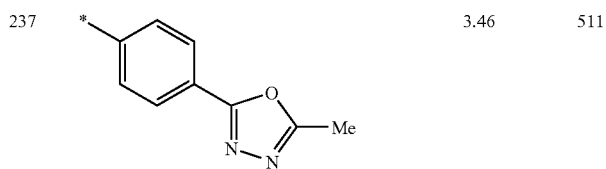 | 3.40 | 550 |
| 237 | | 3.46 | 511 |
*Analytical HPLC Method B
**Analytical HPLC Method C

Example 238

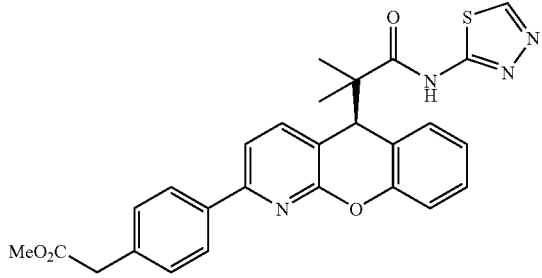

To a solution of the title compound of Example 231 (11 mg, 0.023 mmol) in benzene (0.3 mL) and methanol (0.3 mL) at room temperature was added trimethylsilyl diazomethane (0.037 mL, 0.2 mmol). The reaction mixture was allowed to sit at room temperature for 30 min, then quenched with the addition of 2 drops of glacial acetic acid. The reaction mixture was concentrated, and purified by preparative TLC (0.5 mm silica, 100 cm×100 cm, 40% ethyl acetate in hexanes). The lower of the two bands was isolated, giving the title compound (6 mg, Y=52%) as a colorless solid. MS (ES+) m/z: 501; LC retention time: 3.50 min. $^1$H NMR (400 MHz, CHLOROFORM-D) δ ppm 1.23 (s, 3 H) 1.25 (s, 3 H) 3.67 (s, 2 H) 3.69 (s, 3 H) 4.71 (s, 1 H) 6.99-7.05 (m, 1 H) 7.19 (d, J=7.63 Hz, 1 H) 7.28-7.33 (m, 2H) 7.37 (d, J=8.14 Hz, 2 H) 7.48 (d, J=8.14 Hz, 1 H) 7.67 (d, J=7.63 Hz, 1 H) 7.98 (d, J=8.14 Hz, 2 H) 8.88 (s, 1 H).

Example 239

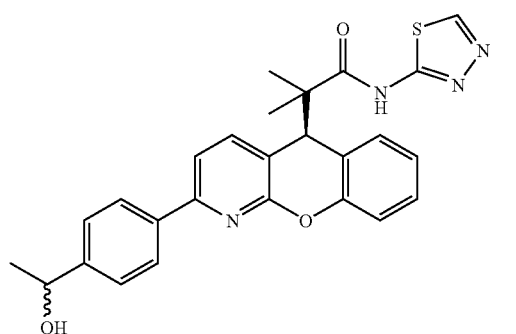

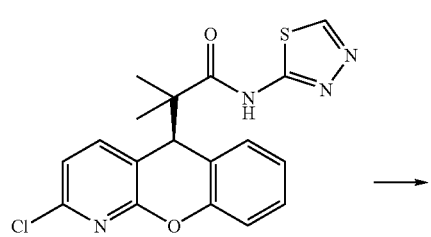

-continued

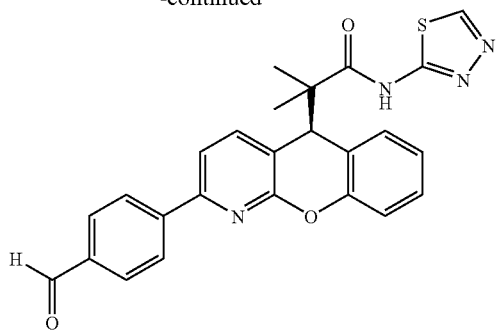

Step 1

The product of Step 1 was prepared in the manner described above for the preparation of the title compounds of Examples 169 to 237. MS (ES+) m/z: 457; LC retention time: 3.44 min.

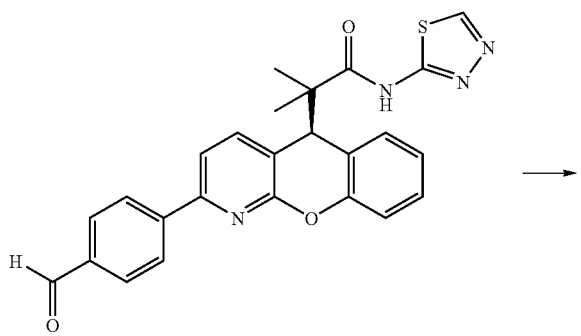

Step 2

To a solution of the product of Step 1 (20 mg, 0.044 mmol) in THF (1 mL) was added methylmagnesium bromide (3M in diethyl ether, 0.04 mL) dropwise. The reaction mixture was stirred at room temperature for 1 h, then quenched with the addition of methanol, concentrated, and purified by preparative HPLC to afford the title compound as a mixture of coeluting diastereoisomers (16 mg, Y=77%). MS (ES+) m/z: 473; LC retention time: 3.34 min.

Example 239

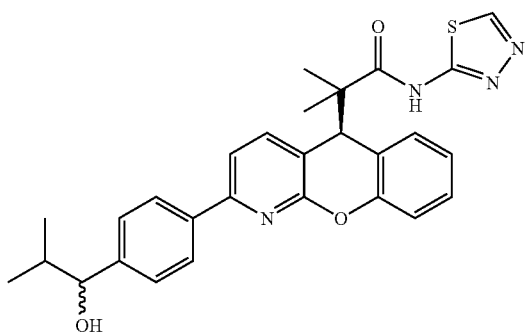

The title compound was obtained from the product of Step 1 of Example 239 in the manner described for the preparation of the title compound of Example 239. MS (ES+) m/z: 501; LC retention time: 3.65 min.

Example 241

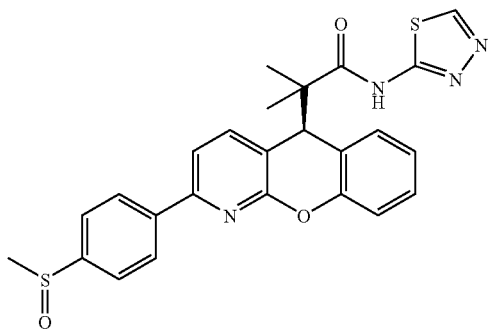

To a solution of the title compound of Example 199 (20 mg, 0.042 mmol) in dichloromethane (1 mL) at 0° C. was added m-chloroperbenzoic acid (containing ~30% 3-chlorobenzoic acid, 10 mg, 0.042 mmol). After 5 min at 0° C., the solvent was removed and exchanged with methanol. This solution was purified by preparative HPLC to provide the product, which was lyophilized from acetonitrile/water to give the title compound (10 mg, Y=39%) as a white powder. MS (ES+) m/z: 491; LC retention time: 3.08 min.

Example 242

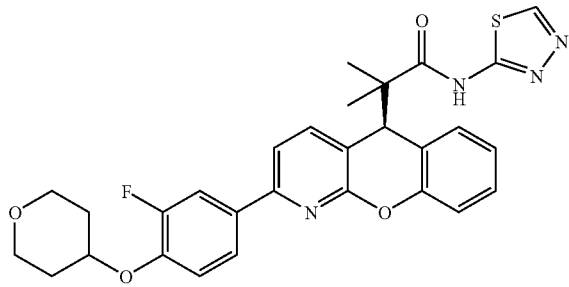

The title compound of Example 223 (21 mg, 0.045 mmol) was azeotroped to dryness from toluene, then dissolved in THF (0.5 mL). To this solution were sequentially added tetrahydro-4H-pyran-4-ol (0.0065 mL, 0.068 mmol), triphenyl phosphine (18 mg, 0.068 mmol), and diisopropyldiazodicarboxylate (DIAD) (0.013 mL, 0.068 mmol). The reaction mixture was allowed to stir at room temperature for 3 h 20 min, then concentrated and purified by preparative TLC (silica, 0.5 mm, 100 cm×100 cm, 50% ethyl acetate in hexanes) to give the title compound (11 mg, Y=45%) as a white powder. MS (ES+) m/z: 547; LC retention time: 3.69 min. $^1$H NMR (500 MHz, Solvent) δ ppm 1.09 (s, 3 H) 1.17 (s, 3 H) 1.68-1.75 (m, 1 H) 1.76-1.83 (m, 1 H) 2.04-2.20 (m, 2 H) 3.39-3.49 (m, 2 H) 3.96 (dd, J=11.68, 3.71 Hz, 1 H) 4.04 (dd, J=11.68, 3.71 Hz, 1 H) 4.48 (s, 1 H) 4.77-4.86 (m, 1 H) 7.00-7.05 (m, 2 H) 7.14 (d, J=7.15 Hz, 1 H) 7.24-7.26 (m, 3 H) 7.29 (d, J=7.70 Hz, 1 H) 7.43 (d, J=8.25 Hz, 1 H) 7.64-7.68 (m, 1 H) 7.82 (dd, J=11.96, 2.06 Hz, 1 H) 8.33 (s, 1 H).

Examples 243 to 244

The following Examples 243 to 244 were prepared in the manner described above for the preparation of the title compound of Example 242.

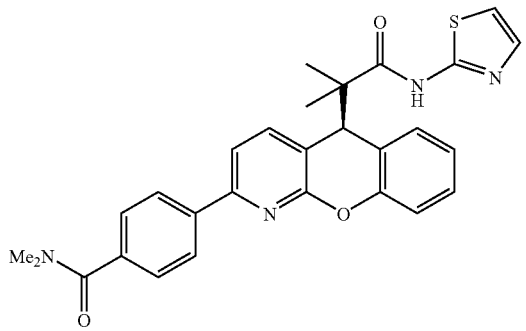

| Example No. | R | Rt (min) | Obs. MS Ion |
|---|---|---|---|
| 243 | cyclohexyl | 4.20 | 545 |
| 244 | cyclopentyl | 4.13 | 531 |

Example 245

Step 1

A stream of nitrogen gas was bubbled through mixture of the title compound of Preparation 30b (40 mg, 0.13 mmol), 4-(dimethylcarbamoyl)phenylboronic acid (50 mg, 0.26 mmol), potassium phosphate (2.0 M, 0.36 mL) and tetrakis (triphenylphosphine)palladium(0) (15 mg, 0.014 mmol) for 10 min. The mixture was then heated at 100° C. for 2 h, then filtered through a syringe-tip filter (0.45 micron, PTFE), and purified by preparative HPLC to give the product (245 a, (S)-2-(2-(4-(dimethylcarbamoyl)phenyl)-5H-chromeno[2,3-b]pyridine-5-yl)-2-methylpropanoic acid, 43 mg, 79% yield) as a white powder. MS (ES+) m/z: 417; LC retention time: 3.29 min.

Step 2

The title compound (245b) was prepared from 245a in a similar manner as described above for the preparation of Examples 73 to 76. MS (ES+) m/z: 499; LC retention time: 3.42 min.

Example 246

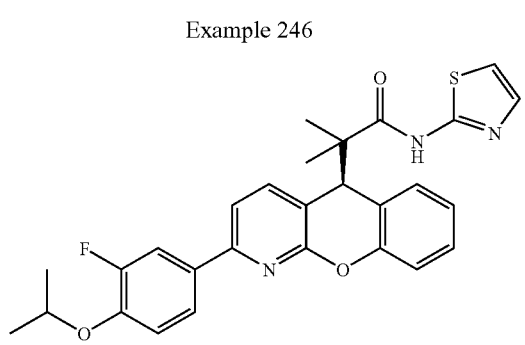

The title compound was prepared in the manner described above for the preparation of the title compound of Example 246. MS (ES+) m/z: 504; LC retention time: 4.07 min. $^1$H NMR (400 MHz, CHLOROFORM-D) δ ppm 1.15 (s, 3 H) 1.17 (s, 3 H) 1.38 (d, J=6.10 Hz, 6 H) 4.57 (s, 1 H) 4.58-4.66 (m, 1 H) 7.17 (d, J=7.12 Hz, 1 H) 7.26-7.32 (m, 2 H) 7.37 (d, J=8.14 Hz, 1 H) 7.40 (d, J=3.56 Hz, 1 H) 7.58 (d, J=8.14 Hz, 1 H) 7.72 (d, J=9.66 Hz, 1 H) 7.77 (dd, J=12.46, 2.29 Hz, 1 H).

Example 247

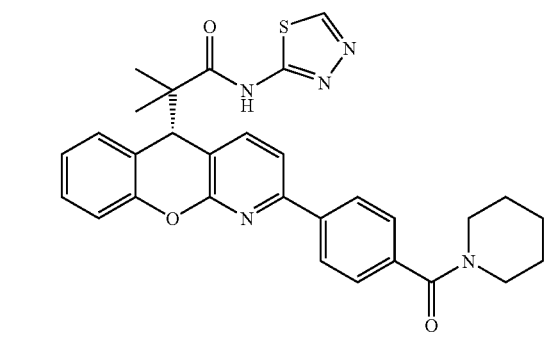

A solution of the title compound of Example 174 (31 mg, 0.066 mmol), triethylamine (0.028 mL, 0.20 mmol), HOBT monohydrate (12 mg, 0.086 mmol), EDC (16 mg, 0.086 mmol) and piperidine (0.013 mL, 0.132 mmol) in acetonitrile (0.5 mL) was heated for 12 h at 45° C. Purification by preparative HPLC gave the title compound (15 mg, 35%), which was lyophilized from acetonitrile/water to give an amorphous, white solid. MS (ES+) m/z: 540; LC retention time: 3.57 min.

$^1$H NMR (400 MHz, CHLOROFORM-D) δ ppm 1.24 (s, 3 H) 1.26 (s, 3H) 1.52 (s, 2 H) 1.68 (s, 4 H) 3.35 (s, 2 H) 3.73 (s, 2 H) 4.71 (s, 1 H) 6.98-7.10 (m, 1H) 7.19 (d, J=7.12 Hz, 1 H) 7.30 (d, J=2.54 Hz, 2 H) 7.49 (t, J=8.39 Hz, 3 H) 7.69 (d, J=7.63 Hz, 1 H) 8.04 (d, J=8.14 Hz, 2 H) 8.88 (s, 1 H)

Examples 248 to 361

The following Examples 248 to 362 were prepared from the title compounds of Examples 174 and 213, and Preparations 53 and 54 in a manner similar to that described for the preparation of the title compound of Example 247.

| Example No. | NR$_a$R$_b$ | X$^3$ | Rt (min) | M/z (MH)$^+$ |
|---|---|---|---|---|
| 248 | NEt$_2$ | H | 3.66 | 542 |
| 249 | piperidine | F | 3.66 | 558 |
| 250 | NMe$_2$ | F | 3.30 | 518 |
| 251 | NMeEt | H | 3.38* | 514 |
| 252 | pyrrolidine | H | 3.42* | 526 |
| 253 | NHMe | F | 3.16 | 504 |
| 254 | NMe(n-Pr) | H | 3.53* | 528 |
| 255 | NMe(Bn) | H | 3.73* | 576 |
| 256 | N-methylpiperazine | H | 2.66* | 555 |
| 257 | morpholine | H | 3.21* | 542 |

-continued
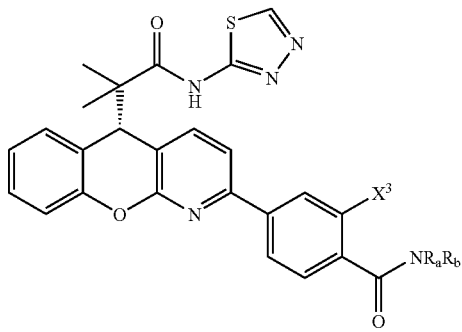
| Example No. | NR$_a$R$_b$ | X$^3$ | Rt (min) | M/z (MH)$^+$ |
|---|---|---|---|---|
| 258 | NMe(i-Pr) | H | 3.50* | 528 |
| 259 | NEt2 | F | 3.56 | 546 |
| 260 | NMe2 | Cl | 3.41 | 534 |
| 261 | piperidine | H | 3.57 | 540 |
| 262 | NEt$_2$ | Ome | 3.51 | 558 |
| 263 | NEt$_2$ | Cl | 3.67 | 562 |
| 264 | piperidine | Cl | 3.58 | 575 |
| 265 | piperidine | Ome | 3.58 | 570 |
| 266 | piperidine | F | 3.66 | 558 |
| 267 | NMe(CH$_2$)$_2$CN | H | 3.08* | 539 |
| 268 | 4-Me-piperidine | H | 3.73* | 554 |
| 269 | 4-OH-piperidine | H | 3.11* | 556 |
| 270 | NMe(CH$_2$)$_2$CH(CH$_3$)$_2$ | H | 3.80* | 556 |
| 271 | 3,3-dimethylpiperidinyl | H | 3.81* | 568 |
| 272 | 2-(methoxymethyl)pyrrolidinyl | H | 3.49* | 570 |
| 273 | 2,6-dimethylmorpholinyl | H | 3.49* | 570 |
| 274 | 4-acetylpiperazinyl | H | 3.04* | 583 |
| 275 | 4-(2-hydroxyethyl)piperazinyl | H | 3.30* | 584 |
| 276 | N(Me)(CH$_2$)$_2$Ph | H | 3.75* | 590 |

-continued
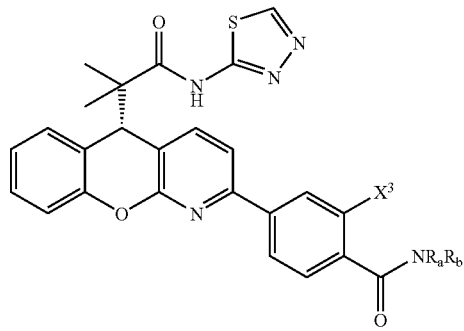
| Example No. | NRaRb | X³ | Rt (min) | M/z (MH)+ |
|---|---|---|---|---|
| 277 | (acetyl-diazepane) | H | 3.05* | 597 |
| 278 | 4-Bn-piperidine | H | 4.04* | 630 |
| 279 | (4-hydroxymethyl-piperidine) | H | 3.19* | 570 |
| 280 | (tetrahydroisoquinoline) | H | 3.80* | 588 |
| 281 | 4-Ph-piperidine | H | 3.92* | 616 |
| 282 | (prolinamide) | H | 3.03* | 569 |
| 283 | (4-ethylsulfonyl-piperazine) | H | 3.19* | 633 |
| 284 | (3-hydroxy-piperidine) | H | 3.17* | 556 |
| 285 | (2-methoxymethyl-pyrrolidine) | H | 3.48* | 570 |
| 286 | NMe(CH₂)₂SO₂Me | H | 3.03* | 592 |
| 287 | (4,4-difluoro-piperidine) | H | 349* | 576 |

-continued
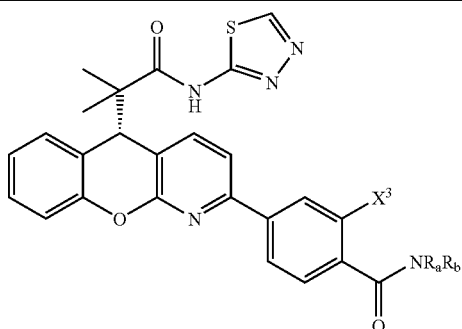
| Example No. | NRₐRᵦ | X³ | Rt (min) | M/z (MH)⁺ |
|---|---|---|---|---|
| 288 | 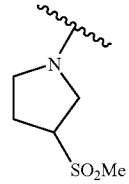 | H | 3.00* | 604 |
| 289 | 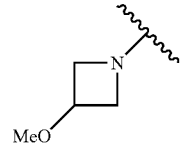 | H | 3.30* | 542 |
| 290 | 4-(CF₃)-piperidine | H | 3.71* | 608 |
| 291 | 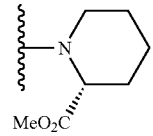 | H | 359* | 598 |
| 292 | NMe(n-Bu) | H | 3.67* | 542 |
| 293 | NMeCH₂CO₂Me | H | 3.22* | 558 |
| 294 | NMe(CH₂)₂OH | H | 3.02* | 530 |
| 295 | NMe(CH₂)₂OMe | H | 3.27* | 544 |
| 296 | 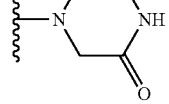 | H | 2.91* | 555 |
| 297 | 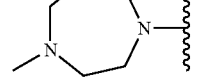 | H | 2.56* | 569 |
| 298 | 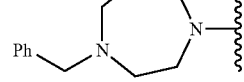 | H | 2.80* | 645 |
| 299 | 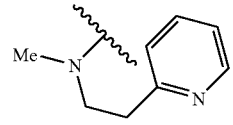 | H | 2.67* | 591 |

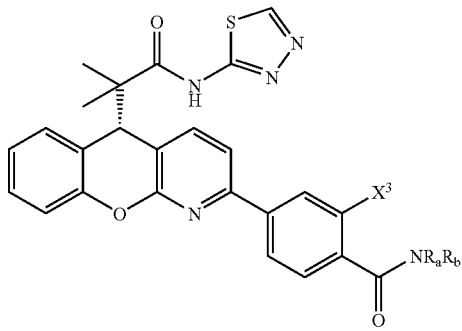
| Example No. | NRaRb | X³ | Rt (min) | M/z (MH)+ |
|---|---|---|---|---|
| 300 | ![piperidine with 4,4-F2] | H | 3.53* | 576 |
| 301 | Me-N(CH2-4-pyridyl) | H | 2.66* | 577 |
| 302 | NMe(CH2)2O(t-Bu) | H | 3.70* | 586 |
| 303 | HO-CH2CH2-N(diazepane) | H | 2.58* | 599 |
| 304 | N((CH2)2OH)2 | H | 2.90* | 560 |
| 305 | 3,5-diMe-piperidine | H | 3.90* | 568 |
| 306 | 3-AcHN-pyrrolidine | H | 3.05* | 583 |
| 307 | 3-Me2N-pyrrolidine | H | 2.58* | 569 |
| 308 | 3-Me2N-pyrrolidine (ent) | H | 2.58* | 570 |
| 309 | 4-OMe-piperidine | H | 3.39* | 570 |

-continued
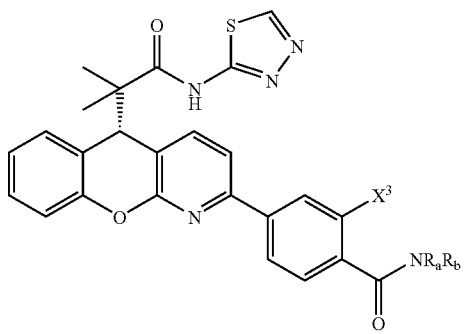
| Example No. | NR$_a$R$_b$ | X$^3$ | Rt (min) | M/z (MH)$^+$ |
|---|---|---|---|---|
| 310 |  | H | 2.99* | 590 |
| 311 |  | H | 2.95* | 569 |
| 312 |  | H | 3.03* | 569 |
| 313 | 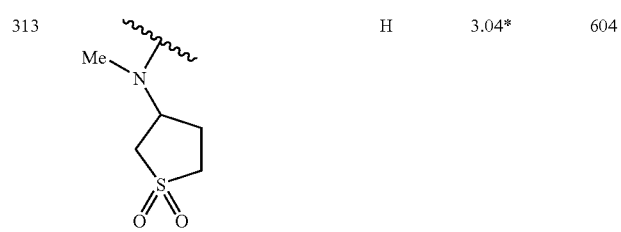 | H | 3.04* | 604 |
| 314 | 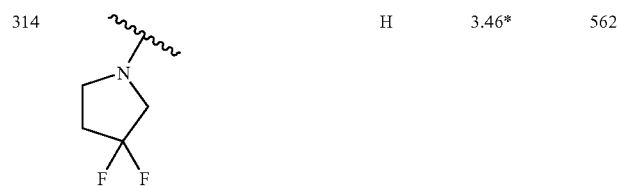 | H | 3.46* | 562 |
| 315 | 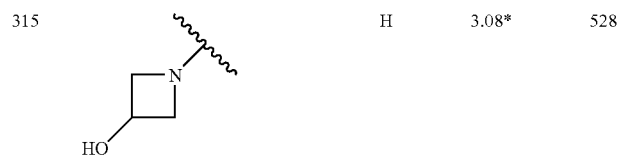 | H | 3.08* | 528 |
| 316 | 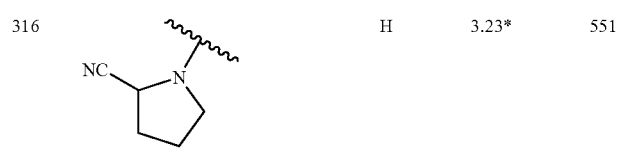 | H | 3.23* | 551 |

-continued
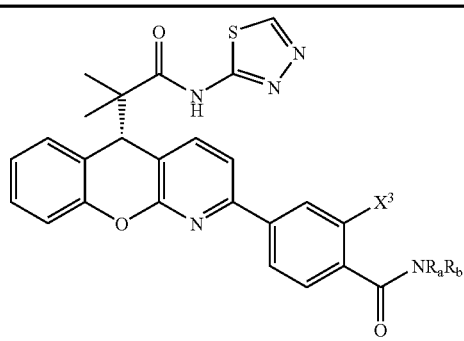
| Example No. | NR$_a$R$_b$ | X$^3$ | Rt (min) | M/z (MH)$^+$ |
|---|---|---|---|---|
| 317 | (2-isobutylpyrrolidin-1-yl) | H | 3.94* | 582 |
| 318 | (2-isopropylpyrrolidin-1-yl) | H | 3.83* | 568 |
| 319 | MeN(CH$_2$C(O)NMe$_2$)- | H | 3.03* | 571 |
| 320 | NEt(CH$_2$)$_2$OH | H | 3.16* | 544 |
| 321 | 4-(N-methylcarbamoyl)piperidin-1-yl | H | 3.08* | 597 |
| 322 | 4-oxoazepan-1-yl | H | 3.14* | 568 |
| 323 | 1,4-oxazepan-4-yl | H | 3.23* | 556 |
| 324 | 4-acetylpiperazin-1-yl | F | 3.12 | 601 |
| 325 | (2-(methoxymethyl)pyrrolidin-1-yl) | F | 3.58 | 588 |
| 326 | NMe(CH$_2$)$_2$CN | F | 3.14 | 557 |
| 327 | morpholine | F | 3.27 | 560 |

-continued
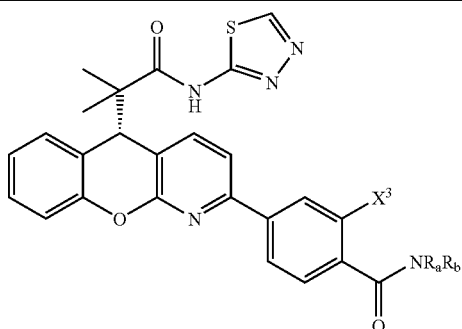
| Example No. | NRₐRᵦ | X³ | Rt (min) | M/z (MH)⁺ |
| --- | --- | --- | --- | --- |
| 328 | morpholine | Cl | 3.39 | 576 |
| 329 | NMe(i-Pr) | F | 3.57 | 546 |
| 330 | (S)-2-(methoxymethyl)pyrrolidinyl | Cl | 3.70 | 604 |
| 331 | (S)-2-(hydroxymethyl)pyrrolidinyl | H | 3.25 | 556 |
| 332 | (R)-2-(methoxymethyl)pyrrolidinyl | H | 3.25 | 556 |
| 333 | pyrrolidine | F | 3.44 | 544 |
| 334 | 4,4-difluoropiperidinyl | F | 3.61 | 594 |
| 335 | 3,3-difluoropyrrolidinyl | F | 3.51 | 580 |
| 336 | NEtMe | F | 3.47 | 532 |
| 337 | 3,3,4,4-tetrafluoropyrrolidinyl | F | 3.69 | 616 |
| 338 | NMe(CH₂)CO₂H | H | 3.06 | 544 |
| 339 | 4,4-difluoropiperidinyl | Cl | 3.69 | 610 |

-continued
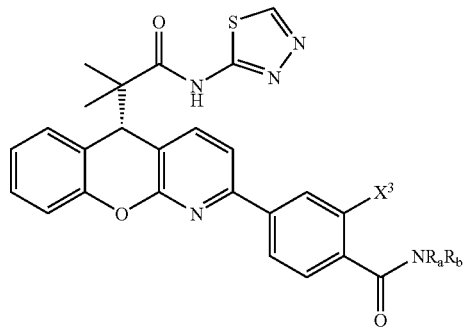
| Example No. | NRₐRᵦ | X³ | Rt (min) | M/z (MH)⁺ |
|---|---|---|---|---|
| 340 | 3,3-difluoropyrrolidinyl | Cl | 3.59 | 596 |
| 341 | pyrrolidine | Cl | 3.57 | 560 |
| 342 | 2-(methoxymethyl)pyrrolidinyl | F | 3.30 | 574 |
| 343 | NMe(n-Pr) | F | 3.60 | 546 |
| 344 | 2-(hydroxymethyl)pyrrolidinyl | F | 3.30 | 574 |
| 345 | NMeEt | Cl | 3.49 | 548 |
| 346 | NMe(n-Pr) | Cl | 3.69 | 562 |
| 347 | NMe₂ | Ome | 3.24 | 530 |
| 348 | NHMe | H | 3.17 | 486 |
| 349 | NHBn | H | XX* | XX |
| 350 | NH-cyclopropyl | H | 3.35* | 512 |
| 351 | NH-cyclopentyl | H | 3.43* | 540 |
| 352 | NH-t-Bu | H | 3.61* | 528 |
| 353 | NHiPr | H | 3.41* | 514 |
| 354 | NH(CH₂)₂Ph | H | 3.74* | 576 |
| 355 | NH(CH₂)₂Ome | H | 3.26* | 530 |
| 356 | NH(CH₂)₂C(CH₃)₃ | H | 3.70* | 542 |
| 357 | NH(CH₂)₂OH | H | 3.06* | 516 |
| 358 | NH(n-Pr) | H | 3.45* | 514 |

-continued

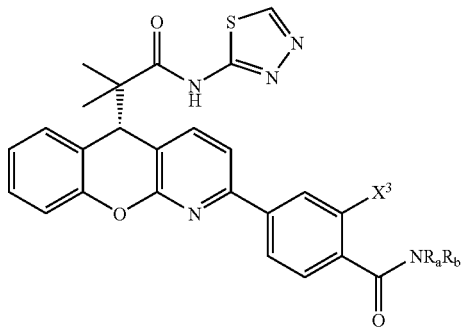

| Example No. | NR$_a$R$_b$ | X$^3$ | Rt (min) | M/z (MH)$^+$ |
|---|---|---|---|---|
| 359 | NH(CH$_2$)$_3$OH | H | 3.15* | 530 |
| 360 |  | H | 3.36* | 583 |
| 361 | NHMe | OMe | 3.30 | 516 |

*Analytical HPLC Method B

Examples 362 to 368

The following compounds 362 to 368 were prepared from the title compound of Preparation 57 in the same manner as described for the preparation of the title compound of Preparation 53a.

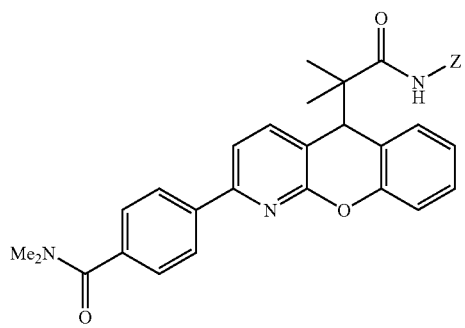

| Example No. | Z | Rt (min) | M/z (MH)$^+$ |
|---|---|---|---|
| 362 | t-Bu | 2.47* | 472 |
| 363 | 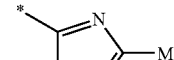 | 2.41* | 513 |
| 364 | 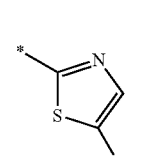 | 2.45* | 513 |

-continued

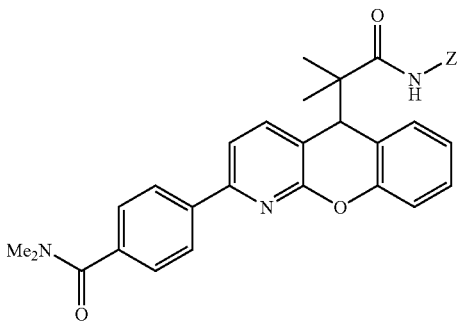

| Example No. | Z | Rt (min) | M/z (MH)$^+$ |
|---|---|---|---|
| 365 | 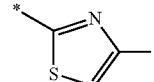 | 2.59* | 527 |
| 366 | 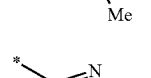 | 1.98* | 496 |
| 367 | CH$_2$CF$_3$ | 2.29* | 498 |
| 378 | 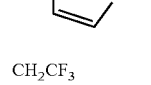 | 2.07* | 514 |

*Analytical HPLC Method B

Example 369

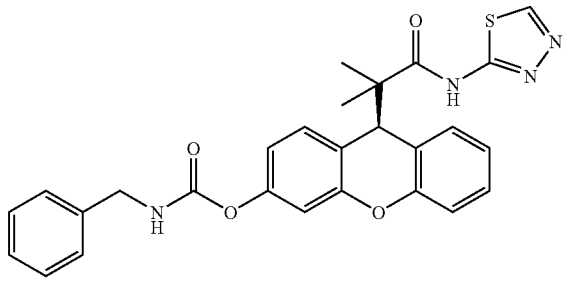

To a solution of the product of Example 90 (20 mg, 0.054 mmol) in dioxane (1 mL) was added diisopropylethyl amine (0.028 mL, 0.163 mmol) and (isocyanatomethyl)benzene (6.8 µL, 0.054 mmol), respectively. The resulting mixture was stirred at room temperature for 2 h. The reaction mixture was purified by prep-HPLC to yield pure (s)-9-(1-(1,3,4-thiadiazole-2ylamino)-2-methyl-1-oxopropan-2-yl)-9H-xanthen-3-yl benzylcarbamate (17 mg, 62% yield): MS (E+) m/z: 501 (M+H)$^+$; LC retention time: 3.54 min.

Examples 370 to 372

The following Examples 370 to 372 were prepared in the manner described above for the preparation of the title compound of Example 369.

| Example No. | Structure | Rt (min) | m/z (M + H)$^+$ |
|---|---|---|---|
| 370 | 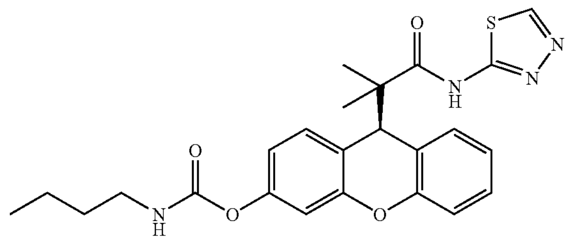 | 3.61 | 467 |
| 371 | 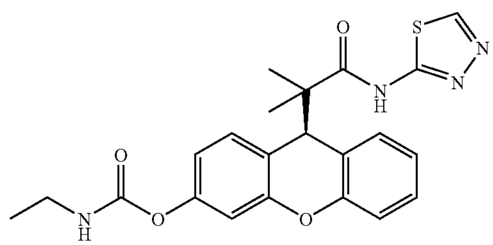 | 3.27 | 439 |
| 372 | 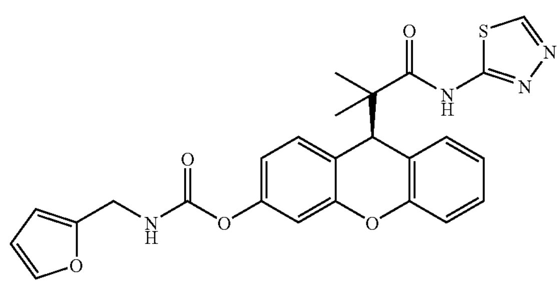 | 3.36 | 491 |

Examples 373 to 393

The following compounds 373 to 393 were prepared from the product of Step 2 of Example 101 (101b) in the manner described above for the preparation of the title compounds of Examples 370 to 372, using commercially available amines.

| Example No. | R^q | Rt (min) | M/z (MH)+ |
|---|---|---|---|
| 373 | cyclohexyl | 2.69* | 493 |
| 374 | n-octyl | 3.31* | 523 |
| 375 | (CH$_2$)$_2$Ph | 2.61* | 515 |
| 376 | *-CH$_2$CH$_2$-(2-thienyl) | 2.59* | 521 |
| 377 | *-CH$_2$-(4-F-phenyl) | 2.55* | 519 |
| 378 | *-CH(Me)-Ph | 2.63* | 515 |
| 379 | *-CH$_2$-(3,4-diCl-phenyl) | 2.87* | 569 |
| 380 | (CH$_2$)$_3$Ph | 2.74* | 529 |
| 381 | *-CH$_2$CH$_2$-(4-F-phenyl) | 2.61* | 533 |
| 382 | t-Bu | 2.57* | 467 |
| 383 | CH(CH$_3$)Et | 2.51* | 467 |
| 384 | *-CH$_2$CH$_2$-(4-OMe-phenyl) | 2.57* | 545 |
| 385 | Cyclohexyl | 3.90 | 493 |
| 386 | Me | 3.23 | 425 |
| 387 | Et | 3.26 | 439 |
| 388 | n-Bu | 3.61 | 467 |
| 389 | CH$_2$Ph | 3.60 | 501 |

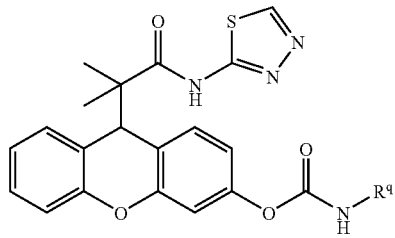

| Example No. | R^q | Rt (min) | M/z (MH)+ |
|---|---|---|---|
| 390 | (p-OMe)Ph | 3.56 | 517 |
| 391 | (p-OMe)PhCH$_2$ | 2.54* | 531 |
| 392 | CH$_2$(cyclohexyl) | 2.92* | 507 |
| 393 | *-CH$_2$-(2-furyl) | 2.36* | 491 |

*Analytical HPLC Method B

Example 394

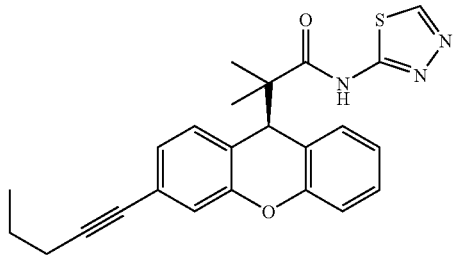

A mixture of the title compound of Preparation 53a (42 mg, 0.11 mmol), bis(triphenylphosphine)-palladium(II) chloride (7.6 mg, 0.011 mmol) and cuprous iodide (2.1 mg, 0.011 mmol) in diisopropyl amine (0.39 mL) and DMF (0.49 mL) was purged with a stream of nitrogen for 30 min. 1-Pentyne (0.012 mL, 0.12 mmol) was then added dropwise via syringe. The mixture was heated with stirring under nitrogen at 80° C. for 3 h 20 min, then purified by preparative HPLC, to give an oil which was lyophilized from acetonitrile/water to give an off-white solid (4.4 mg, 10%Y). MS (ES+) m/z: 420 (M+H); LC retention time: 3.63 min.

Example 395

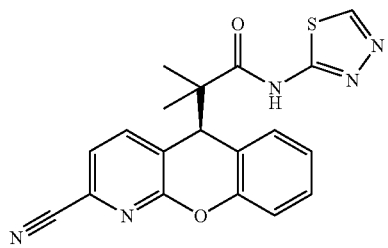

A stream of nitrogen gas was bubbled through a mixture of the product of Preparation 53a (50 mg, 0.13 mmol), Zn (CN)$_2$ (31 mg, 0.26 mmol), and tetrakis(triphenylphosphine)palladium(0) (30 mg, 0.026 mmol) in DMF (1 mL) for 10 min. The mixture was heated at 100° C. for 2.5 h, then filtered through a syringe-tip filter (0.45 micron, PTFE) and purified by preparative HPLC, giving material which contained residual triphenylphosphine oxide. The semipurified material was further purified by flash column chromatography (12 g silica, 60% ethyl acetate in hexanes to 70% ethyl acetate in hexanes) to give the title compound (21 mg, Y=43%) as a white powder. MS (ES+) m/z: 378 (M+H); LC retention time: 2.90 min. $^1$H NMR (400 MHz, MeOD) δ ppm 1.12 (s, 3 H) 1.15 (s, 3 H) 4.66 (s, 1 H) 7.14 (t, J=7.38 Hz, 1 H) 7.21-7.28 (m, 2 H) 7.37 (t, J=8.65 Hz, 1 H) 7.62 (d, J=7.63 Hz, 1 H) 7.83 (d, J=7.63 Hz, 1 H) 9.09 (s, 1 H)

Example 396

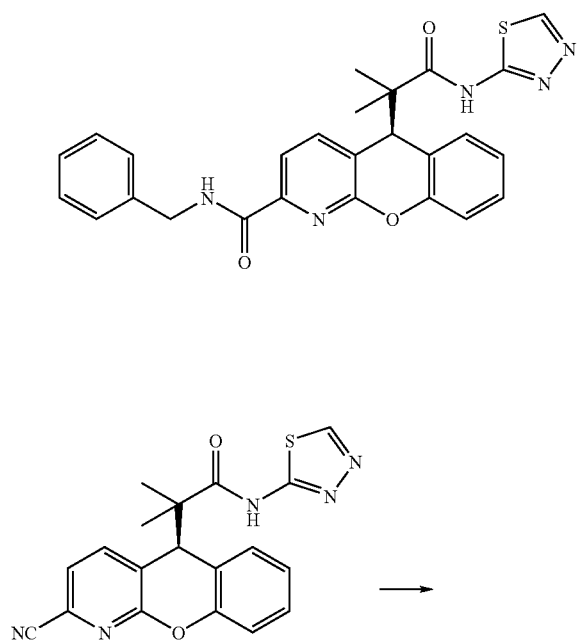

Step 1

A suspension of the title compound of Example 395 (8 mg, 0.021 mmol) in 1,4-dioxane (0.20 mL) and aqueous KOH (4N, 0.053 mL) was heated at 80° C. for 4.5 h. The reaction mixture was then partitioned between ethyl acetate and 1N aqueous HCl. The organic layer was dried over sodium sulfate and concentrated to give the product (398a) as a white solid (7 mg, Y=84%). MS (ES+) m/z: 397 (M+H); LC retention time: 2.75 min.

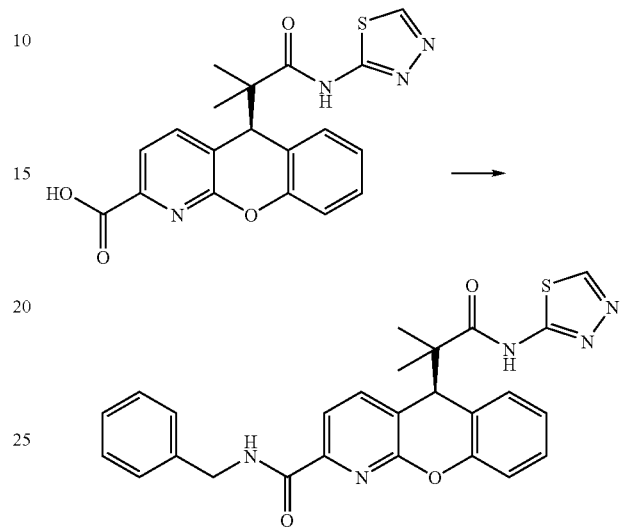

Step 2

To a soln of the product of Step 1 (396a) (10 mg, 0.025 mmol) in acetonitrile (1 mL) was added benzylamine (2.70 mg, 0.025 mmol), diisopropylethyl amine (0.013 mL, 0.076 mmol) and 1-(3-(dimethylamino)propyl)-3-ethyl-carbodiimide hydrochloride (7.25 mg, 0.038 mmol) and 1-hydroxybenzotriazole (5.79 mg, 0.038 mmol). The resulted mixture was heated to 50° C. for 2 h with stirring, then purified by preparative HPLC to give the desired product, which was lyophilized from acetonitrile/water to afford the title compound (12.25 mg, Y=86%) as a white solid. MS (ES+) m/z: 486 (M+H); LC retention time: 3.47 min. $^1$H NMR (400 MHz, CDCl$_3$) δ ppm 1.16 (d, J=5.54 Hz, 6 H) 4.51-4.66 (m, 2 H) 4.68 (s, 1 H) 6.98-7.04 (m, 1 H) 7.11-7.34 (m, 8 H) 7.74 (d, J=7.81 Hz, 1 H) 7.94 (d, J=7.81 Hz, 1 H) 8.15 (t, J=6.04 Hz, 1 H) 8.80 (s, 1 H).

Example 397

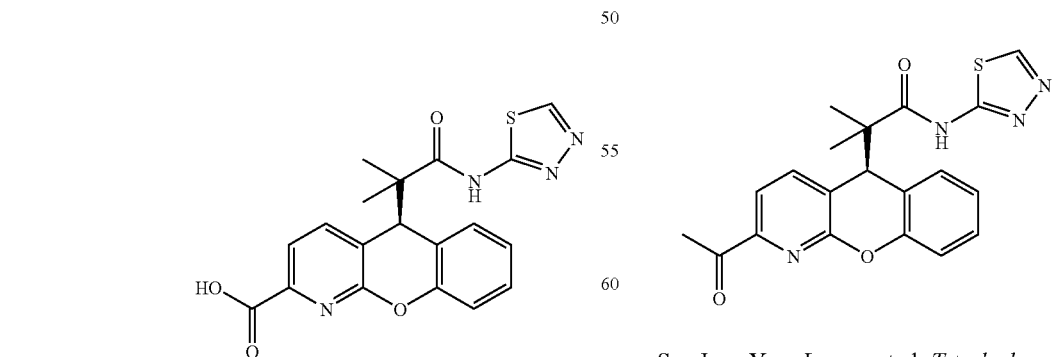

See Jean-Yves Legros et al. *Tetrahedron*, 2001, 57, 2507. To a solution of the product of the first step of Preparation 53 (53a) (30 mg, 0.078 mmol) in toluene (1 mL) was added triphenylphosphine (2.03 mg, 0.008 mmol) and Pd(dba)$_2$ (7.10 mg, 0.008 mmol). The resulting mixture was stirred at room temperature under argon (bubbling) for 15 min. Tributyl (1-ethoxyvinyl)stannane (28.0 mg, 0.078 mmol) was added and the resulting mixture was stirred at 110° C. for 3 h, then cooled to room temperature. Three drops of 1M HCl was added, and stirring was continued for 10 min at room temperature. The solvent was removed in vacuo, and the residue suspended in methanol, then filtered through a syringe-tip filter (0.45 micron, PTFE) and purified by preparative HPLC to afford the product which was lyophilized from acetonitrile/water to afford the title compound as a TFA salt. (22 mg, Y=72%). MS (ES+) m/z: 395 (M+H); LC retention time: 4.60 min. $^1$H NMR (400 MHz, chloroform-D) δ ppm 1.16 (s, 6 H) 2.67 (s, 3 H) 4.72 (s, 1 H) 6.97-7.03 (m, 1 H) 7.13-7.17 (m, 1 H) 7.23-7.28 (m, 2 H) 7.73 (s, 2 H) 8.82 (s, 1 H).

Example 398

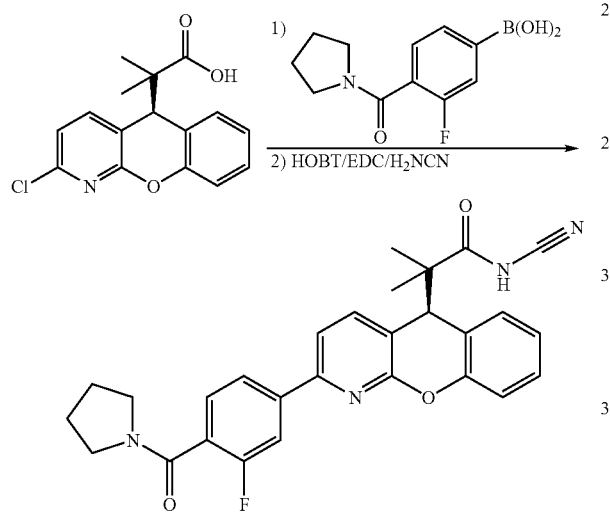

Step 1

A mixture of the product of Preparation 30b (800 mg, 2.6 mmol), 3-fluoro-4-(pyrrolidine-1-carbonyl)phenylboronic acid (1.7 g, 7.2 mmol), 2 M aqueous solution of potassium phosphate (9 mL, 18 mmol), and DMF (24 mL) was bubbled with nitrogen for 5 min before tetrakis(triphenylphosphine)palladium(0) (300 mg, 0.26 mmol) was added. The mixture was bubbled with nitrogen for an additional 5 min. The reaction mixture was stirred at 90° C. under nitrogen for 3 hr before concentrated in vacuo. The residue was mixed with water (50 mL), washed with 1:1 ethyl acetate/heptane mixture (30 mL). The organic mixture was extracted with water (3×15 mL). The combined aqueous solutions were decolorized with active charcoal, neutralized to pH=6-7 with 6N aqueous HCl solution (4 mL) and then 10% aqueous citric acid solution. Ethyl acetate (15 mL) was added and the mixture was stirred for 1 hr. The solid formed was filtered, washed with water (3×2 mL) and ethyl acetate (2×1 mL), and dried to give the product (1.1 g, Y=88%) as a white solid. MS (E+) m/z: 461 (M+H); LC retention time: 3.41 min.

Step 2

To a stirred mixture of the product of Step 1 (398a) (33 mg, 0.072 mmol), HOBT hydrate (22 mg, 0.14 mmol), anhydrous acetonitrile (1 ml), and N,N-diisopropylethylamine (0.13 ml, 0.72 mmol) was added EDC (41 mg, 0.22 mmol) at RT under nitrogen. The mixture was stirred at RT over night before concentrated. The residue was partitioned between dichloromethane (1 mL) and water (2 mL). The aqueous layer was separated and extracted with methylene chloride (2×1 mL). The combined organic solutions were dried (Na$_2$SO$_4$). Silica gel flash chromatography (20=>100% ethyl acetate in hexanes) gave the HOBT ester, which was dissolved in THF (2 mL). The obtained solution and 2 N aqueous NaOH (0.11 ml, 0.22 mmol) were added dropwise to a vigorously stirred cyanamide (20 mg, 0.48 mmol) solution in water (2.5 ml) simultaneously at 0° C. The reaction mixture was then stirred at RT for 1.5 h and concentrated in vacuo to remove THF. The aqueous residue was washed with diethyl ether (3 mL), neutralized with 6N aqueous HCl (0.036 mL), and extracted with ethyl acetate (3×1 mL). The combined ethyl acetate extracts were dried (Na$_2$SO$_4$) and concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title product (20 mg, Y=47%) as a TFA salt. MS (E+) m/z: 485 (M+H); LC retention time: 3.22 min. $^1$H NMR (400 MHz, MeOD) δ ppm 7.91-8.01 (m, 2 H) 7.79-7.86 (m, 2 H) 7.54 (t, J=7.43 Hz, 1 H) 7.41 (td, J=7.70, 1.50 Hz, 1 H) 7.26-7.33 (m, 2 H) 7.23 (td, J=7.37, 1.13 Hz, 1 H) 4.46 (s, 1 H) 3.63 (t, J=6.92 Hz, 2 H) 3.39 (t, J=6.55 Hz, 2 H) 1.99-2.06 (m, 2 H) 1.91-1.98 (m, 2 H) 1.06 (s, 3 H) 1.04 (s, 3 H).

Example 399

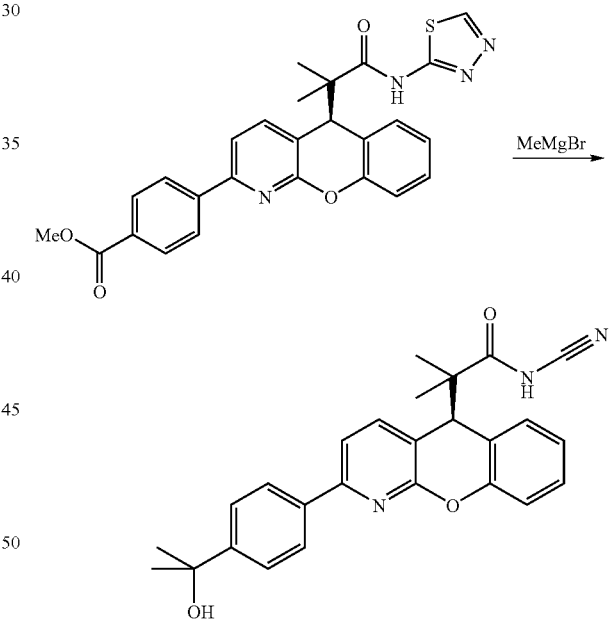

To a clear solution of the title compound of Example 192 (TFA salt, 13 mg, 0.022 mmol) in anhydrous THF (1 mL) was added methylmagnesium bromide solution (3 M in diethyl ether, 0.25 mL, 0.75 mmol) dropwise at −78° C. under nitrogen. The mixture was stirred at the same temperature for 20 min before ethyl acetate (0.2 mL) was added to quench the reaction at −78° C. After the reaction mixture was stirred at RT for 10 min, acetic acid (0.06 mL) was added. Concentration in vacuo and purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 4.5 mg, Y=32%) as a white solid. MS (E+) m/z: 428 (M+H); LC retention time: 3.18 min. $^1$H NMR (400 MHz, MeOD) δ ppm 8.00 (dt, J=8.60, 2.00 Hz, 2 H) 7.80 (d, J=8.00 Hz, 1 H) 7.73 (d, J=8.00 Hz, 1 H) 7.62 (dt, J=8.60, 2.00 Hz, 2 H) 7.38-7.43 (m, 1 H) 7.28-7.33 (m, 2H) 7.22 (td, J=7.40, 1.20 Hz, 1 H) 4.44 (s, 1 H) 1.58 (s, 6 H) 1.06 (s, 3 H) 1.05 (s, 3H).

Example 400

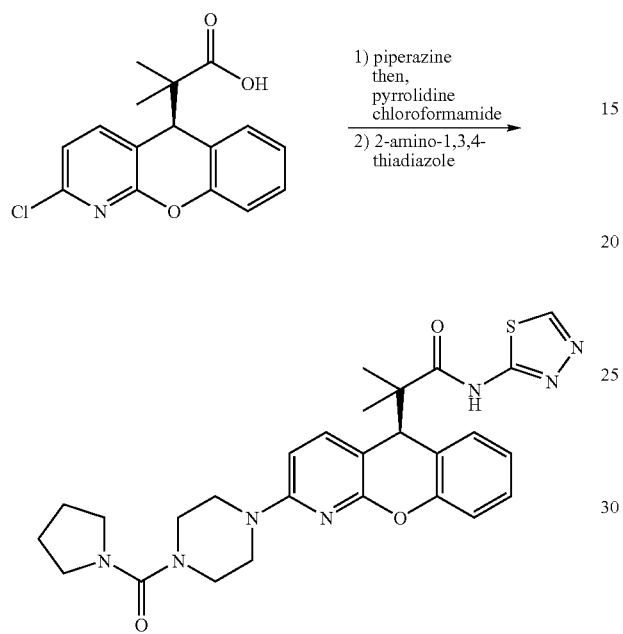

Step 1

A mixture of the product of Preparation 30b (14 mg, 0.046 mmol) and piperazine (140 mg, 1.6 mmol) in a sealed tube was heated at 150° C. under nitrogen for 30 min. Most of the piperidine was then removed at 160° C. by passing nitrogen stream through the mixture to obtain a solid, which was dissolved anhydrous dichloromethane (1 mL). 1-pyrrolidinecarbonyl chloride (0.1 mL, 0.9 mmol) was added dropwise, followed by N,N-diisopropylethylamine (0.25 mL). The mixture was stirred at RT for 2 h, quenched with aqueous sodium hydroxide solution (1 M, 1 mL), concentrated in vacuo, and purified using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the product (TFA salt, 20 mg, Y=77%) as a white solid. MS (E+) m/z: 451 (M+H); LC retention time: 3.32 min.

Step 2

A mixture of the product of Step 1 (400a) (20 mg, 0.052 mmol), 2-amino-1,3,4-thiadiazole (18 mg, 0.18 mmol), HOBT hydrate (14 mg, 0.09 mmol), diisopropylethylamine (0.093 mL, 0.53 mmol), and EDC (27 mg, 0.14 mmol) in anhydrous acetonitrile (1.0 mL) was heated for 3 h at 80° C. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title product (TFA salt, 12 mg, Y=50%) as a white solid. MS (E+) m/z: 534 (M+H); LC retention time: 3.26 min. $^1$H NMR (400 MHz, MeOD) δ ppm 9.09 (s, 1 H) 7.38 (d, J=8.56 Hz, 1 H) 7.27-7.33 (m, 1 H) 7.16 (dd, J=8.18, 1.13 Hz, 2 H) 7.04 (td, J=7.50, 1.30 Hz, 1 H) 6.52 (d, J=8.56 Hz, 1 H) 4.43 (s, 1 H) 3.54-3.59 (m, 4 H) 3.38-3.44 (m, 8 H) 1.85-1.90 (m, 4 H) 1.12 (s, 3 H) 1.10 (s, 3 H).

Example 401

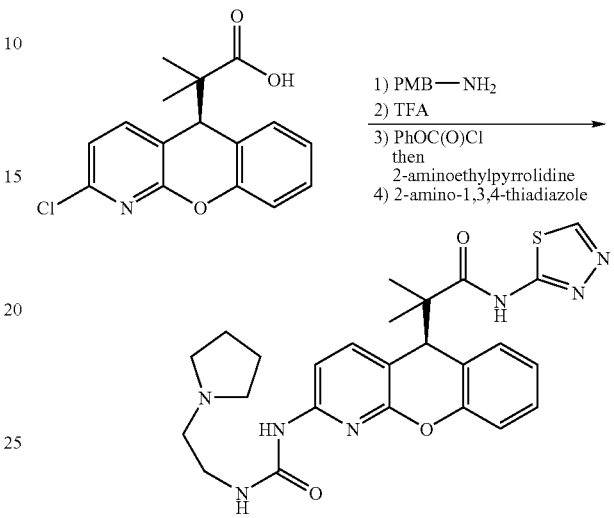

Step 1

A mixture of the product of Preparation 30b (50 mg, 0.17 mmol) and (4-methoxyphenyl)methanamine (0.4 mL) was stirred at 150° C. under nitrogen for 26 hr. The mixture was concentrated in vacuo, and purified by preparative HPLC. The product (60 mg, Y=62%) was obtained as a solid, TFA salt. MS (E+) m/z: 405 (M+H); LC retention time: 3.34 min.

Step 2

A mixture of the product of Step 1 (23 mg, 0.044 mmol), dichloromethane (0.5 mL), and TFA (0.5 mL) was stirred at room temperature for 3 hr before concentrating in vacuo. The residue was mixed with ethyl acetate (0.5 mL) and saturated aqueous sodium bicarbonate solution (0.5 mL). Solid potassium carbonate was added to make the mixture basic. The aqueous solution was separated, neutralized with 10% aqueous citric acid solution, and extracted with ethyl acetate (3×0.5 mL). The combined ethyl acetate extracts were dried (Na$_2$SO$_4$) and concentrated to gave an oil. MS (E+) m/z: 285 (M+H); LC retention time: 2.21 min.

Step 3

The above product of Step 2 was mixed with pyridine (0.08 mL, 1 mmol) and anhydrous dichlormethane (0.5 mL). Phenyl chloroformate (0.03 mL, 0.24 mmol) was added at 0° C. under nitrogen. The mixture was stirred at 0° C. for 40 min before 1-(2-aminoethyl)pyrrolidine (0.15 mL, 1.2 mmol) was added. The reaction mixture was heated to 100° C. (dichloromethane was distilled off during the heating), stirred at 100° C. for 40 min, and then concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave a solid (2TFA salt, 17 mg, Y=59% for step 2+3). MS (E+) m/z: 425 (M+H); LC retention time: 2.29 min.

Step 4

A mixture of the product of Step 3 (16 mg, 0.025 mmol), 2-amino-1,3,4-thiadiazole (15 mg, 0.15 mmol), HOBT hydrate (13 mg, 0.086 mmol), pyridine (0.12 mL, 1.5 mmol), and EDC (24 mg, 0.12 mmol) in acetonitrile (1.0 mL) was heated for 6 h at 80° C. Concentration in vacuo and purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title product, which was lyophilized to give a white solid (7 mg, Y=37%) as a 2 TFA salt. MS (E+) m/z: 508 (M+H); LC retention time: 2.30 min. $^1$H NMR (400 MHz, MeOD) δ ppm 9.09 (s, 1 H) 7.54 (d, J=8.31 Hz, 1 H) 7.32-7.37 (m, 1 H) 7.17-7.24 (m, 2 H) 7.11 (td, J=7.40, 1.40 Hz, 1 H) 6.83 (d, J=8.31 Hz, 1 H) 4.51 (s, 1 H) 3.77-3.86 (m, 2 H) 3.74 (t, J=5.54 Hz, 2 H) 3.44 (t, J=5.79 Hz, 2 H) 3.12-3.21 (m, 2 H) 2.18 (br. s., 2 H) 1.99-2.09 (m, 2 H) 1.15 (s, 3 H) 1.07-1.12 (m, 3 H).

Example 402

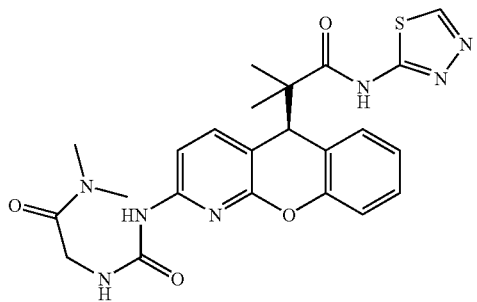

The title compound was prepared in the same manner as described for the preparation of the title compound of Example 401. MS (E+) m/z: 496 (M+H); LC retention time: 2.76 min. $^1$H NMR (400 MHz, MeOD) δ ppm 9.09 (s, 1 H) 7.49 (d, J=8.31 Hz, 1 H) 7.30-7.36 (m, 1 H) 7.17-7.26 (m, 2 H) 7.05-7.10 (m, 1 H) 6.88 (d, J=8.06 Hz, 1 H) 4.48 (s, 1 H) 4.24 (s, 2 H) 3.10 (s, 3 H) 3.01 (s, 3 H) 1.15 (s, 3 H) 1.12 (s, 3 H).

Example 403

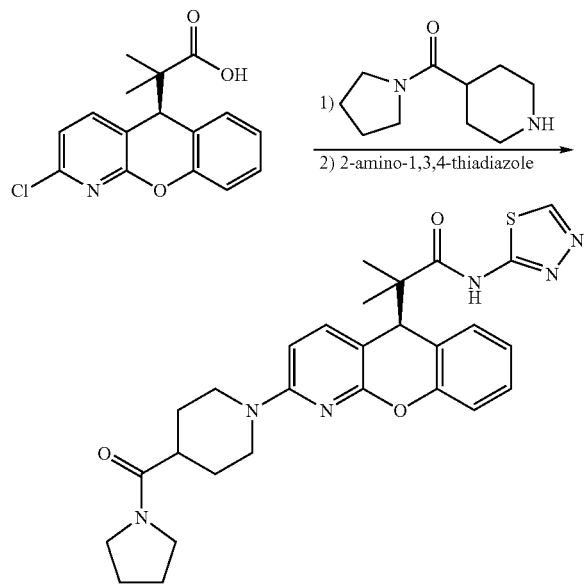

Step 1

A mixture of the product of Preparation 30b (14 mg, 0.046 mmol), piperidin-4-yl(pyrrolidin-1-yl)methanone (95 mg, 0.521 mmol), and anhydrous DMA (0.1 mL) was stirred at 150° C. under nitrogen for 3 hr. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the product (TFA salt, 22 mg, Y=85%) as a solid. MS (E+) m/z: 450 (M+H); LC retention time: 3.16 min.

Step 2

The step was completed in the same manner as described in Example 400, Step 2 to obtain the title compound as a white solid, a TFA salt. MS (ES+) m/z: 533 (M+H); LC retention time: 3.15 min. $^1$H NMR (400 MHz, MeOD) δ ppm 9.09 (s, 1H) 7.37 (d, J=8.31 Hz, 1 H) 7.27-7.32 (m, 1 H) 7.13-7.19 (m, 2 H) 7.03 (td, J=7.40, 1.20 Hz, 1 H) 6.53 (d, J=8.56 Hz, 1 H) 4.42 (s, 1 H) 4.35 (d, J=13.35 Hz, 2 H) 3.62 (t, J=6.80 Hz, 2 H) 3.41 (t, J=6.92 Hz, 2 H) 2.93 (t, J=12.72 Hz, 2 H) 2.75-2.84 (m, 1H) 1.96-2.04 (m, 2 H) 1.85-1.94 (m, 2 H) 1.66-1.84 (m, 4 H) 1.12 (br. s., 3 H) 1.11 (br. s., 3 H).

Example 404

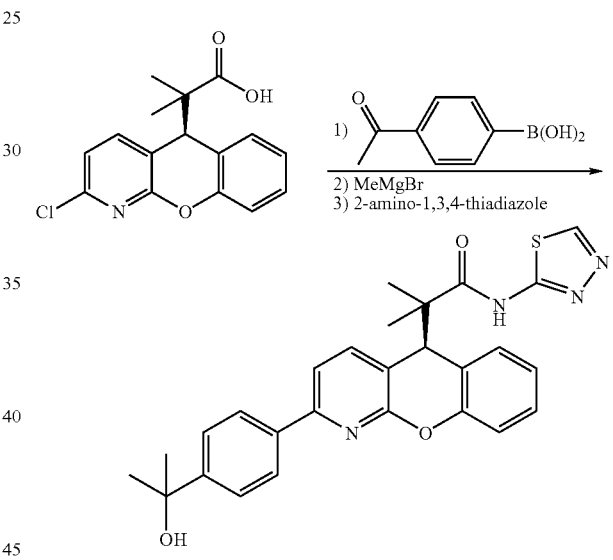

Step 1

A mixture of the product of Preparation 30b (45 mg, 0.15 mmol), 4-acetylphenylboronic acid (73 mg, 0.44 mmol), 2 M aqueous solution of potassium phosphate (0.52 mL, 1.0 mmol), and DMF (1 mL) was bubbled with nitrogen for 5 min before tetrakis(triphenylphosphine)palladium(0) (13 mg, 0.011 mmol) was added. The mixture was bubbled with nitrogen for an additional 5 min. After stirred at 90° C. under nitrogen for 1.5 h, the mixture was partitioned between saturated aqueous sodium bicarbonate solution (3 mL) and diethyl ether (4 mL). The aqueous was separated, acidified to pH=6, and extracted with ethyl acetate (3×2 mL). The combined ethyl acetate extracts were dried (Na$_2$SO$_4$) and concentrated in vacuo to give the product mixture as a liquid.

Step 2

The product mixture of Step 1 was dissolved in anhydrous THF (2 mL) and treated with methyl magnesium bromide solution (3 M in diethyl ether, 0.49 mL, 1.5 mmol) at −78° C. under nitrogen. After the mixture was stirred at RT for 30 min, 10% aqueous citric acid solution was added to make the pH=6. The mixture was extracted with ethyl acetate (3×1 mL). The combined ethyl acetate extracts were dried (Na$_2$SO$_4$) and concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the product (TFA salt, 34 mg, Y=44% for steps 1+2) as a white solid. MS (ES+) m/z: 404 (M+H); LC retention time: 3.33 min.

Step 3

A mixture of the product of Step 2 (18 mg, 0.045 mmol), 2-amino-1,3,4-thiadiazole (23 mg, 0.22 mmol), HOBT hydrate (17 mg, 0.11 mmol), diisopropylethylamine (0.12 mL, 0.67 mmol), and EDC (34 mg, 0.18 mmol) in anhydrous acetonitrile (1.0 mL) was stirred at 80° C. for 1 h and at RT overnight. The mixture was concentrated in vacuo. The residue was mixed with ethyl acetate (2 mL), washed with water (1 mL) and saturated aqueous sodium bicarbonate solution (2×1 mL), dried over sodium sulfate, and concentrated in vacuo. Purification using prep TLC gave the product (12 mg, Y=47%) as a solid. MS (ES+) m/z: 487 (M+H); LC retention time: 3.34 min. $^1$H NMR (400 MHz, CHLOROFORM-d) δ ppm 8.91 (s, 1H) 8.01 (d, J=8.31 Hz, 2 H) 7.74 (d, J=7.81 Hz, 1 H) 7.58 (d, J=8.56 Hz, 2 H) 7.50 (d, J=7.81 Hz, 1 H) 7.27-7.36 (m, 2 H) 7.24 (d, J=7.30 Hz, 1 H) 7.01-7.08 (m, 1 H) 4.82 (s, 1 H) 1.62 (s, 6 H) 1.30 (s, 3 H) 1.26 (s, 3 H).

Example 405

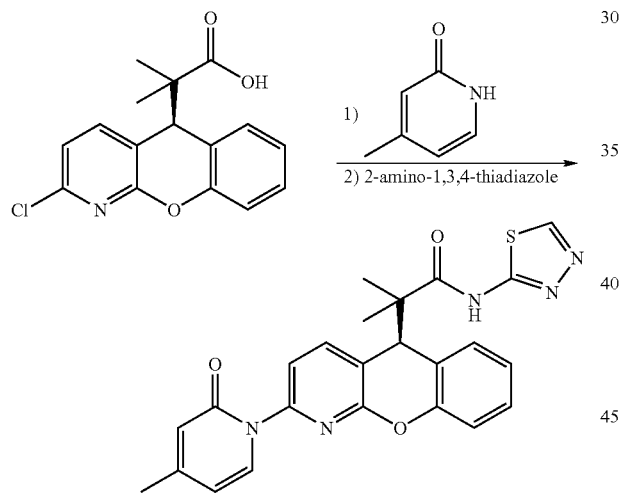

Step 1

To mixture of the product of Preparation 30b (15 mg, 0.049 mmol), 4-methylpyridin-2(1 H)-one (11 mg, 0.099 mmol), copper(I) iodide (4.7 mg, 0.025 mmol), and potassium carbonate (20 mg, 0.15 mmol) was added a solution of N,N'-dimethylcyclohexane-1,2-diamine (11 mg, 0.077 mmol) in anhydrous DMA (0.2 mL) under nitrogen. The mixture was stirred at 120° C. for 6 h and at 60° C. overnight. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) and neutralization gave the product (7 mg, Y=40%) as a solid. MS (ES+) m/z: 377 (M+H); LC retention time: 2.94 min.

Step 2

The step was completed in the same manner as described in Example 400, step 2 to obtain the product as a solid, a TFA salt. MS (ES+) m/z: 460 (M+H); LC retention time: 2.88 min. $^1$H NMR (400 MHz, MeOD) δ ppm 9.09 (s, 1 H) 7.85 (d, J=8.06 Hz, 1 H) 7.80 (d, J=7.05 Hz, 1 H) 7.52 (d, J=7.81 Hz, 1 H) 7.36 (t, J=7.68 Hz, 1 H) 7.24 (br. s., 1 H) 7.22 (br. s., 1 H) 7.11 (t, J=7.30 Hz, 1 H) 6.45 (br. s., 1 H) 6.40 (d, J=7.05 Hz, 1 H) 4.67 (s, 1 H) 2.30 (s, 3 H) 1.20 (s, 3 H) 1.17 (s, 3 H).

Example 406

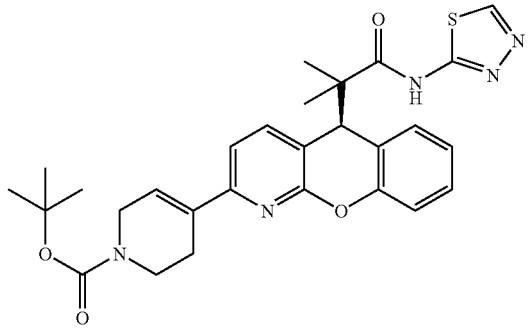

The title compound was prepared from the S isomer of Preparation 30 (30b) in the manner described for the preparation of the title compound of Example 162, using commercially available (N-tert-butoxycarbonyl)-1,2,3,6-tetrahydropyridine-4-boronic acid pinacol ester. MS (ES+) m/z: 534 (M+H); LC retention time: 3.67 min. $^1$H NMR (400 MHz, CHLOROFORM-d) δ ppm 12.14 (br. s., 1 H) 8.93 (s, 1 H) 7.71 (d, J=7.81 Hz, 1 H) 7.24-7.30 (m, 3 H) 7.12 (d, J=7.81 Hz, 1 H) 6.99-7.06 (m, 1 H) 6.72 (br. s., 1 H) 4.89 (s, 1 H) 4.14 (br. s., 2 H) 3.58-3.69 (m, 2 H) 2.63 (br. s., 2 H) 1.49 (s, 9 H) 1.28 (s, 3 H) 1.26 (s, 3 H).

Example 407

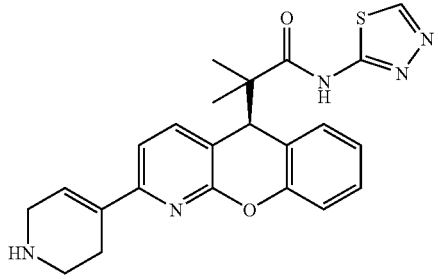

The title compound of Example 406 (57 mg, 0.11 mmol) was mixed with dichloromethane (6 mL) and TFA (3 mL). The mixture was stirred at RT for 1 h before concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (2 TFA salt, 47 mg, Y=67%) as a white solid. MS (ES+) m/z: 434 (M+H); LC retention time: 2.19 min. $^1$H NMR (400 MHz, MeOD) δ ppm 9.10 (s, 1 H) 7.65 (d, J=7.81 Hz, 1 H) 7.35 (d, J=7.81 Hz, 2 H) 7.23 (td, J=7.93, 1.26 Hz, 2 H) 7.08-7.14 (m, 1 H) 6.69-6.74 (m, 1 H)

4.60 (s, 1 H) 3.88-3.94 (m, 2 H) 3.47 (t, J=6.17 Hz, 2 H) 2.84-2.94 (m, 2 H) 1.17 (s, 3 H) 1.10 (s, 3 H).

Example 408

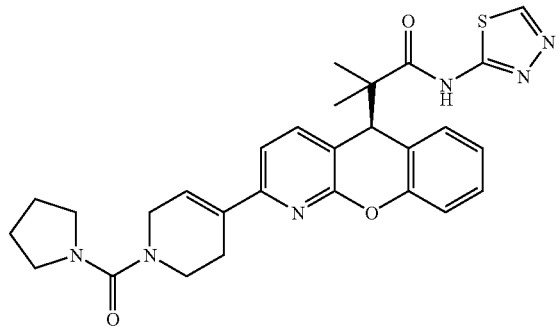

To a stirred solution of the title compound of Example 407 (14 mg, 0.021 mmol) and N,N-diisopropylethylamine (0.1 mL) in anhydrous THF (1 mL) was added 1-pyrrolidinecarbonyl chloride (0.01 mL, 0.09 mmol) under nitrogen. The mixture was stirred at RT for 45 min before water (0.1 mL) and methanol (1 mL) were added to quench the reaction. The mixture was concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 10 mg, Y=73%) as a solid. MS (ES+) m/z: 531 (M+H); LC retention time: 3.36 min. $^1$H NMR (400 MHz, MeOD) δ ppm 9.09 (s, 1 H) 7.61 (d, J=7.81 Hz, 1 H) 7.31-7.37 (m, 1 H) 7.19-7.29 (m, 3 H) 7.06-7.11 (m, 1 H) 6.69 (br. s., 1 H) 4.57 (s, 1 H) 4.01-4.05 (m, 2 H) 3.53 (t, J=5.54 Hz, 2 H) 3.39-3.45 (m, 4 H) 2.66 (br. s., 2 H) 1.85-1.91 (m, 4 H) 1.15 (s, 3 H) 1.12 (s, 3 H).

Example 409

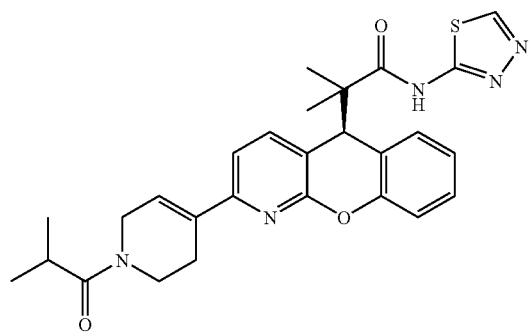

To a stirred solution of HOBT hydrate (20 mg, 0.13 mmol), and N,N-diisopropylethylamine (0.10 mL, 0.57 mmol) in anhydrous acetonitrile (1 mL) was added isobutyryl chloride (0.010 mL, 0.095 mmol) under nitrogen. The mixture was stirred at RT for 10 min before the title compound of Example 10 (11 mg, 0.017 mmol) was added. After the mixture was stirred at RT for 2 h, water (0.1 mL) was added to quench the reaction. The mixture was concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 7.6 mg, Y=74%) as a white solid. MS (ES+) m/z: 504 (M+H); LC retention time: 3.32 min. $^1$H NMR (400 MHz, MeOD) δ ppm 9.09 (s, 1 H) 7.61 (d, J=7.81 Hz, 1 H) 7.26-7.37 (m, 2 H) 7.22 (dt, J=7.81, 2.27 Hz, 2 H) 7.06-7.12 (m, 1 H) 6.69 (br. s., 1 H) 4.57 (s, 1 H) 4.34 (br. s., 1 H) 4.25 (br. s., 1 H) 3.81 (t, J=5.67 Hz, 2 H) 2.94-3.08 (m, 1 H) 2.72 (br. s., 1 H) 2.61 (br. s., 1 H) 1.11-1.16 (m, 12 H).

Example 410

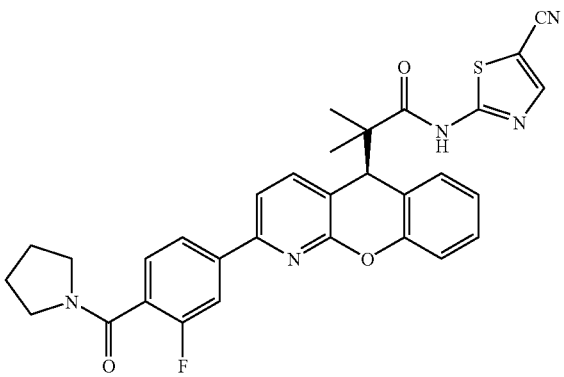

The product of Step 1 of Example 398 (398a) (12 mg, 0.026 mmol) was mixed with DMF (0.2 mL), N,N-diisopropylethylamine (0.050 mL, 0.29 mmol), HATU (30 mg, 0.078 mmol), and 2-amino-5-cyanothiazole (16 mg, 0.13 mmol). The reaction mixture was stirred at 80° C. for 6 hr. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 5.7 mg, Y=25%) as a yellow solid. MS (ES+) m/z: 568 (M+H); LC retention time: 3.66 min. $^1$H NMR (400 MHz, MeOD) δ ppm 8.15 (s, 1 H) 7.91-7.98 (m, 2 H) 7.73 (d, J=2.77 Hz, 2 H) 7.53 (t, J=7.43 Hz, 1 H) 7.35-7.41 (m, 1 H) 7.21-7.30 (m, 2 H) 7.10-7.16 (m, 1 H) 4.62 (s, 1 H) 3.63 (t, J=6.92 Hz, 2 H) 3.36-3.42 (m, 2 H) 1.91-2.06 (m, 4 H) 1.18 (s, 3 H) 1.15 (s, 3 H).

Examples 411 to 414

The following Examples 411 to 414 were prepared in the same manner as described for the preparation of the title compound of Example 410.

| Example No. | Structure | Rt (min) | M/z (MH)+ |
|---|---|---|---|
| 411 | 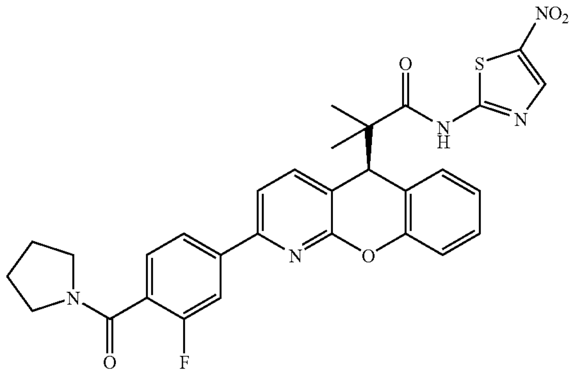 | 3.78 | 588 |
| 412 | 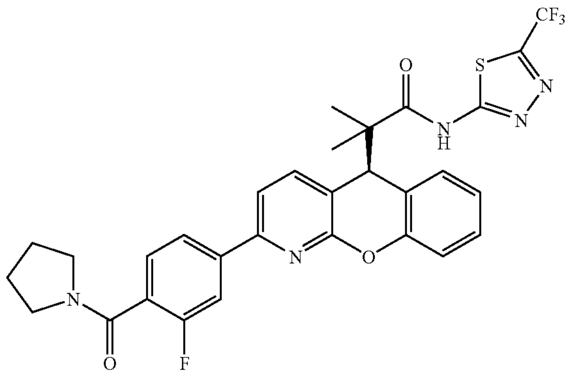 | 3.88 | 612 |
| 413 | 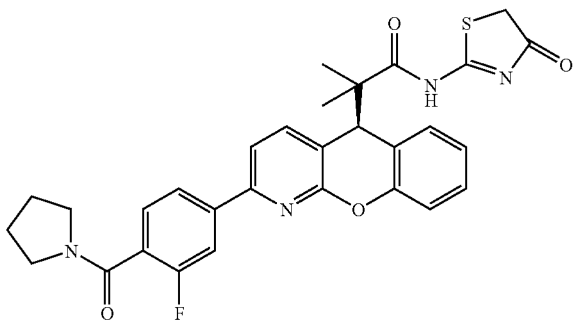 | 3.38 | 559 |
| 414 | 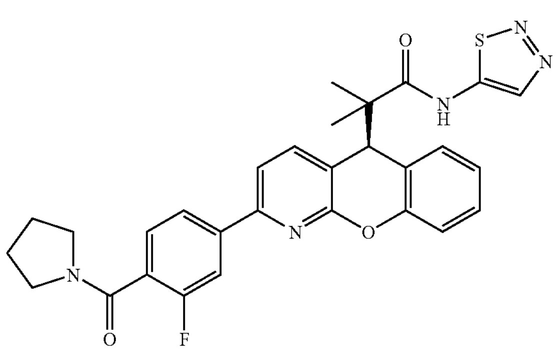 | 3.49 | 544 |

Example 415

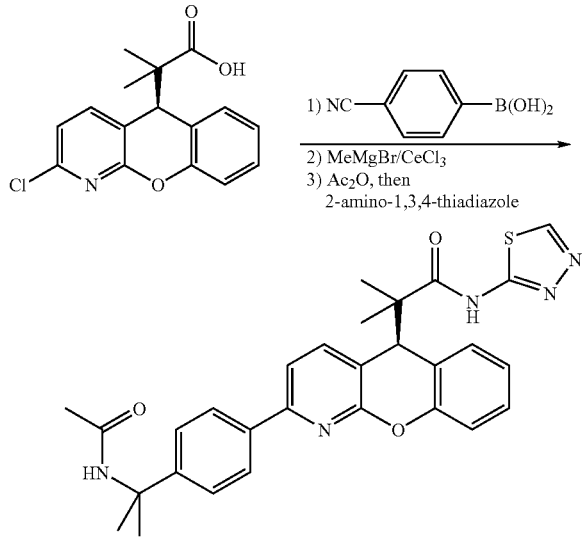

Step 1

A mixture of the product of Preparation 30b (183 mg, 0.60 mmol), 4-cyanophenylboronic acid (240 mg, 1.6 mmol), 2 M aqueous solution of potassium phosphate (2.1 mL, 4.2 mmol), and DMF (6 mL) was bubbled with nitrogen for 5 min before tetrakis(triphenylphosphine)palladium(0) (70 mg, 0.060 mmol) was added. After bubbled with nitrogen for an additional 5 min, the reaction mixture was stirred at 90° C. under nitrogen for 4 h. The mixture was concentrated in vacuo, mixed with water (5 mL), neutralized with 6N aqueous HCl solution, and extracted with ethyl acetate (3×2 mL). The combined ethyl acetate extracts were dried ($Na_2SO_4$) and concentrated in vacuo. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave the product (195 mg, Y=87%) as a solid. MS (ES+) m/z: 371 (M+H); LC retention time: 3.41 min.

Step 2

To a stirred cerium(III) chloride (340 mg, 1.4 mmol) in a dry flask was added anhydrous THF (6 mL) under nitrogen. The mixture was stirred at room temperature for 40 min before methyllithium (0.85 mL, 1.4 mmol) was added dropwise at −78° C. under nitrogen. After the mixture was stirred at −78° C. for 40 min, the product of Step 1 (93 mg, 0.25 mmol) was added. The reaction mixture was stirred at −78° C. for 40 min and at RT for 2 hr before water (3 mL) was added. The aqueous layer was neutralized with 10% aqueous citric acid to pH=8, extracted with ethyl acetate (2×2 mL), and then neutralized with 10% aqueous citric acid to pH=6, extracted with ethyl acetate (2×2 mL). The combined organic solutions were dried ($Na_2SO_4$) and concentrated under reduced pressure. The residue was dissolved in methanol (1.8 mL) and trifluoroacetic acid (0.2 mL). Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave the product (TFA salt, 18 mg, Y=14%) as a yellow solid. (ES+) m/z: 403 (M+H); LC retention time: 2.46 min.

Step 3

To a clear solution of the product of Step 2 (8.0 mg, 0.015 mmol) and N,N-diisopropylethylamine (0.10 mL, 0.57 mmol) in anhydrous dichloromethane (1 mL) was added acetic anhydride (10 μL, 0.11 mmol) under nitrogen. The reaction mixture was stirred at RT for 1 hr and concentrated in vacuo. The residue was mixed with anhydrous MeCN (1 mL), HOBT (40 mg, 0.26 mmol), 2-Amino-1,3,4-thiadiazole (60 mg, 0.59 mmol), EDC (100 mg, 0.52 mmol), and N,N-diisopropylethylamine (0.20 mL, 1.1 mmol). After stirred at 80° C. under nitrogen for 2 hr, the mixture was concentrated, mixed with saturated aqueous sodium bicarbonate solution (5 mL), and extracted with dichloromethane (3×1 mL). The combined methylene chloride extracts were dried ($Na_2SO_4$). Flash chromatography purification (0% to 100% ethyl acetate in hexanes then 0=>10% MeOH in ethyl acetate) afforded a crude product, which was purified using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) to give the title compound (TFA salt, 3 mg, Y=30%) MS (ES+) m/z: 528 (M+H); LC retention time: 3.24 min. $^1$H NMR (400 MHz, MeOD) δ ppm 9.10 (s, 1 H) 7.94 (d, J=8.31 Hz, 2 H) 7.70 (d, J=7.81 Hz, 1 H) 7.59 (d, J=7.81 Hz, 1 H) 7.48 (d, J=8.31 Hz, 2 H) 7.36 (t, J=7.68 Hz, 1 H) 7.20-7.29 (m, 2 H) 7.10 (t, J=7.43 Hz, 1 H) 4.61 (s, 1 H) 1.96 (s, 3 H) 1.66 (s, 6 H) 1.18 (s, 3 H) 1.16 (s, 3 H)

Example 416

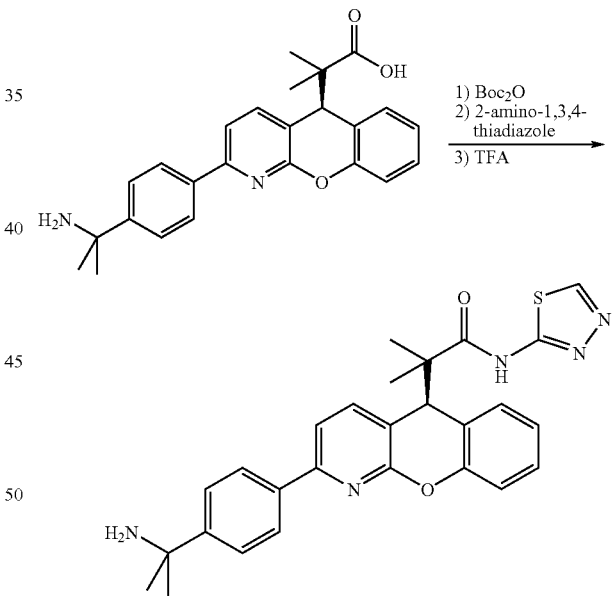

Step 1

To a stirred solution of the product of Step 2 in Example 415 (415b)(12 mg, 0.024 mmol), dioxane (0.5 mL), NaOH (0.097 mL, 0.048 mmol), and acetonitrile (2 mL) was added Boc2O (8.4 μL, 0.036 mmol). The reaction mixture was stirred at RT for 4 h. After more Boc2O (30 mg) was added, the mixture was stirred at RT for 2 hr and then concentrated in vacuo. The residue was mixed with water (0.5 mL), acidified with 10% aqueous citric acid solution to pH=5, and extracted with ethyl acetate. The combined ethyl acetate extracts were dried ($Na_2SO_4$) and concentrated under reduced pressure to give a crude product as a yellow liquid.

Step 2

The step was completed in the same manner as described in Example 400, step 2. using the product of Step 1 (416a).

Step 3

The product of Step 2 was dissolved in methylene chloride (1 mL) and TFA (0.5 mL). The mixture was stirred at RT for 1 hr before concentrated. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (2TFA, 7 mg, Y=40% for steps 1+2+3) as a white solid. MS (ES−) m/z: 484 (M−H); LC retention time: 2.66 min. $^1$H NMR (400 MHz, MeOD) δ ppm 9.11 (s, 1 H) 8.12 (d, J=8.56 Hz, 2 H) 7.73 (d, J=8.00 Hz, 1 H) 7.61-7.68 (m, 3 H) 7.35-7.40 (m, 1 H) 7.24-7.29 (m, 2 H) 7.13 (td, J=7.43, 1.26 Hz, 1 H) 4.64 (s, 1 H) 1.78 (s, 6 H) 1.20 (s, 3 H) 1.15 (s, 3 H).

Example 417

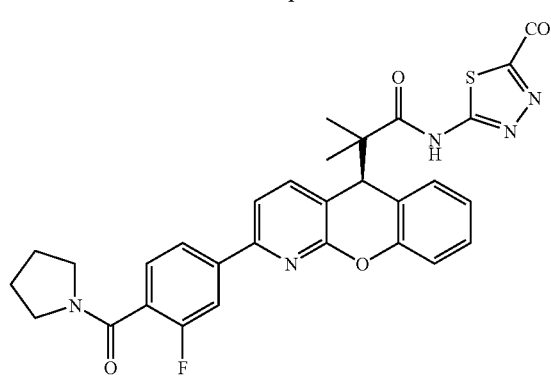

To a stirred mixture of the product of Step 1 in Example 398 (400 mg, 0.87 mmol), ethyl 5-amino-1,3,4-thiadiazole-2-carboxylate (400 mg, 2.3 mmol), HOBT hydrate (140 mg, 0.91 mmol), and anhydrous MeCN (10 mL) was added EDC (340 mg, 1.8 mmol) at RT under nitrogen, followed by N,N-diisopropylethylamine (0.2 mL, 1.1 mmol). After stirring at 80° C. for 4.5 h, the reaction mixture was concentrated, mixed with water (15 mL) and ethyl acetate (15 mL). The aqueous layer was extracted with ethyl acetate (3×10 mL). The combined organic solutions were dried (Na$_2$SO$_4$), concentrated in vacuo, and purified by flash chromatography (20-100% ethyl acetate in hexanes) gave the title product (410 mg, Y=77%) as a yellow solid. MS (ES+) m/z: 616 (M+H); LC retention time: 3.70 min. $^1$H NMR (400 MHz, CHLOROFORM-d) δ ppm 10.16 (br. s., 1 H) 8.04 (br. s., 1 H) 7.82-7.88 (m, 2 H) 7.53 (t, J=8.31 Hz, 2 H) 7.31-7.34 (m, 1 H) 7.22 (d, J=7.55 Hz, 1 H) 7.05 (ddd, J=7.87, 5.10, 3.15 Hz, 1 H) 4.86 (s, 1 H) 4.56 (q, J=7.13 Hz, 2 H) 3.68 (t, J=6.92 Hz, 2 H) 3.36 (t, J=6.55 Hz, 2 H) 1.87-2.06 (m, 4 H) 1.48 (t, J=7.18 Hz, 3 H) 1.35 (s, 3H) 1.23 (s, 3 H).

Example 418

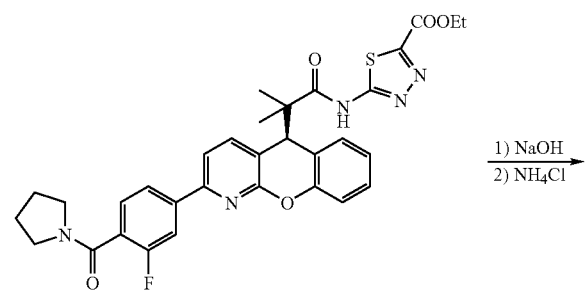

Step 1

To a stirred solution of the title compound of Example 417 (183 mg, 0.30 mmol) in MeOH (1.5 mL) was added 1M aqueous sodium hydroxide solution (1.0 ml, 1.0 mmol). The reaction mixture was stirred at RT for 1.5 hr before concentrated under reduced pressure to remove methanol and lypholized to remove water to give a yellow solid (207 mg).

Step 2

To a dry flask were added the product of Step 1 (21 mg, 0.029 mmol) ammonium chloride (18 mg, 0.34 mmol), N,N-diisopropylethylamine (50 μL, 0.29 mmol), and anhydrous DMF (0.3 mL) at RT under nitrogen. The mixture was stirred at RT for 2 min before PyBOP (20 mg, 0.038 mmol) was added. The mixture was at RT for 1 h. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title product (TFA salt, 16 mg, Y=79%) as a white solid. MS (ES+) m/z: 587 (M+H); LC retention time: 3.34 min. $^1$H NMR (400 MHz, MeOD) δ ppm 7.90-7.97 (m, 2 H) 7.69-7.76 (m, 2 H) 7.52 (t, J=7.43 Hz, 1 H) 7.35-7.40 (m, 1 H) 7.23-7.30 (m, 2 H) 7.13 (t, J=7.43 Hz, 1 H) 4.63 (s, 1 H) 3.63 (t, J=6.92 Hz, 2 H) 3.39 (t, J=6.55 Hz, 2 H) 1.91-2.06 (m, 4 H) 1.20 (s, 3 H) 1.16 (s, 3H).

Example 419 TO 422

The following Examples 419 to 422 can be prepared in the same manner as described for the preparation of the title compound of Example 418 from the corresponding amine.

| Example No. | Structure | Rt(min) | M/z (MH)+ |
|---|---|---|---|
| 419 | 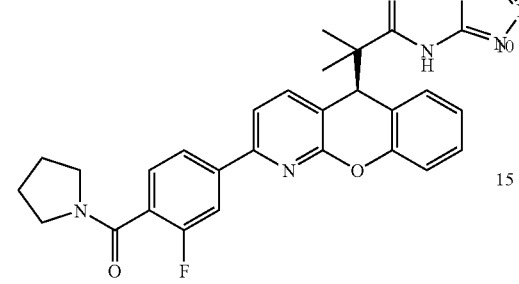 | 3.41 | 601 |
| 420 | 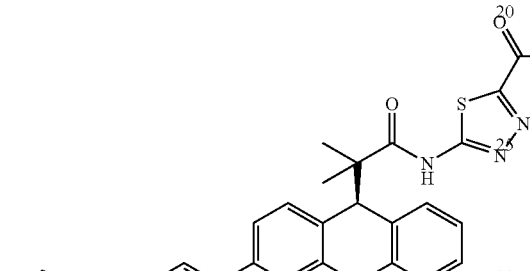 | 3.44 | 615 |
| 421 | 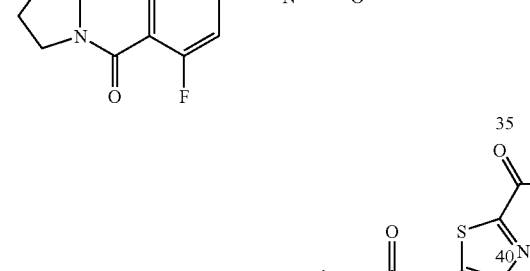 | 3.49 | 615 |
| 422 | 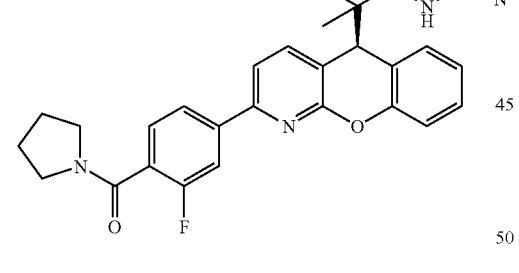 | 3.52 | 627 |

Example 422[a]

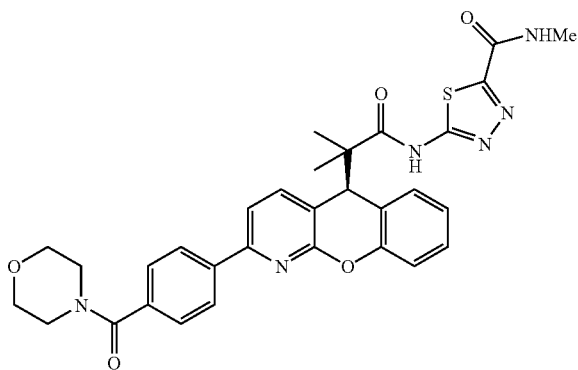

The title compound was prepared in the same manner described above for the preparation of the title compounds of Examples 419-422, substituting commercially available boronic acid (4-(morpholine-4-carbonyl)phenylboronic acid) in place of 3-fluoro-4-(pyrrolidine-1-carbonyl)phenylboronic acid in the first step of Example 398. MS (ES+) m/z: 599 (M+H); LC retention time: 3.15 min.

Example 422[b]

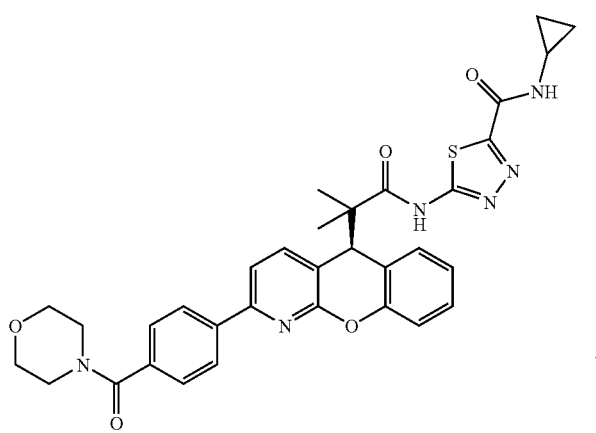

The title compound was prepared in the same manner described above for the preparation of the title compound of Examples 422a. MS (ES+) m/z: 625 (M+H); LC retention time: 3.28 min.

Example 423

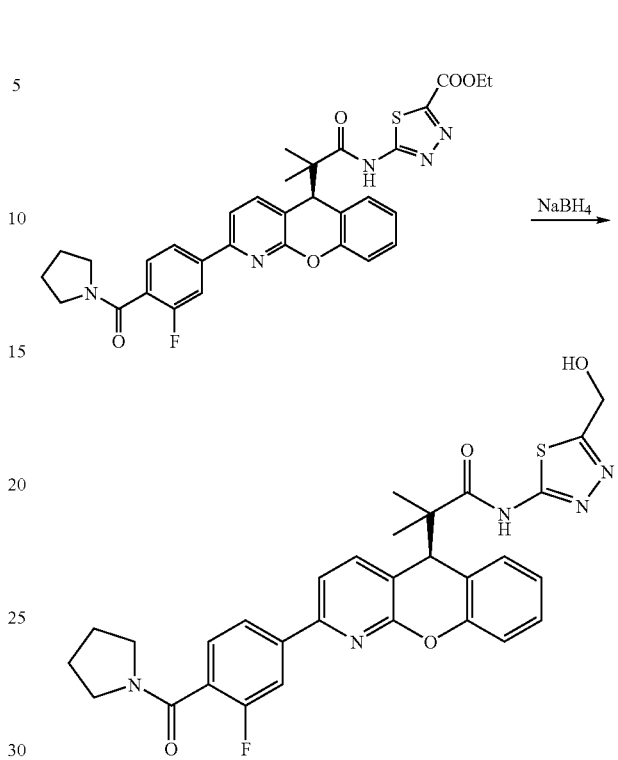

To a stirred solution of the title compound of Example 417 (17 mg, 0.028 mmol) in THF (0.5 mL) and ethanol (0.5 mL) was added NaBH$_4$ (17 mg, 0.45 mmol) portionwise. The mixture was stirred at RT for 1 hr before acetone (1 mL) was added to quench the reaction. The mixture was concentrated in vacuo. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 12 mg, Y=63%) as a white solid. MS (ES+) m/z: 574 (M+H); LC retention time: 3.28 min. $^1$H NMR (400 MHz, MeOD) δ ppm 7.90-7.98 (m, 2 H) 7.69-7.77 (m, 2 H) 7.53 (t, J=7.43 Hz, 1 H) 7.35-7.40 (m, 1 H) 7.23-7.30 (m, 2 H) 7.13 (td, J=7.43, 1.26 Hz, 1 H) 4.92 (s, 2 H) 4.63 (s, 1 H) 3.63 (t, J=6.92 Hz, 2 H) 3.39 (t, J=6.55 Hz, 2 H) 1.91-2.06 (m, 4 H) 1.18 (s, 3 H) 1.15 (s, 3 H).

Example 424

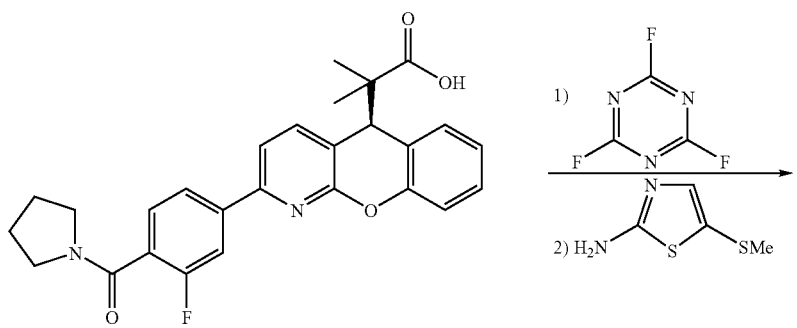

-continued

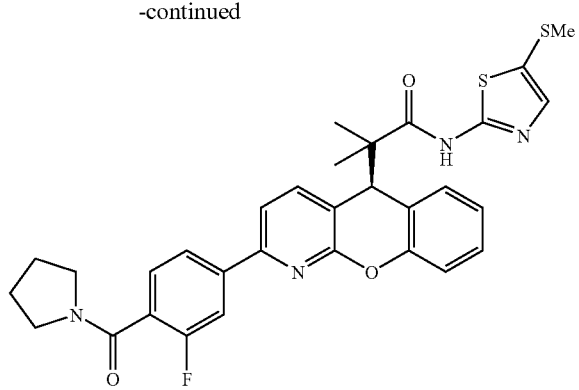

Step 1

To a solution of the product of Step 1 in Example 398 (170 mg, 0.37 mmol) and pyridine (0.060 mL, 0.74 mmol) in anhydrous dichloromethane (2 mL) was added 2,4,6-trifluoro-1,3,5-triazine (0.062 mL, 0.74 mmol) dropwise at 0° C. under nitrogen. After stirred at 0° C. for 30 min and at RT for 1.5 hr, the mixture was poured into water (2 mL) at 0° C. The aqueous layer was separated and extracted with methylene chloride (3×1 mL). The combined methylene chloride solutions were dried ($Na_2SO_4$). Flash chromatography purification (20=>100% ethyl acetate in hexanes) afforded the product (153 mg, Y=90%) as a white solid. MS (ES+) m/z: 463 (M+H); LC retention time: 3.56 min.

Step 2

A mixture of the product of Step 1 (30 mg, 0.065 mmol), 5-(methylthio)thiazol-2-amine (19 mg, 0.13 mmol), pyridine (50 μL, 0.60 mmol), and anhydrous acetonitrile (1 mL) was stirred at RT under nitrogen for 60 h. EDC (15 mg) was added. The mixture was stirred at 80° C. 4 h and at 90° C. for 2 h. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave the title product (32 mg, Y=83% yield) as a yellowish solid. MS (ES+) m/z: 589 (M+H); LC retention time: 3.82 min. $^1$H NMR (400 MHz, MeOD) δ ppm 7.88-7.95 (m, 2 H) 7.73 (d, J=8.0 Hz, 1 H) 7.69 (d, J=8.0 Hz, 1 H) 7.51 (t, J=7.43 Hz, 1 H) 7.43 (s, 1 H) 7.36 (td, J=7.8, 1.2 Hz, 1 H) 7.26 (d, J=8.56 Hz, 2 H) 7.12 (td, J=7.5, 1.0 Hz, 1 H) 4.61 (s, 1 H) 3.62 (t, J=6.80 Hz, 2 H) 3.38 (t, J=6.67 Hz, 2 H) 2.45 (s, 3 H) 1.91-2.06 (m, 4 H) 1.15 (s, 3 H) 1.10 (s, 3 H).

Example 425

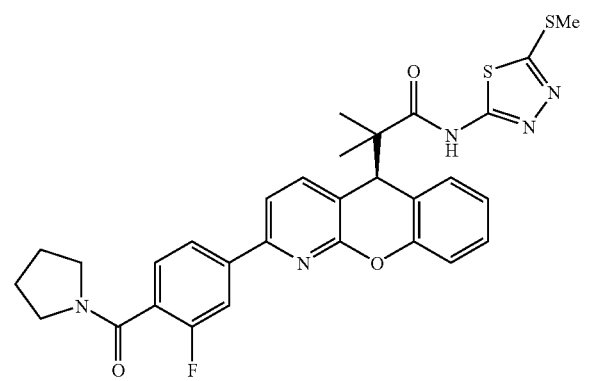

The title compound was prepared in the same manner as described for the preparation of the title compound of Example 424 from 5-(methylthio)thiadiazol-2-amine. MS (ES+) m/z: 590 (M+H); LC retention time: 3.71 min. $^1$H NMR (400 MHz, MeOD) δ ppm 7.91-7.98 (m, 2 H) 7.75 (d, J=8.0 Hz, 1 H) 7.72 (d, J=8.0 Hz, 1H) 7.53 (t, J=7.55 Hz, 1 H) 7.35-7.41 (m, 1 H) 7.23-7.30 (m, 2 H) 7.14 (t, J=7.43 Hz, 1 H) 4.61 (s, 1 H) 3.63 (t, J=6.92 Hz, 2 H) 3.39 (t, J=6.67 Hz, 2 H) 2.76 (s, 3 H) 1.92-2.05 (m, 4 H) 1.17 (s, 3 H) 1.13 (s, 3 H).

Examples 426 and 427

EXAMPLE 426

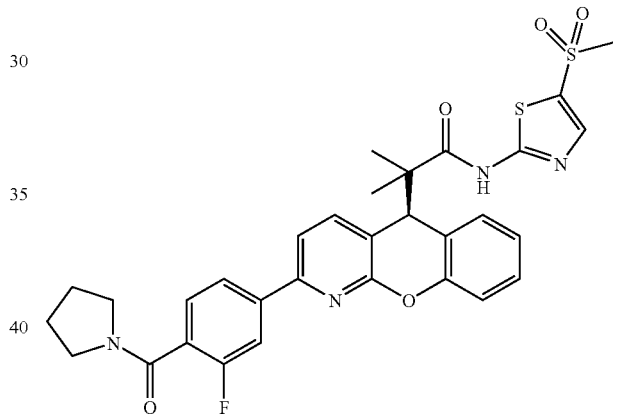

EXAMPLE 427

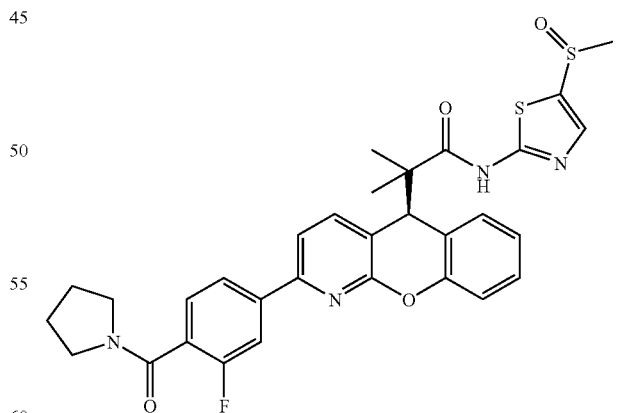

To a clear solution of the title compound of Example 424 (22 mg, 0.038 mmol) and TFA (15 μL, 0.20 mmol) in dichloromethane (1 mL) was added mCPBA (57-86%, 14 mg) at 0° C. The reaction mixture was stirred at the same temperature for 1.5 h and at RT for 1 h before saturated aqueous sodium bicarbonate solution (1 mL) was added. The aqueous solution was extracted with dichloromethane (2×1 mL). The combined dichloromethane solutions were dried (Na$_2$SO$_4$). Flash chromatography purification (50=>100% ethyl acetate in heptanes; then 0-20% methanol in ethyl acetate) afforded the sulfoxide (5 mg) and the sulfone (24 mg). Each of them was separately purified using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) to give the title compound of Example 427 (TFA salt, 3 mg, Y=11%) as a white solid. (MS (ES+) m/z: 605 (M+H); LC retention time: 3.27 min, $^1$H NMR (400 MHz, MeOD) δ ppm 7.91-7.98 (m, 3 H) 7.70-7.78 (m, 2H) 7.53 (t, J=7.43 Hz, 1 H) 7.35-7.40 (m, 1 H) 7.24-7.30 (m, 2 H) 7.13 (td, J=7.50, 1.20 Hz, 1 H) 4.64 (s, 1 H) 3.63 (t, J=6.92 Hz, 2 H) 3.39 (t, J=6.55 Hz, 2 H) 3.09 (s, 3H) 1.91-2.06 (m, 4 H) 1.18 (d, J=3.53 Hz, 3 H) 1.14 (d, J=3.78 Hz, 3 H)) and the title compound of Example 426 (TFA salt, 19 mg, Y=69%) as a white solid. (MS (ES+) m/z: 621 (M+H); LC retention time: 3.36 min, $^1$H NMR (400 MHz, MeOD) δ ppm 8.06 (s, 1 H) 7.89-7.96 (m, 2 H) 7.74 (d, J=8.0 Hz, 1 H) 7.71 (d, J=8.0 Hz, 1 H) 7.52 (t, J=7.43 Hz, 1 H) 7.37 (td, J=7.7, 1.3 Hz, 1 H) 7.23-7.29 (m, 2 H) 7.11-7.16 (m, 1 H) 4.62 (s, 1 H) 3.63 (t, J=6.92 Hz, 2 H) 3.39 (t, J=6.55 Hz, 2 H) 3.30 (s, 3 H) 1.92-2.05 (m, 4 H) 1.18 (s, 3 H) 1.14 (s, 3 H)).

Example 428

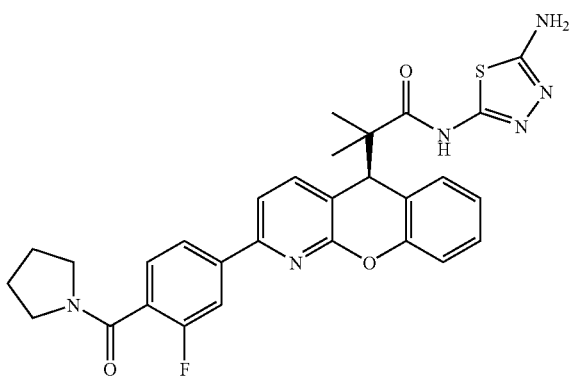

A mixture of the product of Step 1 of Example 398 (15 mg, 0.032 mmol), 1,3,4-thiadiazole-2,5-diamine (20 mg, 0.17 mmol), and anhydrous DMF (0.2 mL) was sonicated and stirred at RT overnight under nitrogen. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 20 mg, 90% yield) as a white solid. MS (E+) m/z: 559 (M+H); LC retention time: 3.02 min. $^1$H NMR (400 MHz, MeOD) δ ppm 7.97 (dd, J=8.0, 1.6 Hz, 1 H) 7.94 (dd, J=11.21, 1.38 Hz, 1 H) 7.79 (d, J=8.0 Hz, 1 H) 7.76 (d, J=8.0 Hz, 1 H) 7.54 (t, J=7.55 Hz, 1 H) 7.39 (td, J=7.8, 1.6 Hz, 1 H) 7.25-7.30 (m, 2 H) 7.17 (td, J=7.6, 1.2 Hz, 1 H) 4.54 (s, 1 H) 3.63 (t, J=6.92 Hz, 2 H) 3.39 (t, J=6.55 Hz, 2 H) 1.91-2.06 (m, 4 H) 1.15 (s, 3 H) 1.14 (s, 3 H).

Example 429

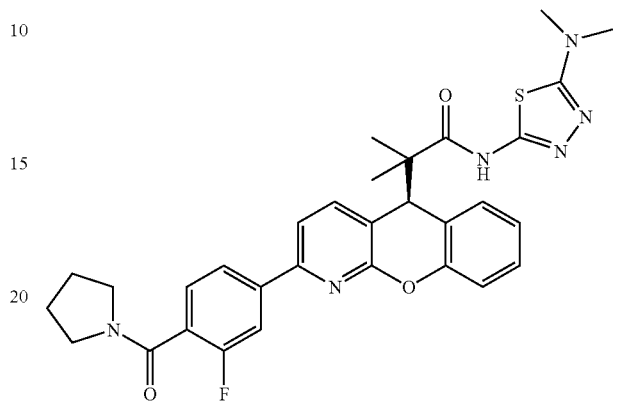

A mixture of 5-bromo-1,3,4-thiadiazol-2-amine (90 mg, 0.50 mmol), dimethylamine hydrochloride (410 mg, 5.0 mmol), 2-propanol (0.6 mL), and N,N-diisopropylethylamine (0.90 mL, 5.0 mmol) was stirred at 150° C. for 1 h under nitrogen in a CEM microwave reactor. Saturated aqueous sodium bicarbonate solution (6 mL) was added with caution, and the mixture was extracted with ethyl acetate (4×2 mL). The combined ethyl acetate extracts were dried (Na$_2$SO$_4$) and concentrated under reduced pressure to give a crude product (16 mg, N2,N2-dimethyl-1,3,4-thiadiazole-2,5-diamine), which was mixed with anhydrous acetonitrile (1 mL), N,N-diisopropylethylamine (0.1 mL, 0.57 mmol), and the product of Step 1 in Example 426 (15 mg, 0.032 mmol). The mixture was stirred at RT under nitrogen overnight. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave the title compound (TFA salt, 4 mg, Y=18%) as a white solid. MS (E+) m/z: 587 (M+H); LC retention time: 3.32 min. $^1$H NMR (400 MHz, MeOD) δ ppm 7.91-7.99 (m, 2 H) 7.79 (d, J=8.0 Hz, 1 H) 7.75 (d, J=8.0 Hz, 1 H) 7.54 (t, J=7.55 Hz, 1 H) 7.39 (td, J=7.7, 1.2 Hz, 1 H) 7.25-7.30 (m, 2 H) 7.16 (td, J=7.7, 1.2 Hz, 1 H) 4.56 (s, 1 H) 3.63 (t, J=6.92 Hz, 2 H) 3.39 (t, J=6.67 Hz, 2 H) 3.26 (s, 6 H) 1.91-2.07 (m, 4 H) 1.16 (s, 3 H) 1.14 (s, 3 H).

Example 430

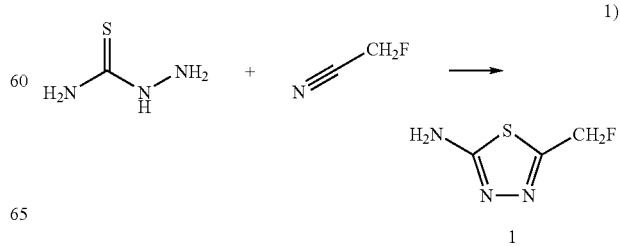

1

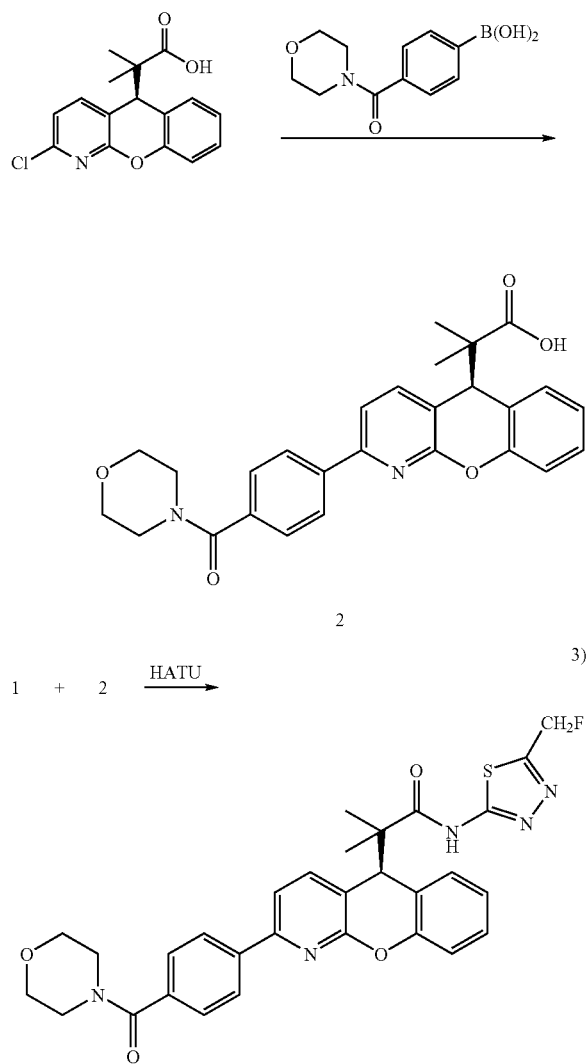

Step 1

A mixture of hydrazinecarbothioamide (550 mg, 6.0 mmol), 2-fluoroacetonitrile (0.34 mL, 6.0 mmol), and TFA (3 mL) was stirred at 60° C. for 4 hr. The mixture was concentrated in vacuo. The residue was dissolved in water (15 mL), basified with saturated aqueous sodium bicarbonate solution (20 mL) and saturated aqueous potassium phosphate solution, and mixed with ethyl acetate (10 mL). The solid was filtered, washed with water and ethyl acetate, and dried to give a white solid (100 mg). The filtrate was extracted with ethyl acetate (3×10 mL). All organic solutions were combined, dried ($Na_2SO_4$), and concentrated under reduced pressure. The solid residue obtained was triturated with ethyl acetate to give a white solid (210 mg). Both of the solid were the desired 5-(fluoromethyl)-1,3,4-thiadiazol-2-amine (310 mg, 39% yield). MS (E+) m/z: 134 (M+H); LC retention time: 0.28 min.

Step 2

The step was completed in the same manner as described in Example 398 Step 1 to obtain the product as a white solid. MS (ES+) m/z: 459 (M+H); LC retention time: 3.10 min.

Step 3

A mixture of the product of Step 2 (20 mg, 0.044 mmol), the product of Step 1 (17 mg, 0.13 mmol), DMAP (11 mg, 0.087 mmol), HATU (33 mg, 0.087 mmol) and DMF (0.3 mL) was stirred at 80° C. under nitrogen for 2 h. After more (10 mg) of the product of Step 1 was added, the mixture was stirred at 80° C. for an additional 1 h. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave the title compound (TFA salt, 20 mg, Y=67%) as a white solid. MS (E+) m/z: 574 (M+H); LC retention time: 3.25 min. $^1$H NMR (400 MHz, MeOD) δ ppm 8.13 (d, J=8.31 Hz, 2 H) 7.74 (d, J=8.0 Hz, 1 H) 7.68 (d, J=8.0 Hz, 1 H) 7.55 (d, J=8.56 Hz, 2 H) 7.37 (td, J=7.7, 1.4 Hz, 1 H) 7.23-7.30 (m, 2 H) 7.12 (td, J=7.5, 1.0 Hz, 1 H) 5.74 (d, J=47.0 Hz, 2 H) 4.63 (s, 1 H) 3.45-3.84 (m, 8H) 1.19 (s, 3 H) 1.16 (s, 3 H).

Example 431 to 433

The following Examples 431 to 433 were prepared in the same manner as described for the preparation of the title compound of Example 430 from the corresponding commercially available boronic acids.

| Example No. | Structure | Rt (min) | M/z (MH)+ |
|---|---|---|---|
| 431 | 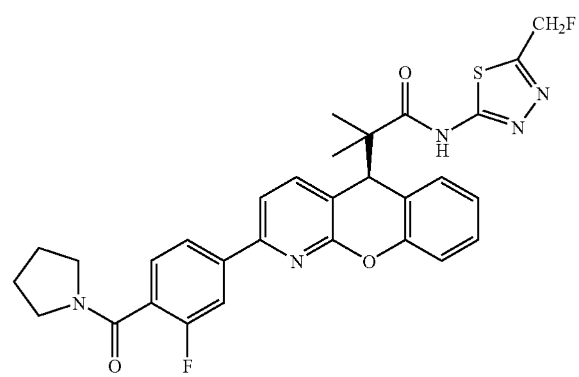 | 3.52 | 576 |

-continued

| Example No. | Structure | Rt (min) | M/z (MH)+ |
|---|---|---|---|
| 432 | CH₂F | 3.32 | 532 |
| 433 | CH₂F | 3.46 | 558 |

Example 434

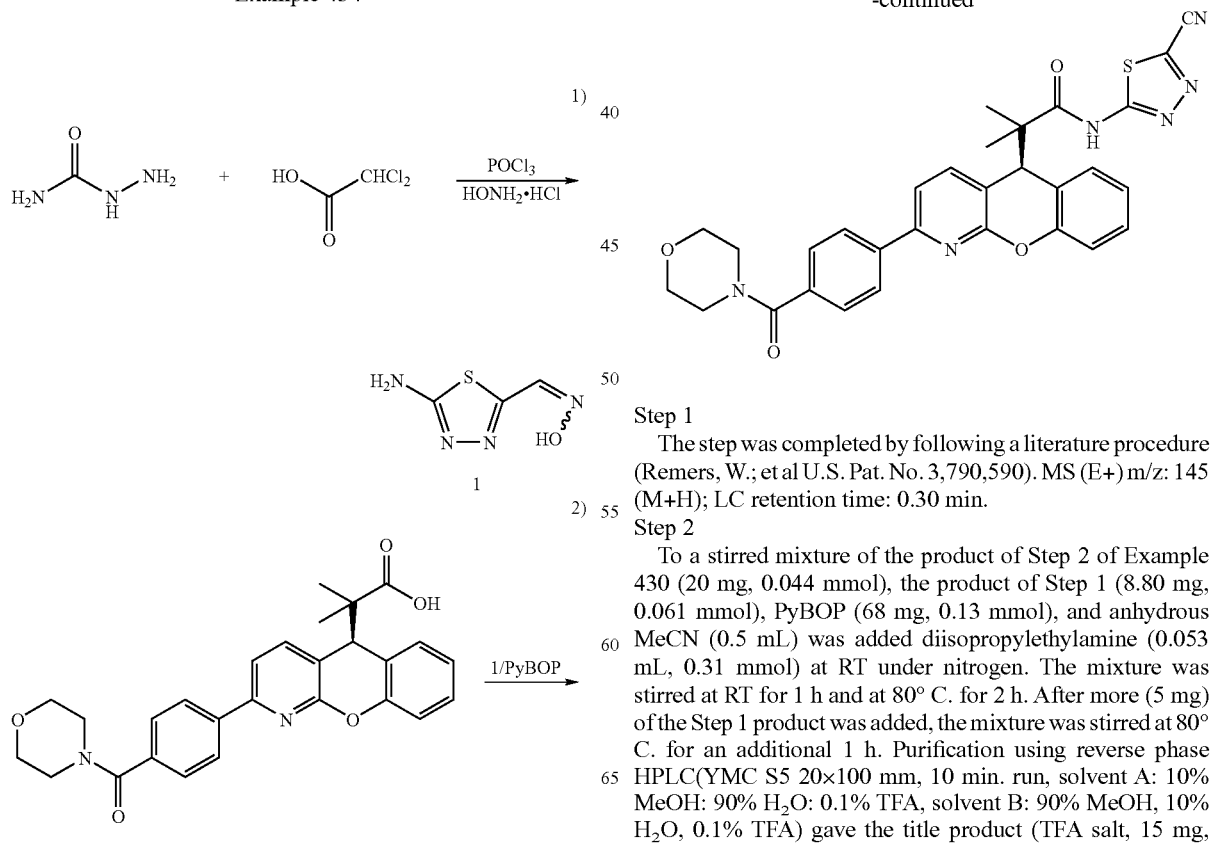

Step 1

The step was completed by following a literature procedure (Remers, W.; et al U.S. Pat. No. 3,790,590). MS (E+) m/z: 145 (M+H); LC retention time: 0.30 min.

Step 2

To a stirred mixture of the product of Step 2 of Example 430 (20 mg, 0.044 mmol), the product of Step 1 (8.80 mg, 0.061 mmol), PyBOP (68 mg, 0.13 mmol), and anhydrous MeCN (0.5 mL) was added diisopropylethylamine (0.053 mL, 0.31 mmol) at RT under nitrogen. The mixture was stirred at RT for 1 h and at 80° C. for 2 h. After more (5 mg) of the Step 1 product was added, the mixture was stirred at 80° C. for an additional 1 h. Purification using reverse phase HPLC(YMC S5 20×100 mm, 10 min. run, solvent A: 10% MeOH: 90% H₂O: 0.1% TFA, solvent B: 90% MeOH, 10% H₂O, 0.1% TFA) gave the title product (TFA salt, 15 mg, 0.022 mmol, 51% yield) as a yellow solid. MS (E+) m/z: 567 (M+H); LC retention time: 3.35 min. ¹H NMR (400 MHz, MeOD) δ ppm 8.13 (d, J=8.56 Hz, 2 H) 7.73 (d, J=8.0 Hz, 1 H) 7.69 (d, J=8.0 Hz, 1 H) 7.56 (d, J=8.31 Hz, 2 H) 7.38 (td, J=7.7, 1.4 Hz, 1 H) 7.28 (dd, J=8.06, 1.01 Hz, 1 H) 7.23 (dd, J=7.68, 1.38 Hz, 1 H) 7.13 (td, J=7.5, 1.2 Hz, 1H) 4.61 (s, 1 H) 3.46-3.84 (m, 8 H) 1.20 (s, 3 H) 1.18 (s, 3 H).

Example 435

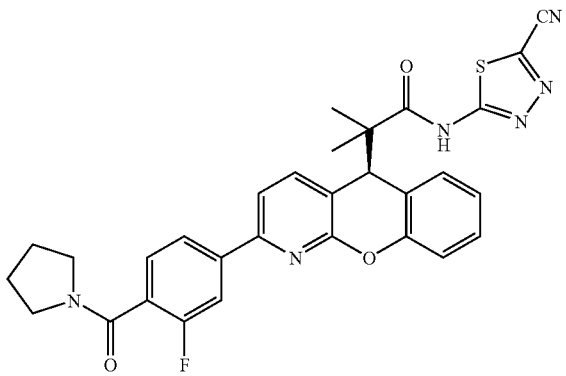

The title compound was prepared in the same manner as described for the preparation of the title compound of Example 434 from the product of Step 1 in Example 398. MS (ES+) m/z: 569 (M+H); LC retention time: 3.59 min. ¹H NMR (400 MHz, MeOD) δ ppm 7.89-7.99 (m, 2 H) 7.74 (d, J=8.0 Hz, 1 H) 7.72 (d, J=8.0 Hz, 1 H) 7.53 (t, J=7.43 Hz, 1 H) 7.35-7.41 (m, 1 H) 7.28 (d, J=8.06 Hz, 1 H) 7.22 (d, J=7.55 Hz, 1 H) 7.13 (t, J=6.92 Hz, 1 H) 4.62 (s, 1 H) 3.63 (t, J=6.80 Hz, 2 H) 3.39 (t, J=6.55 Hz, 2 H) 1.89-2.08 (m, 4 H) 1.20 (s, 3 H) 1.18 (s, 3 H).

Example 436

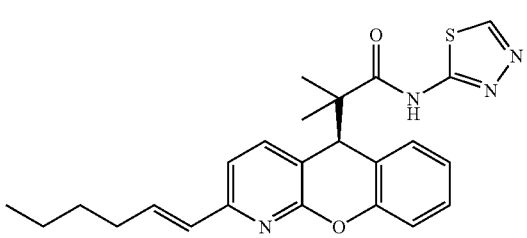

A stream of nitrogen gas was bubbled through a mixture of the product of the Step 1 of Preparation 53 (53a) (100 mg, 0.26 mmol), trans-1-hexen-1-yl boronic acid (66 mg, 0.52 mmol) and (triphenylphosphine)palladium(0) (10 mg, 0.009 mmol) in DMF (1.5 mL) and aqueous potassium phosphate (2.0M, 0.3 mL) for 10 min. The mixture was heated at 100° C. for 2.5 h, then purified by preparative HPLC to give the title compound as a light yellow TFA salt (24 mg, Y=17%). MS (ES+) m/z: 435 (M+H); LC retention time: 3.95 min.

Example 437

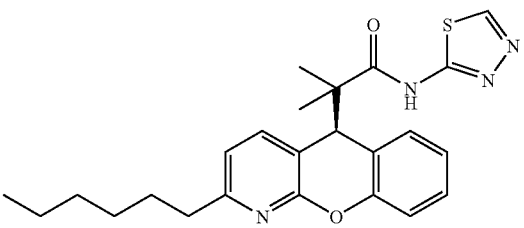

To a solution of the title compound of Example 436 (10 mg, 0.023 mmol) in methanol (2 mL) was added palladium on carbon (10% w/w, 10 mg). The mixture was evacuated, then placed under an atmosphere of hydrogen, and stirred overnight at room temperature. The mixture was then filtered (syringe-tip 0.45 micron PTFE filter), and purified by reverse phase preparative HPLC to afford the title compound (6.1 mg, Y=48%) as a white powder, TFA salt. MS (ES+) m/z: 437 (M+H); LC retention time: 3.94 min.

Example 438

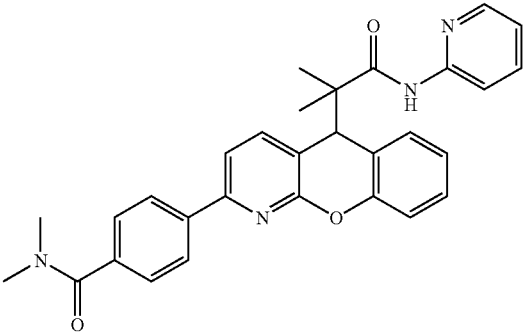

Step 1

A 1 M CH₂Cl₂ solution of oxalyl chloride (0.7 mL, 3 eq) was added to a suspension of the acid from Preparation 101 (200 mg, 0.24 mmol) and trace amount of DMF in CH₂Cl₂ (20 mL) at room temperature. After 20 min, the mixture was concentrated to give the expected acid chloride as an off-white solid.

Step 2

To a CH₂Cl₂ (1.4 mL) solution of the acid chloride from the last step (40 mg, 0.092 mmol) was added 2-aminopyridine (25 mg, 2.9 eq) at room temperature. After 1 h, the mixture was concentrated and purified by preparative reverse-phase HPLC (using Shimadzu 10A liquid chromatographs and Waters Sunfire S10 30×250 mm column) to give Example 501 as a white solid (28.8 mg, 43%). ¹H NMR (400 MHz, CDCl3) δ ppm 12.14 (s, 1 H), 8.75 (d, J=8.81 Hz, 1 H), 8.18-8.37 (m, 2 H), 8.08 (d, J=8.31 Hz, 2 H), 7.83 (d, J=7.81 Hz, 1 H), 7.55 (dd, J=13.22, 8.18 Hz, 3 H), 7.44 (t, J=6.17 Hz, 1 H), 7.28-7.38 (m, 2 H), 7.22 (d, J=7.30 Hz, 1 H), 7.03-7.14 (m, 1 H), 4.77 (s, 1 H), 3.18 (s, 3 H), 3.04 (s, 3 H), 1.22 (s, 3 H), 1.14 (s, 3 H); MS (ES+) m/z: 493 (M+H); LC retention time: 3.69 min (Analytical HPLC Method D).

(s, 3 H), 2.95 (s, 3 H), 1.02 (s, 3 H), 0.98 (s, 3H); MS (ES+) m/z: 483 (M+H); LC retention time: 3.55 min (Analytical HPLC Method D).

Example 439

Example 440

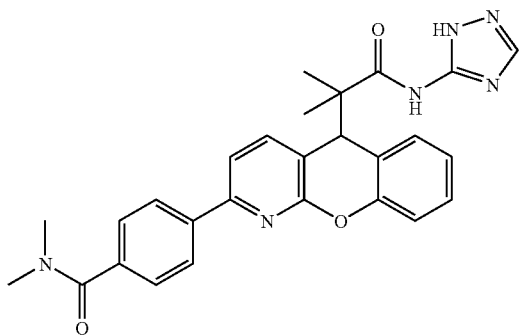

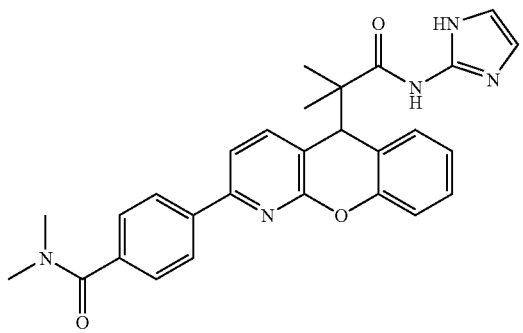

Step 1

To a CH$_2$Cl$_2$ (2 mL) solution of 2-methyl-2-thioisourea sulfate (68.9 mg, 0.366 mmol) and 1 N NaOH (405 µL, 0.405 mmol) at 0° C. was added a solution of the acid chloride from Step 1 of Example 501 (63.7 mg, 0.135 mmol) in CH$_2$Cl$_2$ (2 mL). After 1 h at 0° C., the biphasic mixture was separated and the aqueous layer was extracted with CH$_2$Cl$_2$ (2 mL). The combined CH$_2$Cl$_2$ phase was concentrated to give the expected product as a light brown solid. MS (ES+) m/z: 489 (M+H); LC retention time: 3.34 min (Analytical HPLC Method D).

Step 2

A pyridine (1.5 mL) solution of the crude product from the last step, formohydrazide (14 mg, 0.233 mmol) and (S)-camphorsulfonic acid (56 mg, 0.241 mmol) was heated at 100° C. in a sealed tube. After 3 h at 100° C., the mixture was purified by preparative reverse-phase HPLC (using Shimadzu 10A liquid chromatographs and Waters Sunfire S10 30×250 mm column) to give the title compound as a white solid (13 mg, 15% yield for 2 steps). $^1$H NMR (400 MHz, DMSO-d$_6$) δ ppm 8.16 (d, J=8.56 Hz, 2 H), 7.87 (d, J=7.81 Hz, 1 H), 7.74 (d, J=8.06 Hz, 1 H), 7.52 (d, J=8.31 Hz, 2 H), 7.33-7.42 (m, 2 H), 7.23-7.33 (m, 2 H), 7.12-7.21 (m, 1 H), 4.82 (s, 1 H), 3.01

An acetonitrile (2 mL) solution of the product from Preparation 101 (35.8 mg, 0.086 mmol), 1-trityl-2-aminoimidazole (66.2 mg, 2.4 eq, prepared following a known procedure *J. Med. Chem.* 2000, 43, 27-40), HOBt (30.5 mg, 2.6 eq), EDC (52.5 mg, 3.2 eq) and DIPEA (75 µL, 5 eq) was heated at 60° C. for 16 h. The crude mixture was poured into saturated NH$_4$Cl (20 mL) and extracted with ethyl acetate (10 mL). The ethyl acetate extract was concentrated, dissolved in CH$_2$Cl$_2$ (0.5 mL), treated with TFA (0.5 mL) for 20 min and concentrated. Purification by preparative reverse-phase HPLC (using Shimadzu 10A liquid chromatographs and Waters Sunfire S10 30×250 mm column) gave Example 503 as a white solid (15.5 mg, 37%). 1H NMR (400 MHz, CDCl3) δ ppm 14.11 (s, 1 H), 8.08 (d, J=8.56 Hz, 2 H), 7.77 (d, J=7.81 Hz, 1 H), 7.55 (dd, J=16.37, 8.06 Hz, 3 H), 7.28-7.38 (m, 2 H), 7.15-7.22 (m, 1 H), 7.05-7.14 (m, 1 H), 6.99 (s, 2 H), 4.66 (s, 1 H), 3.16 (s, 3 H), 3.03 (s, 3 H), 1.21 (s, 3 H), 1.14 (s, 3 H); MS (E+) m/z: 482 (M+H); LC retention time: 3.09 min (Analytical HPLC Method D).

Examples 441 to 449

Following procedure analogous to the preparation of Example 440, the following examples were prepared by couplings between appropriate amines (commercially available) and the acid from Preparation 57 or 65.

| Example No. | Structure | Rt (min)* | M/z M + H |
|---|---|---|---|
| 441 | 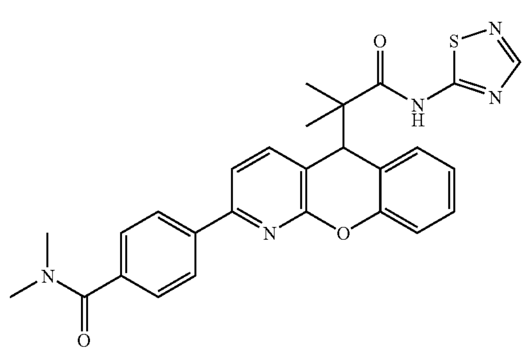 | 3.97 | 500 |

-continued
| Example No. | Structure | Rt (min)* | M/z M + H |
|---|---|---|---|
| 442 | 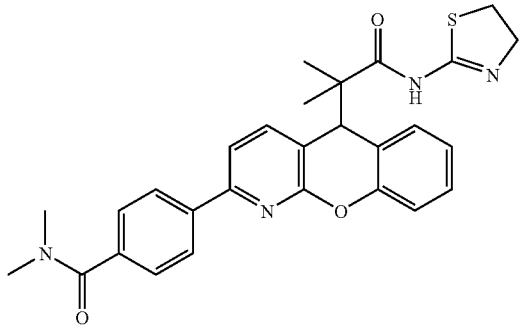 | 3.29 | 501 |
| 443 | 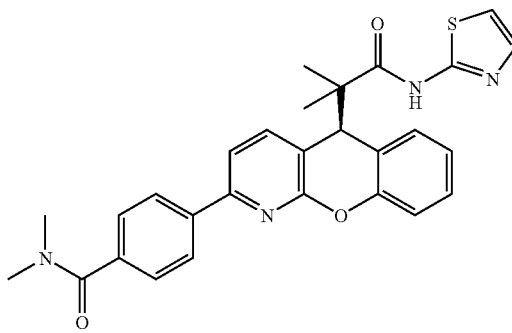 | 4.10 | 513 |
| 444 | 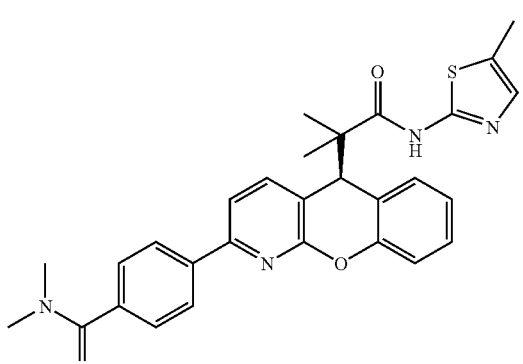 | 4.12 | 513 |
| 445 | 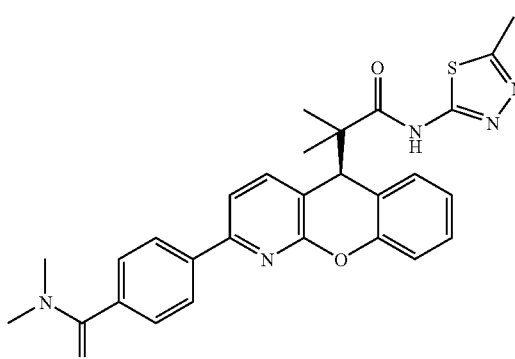 | 3.90 | 514 |

-continued

| Example No. | Structure | Rt (min)* | M/z M + H |
|---|---|---|---|
| 446 | 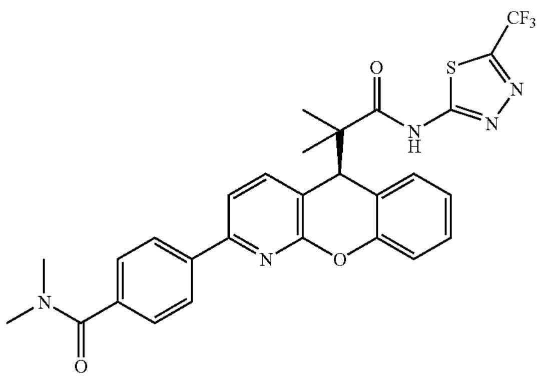 | 4.40 | 568 |
| 447 | 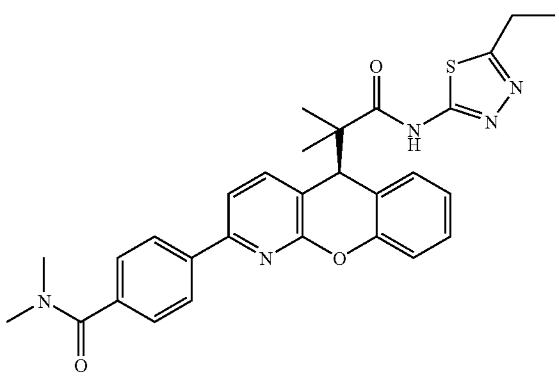 | 4.06 | 528 |
| 448 | 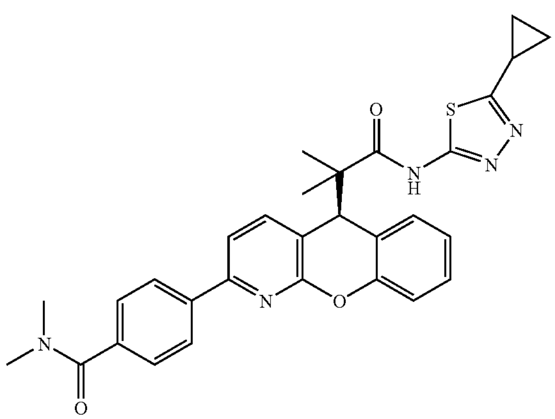 | 4.12 | 540 |
| 449 | 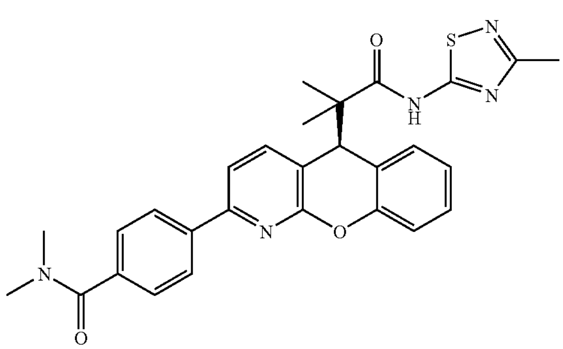 | 4.02 | 514 |

*Analytical HPLC Method D.

Examples 450 to 452

The following Examples 450 to 452 were prepared in the same manner described for the preparation of the title compounds of Examples 168 to 236, using commercially available boronic acids and the product of Preparation 53a. For Example 451, see *Bioorg. & Med. Chem. Lett.* 2003, 13, 4143-4145.

| Example No. | Structure | Rt (min)* | M/z (M + H) |
|---|---|---|---|
| 450 | 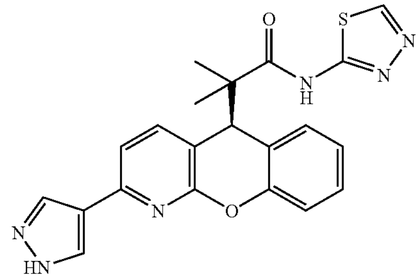 | 3.52 | 419 |
| 451 | 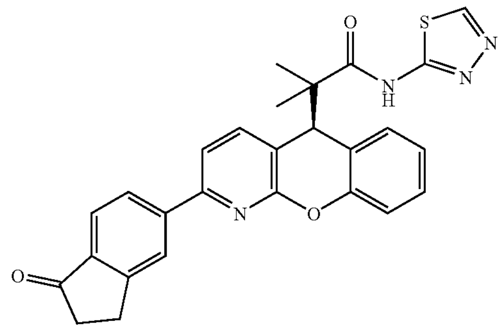 | 4.01 | 483 |
| 452 | 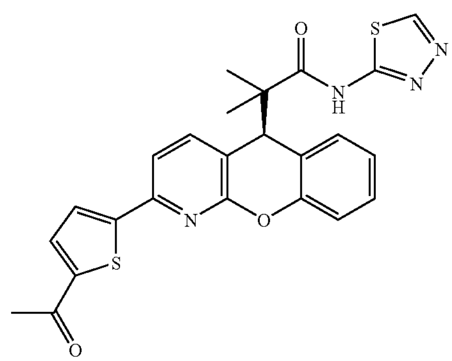 | 3.96 | 477 |

*Analytical HPLC Method D.

Example 453

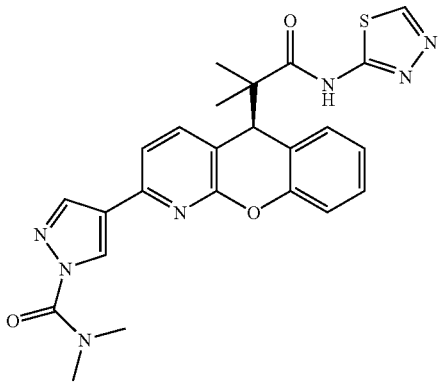

To a THF (1.5 mL) solution of Example 450 (8.1 mg, 0.019 mmol) and dimethylcarbamyl chloride (14 mg, 6.7 eq) was added DBU (20.2 µL, 7 eq). The resulting mixture was heated at 60° C. for 1 h, concentrated and purified by flash column chromatography (ISCO, 4 g silica gel cartridge, 20 to 100% ethyl acetate-hexanes) to give the title compound as a white solid (2.5 mg, 26%). 1H NMR (400 MHz, CDCl3) δ ppm 8.89 (s, 1 H), 8.62 (s, 1 H), 8.19 (s, 1 H), 7.61 (d, J=7.81 Hz, 1H), 7.26-7.37 (m, 3 H), 7.15-7.21 (m, 1 H), 7.01-7.09 (m, 1 H), 4.63 (s, 1 H), 3.26 (s, 6 H), 1.24 (s, 3 H), 1.23 (s, 3 H); MS (E+) m/z: 490 (M+H); LC retention time: 3.74 min (Analytical HPLC Method D).

Examples 454 to 461

Following procedure analogous to preparation of Example 440, the following examples were prepared by couplings between 5-amino-1,2,4-thiadiazole or 2-amino-5-methyl-1,3,4-thiadiazole and the acids from Preparations 67 to 70 and 72 to 73.

| Example No. | Structure | Rt (min)* | M/z M + H |
|---|---|---|---|
| 454 | 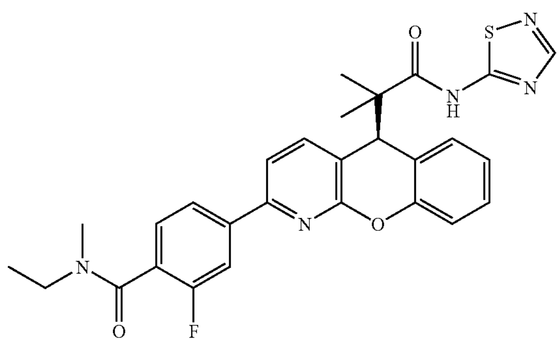 | 4.18 | 532 |
| 455 | 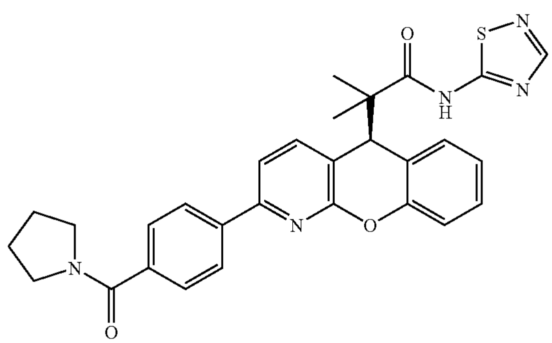 | 4.12 | 526 |
| 456 | 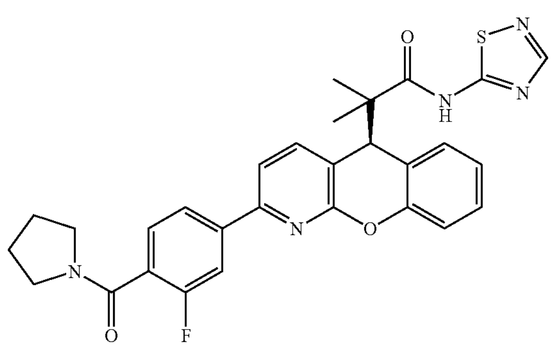 | 4.21 | 544 |

| Example No. | Structure | Rt (min)* | M/z M + H |
|---|---|---|---|
| 457 | 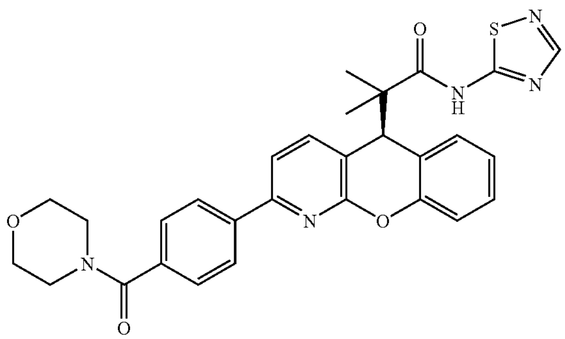 | 3.95 | 542 |
| 458 | 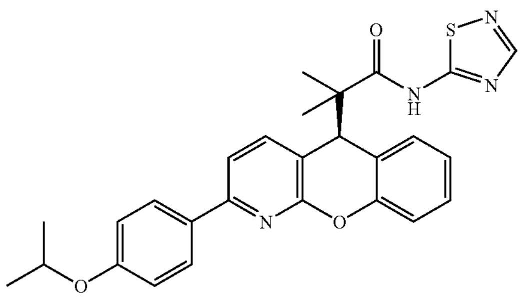 | 4.60 | 487 |
| 459 | 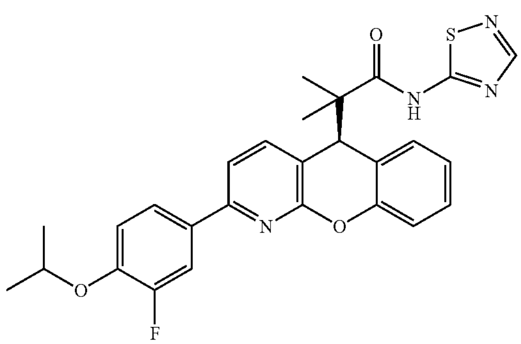 | 4.60 | 505 |
| 460 | 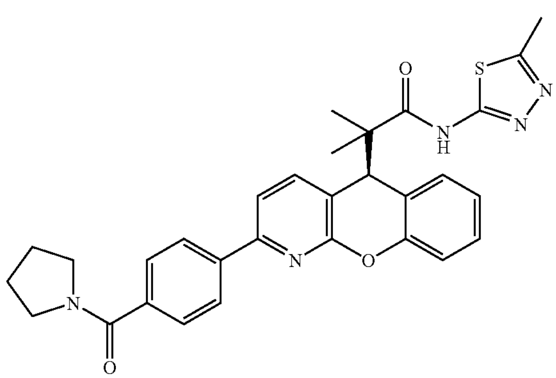 | 4.07 | 540 |

-continued

| Example No. | Structure | Rt (min)* | M/z M + H |
|---|---|---|---|
| 461 | 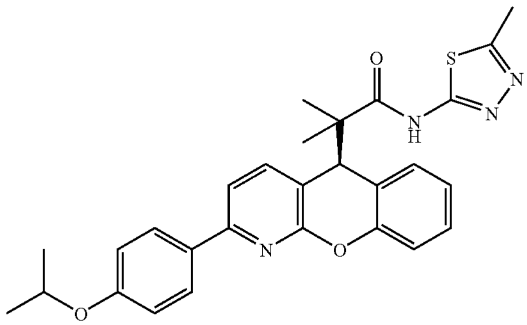 | 4.52 | 501 |

*Analytical HPLC Method D.

Examples 462 to 469

Following procedure analogous to preparation of Example 440, the following examples were prepared by coupling between commercially available amines and the acid from Preparations 78 to 82.

| Example No. | Structure | Rt (min)* | M/z (M + H) |
|---|---|---|---|
| 462 | 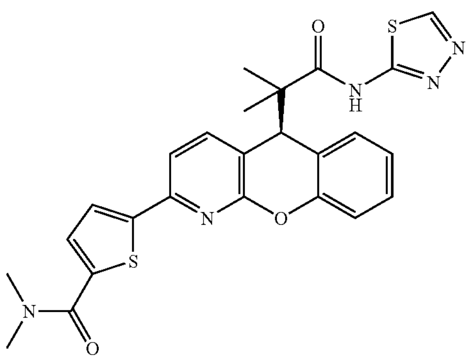 | 3.78 | 506 |
| 463 | 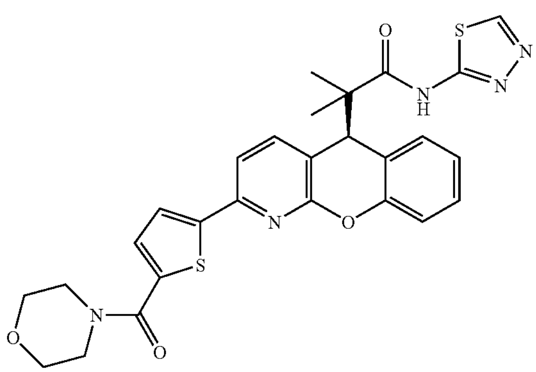 | 3.77 | 548 |

-continued
| Example No. | Structure | Rt (min)* | M/z (M + H) |
|---|---|---|---|
| 464 | 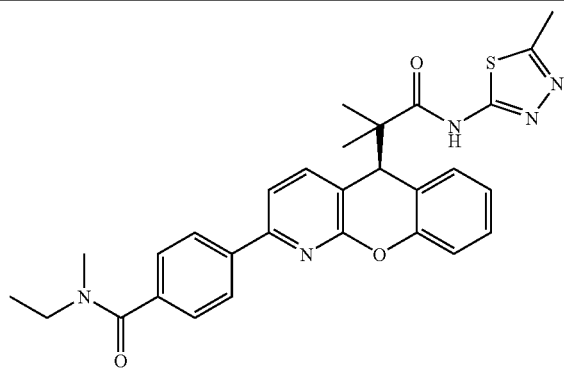 | 4.02 | 528 |
| 465 | 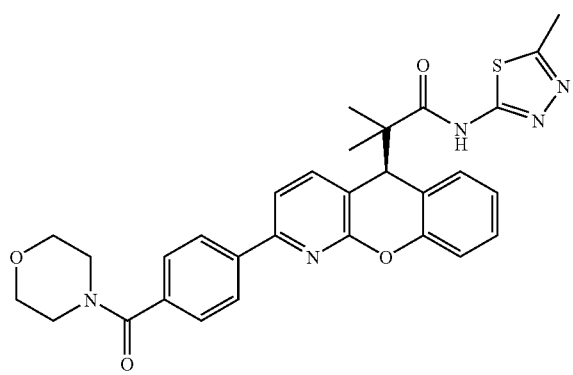 | 3.89 | 556 |
| 466 | 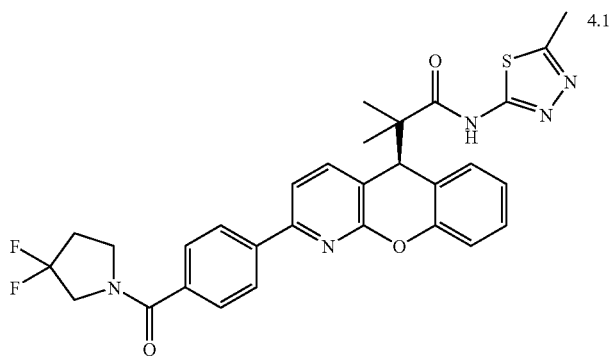 | 4.10 | 576 |
| 467 | 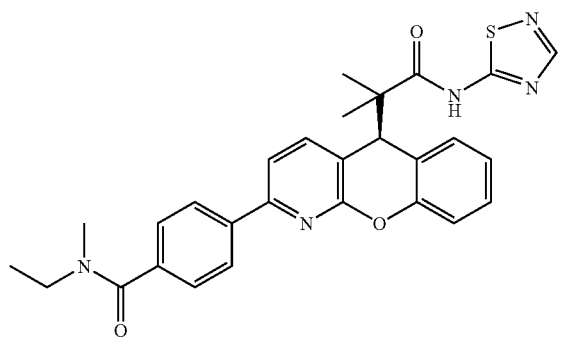 | 4.09 | 514 |

-continued

| Example No. | Structure | Rt (min)* | M/z (M + H) |
|---|---|---|---|
| 468 | 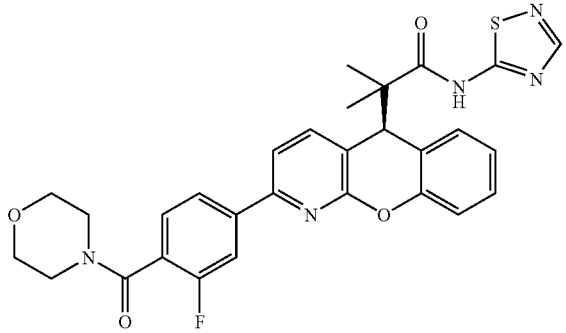 | 4.07 | 560 |
| 469 | 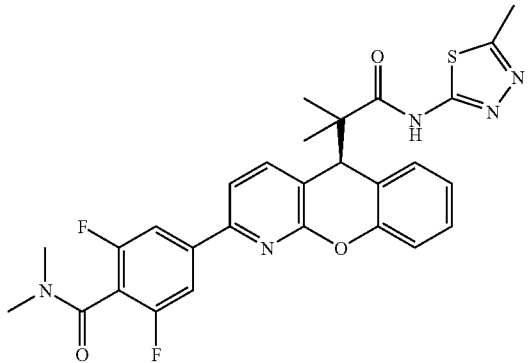 | 4.00 | 550 |

*Analytical HPLC Method D.

Example 470

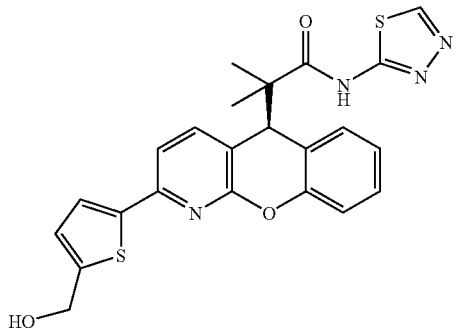

Using procedure analogous to preparation of Example 440, the title compound was prepared by coupling between 2-amino-1,3,4-thiadiazole and the acid from Preparation 66. $^1$H NMR (400 MHz, CDCl3) δ ppm 8.87 (s, 1 H), 7.49-7.60 (m, 2 H), 7.36-7.40 (m, 1 H), 7.28-7.33 (m, 2 H), 6.99-7.12 (m, 3 H), 4.86 (s, 2H), 4.48 (s, 1 H), 1.26 (s, 3 H), 1.21 (s, 3 H); MS (E+) m/z: 465 (M+H); LC retention time: 3.73 min (Analytical HPLC Method D).

Examples 471 to 478

Following procedure analogous to Preparation 57, the following examples were prepared by Suzuki coupling between boronic acids (commercially available or prepared in Preparations 58, 61 and 64) and intermediates from Preparations 75 to 77.

| Example No. | Structure | Rt (min)* | M/z (M + H) |
|---|---|---|---|
| 471 | 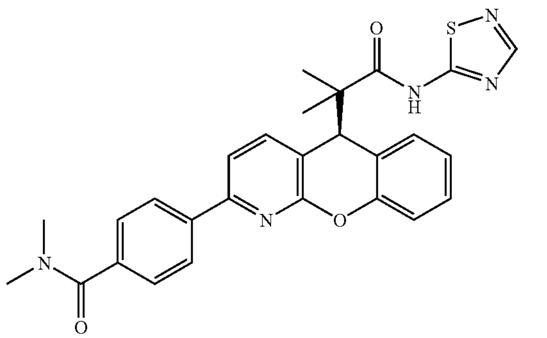 | 3.97 | 500 |
| 472 | 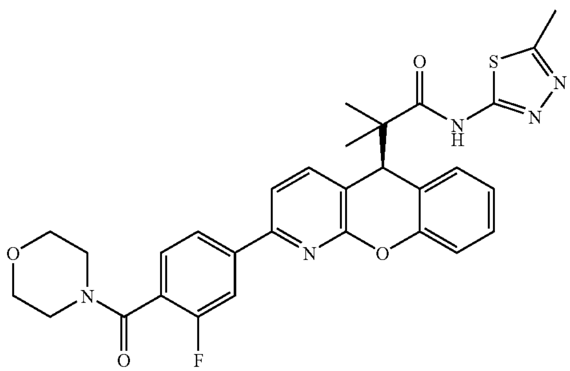 | 4.00 | 574 |
| 473 | 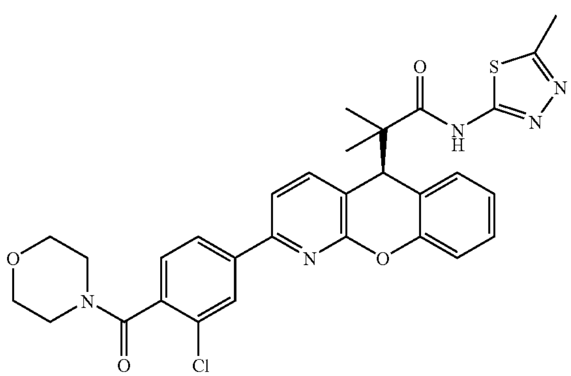 | 4.07 | 590 |
| 474 | 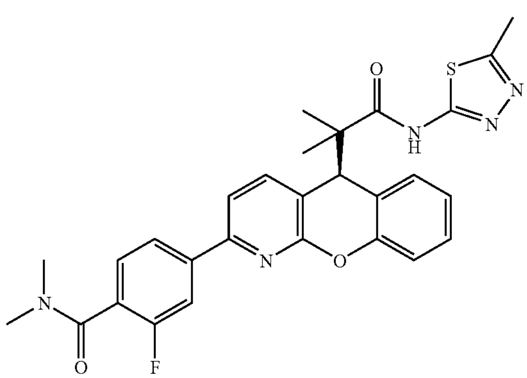 | 3.98 | 532 |

-continued
| Example No. | Structure | Rt (min)* | M/z (M + H) |
|---|---|---|---|
| 475 | 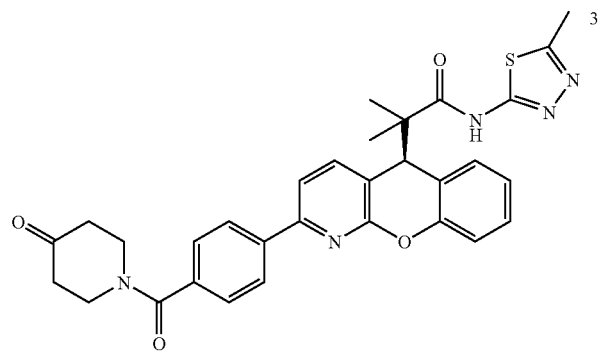 | 3.85 | 568 |
| 476 | 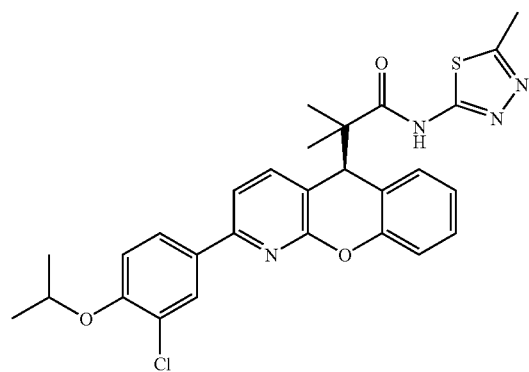 | 4.68 | 535 |
| 477 | 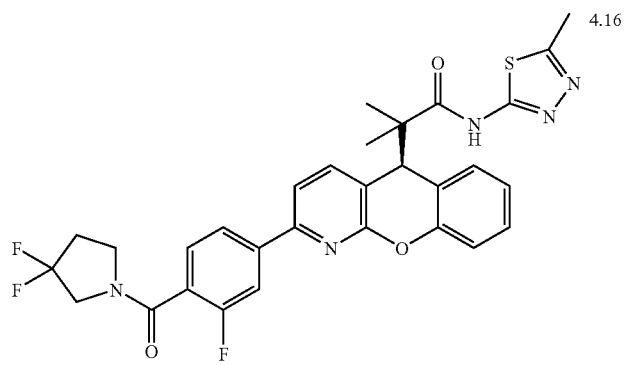 | 4.16 | 594 |
| 478 | 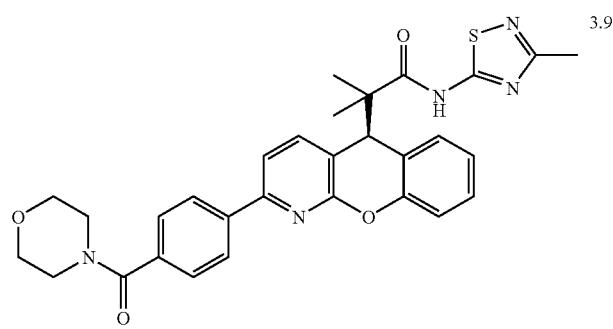 | 3.99 | 556 |
*Analytical HPLC Method D.

Example 479

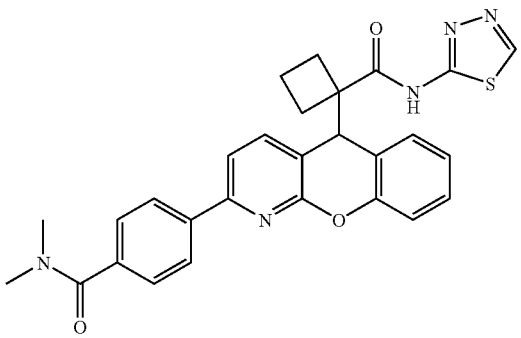

Step 1
A 1.6 M hexane solution of n-butyllithium (2.72 mL, 4.34 mmol) was added to a solution of diisopropylamine (440 mg, 4.34 mmol) in THF (6 mL) at −78° C. over 5 minutes. The resultant solution was warmed to 0° C. for 30 min and cooled to −78° C. A solution of ethyl cyclobutanecarboxylate (464 mg, 3.62 mmol) in THF (1 mL) was added dropwise. The mixture was stirred at −78° C. for 30 min. Chlorotrimethylsilane (0.597 mL, 4.71 mmol) was added. The mixture was warmed to room temperature over 1 h, quenched with saturated NaHCO$_3$ (5 mL), diluted with diethyl ether (200 mL), washed with water (20 mL), brine (20 mL), dried (MgSO$_4$) and concentrated to give (cyclobutylidene(ethoxy)methoxy)trimethylsilane, which was taken to next step without further purification.

Step 2
A 1.0 M dichloromethane solution titanium(IV) chloride (0.254 mL, 0.254 mmol) was added to a solution of the product from Preparation 83 (80 mg, 0.231 mmol) in dichloromethane (10 mL) at 0° C. After 10 min at 0° C., the crude (cyclobutylidene(ethoxy)methoxy)trimethylsilane (350 mg, ~1.75 mmol) was added. After 1 h at 0° C., the mixture was quenched with saturated NaHCO$_3$ (5 mL), diluted with dichloromethane (80 mL), washed with water (10 mL), brine (10 mL), dried (MgSO$_4$) and concentrated. Purification by flash column chromatography (silica gel, 50-100% ethyl acetate in hexanes) gave ethyl 1-(2-(4-(dimethylcarbamoyl)phenyl)-5H-chromeno[2,3-b]pyridin-5-yl)cyclobutanecarboxylate (80 mg, 76%). MS (ES+) m/z: 457 (M+H).

Step 3
Sodium propane-2-thiolate (172 mg, 1.75 mmol) was added to a solution of the product from Step 2 (80 mg, 0.175 mmol) in DMF (5 mL) at room temperature. After 15 h at 60° C., the mixture was cooled to room temperature and adjusted pH2-3 with 1 N aqueous HCl. After addition of ethyl acetate (100 mL), the mixture was washed with water (10 mL), brine (10 mL), dried (MgSO$_4$) and concentrated. Purification by preparative HPLC gave the desired 1-(2-(4-(dimethylcarbamoyl)phenyl)-5H-chromeno[2,3-b]pyridin-5-yl)cyclobutanecarboxylic acid (45 mg, 60%). MS (ES+) m/z: 429 (M+H).

Step 4
The mixture of the product from Step 3 (22 mg, 0.051 mmol), 1,3,4-thiadiazol-2-amine (10.4 mg, 0.103 mmol), EDC (19.7 mg, 0.103 mmol), HOBT (15.7 mg, 0.103 mmol) and DIEA (0.036 mL, 0.205 mmol) in acetonitrile (2 mL) was heated to 70° C. for 15 h. Then the mixture was cooled to room temperature, quenched with saturated NaHCO$_3$ (2 mL), diluted with ethyl acetate (60 mL), washed with water (10 mL), brine (10 mL), dried (MgSO$_4$) and concentrated. The residue was purified by preparative HPLC to give the title compound (12 mg, 46%). $^1$H-NMR (400 MHz, CDCl$_3$) δ 11.93 (s, 1 H), 8.93 (s, 1 H), 8.06 (d, J=8.4 Hz, 2 H), 7.85 (d, J=7.6 Hz, 1 H), 7.53 (m, 2 H), 7.37 (d, J=7.6 Hz, 1 H), 7.28 (m, 3 H), 7.07 (m, 1 H), 4.69 (s, 1 H), 3.14 (s, 3 H), 3.01 (s, 3 H), 2.45 (m, 4 H), 1.67 (m, 1 H), 1.31 (m, 1 H); MS (ES+) m/z: 512 (M+H); HPLC retention time: 1.65 min (Analytical HPLC Method F).

Examples 480 and 481

EXAMPLE 480

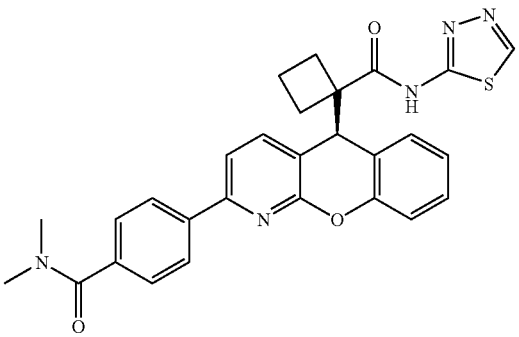

EXAMPLE 481

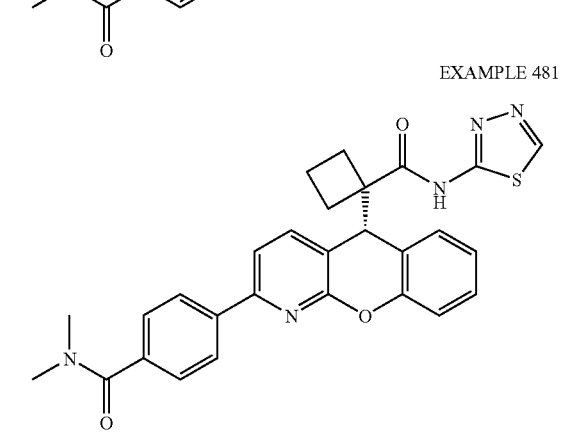

The title compound of Example 480 (400 mg, 0.783 mmol) was purified by chiral SFC (AD-H column, CO$_2$/MeOH=65/35) to provide Example 480 (fast eluting enantiomer, 113 mg, 28%) and Example 481 (slow eluting enantiomer, 120 mg, 30%). Data for Example 480: $^1$H-NMR (400 MHz, MeOH-d$_4$) δ 9.10 (s, 1H), 8.12 (d, J=8.4 Hz, 2H), 7.75 (m, 2H), 7.56 (d, J=8.4 Hz, 2H), 7.39 (m, 2H), 7.25 (m, 2H), 4.58 (s, 1H), 3.15 (s, 3H), 3.07 (s, 3H), 2.37 (m, 3H), 2.29 (m, 1H), 1.56 (m, 1H), 1.20 (m, 1H); MS (ES+) m/z: 512 (M+H); HPLC retention time: 1.65 min (Analytical HPLC Method F). Data for Example 481: MS (ES+) m/z: 512 (M+H); HPLC retention time 1.65 min (Analytical HPLC Method F). Both enantiomers were analyzed using chiral HPLC (Chiralpak AD-H column: 0.46×25 cm, 5 μm; temperature: 40° C.; flow rate: 2.0 mL/min; mobile phase: CO$_2$/MeOH (65/35); detector wavelength: 252 nm). Retention times for Examples 480 and 481 are 13.0 and 18.0 min, respectively.

Examples 482 to 485

Examples 482 to 485 were prepared in a sequence similar to Example 479, substituting methyl propionate and ethyl cyclobutanecarboxylate for ethyl cyclobutanecarboxylate. Example 484 and 485 were prepared following a sequence similar to Preparation 17, substituting (cyclopentylidene (methoxy)methoxy)trimethylsilane for methyl trimethylsilyl dimethylketene acetal, Preparation 57 and coupling with 2-amino-1,3,4-thiadiazole or 5-amino-1,2,4-thiadiazole.

| Example No. | Structure | Rt (min)* | M/z (M + H) |
|---|---|---|---|
| 482 | 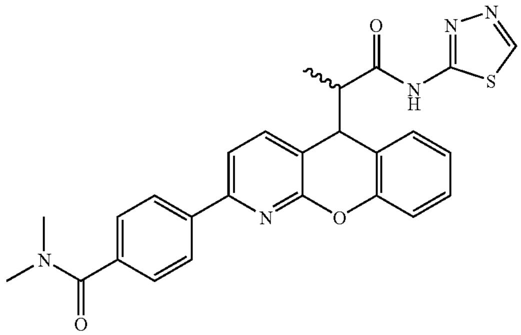 | 3.65* | 486 |
| 483 | 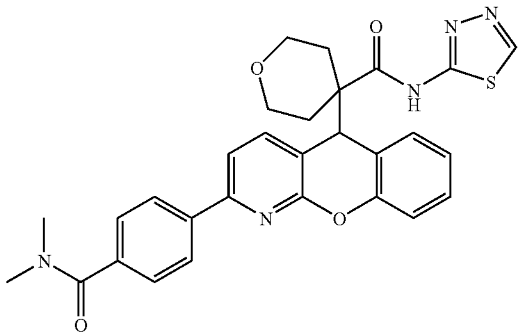 | 1.89** | 542 |
| 484 | 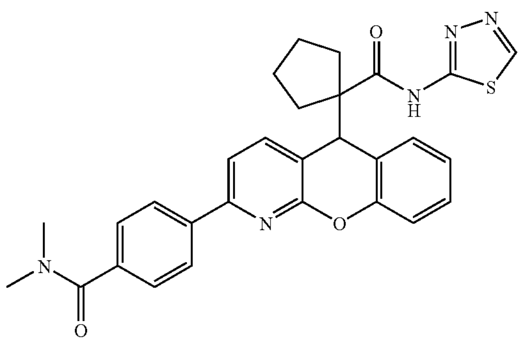 | 3.86* | 526 |
| 485 | 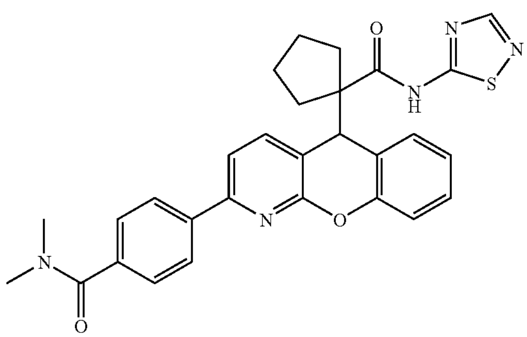 | 4.04* | 526 |

*Analytical HPLC Method D.
**Analytical HPLC Method F.

Examples 486 and 487

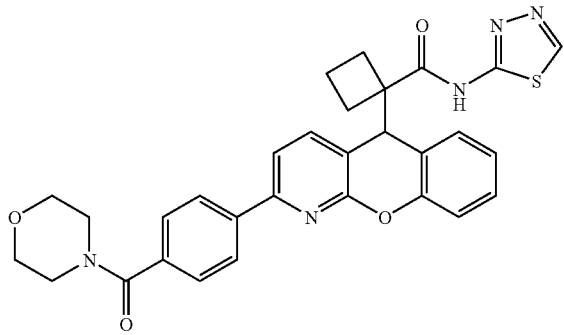

Step 1

Following procedure similar to Step 2 of Example 479, the alcohol from Preparation 84 (700 mg, 2.10 mmol) was reacted with (cyclobutylidene(ethoxy)methoxy)trimethylsilane to give methyl 4-(5-(1-(ethoxycarbonyl)cyclobutyl)-5H-chromeno[2,3-b]pyridin-2-yl)benzoate (250 mg, 27%). MS (ES+) m/z: 444 (M+H).

Step 2

A 1 N aqueous solution of NaOH (5 mL, 5.00 mmol) was added to a solution of the product from Step 1 (250 mg, 0.564 mmol) in MeOH (10 mL) at room temperature. After 24 h at 80° C., the mixture was cooled to room temperature and adjusted pH2-3 with 1 N aqueous HCl. MeOH was evaporated in vacuo. The brown precipitate in the aqueous residue was collected by filtration and dried under vacuum to give 4-(5-(1-carboxycyclobutyl)-5H-chromeno[2,3-b]pyridin-2-yl)benzoic acid (210 mg, 93%). MS (ES+) m/z: 402 (M+H).

Step 3

A mixture of the product from Step 2 (50 mg, 0.125 mmol), EDC (71.6 mg, 0.374 mmol), HOBT (57.2 mg, 0.374 mmol) and DIEA (0.131 mL, 0.747 mmol) in acetonitrile (2 mL) was stirred at room temperature for 10 min and cooled to 0° C.

A solution of morpholine (13.1 mg, 0.149 mmol) in acetonitrile (1 mL) was added dropwise. The resultant mixture was stirred at 0° C. for 1 h, quenched with saturated $NH_4Cl$ (2 mL). After addition of ethyl acetate (60 mL), the mixture was washed with water (5 mL), brine (5 mL), dried ($MgSO_4$) and concentrated to provide 1H-benzo[d][1,2,3]triazol-1-yl 1-(2-(4-(morpholine-4-carbonyl)phenyl)-5H-chromeno[2,3-b]pyridin-5-yl)cyclobutanecarboxylate (75 mg), which was taken to next step without further purification. MS (ES+) m/z: 588 (M+H).

Step 4

Following similar procedure as Step 4 of Example 479, the product from Step 3 (73.5 mg, 0.125 mmol) was converted to the desired product (32 mg, 46%). The racemic mixture was separated by chiral SFC (AD-H column, $CO_2$/MeOH=65/35) to provide Example 486 (fast eluting enantiomer, 10 mg) and Example 487 (slow eluting enantiomer, 10 mg). Data for Example 486: $^1$H-NMR (400 MHz, MeOH-$d_4$) δ 8.99 (s, 1H), 8.02 (d, J=8.4 Hz, 2H), 7.63 (m, 2H), 7.45 (d, J=8.4 Hz, 2H), 7.27 (m, 2H), 7.13 (m, 2H), 4.45 (s, 1H), 3.40-3.80 (m, 8H), 2.25 (m, 3H), 2.15 (m, 1H), 1.40 (m, 1H), 1.15 (m, 1H); MS (ES+) m/z: 554 (M+H); HPLC retention time: 2.01 min (Analytical HPLC Method E). Data for Example 487: MS (ES+) m/z: 554 (M+H); HPLC retention time: 2.02 min (Analytical HPLC Method E). Both enantiomers were analyzed using chiral HPLC (Chiralpak AD-H column: 0.46×25 cm, 5 μm; temperature: 40° C.; flow rate: 3.0 mL/min; mobile phase: $CO_2$/MeOH (65/35); detector wavelength: 270 nm). Retention times for Examples 486 and 487 are 9.2 and 13.4 min, respectively.

Example 488

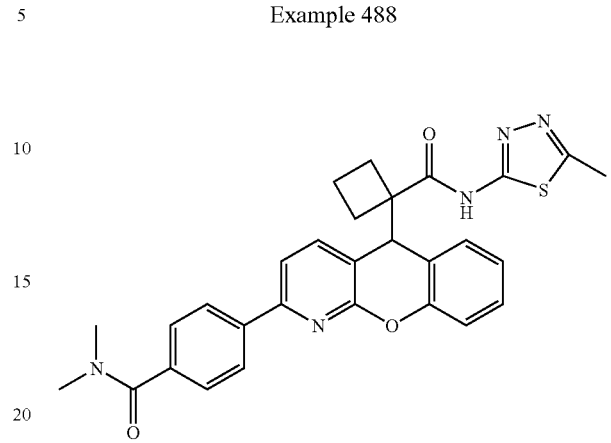

Following similar procedure to Steps 3 and 4 of Examples 486 and 487, the product from Step 2 of Examples 486 and 487 (50 mg, 0.125 mmol) was converted to the title compound (5.8 mg, 7%). MS (ES+) m/z: 526 (M+H); HPLC retention time: 2.03 min (Analytical HPLC Method E).

Example 489

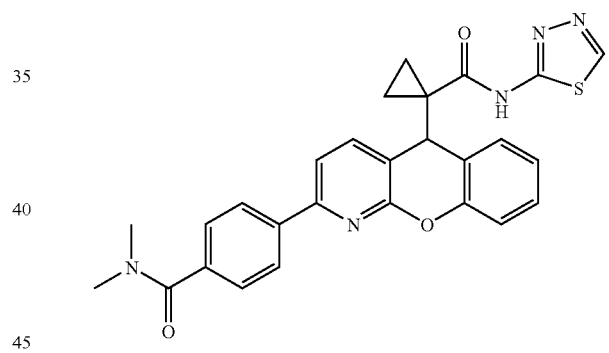

Step 1

Following similar procedure to Step 2 of Example 479, alcohol from Preparation 83 (160 mg, 0.462 mmol) was converted to methyl 2-(2-(4-(dimethylcarbamoyl)phenyl)-5H-chromeno[2,3-b]pyridin-5-yl)acetic acid (170 mg, 92%). MS (ES+) m/z: 403 (M+H); HPLC retention time: 1.65 min (Analytical HPLC Method F).

Step 2

A 1.6 M hexane solution of n-butyllithium (0.38 mL, 0.62 mmol) was added to a solution of diisopropylamine (0.089 mL, 0.62 mmol) in THF (5 mL) at −78° C. over 5 min. The resultant solution was warmed to 0° C. for 30 min and cooled to −78° C. A solution of the product from Step 1 (100 mg, 0.248 mmol) in THF (1 mL) was added dropwise. The mixture was stirred at −78° C. for 30 min and at −30° C. for 30 min. Formaldehyde (60 mg) was bubbled into the mixture by a stream of N2 at −30° C. The resultant mixture was stirred at −30° C. for 30 min, quenched with MeOH (1 mL) and warmed to room temperature. After addition of ethyl acetate (80 mL), the mixture was washed with saturated $NaHCO_3$ (10 mL), water (10 mL), brine (10 mL), dried (MgSO₄) and concentrated. The residue was purified by flash column chromatography (silica, 50-100% ethyl acetate in hexanes) to provide methyl 2-(2-(4-(dimethylcarbamoyl)phenyl)-5H-chromeno[2,3-b]pyridin-5-yl)-3-hydroxypropanoate (80 mg, 74%). MS (ES+) m/z: 433 (M+H).

Step 3

Methanesulfonyl chloride (0.072 mL, 0.925 mmol) was added to a mixture of the product from Step 2 (80 mg, 0.185 mmol), TEA (0.258 mL, 1.85 mmol) and DMAP (24.9 mg, 0.203 mmol) in DCM (2 mL) at 0° C. After 1 h at this temperature, the mixture was concentrated in vacuo. The residue was suspended in benzene (4 mL), treated with DBU (0.139 mL, 0.925 mmol) and stirred at room temperature for 1 h. Saturated NaHCO₃ (5 mL) and ethyl acetate (100 mL) were added. The mixture was washed with water (2×10 mL), brine (10 mL), dried (MgSO₄) and concentrated. The residue was purified by flash column chromatography (silica, 50-100% ethyl acetate in hexanes) to provide methyl 2-(2-(4-(dimethylcarbamoyl)phenyl)-5H-chromeno[2,3-b]pyridin-5-yl)acrylate (45 mg, 59%). MS (ES+) m/z: 415 (M+H); HPLC retention time: 1.73 min (Analytical HPLC Method F).

Step 4

Sodium hydride (5.2 mg, 0.13 mmol, 60% in mineral oil) was added to a solution of trimethyl sulfoxonium iodide (28.7 mg, 0.13 mmol) in DMSO (1 mL) at room temperature. After 30 min at room temperature, the mixture was added to a solution of the product from Step 3 (45 mg, 0.109 mmol) in DMSO (1 mL). The resultant mixture was stirred at room temperature for 10 min and quenched with saturated NaHCO₃ (1 mL). After addition of ethyl acetate (80 mL), the mixture was washed with water (2×10 mL), brine (10 mL), dried (MgSO₄) and concentrated. The residue was purified by flash column chromatography (silica, 50-100% ethyl acetate in hexanes) to provide methyl 1-(2-(4-(dimethylcarbamoyl)phenyl)-5H-chromeno[2,3-b]pyridin-5-yl)cyclopropanecarboxylate (12 mg, 26%). MS (ES+) m/z: 429 (M+H).

Step 5

A 1 N aqueous solution of NaOH (0.5 mL, 0.500 mmol) was added to a solution of the product from Step 4 (11 mg, 0.026 mmol) in MeOH (1 mL) at room temperature. The mixture was heated to 60° C. for 3 h, cooled to room temperature and adjusted pH2-3 with 1 N aqueous HCl. Following addition of ethyl acetate (60 mL), the mixture was washed with brine (10 mL), dried (MgSO₄) and concentrated to give 1-(2-(4-(dimethylcarbamoyl)phenyl)-5H-chromeno[2,3-b]pyridin-5-yl)cyclopropanecarboxylic acid as crude material (11 mg), which was taken to the next step directly. MS (ES+) m/z: 415 (M+H).

Step 6

Following similar procedure to Step 4 of Example 479, the product from Step 5 (11 mg, 0.027 mmol) was converted to the title compound (5.0 mg, 40%). ¹H-NMR (400 MHz, MeOH-d₄) δ 8.90 (s, 1H), 8.42 (s, 1H), 8.00 (d, J=8.4 Hz, 2H), 7.85 (m, 1H), 7.58 (m, 1H), 7.43 (d, J=8.4 Hz, 2H), 7.24 (m, 2H), 7.10 (m, 2H), 4.65 (s, 1H), 3.02 (s, 3H), 2.94 (s, 3H), 1.13 (m, 4H); MS (ES+) m/z: 498 (M+H); HPLC retention time: 2.04 min (Analytical HPLC Method E).

Example 490

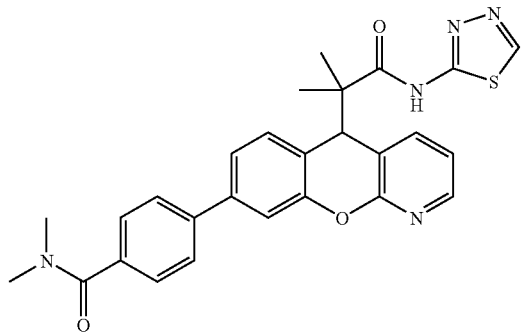

Step 1

A 1.6 M hexane solution of n-butyllithium (39.8 mL, 63.6 mmol) was added to a solution of diisopropylamine (9.45 mL, 66.3 mmol) in THF (100 mL) at −78° C. over 10 min. The resultant solution was stirred at 0° C. for 30 min and cooled to −78° C. Acetonitrile (3.32 mL, 63.6 mmol) dropwise. The mixture was stirred at −78° C. for 30 min and then added a solution of 4-chloro-2-fluorobenzoate (5.00 g, 26.5 mmol) in THF (5 mL) at −78° C. dropwise. After stirring for 1 h at −78° C., the reaction mixture was quenched with brine (20 mL), warmed to room temperature and adjusted to pH 1-2 with 1N aqueous HCl. Following addition of ethyl acetate (400 mL), the mixture was washed with water (40 mL), brine (40 mL), dried (MgSO₄) and concentrated to provide 3-(4-chloro-2-fluorophenyl)-3-oxopropanenitrile as tan solid (5.10 g, 97%). MS (ES+) m/z: 198 (M+H).

Step 2

A mixture of (E)-3-(dimethylamino)acrylaldehyde (3.26 g, 32.9 mmol), the product from Step 1 (5.00 g, 25.3 mmol) and acetic acid (7.24 mL, 127 mmol) in DMF (40 mL) was heated to 120° C. for 48 h and cooled to room temperature. Ethyl acetate (400 mL) was added and the mixture washed with saturated NaHCO₃ (40 mL), water (40 mL), brine (40 mL), dried (MgSO₄) and concentrated. The residue was purified by flash column chromatography (silica, 10-40% ethyl acetate in hexanes) to provide 8-chloro-5H-chromeno[2,3-b]pyridin-5-one (600 mg, 10%). MS (ES+) m/z: 232 (M+H).

Step 3

Sodium borohydride (490 mg, 13.0 mmol) was added to a solution of the product from Step 2 (600 mg, 2.59 mmol) in MeOH (16 mL) and dichloromethane (4 mL) at 0° C. After 2 h at this temperature, the mixture was quenched with saturated NaHCO₃ (5 mL). The organic solvents were evaporated in vacuo. The residue was dissolved in dichloromethane (100 mL), washed with water (10 mL), brine (10 mL), dried (MgSO₄) and concentrated to crude 8-chloro-5H-chromeno[2,3-b]pyridin-5-ol (600 mg), which was taken directly to the next step. MS (ES+) m/z: 234 (M+H).

Step 4

Following similar procedure as Step 2 of Example 479, the product from step 3 (600 mg, 2.59 mmol) was converted to methyl 2-(8-chloro-5H-chromeno[2,3-b]pyridin-5-yl)-2-methylpropanoate (450 mg, 55%). MS (ES+) m/z: 318 (M+H).

Step 5

A 25 mL flask containing Pd(dba)₂ (25.3 mg, 0.044 mmol) was flushed with N₂. Dioxane (2 mL) and a 1.0 M THF solution of tricyclohexylphosphine (0.106 mL, 0.106 mmol) were added. The resultant black mixture was stirred at room temperature for 30 min. Bis(pinacolato)diboron (123 mg, 0.485 mmol), potassium phosphate (64.9 mg, 0.661 mmol) and the product from Step 4 (140 mg, 0.441 mmol) were added successively. The mixture was heated to 80° C. for 15 h and cooled to room temperature. Following addition of water (5 mL) and dichloromethane (80 mL), the mixture was washed with water (10 mL), brine (10 mL), dried (MgSO$_4$) and concentrated. The residue was purified by flash column chromatography (silica, 0-40% ethyl acetate in hexanes) to provide methyl 2-methyl-2-(8-(4,4,5,5-tetramethyl-1,3,2-dioxaborolan-2-yl)-5H-chromeno[2,3-b]pyridin-5-yl)propanoate (65 mg, 36%). MS (ES+) m/z: 410 (M+H).
Step 6

A mixture of the product from Step 5 (65 mg, 0.159 mmol), 4-bromo-N,N-dimethylbenzamide (72.4 mg, 0.318 mmol), 2.0 M aqueous potassium phosphate (0.397 mL, 0.794 mmol) and Pd(Ph$_3$P)$_4$ (27.5 mg, 0.024 mmol) in DMF (3 mL) was purged with N$_2$, heated to 100° C. for 15 h, and cooled to room temperature. After addition of ethyl acetate (80 mL), the mixture was washed with water (10 mL), brine (10 mL), dried (MgSO$_4$) and concentrated. The residue was purified by flash column chromatography (silica, 30-100% ethyl acetate in hexanes) to provide methyl 2-(8-(4-(dimethylcarbamoyl)phenyl)-5H-chromeno[2,3-b]pyridin-5-yl)-2-methylpropanoate (50 mg, 73%). MS (ES+) m/z: 431 (M+H).
Step 7

Following similar procedures to Step 4 to 5 of Example 479, the product from Step 6 (50 mg, 0.116 mmol) was converted to the title compound (3.0 mg, 5%).

$^1$H-NMR (400 MHz, CDCl$_3$) δ 8.90 (s, 1H), 8.38 (s, 1H), 7.75 (m, 1H), 7.63 (m, 2H), 7.52 (m, 3H), 7.35 (m, 2H), 7.20 (m, 2H), 4.62 (s, 1H), 3.20 (s, 3H), 3.09 (s, 3H), 1.27 (s, 3H), 1.26 (s, 3H); MS (ES+) m/z: 500 (M+H); HPLC retention time: 2.01 min (Analytical HPLC Method E).

Example 491

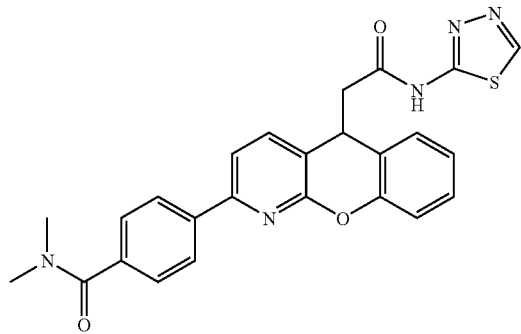

Step 1

Allylchlorodimethylsilane (0.124 mL, 0.85 mmol) and indium chloride (18.8 mg, 0.085 mmol) were added to a yellow solution of the alcohol from Preparation 83 (147 mg, 0.425 mmol) in dichloromethane (25 mL). After 15 h at room temperature, another portion of allylchlorodimethylsilane (0.124 mL, 0.85 mmol) was added. After additional 6 h at rt, the mixture was concentrated and purified by silica gel chromatography (50% to 100% ethyl acetate in hexane) to give 4-(5-allyl-5H-chromeno[2,3-b]pyridin-2-yl)-N,N-dimethylbenzamide as a yellow liquid (160 mg, ~90% pure). MS (ES+) m/z: 371 (M+H); HPLC retention time: 4.05 min (Analytical HPLC Method D).
Step 2

Ozone was bubbled through a solution of the product from Step 1 (40 mg, 0.108 mmol) in dichloromethane (3 mL) and methanol (3 mL) at −78° C. until the solution turned blue. The solution was purged with nitrogen until the blue color disappeared. Polystyrene-supported triphenylphosphine (432 mg, 1 mmol/g) was added. After 6 h of stirring at ambient temperature, the mixture was filtered through a celite plug and the plug rinsed with ethyl acetate. The filtrate was concentrated to crude N,N-dimethyl-4-(5-(2-oxoethyl)-5H-chromeno[2,3-b]pyridin-2-yl)benzamide, which was used without purification. MS (ES+) m/z: 405 (M+MeOH+H).
Step 3

To a mixture of the aldehyde from Step 2, potassium dihydrogenphosphaste (0.047 ml, 0.810 mmol), and sodium chlorite (0.098 g, 1.080 mmol) were added t-butanol (4 ml), a 2 M THF solution of 2-methyl-2-butene (2 ml, 4.00 mmol) and water (2 ml). After stirring at rt for 2 h, the organic solvent was evaporated in vacuo. The residue was taken up in ethyl acetate (50 mL), washed with brine (2×10 mL), dried (MgSO$_4$) and concentrated. Silica gel chromatography, using 0 to 20% of methano in dichloromethane gave impure 2-(2-(4-(dimethylcarbamoyl)phenyl)-5H-chromeno[2,3-b]pyridin-5-yl)acetic acid, which was taken to next step without further purification.
Step 4

To a solution of the impure acid from Step 3 in acetonitrile (5 mL) was added HOBT (24.81 mg, 0.162 mmol), EDC (31.1 mg, 0.162 mmol), 1,3,4-thiadiazol-2-amine (21.84 mg, 0.216 mmol) and Hunig's Base (0.094 ml, 0.540 mmol). The mixture was stirred at room temperature for 3 h and at 60° C. for 1 h. The organic solvents were evaporated in vacuo. The residue was diluted with saturated NH$_4$Cl (10 mL) and extracted with dichloromethane (3×10 mL). The combined extracts were concentrated and purified by reverse-phase HPLC(YMC ODS S5 30×100 mm column) to give the title compound as a TFA salt (11.6 mg, 18% yield over three steps). $^1$H-NMR (400 MHz, MeOH-d$_4$) δ 8.93 (s, 1H), 7.98-7.96 (m, 2H), 7.77 (d, J=7.8 Hz, 1H), 7.56 (d, J=7.8 Hz, 1H), 7.45-7.41 (m, 2H), 7.26-7.18 (m, 2H), 7.12-7.10 (m, 1H), 7.04-7.00 (m, 1H), 4.66 (t, J=6.9 Hz, 1H), 3.02 (s, 3H), 2.93 (s, 3H), 2.88-2.85 (m, 2H); MS (ES+) m/z: 472 (M+H); HPLC retention time: 3.58 min (Analytical HPLC Method D).

Example 492

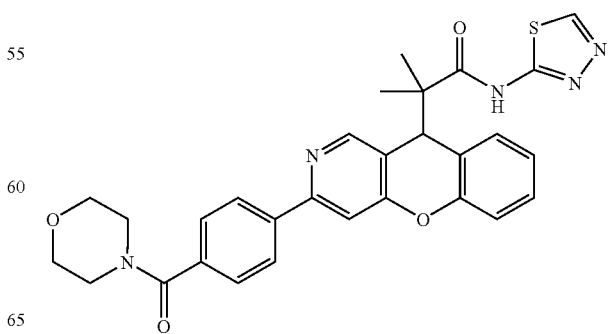

Step 1
A 2.5 M hexane solution of BuLi (16.46 mL, 41.1 mmol) was added dropwise to a solution of diisopropylamine (6.11 mL, 42.9 mmol) in THF (150 mL) at −78° C. The mixture was stirred at 0° C. for 15 min and cooled to −78° C. Acetone (3.02 mL, 41.1 mmol) was added dropwise. After 2 h at −78° C., 2-chlorobenzoyl chloride (3.00 g, 17.14 mmol) in THF (10 mL) was added dropwise. The flask was rinsed with THF (2 mL) and added. After 1 h at −78° C., the mixture was quenched with brine (200 mL) and acidified to pH ~1 with 1 N HCl. The organic solvents were evaporated in vacuo. The aqueous residue was extracted with EtOAc (3×100 mL). The combined extracts were dried (MgSO$_4$) and concentrated to give crude 1-(2-chlorophenyl)butane-1,3-dione as a yellow liquid. The crude material was taken to next step without purification. MS (ES+) m/z: 197 (M+H).

Step 2
A mixture of crude 1-(2-chlorophenyl)butane-1,3-dione from the previous step and 1,1-dimethoxy-N,N-dimethylmethanamine (2.042 g, 17.14 mmol) in toluene (20 mL) was heated to reflux for 2 h and concentrated. Silica gel chromatography, using 70 to 100% ethyl acetate in hexanes gradient, gave 1-(2-chlorophenyl)-2-((dimethylamino)methylene)butane-1,3-dione as a red, viscous oil (2.20 g, 51% yield for 2 steps). MS (ES+) m/z: 252 (M+H); HPLC retention time: 2.51 min (Analytical HPLC Method D).

Step 3
A 1.0 M hexane solution of LiHMDS (19.86 mL, 19.86 mmol) was added dropwise to a solution of 1-(2-chlorophenyl)-2-((dimethylamino)methylene)butane-1,3-dione (2.00 g, 7.95 mmol) and methyl 4-(chlorocarbonyl)benzoate (1.894 g, 9.53 mmol) in THF (100 mL) at −78° C. After 1 h at −78° C., the cold bath was removed and acetic acid (5 mL) and ammonium acetate (1.225 g, 15.89 mmol) were added. The mixture was heated to 70° C. for 1 h, at reflux for 1.5 h, concentrated to dryness in vacuo and taken up in N,N-dimethylacetamide (50 mL). After addition of acetic acid (5 mL), the mixture was heated to 140° C. for 24 h, cooled to room temperature, diluted with MeOH (100 mL) and water (10 mL), cooled to 0° C. for 30 min and filtered. The solid was washed with MeOH three times to give a 7:3 mixture of methyl 4-(10-oxo-10H-chromeno[3,2-c]pyridin-3-yl)benzoate and 4-(10-oxo-10H-chromeno[3,2-c]pyridin-3-yl)benzoic acid.

Step 4
A mixture of the products from Step 3, 1 N solution of NaOH (50 mL, 50.0 mmol), MeOH (50 mL) and THF (50 mL) was heated to reflux. After 1 h, additional MeOH (50 mL) and DMF (10 mL) were added to help dissolving the starting material. After a total of 6 h at reflux, the mixture was cooled to room temperature and acidified to pH ~3 with 1 N HCl. The precipitate was collected by filtration and washed with water three times to give 4-(10-oxo-10H-chromeno[3,2-c]pyridin-3-yl)benzoic acid as a tan solid (906 mg, 36% for 2 steps). MS (ES+) m/z: 318 (M+H).

Step 5
HOBt (145 mg, 0.945 mmol), EDC (181 mg, 0.945 mmol) and Hunig's base (0.550 mL, 3.15 mmol) were added to a suspension of 4-(10-oxo-10H-chromeno[3,2-c]pyridin-3-yl)benzoic acid (200 mg, 0.630 mmol) in DMF (15 mL) and CH$_2$Cl$_2$ (10 mL) at room temperature. After 5 min, morpholine (0.110 mL, 1.261 mmol) was added. After 13 h at rt, the mixture was quenched with saturated NH$_4$Cl (50 mL) and extracted with CH$_2$Cl$_2$ (3×50 mL). The combined extracts were dried (MgSO$_4$) and concentrated to give crude 3-(4-(morpholine-4-carbonyl)phenyl)-10H-chromeno[3,2-c]pyridin-10-one, which was taken to next reaction without purification. MS (ES$^+$) m/z: 387 (M+H).

Step 6
NaBH$_4$ (0.238 g, 6.30 mmol) was added to a suspension of the crude 3-(4-(morpholine-4-carbonyl)phenyl)-10H-chromeno[3,2-c]pyridin-10-one from Step 5 in MeOH (50 mL) and CH$_2$Cl$_2$ (20 mL) at 0° C. After 1 h at 0° C., the mixture remained a suspension, and HPLC and LCMS indicated no product was formed. The cold bath was removed. Additional MeOH (50 mL), CH$_2$Cl$_2$ (30 mL) and NaBH$_4$ (0.5 g) were added. After 2.5 h, another batch of NaBH$_4$ (0.5 g) was added. After 30 min, the mixture was quenched with saturated NH$_4$Cl (100 mL). The organic solvent was evaporated in vacuo. The aqueous residue was extracted with CH$_2$Cl$_2$ (3×100 mL). The combined extracts were dried (MgSO$_4$) and concentrated to give crude (4-(10-hydroxy-110H-chromeno[3,2-c]pyridin-3-yl)phenyl)(morpholino)methanone, which was taken to the next reaction without purification.

Step 7
To a solution of the crude (4-(1'-hydroxy-110H-chromeno[3,2-c]pyridin-3-yl)phenyl)(morpholino)methanone from Step 6 in CH$_2$Cl$_2$ (50 mL) at 0° C. was added a 1 M CH$_2$Cl$_2$ solution of titanium(IV) chloride (1.890 mL, 1.89 mmol). The resultant tan suspension was stirred at 0° C. for 5 min. Methyl trimethylsilyl dimethylketene acetal (0.512 mL, 2.52 mmol) was added. The mixture was stirred at 0° C. for 1 h, quenched with saturated NaHCO$_3$ (50 mL) and filtered through a celite pad to remove the insoluble titanium salt. The filter pad was rinsed with CH$_2$Cl$_2$. The two phases of the filtrate were separated. The aqueous phase was extracted with CH$_2$Cl$_2$ (2×50 mL). The combined CH$_2$Cl$_2$ phase (72170-085-01) was dried (MgSO$_4$) and concentrated. Silica gel chromatography, using 60-100% ethyl acetate in hexane gradient, gave methyl 2-methyl-2-(3-(4-(morpholine-4-carbonyl)phenyl)-110H-chromeno[3,2-c]pyridin-10-yl)propanoate as a white solid (179.2 mg, 60% yield over 3 steps).

Step 8
Sodium 2-propanethiolate (58.5 mg, 0.596 mmol) was added to a solution of methyl 2-methyl-2-(3-(4-(morpholine-4-carbonyl)phenyl)-10H-chromeno[3,2-c]pyridin-10-yl)propanoate (140.9 mg, 0.298 mmol) in DMF (5 mL) and the mixture was heated to 50° C. After 1 h at 50° C., additional sodium 2-propanethiolate (58.5 mg) was added. The mixture was stirred at 50° C. overnight. Another portion of sodium 2-propanethiolate (200 mg) was added. After another hour at 50° C., the mixture was quenched with saturated NH$_4$Cl (20 mL) and extracted with EtOAc (4×20 mL). The combined extracts were washed with brine (5 mL), dried (MgSO$_4$) and concentrated to give 2-methyl-2-(3-(4-(morpholine-4-carbonyl)phenyl)-10H-chromeno[3,2-c]pyridin-10-yl)propanoic acid as a solid (145.5 mg). MS (ES+) m/z: 459 (M+H); HPLC retention time: 3.51 min (Analytical HPLC Method D).

Step 9
Hunig's base (0.072 mL, 0.410 mmol) was added to a mixture of 2-methyl-2-(3-(4-(morpholine-4-carbonyl)phenyl)-10H-chromeno[3,2-c]pyridin-10-yl)propanoic acid (31.3 mg, 0.068 mmol), HOBT (20.91 mg, 0.137 mmol), EDC (26.2 mg, 0.137 mmol) and 1,3,4-thiadiazol-2-amine (20.71 mg, 0.205 mmol) in DMF (2 mL). The mixture was stirred at room temperature for 5 min, at 60° C. for 1 h, at 80° C. for 4 h and concentrated. Purification by preparative reverse-phase HPLC (using Shimadzu 10A liquid chromatographs and Waters Sunfire S10 30×250 mm column) gave Example XX as a white solid (25.5 mg, 57% yield), assumed as TFA salt. 1H NMR (400 MHz, CD3OD) δ ppm 9.13 (s, 1 H), 8.63 (s, 1 H), 8.07 (s, 1 H), 8.05 (d, J=8.26 Hz, 2 H), 7.70

(d, J=8.22 Hz, 2 H), 7.45-7.49 (m, 1 H), 7.36-7.38 (m, 2 H), 7.28-7.30 (m, 1 H), 4.83 (s, 1 H), 3.81 (br s, 4 H), 3.68 (br s, 2 H), 3.50 (br s, 2 H), 1.27 (s, 3 H), 1.25 (s, 3 H); MS (E+) m/z: 542 (M+H); LC retention time: 3.52 min (Analytical HPLC Method D).

Example 493

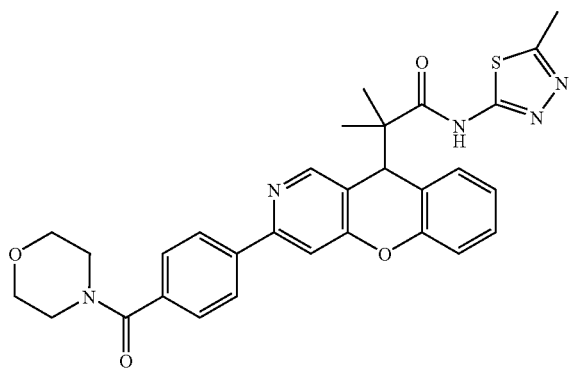

Following procedure analogous to Step 9 of Example 492, the title compound was prepared from 2-methyl-2-(3-(4-(morpholine-4-carbonyl)phenyl)-10H-chromeno[3,2-c]pyridin-10-yl)propanoic acid and 5-methyl 1,3,4-thiadiazol-2-amine. MS (E+) m/z: 556 (M+H); LC retention time: 3.68 min (Analytical HPLC Method D).

Biological Activity Data

The AP-1 activity of Examples 1 to 491 is given where the AP-1 $EC_{50}$ is less than 1 uM. Accompanying AP-1 maximum inhibition values are also given. Where the AP-1 EC50 is greater than 1 uM and/or the maximal inhibition is less than 20%, the glucocorticoid receptor (GR) binding affinity (Ki) is given.

The data presented below were obtained using the assays referred to in the able and described herein in the ASSAY section supra.

| Example No. | GR (Ki, nM) (GR Binding Assay (I)[a]) | GR (Ki, nM) (GR Binding Assay (II)[b]) | AP-1 $EC_{50}$, nM (Cellular Trans-repression Assay) | AP-1 Max % inh (Cellular Trans-repression Assay) |
|---|---|---|---|---|
| 1 | | | 156.90 | 69.29 |
| 2 | | | | 42.73 |
| 3 | | | | 47.84 |
| 4 | | | | 56.46 |
| 5 | | | 58.20 | 65.97 |
| 6 | | | 460.60 | 67.91 |
| 7 | | | 302.70 | 64.91 |
| 8 | | | 546.20 | 69.02 |
| 9 | | 154.20 | | |
| 10 | | | 16.80 | 86.50 |
| 11 | | | 881.90 | 68.50 |
| 12 | | | 460.60 | 67.91 |
| 13 | | | 566.50 | 60.26 |
| 14 | | 5455.00 | | |
| 15 | | | 501.30 | 65.89 |
| 16 | | | 303.40 | 59.92 |
| 17 | | | 334.90 | 67.95 |
| 18 | | | 541.90 | 37.62 |

-continued

| Example No. | GR (Ki, nM) (GR Binding Assay (I)[a]) | GR (Ki, nM) (GR Binding Assay (II)[b]) | AP-1 $EC_{50}$, nM (Cellular Trans-repression Assay) | AP-1 Max % inh (Cellular Trans-repression Assay) |
|---|---|---|---|---|
| 19 | | | | 52.68 |
| 20 | | | 473.30 | 46.87 |
| 21 | | | | 60.79 |
| 22 | | 1637.00 | | |
| 23 | | 445.20 | | |
| 24 | | | 15.72 | 78.77 |
| 25 | | 41.10 | | |
| 26 | | | | 26.90 |
| 27 | | | | 14.96 |
| 28 | | | | 43.67 |
| 29 | | | 139.00 | 66.36 |
| 30 | | | 337.80 | 67.25 |
| 31 | | | 178.70 | 69.38 |
| 32 | | | 301.50 | 67.61 |
| 33 | | | 31.76 | 55.20 |
| 34 | | | 3.52 | 71.85 |
| 35 | | | 80.64 | 72.28 |
| 36 | | 1040.00 | | |
| 37 | | 1.40 | | |
| 38 | | | | 70.38 |
| 39 | | 39.70 | | |
| 40 | | | 461.00 | 47.76 |
| 41 | | | 5.82 | 73.76 |
| 42 | | | 3.70 | 73.41 |
| 43 | | | 13.41 | 71.92 |
| 44 | | | | 69.30 |
| 45 | | | 102.40 | 71.48 |
| 46 | | | 90.23 | 67.62 |
| 47 | | | 534.10 | 66.66 |
| 48 | | 60.90 | | |
| 49 | | | 40.29 | 68.76 |
| 50 | | | 165.20 | 74.75 |
| 51 | | | 6.87 | 77.91 |
| 52 | | | 212.90 | 70.81 |
| 53 | | | 78.51 | 72.00 |
| 54 | | | 13.11 | 71.39 |
| 55 | | | 21.47 | 75.53 |
| 56 | | 233.30 | | |
| 57 | | | 11.54 | 74.78 |
| 58 | | | 3.71 | 70.02 |
| 59 | | | 11.76 | 58.39 |
| 60 | | 35.70 | | |
| 61 | | 909.00 | | |
| 62 | | 58.00 | | |
| 63 | | | | 75.82 |
| 64 | | | 19.86 | 79.28 |
| 65 | | | 345.40 | 32.22 |
| 66 | | 665.20 | | |
| 67 | | 107.00 | | |
| 68 | | 820.20 | | |
| 69 | | 515.40 | | |
| 70 | | 761.70 | | |
| 71 | | 517.20 | | |
| 72 | >1154 | | | |
| 73 | | | 735.40 | 60.62 |
| 74 | | | 318.60 | 71.16 |
| 75 | | 29.00 | | |
| 76 | | 76.40 | | |
| 77 | | | 91.63 | 73.89 |
| 78 | | | 163.80 | 65.08 |
| 79 | | | 9.42 | 62.34 |
| 80 | 56.09 | | | |
| 81 | | 242.90 | | |
| 82 | | | 125.80 | 72.61 |
| 83 | | | 15.03 | 69.64 |
| 84 | | 103.70 | | |
| 85 | | | | 88.40 |
| 86 | | 32.90 | | |
| 87 | | | 91.11 | 45.95 |
| 88 | | | 127.70 | 49.23 |
| 89 | | | 18.08 | 68.32 |
| 90 | | | 6.43 | 59.47 |
| 91 | | 2554.00 | | |

| Example No. | GR (Ki, nM) (GR Binding Assay (I)[a]) | GR (Ki, nM) (GR Binding Assay (II)[b]) | AP-1 EC$_{50}$, nM (Cellular Trans-repression Assay) | AP-1 Max % inh (Cellular Trans-repression Assay) |
|---|---|---|---|---|
| 92 | | 1200.00 | | |
| 93 | | 1266.00 | | |
| 94 | | 403.50 | | |
| 95 | | | 574.10 | 52.19 |
| 96 | | 22.10 | | |
| 97 | | 296.00 | | |
| 98 | | 88.70 | | |
| 99 | | 18.30 | | |
| 100 | | | 256.10 | 71.73 |
| 101 | 19.76 | | | |
| 102 | | | 57.97 | 45.01 |
| 103 | 6.06 | | | |
| 104 | 4.50 | | | |
| 105 | | | 12.19 | 30.54 |
| 106 | | | 24.12 | 48.41 |
| 107 | | | 833.30 | 22.82 |
| 108 | 13.60 | | | |
| 109 | | | 182.50 | 60.22 |
| 110 | | | 183.40 | 35.68 |
| 111 | | | 14.60 | 40.67 |
| 112 | | 9.30 | | |
| 113 | 62.63 | | | |
| 114 | 49.90 | | | |
| 115 | | | 3.90 | 31.34 |
| 116 | 346.10 | | | |
| 117 | 123.10 | | | |
| 118 | 76.60 | | | |
| 119 | | | 83.02 | 45.30 |
| 120 | | | 29.63 | 40.32 |
| 121 | | | 59.45 | 44.82 |
| 122 | 79.97 | | | |
| 123 | 17.82 | | | |
| 124 | 65.14 | | | |
| 125 | | | 94.33 | 33.24 |
| 126 | | | 49.73 | 30.84 |
| 127 | | 29.70 | | |
| 128 | | | 92.02 | 66.34 |
| 129 | | | 307.30 | 39.52 |
| 130 | | | 111.00 | 31.48 |
| 131 | | | 970.00 | 45.65 |
| 132 | | | 95.98 | 50.08 |
| 133 | | | 584.90 | 61.32 |
| 134 | | 444.10 | | |
| 135 | | 537.30 | | |
| 136 | | 141.40 | | |
| 137 | | 221.50 | | |
| 138 | | 11.40 | | |
| 139 | | | 95.54 | 26.80 |
| 140 | | | 93.65 | 64.12 |
| 141 | | | 92.10 | 44.23 |
| 142 | | 156.20 | | |
| 143 | | 744.40 | | |
| 144 | | 5455.00 | | |
| 145 | | 1162.00 | | |
| 146 | | 37.00 | | |
| 147 | | 4026.00 | | |
| 148 | | 11.10 | | |
| 149 | | 11.00 | | |
| 150 | | 26.90 | | |
| 151 | 7.58 | | | |
| 152 | | 10.90 | | |
| 153 | | | 982.50 | 73.55 |
| 154 | | | 236.10 | 46.25 |
| 155 | | 31.80 | | |
| 156 | | 80.90 | | |
| 157 | | 186.40 | | |
| 158 | | | 200.00 | 62.52 |
| 159 | | | 478.80 | 30.33 |
| 160 | | 5455.00 | | |
| 161 | | 36.60 | | |
| 162 | | 255.50 | | |
| 163 | | | 16.78 | 49.60 |
| 163[a] | | | 4.9 | 64.40 |
| 164[a] | | | 8.5 | 57.97 |
| 165[a] | | | 9.8 | 53.39 |
| 166[a] | | | 14.5 | 56.11 |
| 164 | | | 5.58 | 57.26 |
| 165 | | | 25.63 | 56.92 |
| 166 | | | 43.40 | 54.18 |
| 167 | | | 36.57 | 57.94 |
| 168 | | 485.60 | | |
| 169 | | | 92.74 | 48.82 |
| 170 | | | 182.30 | 44.12 |
| 171 | 7.15 | 10.20 | | |
| 172 | | | 13.21 | 59.04 |
| 173 | | | 82.49 | 44.82 |
| 174 | 10.16 | | | |
| 175 | 51.98 | 49.40 | | |
| 176 | | | 118.50 | 43.54 |
| 177 | >1154 | 459.70 | | |
| 178 | 10.58 | 4.70 | | |
| 179 | 64.62 | 37.90 | | |
| 180 | 22.82 | 14.60 | | |
| 181 | >1154 | 182.70 | | |
| 182 | | | 108.60 | 33.12 |
| 183 | 44.43 | 20.40 | | |
| 184 | 6606.00 | 263.10 | | |
| 185 | >1154 | 697.40 | | |
| 186 | 386.10 | 84.60 | | |
| 187 | 33.10 | 34.40 | | |
| 188 | 28.88 | 8.10 | | |
| 189 | 19.63 | 11.70 | | |
| 190 | 11.53 | 5.70 | | |
| 191 | | | 22.64 | 37.51 |
| 192 | 12.33 | 13.10 | | |
| 193 | 11.14 | 8.50 | | |
| 194 | 4.63 | 7.10 | | |
| 195 | 735.70 | 505.30 | | |
| 196 | 6.26 | 15.90 | | |
| 197 | 9.27 | 23.30 | | |
| 198 | | | 22.17 | 34.38 |
| 199 | | | 27.60 | 48.94 |
| 200 | | | 133.80 | 53.76 |
| 201 | | | 36.34 | 65.46 |
| 202 | | | 218.60 | 38.37 |
| 203 | 4.61 | 13.10 | | |
| 204 | | | 42.75 | 44.75 |
| 205 | | | 8.50 | 57.72 |
| 206 | | | 21.31 | 54.73 |
| 207 | | | 32.61 | 37.96 |
| 208 | | | 12.25 | 54.08 |
| 209 | | | 14.30 | 50.21 |
| 210 | | | 77.73 | 39.38 |
| 211 | | | 41.28 | 49.63 |
| 212 | | | 19.59 | 63.05 |
| 213 | 7.95 | | | |
| 214 | 1.37 | | | |
| 215 | 2.50 | | | |
| 216 | 4.14 | | | |
| 217 | | | 41.03 | 45.81 |
| 218 | 1.24 | | | |
| 219 | | | 180.30 | 35.87 |
| 220 | | | 105.20 | 52.23 |
| 221 | | | 28.92 | 62.97 |
| 222 | | | 100.20 | 61.88 |
| 223 | | | 838.90 | 27.87 |
| 224 | 8.06 | | | |
| 225 | | | 919.70 | 45.65 |
| 226 | | | 18.14 | 49.05 |
| 227 | | | 37.94 | 42.50 |
| 228 | | | 51.53 | 28.32 |
| 229 | | | 42.01 | 39.34 |
| 230 | | | 550.10 | 52.33 |
| 231 | | | 733.40 | 38.36 |
| 232 | 4.57 | | | |
| 233 | 11.29 | | | |

| Example No. | GR (Ki, nM) (GR Binding Assay (I)[a]) | GR (Ki, nM) (GR Binding Assay (II)[b]) | AP-1 EC$_{50}$, nM (Cellular Trans-repression Assay) | AP-1 Max % inh (Cellular Trans-repression Assay) |
|---|---|---|---|---|
| 234 | | | 405.40 | 27.08 |
| 235 | 4.85 | | | |
| 236 | 9.44 | | | |
| 237 | 6.04 | | | |
| 238 | | | 601.00 | 62.32 |
| 239 | | | 12.43 | 44.85 |
| 240 | | | 51.87 | 61.72 |
| 241 | | | 25.28 | 46.83 |
| 242 | 412.30 | | | |
| 243 | >1154 | | | |
| 244 | >1154 | | | |
| 245 | 1.01 | | | |
| 246 | | | 325.40 | 81.76 |
| 247 | | | 4.74 | 52.38 |
| 248 | | | 21.45 | 55.87 |
| 249 | | | 11.20 | 42.38 |
| 250 | | | 17.84 | 48.42 |
| 251 | | | 17.45 | 54.92 |
| 252 | | | 34.61 | 60.94 |
| 253 | 6.28 | | | |
| 254 | | | 23.62 | 41.80 |
| 255 | 16.11 | | | |
| 256 | 180.30 | | | |
| 257 | | | 12.44 | 63.96 |
| 258 | | | 533.50 | 40.99 |
| 259 | | | 72.21 | 23.33 |
| 260 | | | 23.14 | 67.28 |
| 261 | | | 4.74 | 52.38 |
| 262 | 18.19 | | | |
| 263 | | | 15.42 | 58.05 |
| 264 | | | 115.20 | 33.74 |
| 265 | 126.20 | | | |
| 266 | | | 11.20 | 42.38 |
| 267 | | | 568.70 | 40.78 |
| 268 | 9.45 | | | |
| 269 | 14.75 | | | |
| 270 | 20.94 | | | 27.98 |
| 271 | 218.00 | | | |
| 272 | 12.58 | | | |
| 273 | 19.91 | | | 20.96 |
| 274 | | | 234.10 | 62.19 |
| 275 | 2.60 | | | 26.02 |
| 276 | 4.05 | | | 27.21 |
| 277 | 81.32 | | | 24.52 |
| 278 | 30.53 | | | |
| 279 | 20.84 | | | |
| 280 | 10.75 | | | 33.52 |
| 281 | 33.50 | | | |
| 282 | 13.41 | | | |
| 283 | 9.21 | | | 24.64 |
| 284 | 17.37 | | | |
| 285 | 5.84 | | | 45.31 |
| 286 | 12.15 | | | 49.83 |
| 287 | 16.82 | | | |
| 288 | 13.80 | | | 35.54 |
| 289 | 19.98 | | | 24.29 |
| 290 | 20.36 | | | 28.80 |
| 291 | 43.96 | | | 26.99 |
| 292 | 10.84 | | | |
| 293 | 10.43 | | | 25.39 |
| 294 | 29.30 | | | 59.35 |
| 295 | 38.73 | | | 24.36 |
| 296 | 19.13 | | | |
| 297 | >1154 | | | |
| 298 | 241.90 | | | 25.36 |
| 299 | 13.28 | | | |
| 300 | | | 14.83 | 61.77 |
| 301 | 20.25 | | | 28.57 |
| 302 | 126.30 | | | |
| 303 | 278.00 | | | 28.59 |
| 304 | 149.00 | | | |
| 305 | 24.71 | | | 38.32 |
| 306 | 9.85 | | | 43.48 |
| 307 | 67.51 | | | 37.14 |
| 308 | 313.00 | | | |
| 309 | | | 41.50 | 34.95 |
| 310 | | | 785.90 | 52.93 |
| 311 | 25.77 | | | |
| 312 | | | 266.70 | 73.06 |
| 313 | 4.65 | | | |
| 314 | | | 18.01 | 69.78 |
| 315 | | | 749.90 | 40.86 |
| 316 | | | 60.90 | 35.90 |
| 317 | 23.69 | | | |
| 318 | | | 63.08 | 27.55 |
| 319 | 110.30 | | | |
| 320 | 13.11 | | | |
| 321 | 30.56 | | | |
| 322 | 18.89 | | | |
| 323 | 3.69 | | | |
| 324 | | | 431.10 | 54.88 |
| 325 | | | 90.21 | 56.09 |
| 326 | 10.49 | | | |
| 327 | | | 8.93 | 59.45 |
| 328 | | | 18.63 | 66.06 |
| 329 | | | 582.70 | 40.81 |
| 330 | | | 21.94 | 60.62 |
| 331 | | | 33.71 | 36.28 |
| 332 | 9.56 | | | |
| 333 | | | 24.69 | 52.71 |
| 334 | | | 3.36 | 36.22 |
| 335 | | | 37.94 | 55.97 |
| 336 | | | 20.40 | 55.80 |
| 337 | | | 102.80 | 51.49 |
| 338 | 311.80 | | | |
| 339 | | | 184.70 | 38.40 |
| 340 | | | 54.77 | 67.61 |
| 341 | | | 14.82 | 50.27 |
| 342 | | | 51.68 | 41.54 |
| 343 | | | 18.44 | 29.68 |
| 344 | | | 39.64 | 44.55 |
| 345 | | | 124.30 | 54.25 |
| 346 | 3.04 | | | |
| 347 | 5.63 | | | |
| 348 | | | 300.30 | 34.37 |
| 349 | 5.88 | | | 31.72 |
| 350 | | | 519.90 | 45.06 |
| 351 | 146.70 | | | |
| 352 | 42.06 | | | |
| 353 | 13.03 | | | |
| 354 | 20.10 | | | 28.93 |
| 355 | 19.56 | | | |
| 356 | 581.90 | | | |
| 357 | 31.36 | | | 29.62 |
| 358 | 40.50 | | | |
| 359 | 30.08 | | | |
| 360 | 154.10 | | | |
| 361 | 14.62 | | | |
| 362 | 804.70 | | | |
| 363 | | | 247.10 | 47.74 |
| 364 | | | 244.20 | 58.90 |
| 365 | 18.25 | | | |
| 366 | 200.00 | | | |
| 367 | 692.30 | | | |
| 368 | | | 38.59 | 46.80 |
| 369 | | | 33.04 | 55.45 |
| 370 | | | 34.22 | 57.60 |
| 371 | | | 22.27 | 48.73 |
| 372 | | | 28.28 | 52.42 |
| 373 | | | 32.80 | 45.61 |
| 374 | | | 30.91 | 50.87 |
| 375 | | | 82.80 | 51.24 |
| 376 | | | 34.42 | 45.09 |
| 377 | | | 32.72 | 49.10 |
| 378 | | | 72.62 | 48.18 |
| 379 | | | 73.97 | 51.21 |

-continued

| Example No. | GR (Ki, nM) (GR Binding Assay (I)[a]) | GR (Ki, nM) (GR Binding Assay (II)[b]) | AP-1 EC$_{50}$, nM (Cellular Trans-repression Assay) | AP-1 Max % inh (Cellular Trans-repression Assay) |
|---|---|---|---|---|
| 380 | | | 100.60 | 53.58 |
| 381 | | | 45.25 | 52.00 |
| 382 | | | 205.80 | 47.22 |
| 383 | | | 46.32 | 41.78 |
| 384 | | | 61.85 | 42.30 |
| 385 | | | 96.47 | 28.99 |
| 386 | | | 89.04 | 34.32 |
| 387 | | | 82.02 | 52.49 |
| 388 | | | 34.22 | 57.60 |
| 389 | | | 50.54 | 55.20 |
| 390 | | | 42.77 | 56.63 |
| 391 | | | 52.02 | 44.08 |
| 392 | | | 49.73 | 44.82 |
| 393 | | | 53.37 | 43.80 |
| 394 | 4.00 | | | |
| 395 | 1.19 | | | |
| 396 | 10.62 | | | |
| 397 | 40.89 | | | |
| 398 | | | 479.60 | 50.00 |
| 399 | | | 332.90 | 69.30 |
| 400 | 37.32 | | | |
| 401 | | | 778.30 | 35.10 |
| 402 | 698.60 | | | |
| 403 | 61.21 | | | |
| 404 | | | 22.49 | 70.62 |
| 405 | 423.70 | | | |
| 406 | 176.30 | | | |
| 407 | 958.20 | | | |
| 408 | | | 363.90 | 24.10 |
| 409 | 78.16 | | | |
| 410 | | | 53.32 | 48.15 |
| 411 | | | 161.10 | 58.47 |
| 412 | 22.27 | | | |
| 413 | 37.74 | | | |
| 414 | 589.00 | | | |
| 415 | 64.10 | | | |
| 416 | 94.46 | | | |
| 417 | | | 67.32 | 54.11 |
| 418 | | | 82.09 | 29.07 |
| 419 | | | 71.86 | 46.63 |
| 420 | | | 41.94 | 42.14 |
| 421 | | | 49.78 | 42.56 |
| 422 | | | 84.14 | 41.58 |
| 422[a] | | | 51.50 | 50.45 |
| 422[b] | | | 46.72 | 63.52 |
| 423 | | | 81.98 | 30.36 |
| 424 | | | 150.30 | 59.58 |
| 425 | | | 84.43 | 49.89 |
| 426 | | | 117.10 | 31.80 |
| 427 | | | 187.80 | 25.13 |
| 428 | | | 30.29 | 26.89 |
| 429 | | | 67.27 | 41.78 |
| 430 | | | 34.69 | 47.22 |
| 431 | | | 69.04 | 41.78 |
| 432 | | | 52.66 | 40.25 |
| 433 | | | 40.97 | 46.21 |
| 434 | | | 197.10 | 38.45 |
| 435 | | | 291.80 | 27.88 |
| 436 | | | 95.67 | 44.01 |
| 437 | 11.06 | | | |
| 438 | 53.10 | | | |
| 439 | 65.80 | | | |
| 440 | 20.97 | | | |
| 441 | | | 63.91 | 52.35 |
| 442 | | | 126.60 | 50.14 |
| 443 | | | 134.40 | 51.70 |
| 444 | | | 44.20 | 57.54 |
| 445 | | | 38.48 | 45.74 |
| 446 | | | 412.60 | 27.69 |
| 447 | | | 95.37 | 53.02 |
| 448 | | | 178.40 | 56.59 |
| 449 | | | 126.40 | 48.87 |
| 450 | | | 59.16 | 26.30 |
| 451 | 5.57 | | | |
| 452 | | | 11.11 | 53.38 |
| 453 | 17.60 | | | |
| 454 | | | 25.34 | 49.46 |
| 455 | | | 24.61 | 58.63 |
| 456 | | | 41.48 | 45.84 |
| 457 | | | 16.56 | 51.89 |
| 458 | | | 53.25 | 35.19 |
| 459 | | | 101.70 | 35.43 |
| 460 | | | 30.33 | 56.91 |
| 461 | | | 53.38 | 50.80 |
| 462 | 3.78 | | | |
| 463 | | | 45.30 | 26.23 |
| 464 | | | 18.20 | 54.01 |
| 465 | | | 16.55 | 61.53 |
| 466 | | | 28.25 | 56.07 |
| 467 | | | 14.97 | 57.51 |
| 468 | | | 35.39 | 53.30 |
| 469 | 49.82 | | | |
| 470 | | | 24.60 | 43.03 |
| 471 | | | 63.91 | 52.35 |
| 472 | | | 26.92 | 47.04 |
| 473 | | | 40.19 | 52.52 |
| 474 | | | 85.40 | 37.88 |
| 475 | 18.31 | | | |
| 476 | 16.37 | | | |
| 477 | | | 39.75 | 44.78 |
| 478 | | | 16.02 | 41.78 |
| 479 | | | 47.00 | 44.36 |
| 480 | | | 27.01 | 43.97 |
| 481 | | | 579.30 | 33.76 |
| 482 | 44.97 | | | |
| 483 | 426.20 | | | |
| 484 | | | 19.32 | 29.79 |
| 485 | | | 42.36 | 38.86 |
| 486 | | | 15.78 | 50.34 |
| 487 | >1154 | | | |
| 488 | | | 42.92 | 34.48 |
| 489 | 143.80 | | | |
| 490 | 14.82 | | | |
| 491 | >1154 | | | |
| 492 | | | 182.00 | 28.40 |
| 493 | 108.90 | | | |

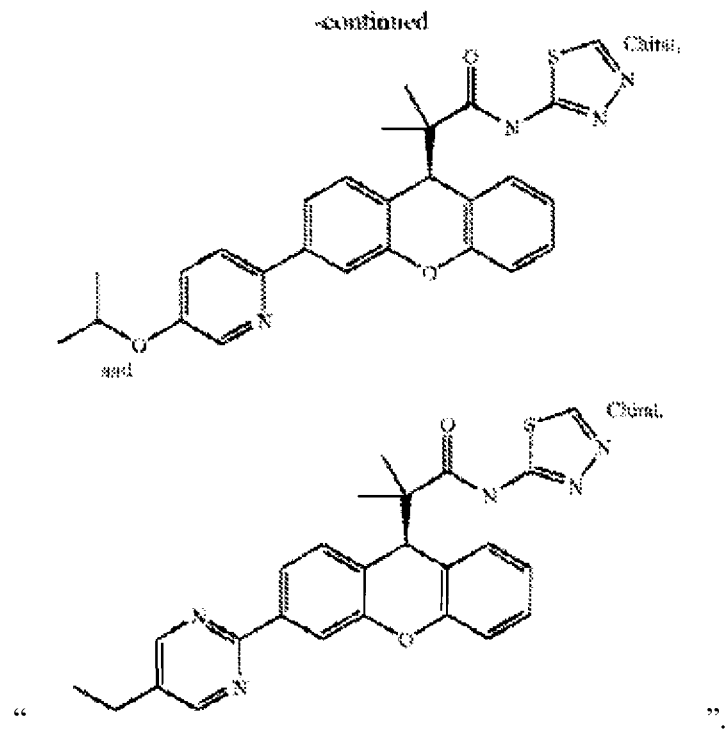

The invention claimed is:

1. A compound having the structure an enantiomer, diastereomer, tautomer, or a pharmaceutically-acceptable salt thereof, wherein:

$X^2$ is halogen, alkoxy, H, or alkyl;

$R^x$ is H, $C(O)NR_2{}^aR_2{}^b$, $OR_2{}^c$, $R_2{}^a$, COOH, $CF_3$,

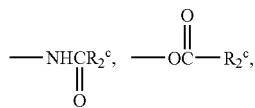

—$NHSO_2R_2{}^c$, aryl, aryloxy, alkylthio, amino, acyl or cyano;

$R_2{}^a$ and $R_2{}^b$ are the same or different and at each occurrence are independently selected from hydrogen, alkyl, substituted alkyl, $C(=O)$alkyl, $CO_2$(alkyl), $SO_2$alkyl, hydrogen, alkenyl, substituted alkenyl, alkoxy, amino, substituted amino, aryl, heteroaryl, heterocyclo, and cycloalkyl;

or $R_2{}^a$ and $R_2{}^b$, where possible can be taken together with the nitrogen to which they are attached to form a 5-, 6- or 7-membered heteroaryl or cycloheteroalkyl ring which contains 1, 2 or 3 hetero atoms which can be N, O, or S;

$R_2{}^c$ is selected from hydrogen, alkyl, substituted alkyl, alkenyl, substituted alkenyl, alkynyl, substituted alkynyl, alkoxy, amino, substituted amino, heteroaryl, heterocyclo, cycloalkyl, and aryl;

$R_9$ and $R_{10}$ are the same or different and at each occurrence are independently selected from (i) hydrogen, alkyl, and substituted alkyl or (ii) together with the atom to which they are attached, $R_9$ and $R_{10}$ are taken together to form a cycloalkyl group;

$R_{11}$ is selected from hydrogen, alkyl, substituted alkyl, $C(=O)$alkyl, $CO_2$(alkyl), $SO_2$alkyl, alkoxy, amino, substituted amino, aryl, heteroaryl, heterocyclo, and cycloalkyl;

Z is selected from

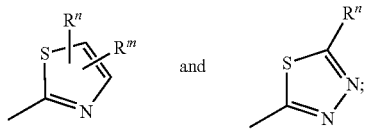

$R^m$ and $R^n$ are the same or different and at each occurrence are independently selected from hydrogen, halogen, alkoxy, —$COR_1{}^a$, —$CO_2R_1{}^a$, $C_{1-6}$alkyl, $CF_3$, substituted alkyl, aryl-NHC(O)-aryl, $N(R_1{}^a)(R_1{}^b)$, aryl, arylalkyl, $CH_2OH$, —$SR_1{}^a$, $CH_2F$, cyano, and $C_{3-6}$cycloalkyl;

$R_1{}^a$ at each occurrence is independently selected from hydrogen, alkyl, substituted alkyl, $C(=O)$alkyl, $CO_2$(alkyl), $SO_2$alkyl, alkenyl, substituted alkenyl, alkoxy, amino, substituted amino, aryl, and cycloalkyl; and $R_1{}^b$ is alkyl.

2. The compound as defined in claim 1, or an enantiomer, diastereomer, tautomer, or a pharmaceutically-acceptable salt thereof, wherein

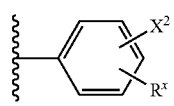 is 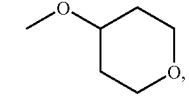

-continued

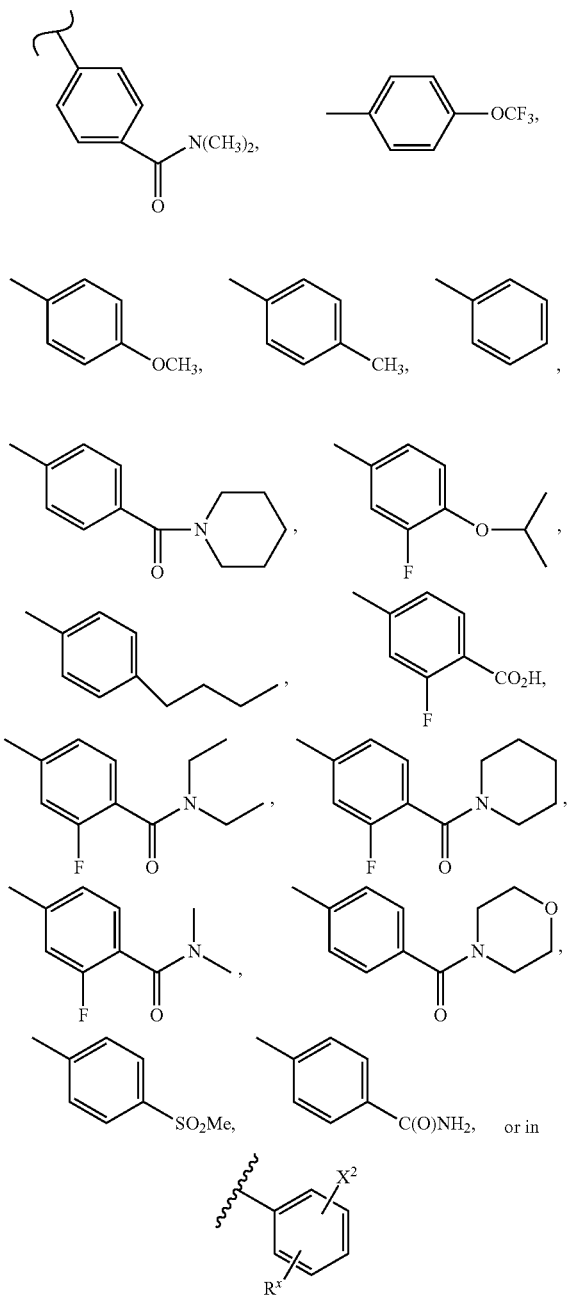

$X^2$ is hydrogen or fluoro, and $R^x$ is selected from cyclohexyl, —O(isopropyl), hydroxyl, hydrogen, —S(ethyl), $SO_2$(ethyl), $SO_2$(isopropyl), $C(O)CH_3$, —O(n-propyl), $CH_2CO_2H$, $SO_2N(CH_3)_2$, $SO_2$(N-morpholinyl), $C(OH)Me_2$, $SO_2NHCH_2CH_3$, $SO_2NH$(cyclopropyl), $SO_2NH$(isopropyl), $CH_2CO_2CH_3$, $CH(OH)CH_3$, $CH(OH)$(Isopropyl), $S(O)CH_3$, O(cyclohexyl), O(cyclopentyl), and

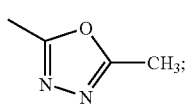

3. The compound as defined in claim 1, or an enantiomer, diastereomer, tautomer, or a pharmaceutically-acceptable salt thereof, wherein:

$R_9$ and $R_{10}$ are alkyl;

or together with the atom to which they are attached, $R_9$ taken together with $R_{10}$ forms a $C_{3-6}$cycloalkyl; and $R_{11}$ is hydrogen.

4. The compound as defined in claim 3, or an enantiomer, diastereomer, tautomer, or a pharmaceutically-acceptable salt thereof, wherein $R_9$ and $R_{10}$ are methyl, or $R_9$ and $R_{10}$ taken together with the carbon to which they are attached form a cyclopropyl, cyclobutyl, or cyclopentyl ring.

5. The compound as defined in claim 1, or an enantiomer, diastereomer, tautomer, or a pharmaceutically-acceptable salt thereof, wherein Z is

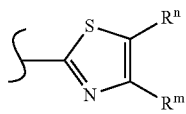 or 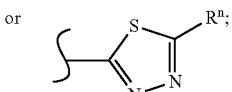

$R^m$ and $R^n$ are the same or different and at each occurrence are independently selected from hydrogen, $C_{1-6}$alkyl, $CF_3$, $CH_2OH$, $—SR_1^a$, $CH_2F$, cyano, and $C_{3-6}$cycloalkyl; and $R_1^a$ at each occurrence is independently selected from hydrogen, $C_{1-6}$alkyl, and $C_{3-6}$cycloalkyl.

6. The compound as defined in claim 1, or an enantiomer, diastereomer, tautomer, or a pharmaceutically-acceptable salt thereof, wherein:

Z is 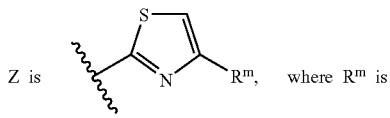 where $R^m$ is

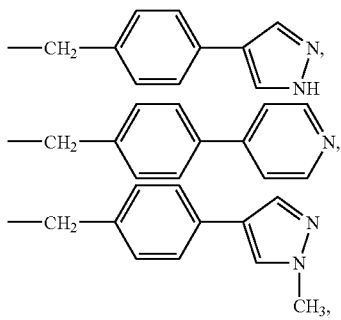

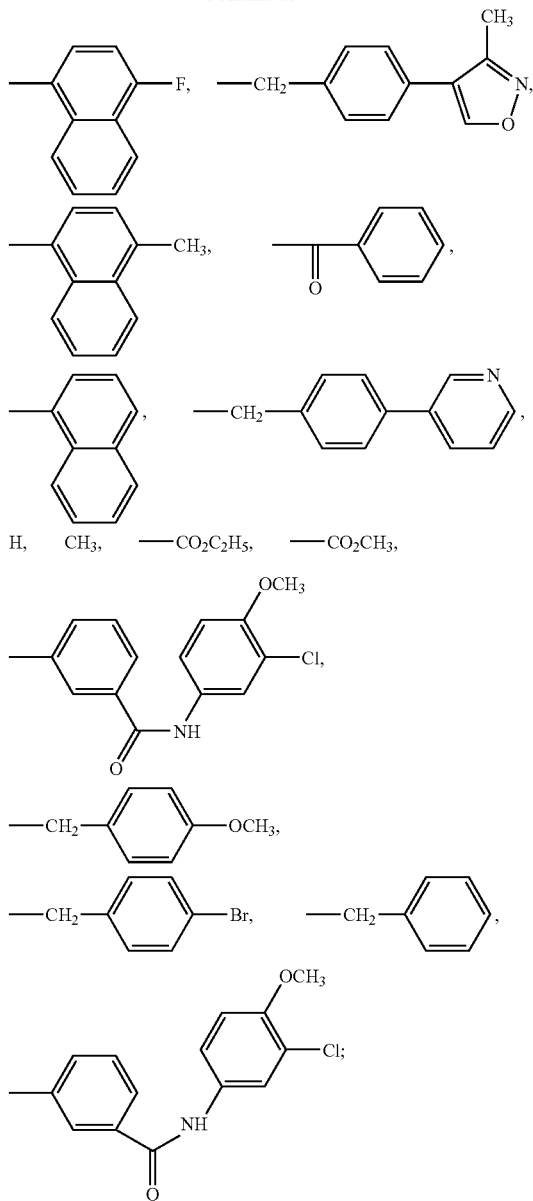

Z is

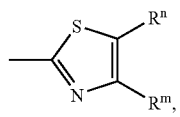

where $R^n$ is $CH_3$, $R^m$ is $CH_3$; or

Z is

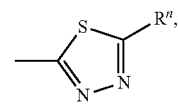

, where R" is CH₃, H, CF₃, C(O)OEt, C(O)NH₂, C(O)NH(cyclopropyl), C(O)NHCH₃, C(O)NHEt, CH₂OH, S(methyl), N(methyl)₂, CH₂F, cyano, ethyl, or cyclopropyl.

7. The compound as defined in claim 1, or an enantiomer, diastereomer, tautomer, or a pharmaceutically-acceptable salt thereof, wherein

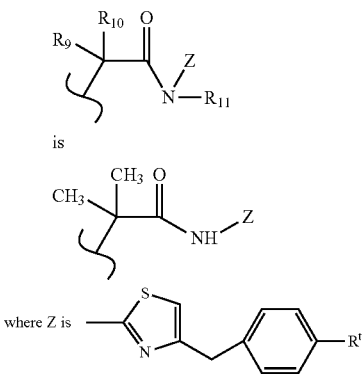

where R' is H or alkyl.

8. The compound as defined in claim 5, or an enantiomer, diastereomer, tautomer, or a pharmaceutically-acceptable salt thereof, having the structure:

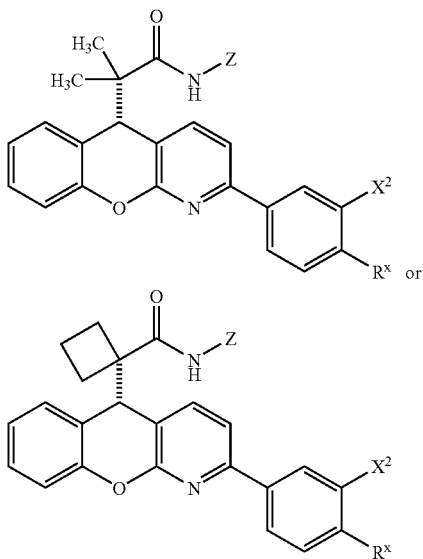

wherein:
X² is H, halogen, or alkyl;
R^x is H, C(O)NR₂^a R₂^b, OR₂^a, R₂^a, COOH, CF₃,

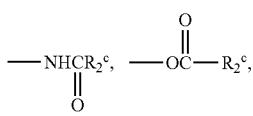

—NHSO₂R₂^c, aryl, aryloxy, alkylthio, amino, acyl or cyano;
R₂^a is selected from hydrogen, alkyl, substituted alkyl, C(=O)alkyl, CO₂(alkyl), SO₂alkyl, hydrogen, alkenyl, substituted alkenyl, alkoxy, amino, substituted amino, aryl, heteroaryl, heterocyclo, and cycloalkyl;
R₂^b is selected from alkyl, substituted alkyl, C(=O)alkyl, CO₂(alkyl), SO₂alkyl, hydrogen, alkenyl, substituted alkenyl, alkoxy, amino, substituted amino, aryl, heteroaryl, heterocyclo, and cycloalkyl;
or R₂^a and R₂^b are taken together with the nitrogen to which they are attached to form a 5-, 6- or 7-membered heteroaryl or cycloheteroalkyl ring which contains 1, 2 or 3 hetero atoms which can be N, O, or S; and
R₂^c is selected from alkyl, substituted alkyl, alkenyl, substituted alkenyl, alkynyl, substituted alkynyl, alkoxy, amino, substituted amino, heteroaryl, heterocyclo, cycloalkyl, and aryl.

9. A compound selected from:
2-(5H-chromeno[2,3-b]pyridin-5-yl)-N-[4-(4-fluoro-1-naphthyl)-1,3-thiazol-2-yl]-2-methylpropanamide,
2-(5H-chromeno[2,3-b]pyridin-5-yl)-2-methyl-N-{4-[4-(4-pyridinyl)benzyl]-1,3-thiazol-2 -yl}propanamide,
2-(5H-chromeno[2,3-b]pyridin-5-yl)-2-methyl-N-1,3,4-thiadiazol-2-ylpropanamide,
2-(5H-chromeno[2,3-b]pyridin-5-yl)-2-methyl-N-1,2,4-thiadiazol-5-ylpropanamide,
2-(5H-chromeno[2,3-b]pyridin-5-yl)-2-methyl-N-1,3-thiazol-2-ylpropanamide,
ethyl 2-{[2-(5H-chromeno[2,3-b]pyridin-5-yl)-2-methyl-propanoyl]amino}-1,3-thiazole-4 -carboxylate,
2-(5H-chromeno[2,3-b]pyridin-5-yl)-2-methyl-N-(5-methyl-1,3-thiazol-2-yl)propanamide,
2-(5H-chromeno[2,3-b]pyridin-5-yl)-2-methyl-N-(4-methyl-1,3-thiazol-2-yl)propanamide,
2-(5H-chromeno[2,3-b]pyridin-5-yl)-2-methyl-N-(5-methyl-1,3,4-thiadiazol-2 -yl)propanamide,
2-(2-chloro-5H-chromeno[2,3-b]pyridin-5-yl)-N-[4-(4-fluoro-1-naphthyl)-1,3-thiazol-2-yl]-2-methylpropanamide,
2-(2-chloro-5H-chromeno[2,3-b]pyridin-5-yl)-2-methyl-N-[4-(1-naphthyl)-1,3-thiazol-2 -yl]propanamide,
2-(2-chloro-5H-chromeno[2,3-b]pyridin-5-yl)-2-methyl-N-1,3-thiazol-2-ylpropanamide,
2-(2-chloro-5H-chromeno[2,3-b]pyridin-5-yl)-2-methyl-N-1,3,4-thiadiazol-2-ylpropanamide,
N-[4-(4-methoxybenzyl)-1,3-thiazol-2-yl]-2-(2-methoxy-5H-chromeno[2,3-b]pyridin-5-yl) -2-methylpropanamide,
N-[4-(4-fluoro-1-naphthyl)-1,3-thiazol-2-yl]-2-(2-methoxy-5H-chromeno[2,3-b]pyridin-5 -yl)-2-methylpropanamide,
2-(2-methoxy-5H-chromeno[2,3-b]pyridin-5-yl)-2-methyl-N-{4-[4-(4-pyridinyl)benzyl]-1,3 -thiazol-2-yl}propanamide,
2-methyl-2-[2-(methylamino)-5H-chromeno[2,3-b]pyridin-5-yl]-N-1,3-thiazol-2-ylpropanamide,
2-{2-[(4-methoxybenzyl)amino]-5H-chromeno[2,3-b]pyridin-5-yl}-2-methyl-N-1,3,4 -thiadiazol-2-ylpropanamide,
2-methyl-2-[2-(4-morpholinyl)-5H-chromeno[2,3-b]pyridin-5-yl]-N-1,3,4-thiadiazol-2 -ylpropanamide,
2-methyl-2-[2-(1-pyrrolidinyl)-5H-chromeno[2,3-b]pyridin-5-yl]-N-1,3,4-thiadiazol-2 -ylpropanamide,
2-methyl-2-[2-(4-methyl-1-piperazinyl)-5H-chromeno[2,3-b]pyridin-5-yl]-N-1,3,4 -thiadiazol-2-ylpropanamide,
2-methyl-2-[2-(1-piperidinyl)-5H-chromeno[2,3-b]pyridin-5-yl]-N-1,3,4-thiadiazol-2 -ylpropanamide,
2-[2-(benzylamino)-5H-chromeno[2,3-b]pyridin-5-yl]-2-methyl-N-1,3,4-thiadiazol-2 -ylpropanamide, 2-methyl-2-[(5R)-2-(1-piperidinyl)-5H-chromeno[2,3-b]pyridin-5-yl]-N-1,3,4-thiadiazol-2-ylpropanamide,
2-[(5R)-2-(1,4-dioxa-8-azaspiro[4.5]dec-8-yl)-5H-chromeno[2,3-b]pyridin-5-yl]-2-methyl -N-1,3,4-thiadiazol-2-ylpropanamide,
2-{(5R)-2-[(4-methoxybenzyl)amino]-5H-chromeno[2,3-b]pyridin-5-yl}-2-methyl-N-1,3,4 -thiadiazol-2-ylpropanamide,
2-methyl-2-[(5R)-2-(1-pyrrolidinyl)-5H-chromeno[2,3-b]pyridin-5-yl]-N-1,3,4-thiadiazol-2 -ylpropanamide,
2-methyl-2-[(5S)-2-(1-piperidinyl)-5H-chromeno[2,3-b]pyridin-5-yl]-N-1,3,4-thiadiazol-2 -ylpropanamide,
2-[(5S)-2-(1,4-dioxa-8-azaspiro[4.5]dec-8-yl)-5H-chromeno[2,3-b]pyridin-5-yl]-2-methyl-N -1,3,4-thiadiazol-2-ylpropanamide,
2-{(5S)-2-[(4-methoxybenzyl)amino]-5H-chromeno[2,3-b]pyridin-5-yl}-2-methyl-N-1,3,4 -thiadiazol-2-ylpropanamide,
2-methyl-2-[(5S)-2-(1-pyrrolidinyl)-5H-chromeno[2,3-b]pyridin-5-yl]-N-1,3,4-thiadiazol-2 -ylpropanamide,
2-methyl-2-[(5S)-2-{[(1S)-1-phenylethyl]amino}-5H-chromeno[2,3-b]pyridin-5-yl]-N-1,3,4 -thiadiazol-2-ylpropanamide,
2-methyl-2-[(5S)-2-{[(1R)-1-phenylethyl]amino}-5H-chromeno[2,3-b]pyridin-5-yl]-N-1,3,4 -thiadiazol-2-ylpropanamide,
2-{(5S)-2-[(2S)-2-(methoxymethyl)-1-pyrrolidinyl]-5H-chromeno[2,3-b]pyridin-5-yl}-2 -methyl-N-1,3,4-thiadiazol-2-ylpropanamide,
2-{(5S)-2-[(2R)-2-(methoxymethyl)-1-pyrrolidinyl]-5H-chromeno[2,3-b]pyridin-5-yl}-2 -methyl-N-1,3,4-thiadiazol-2-ylpropanamide,
2-[(5S)-2-(1-azepanyl)-5H-chromeno[2,3-b]pyridin-5-yl]-2-methyl-N-1,3,4-thiadiazol-2 -ylpropanamide,
2-methyl-2-[(5S)-2-(3-phenyl-1-piperidinyl)-5H-chromeno[2,3-b]pyridin-5-yl]-N-1,3,4 -thiadiazol-2-ylpropanamide,
2-methyl-2-[(5S)-2-(1-piperidinyl)-5H-chromeno[2,3-b]pyridin-5-yl]-N-1,3-thiazol-2 -ylpropanamide,
2-[(5S)-2-(dimethylamino)-5H-chromeno[2,3-b]pyridin-5-yl]-2-methyl-N-1,3,4-thiadiazol-2 -ylpropanamide,
2-methyl-2-[(5S)-2-(3-methyl-1-piperidinyl)-5H-chromeno[2,3-b]pyridin-5-yl]-N-1,3,4 -thiadiazol-2-ylpropanamide,
2-{2-[(4-methoxybenzyl)amino]-5H-chromeno[2,3-b]pyridin-5-yl}-2-methyl-N-1,3-thiazol -2-ylpropanamide,
2-methyl-2-[2-(4-morpholinyl)-5H-chromeno[2,3-b]pyridin-5-yl]-N-1,3-thiazol-2 -ylpropanamide,
2-[2-(butylamino)-5H-chromeno[2,3-b]pyridin-5-yl]-2-methyl-N-1,3-thiazol-2 -ylpropanamide,
2-{2-[benzyl(methyl)amino]-5H-chromeno[2,3-b]pyridin-5-yl}-2-methyl-N-1,3-thiazol-2 -ylpropanamide,
2-[2-(isopropylamino)-5H-chromeno[2,3-b]pyridin-5-yl]-2-methyl-N-1,3-thiazol-2 -ylpropanamide,
2-(2-amino-5H-chromeno[2,3-b]pyridin-5-yl)-2-methyl-N-1,3-thiazol-2-ylpropanamide,
2-(2-amino-5H-chromeno[2,3-b]pyridin-5-yl)-2-methyl-N-1,3,4-thiadiazol-2-ylpropanamide,
2-[2-(dimethylamino)-5H-chromeno[2,3-b]pyridin-5-yl]-2-methyl-N-1,3-thiazol-2 -ylpropanamide,
2-methyl-2-[(5R)-2-(4-oxo-1-piperidinyl)-5H-chromeno[2,3 -b]pyridin-5-yl]-N-1,3-thiazol-2 -ylpropanamide,
2-methyl-2-[(5S)-2-(4-oxo-1-piperidinyl)-5H-chromeno[2,3-b]pyridin-5-yl]-N-1,3-thiazol-2 -ylpropanamide,
2-[(5R)-2-(4-methoxyphenyl)-5H-chromeno[2,3-b]pyridin-5-yl]-2-methyl-N-1,3,4 -thiadiazol-2-ylpropanamide, 2-methyl-2-[(5S)-2-(4-methylphenyl)-5H-chromeno[2,3-b]pyridin-5-yl]-N-1,3,4-thiadiazol -2-ylpropanamide,
2-methyl-2-[(5S)-2-phenyl-5H-chromeno[2,3-b]pyridin-5-yl]-N-1,3,4-thiadiazol-2 -ylpropanamide,

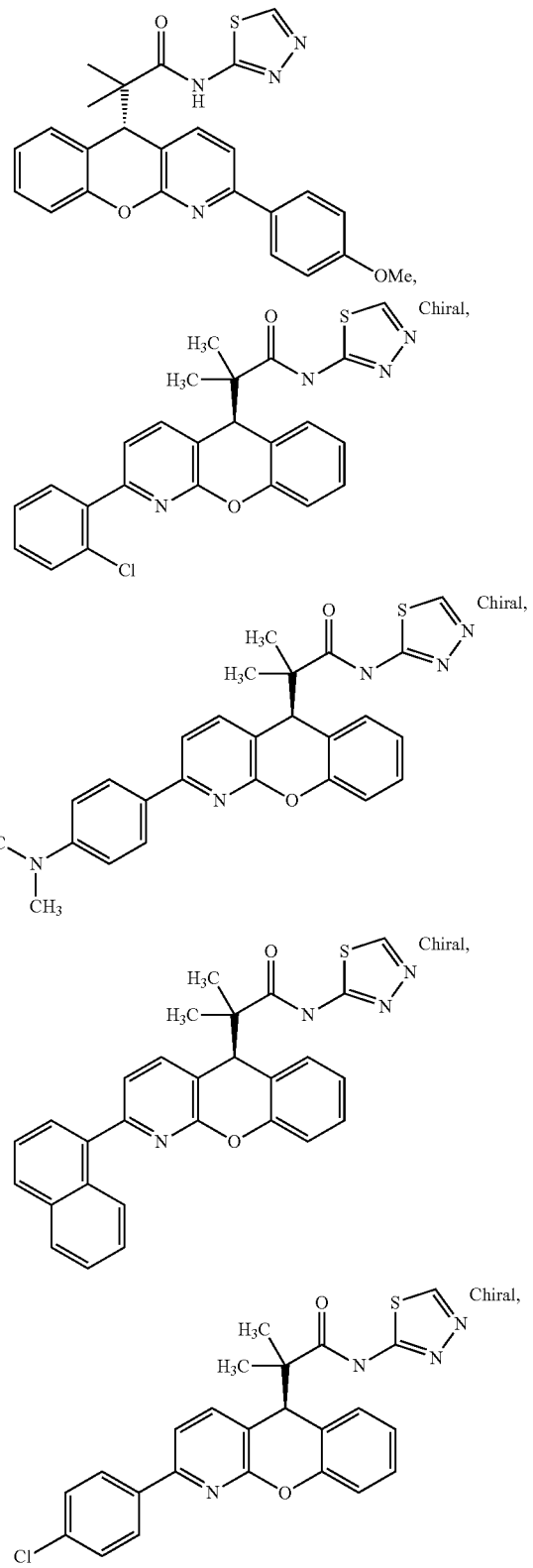

339
-continued
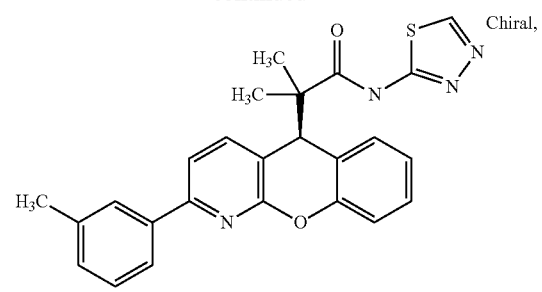
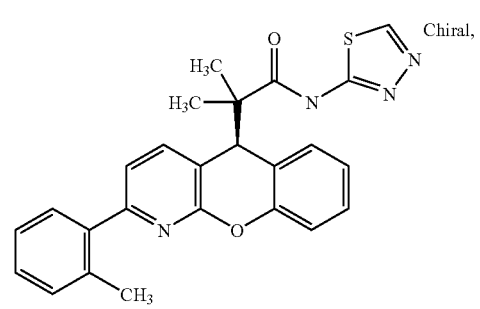
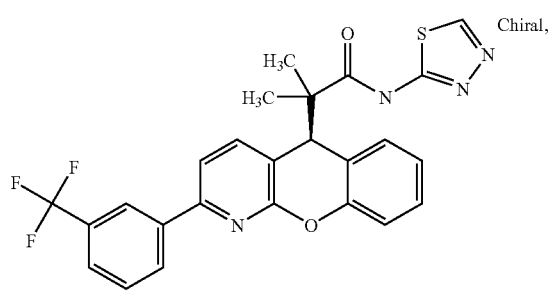
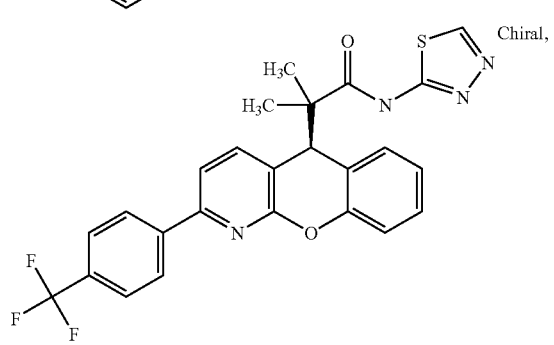
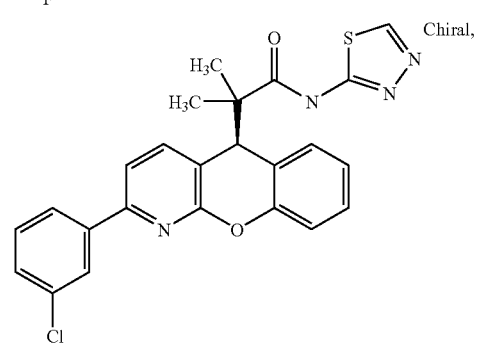
340
-continued
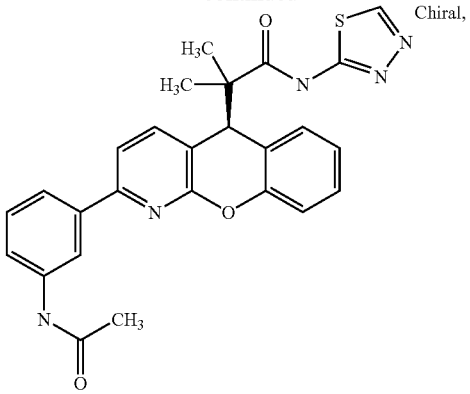
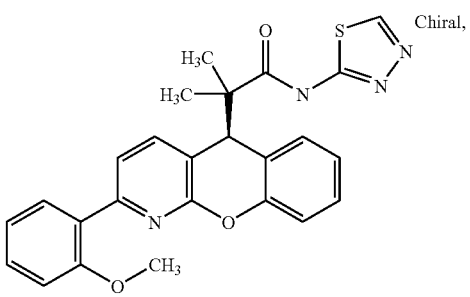
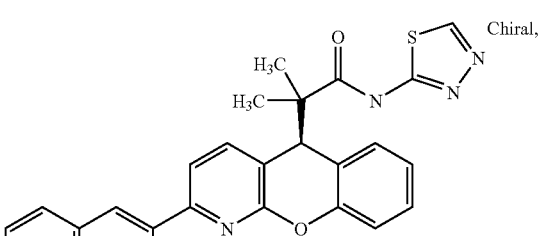
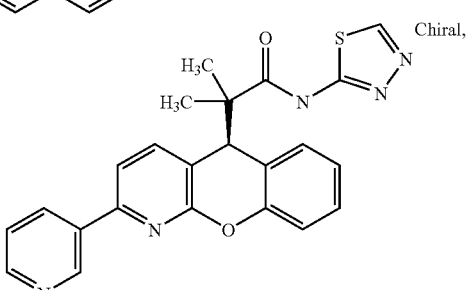
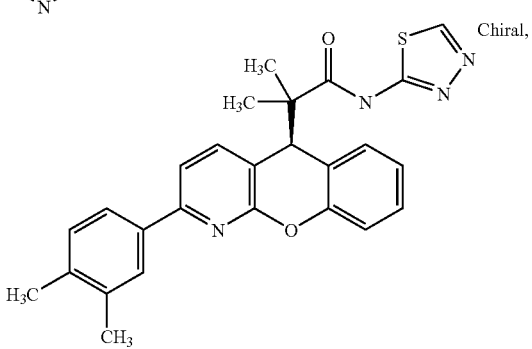

341
-continued
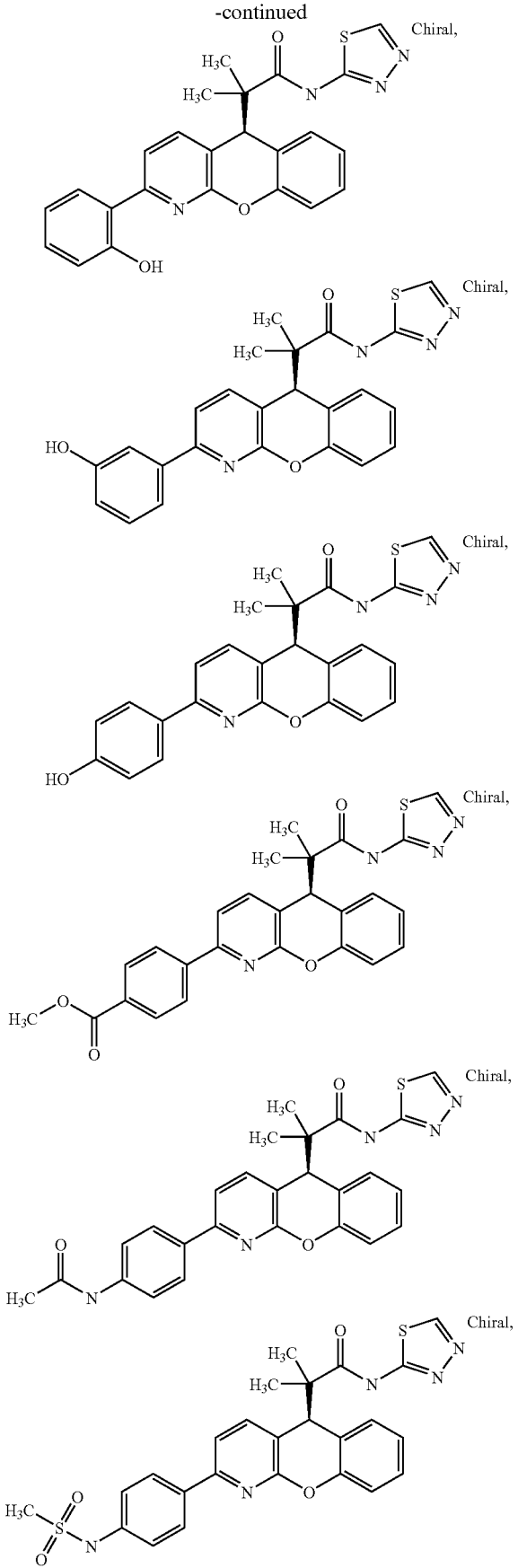
342
-continued
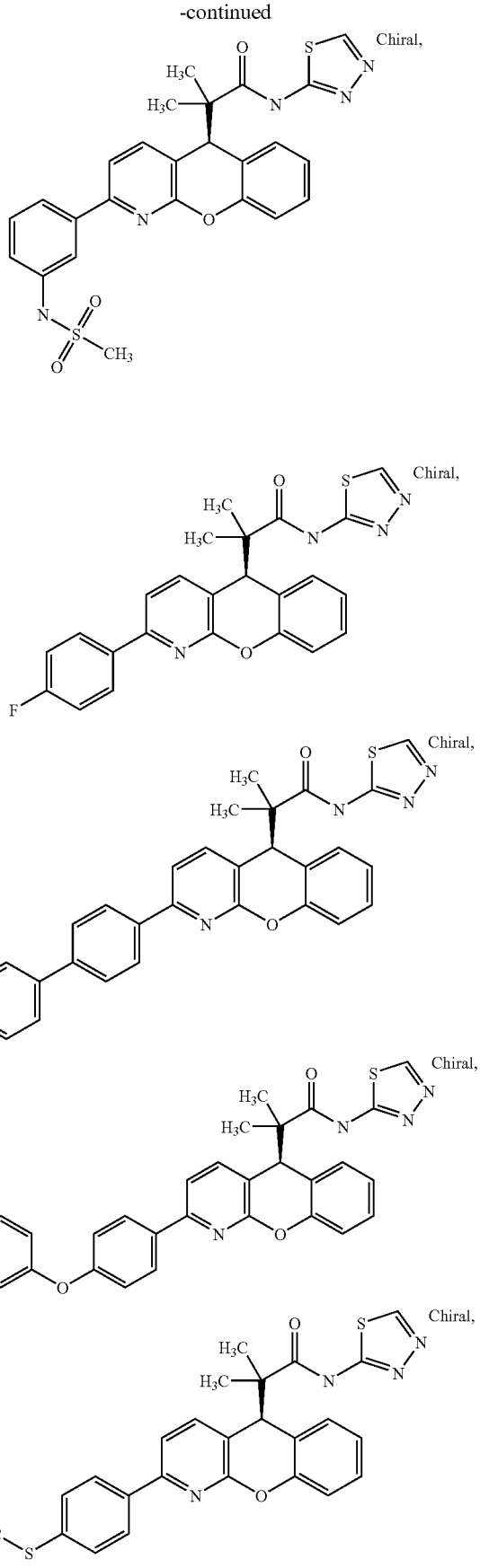

343
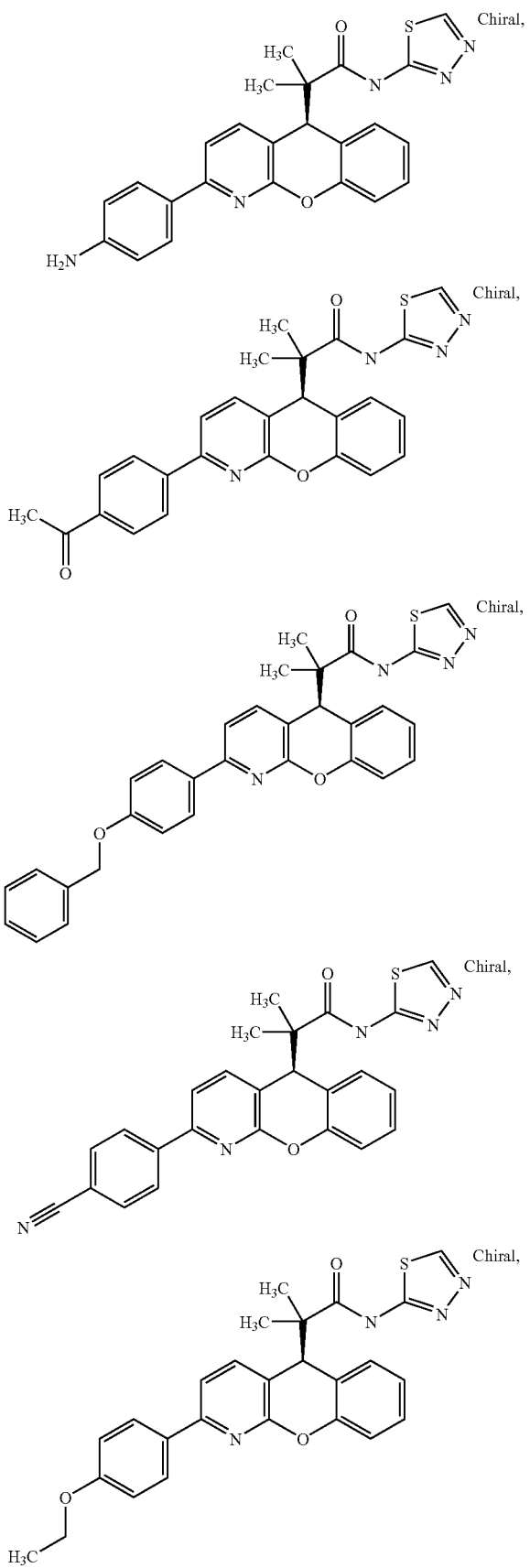
344
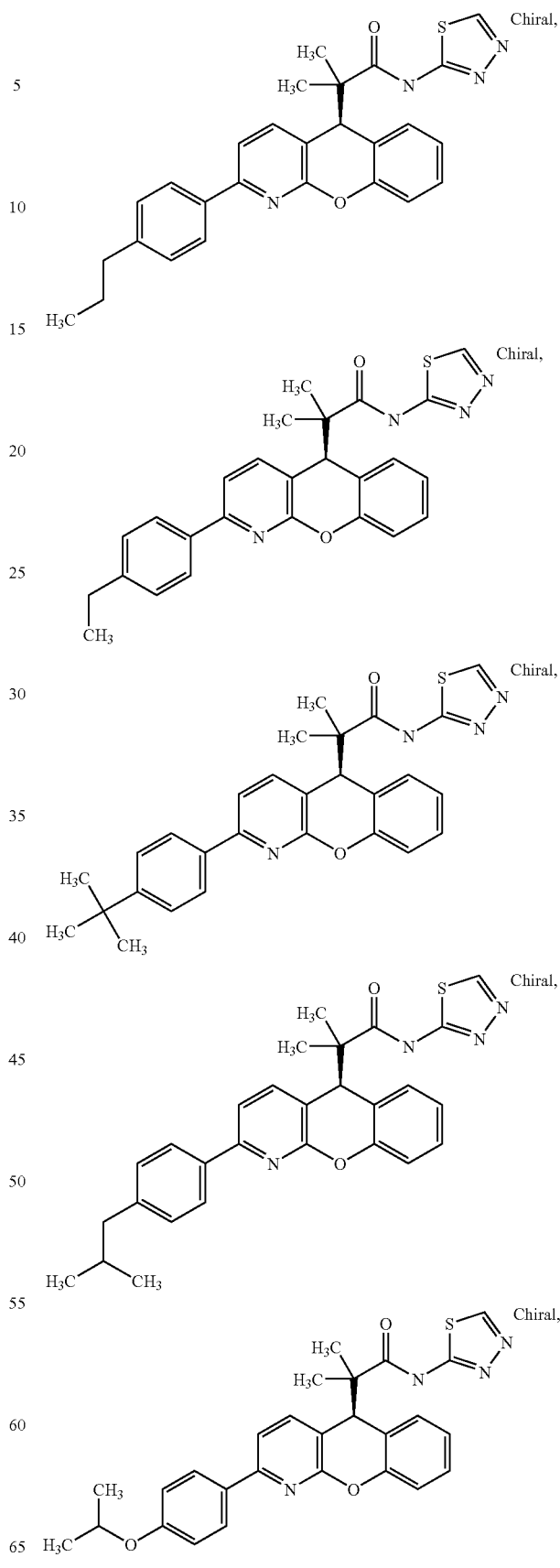

345
-continued
346
-continued
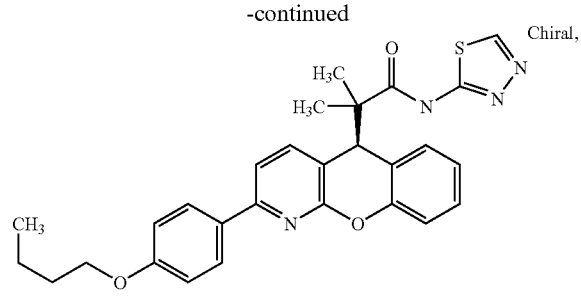
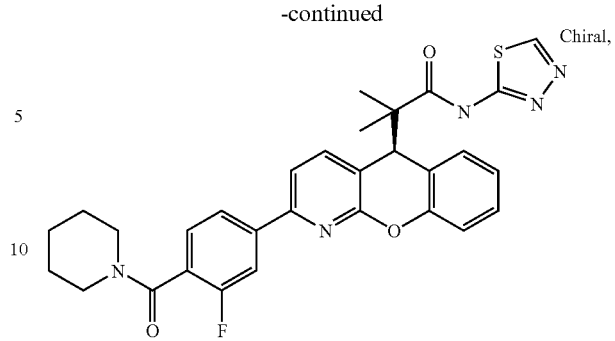
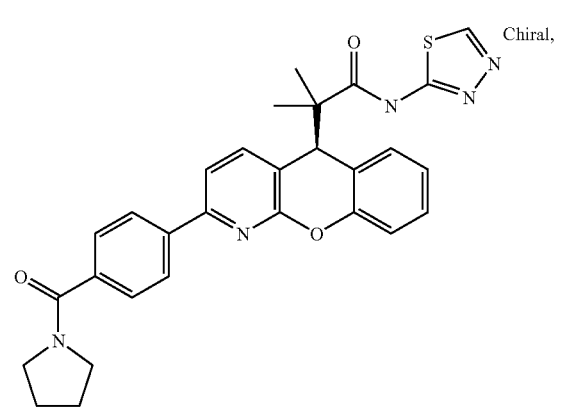
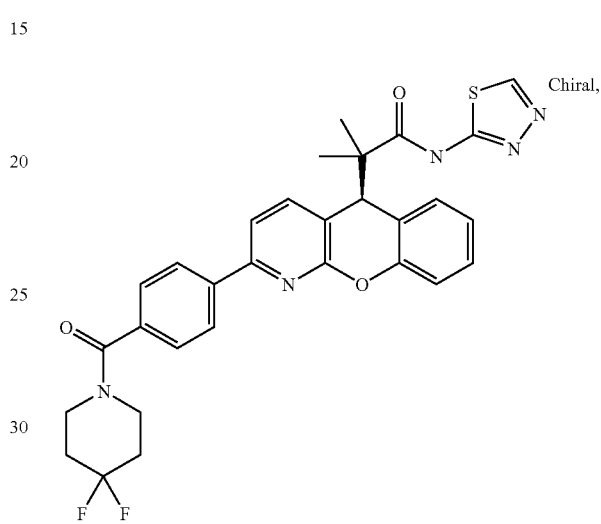
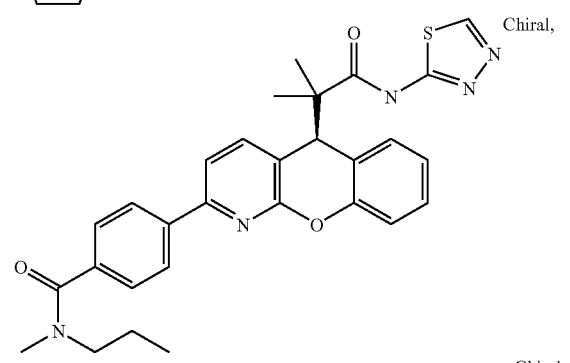
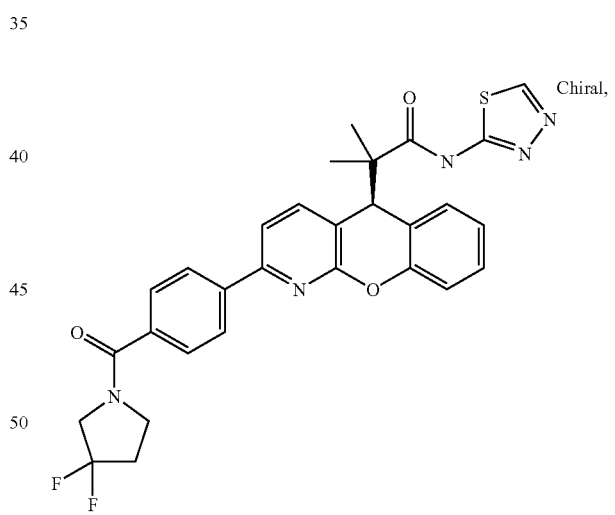
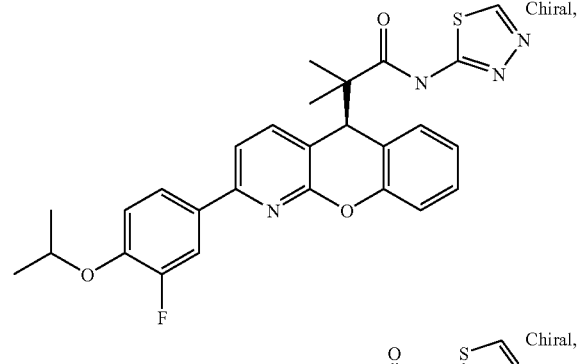
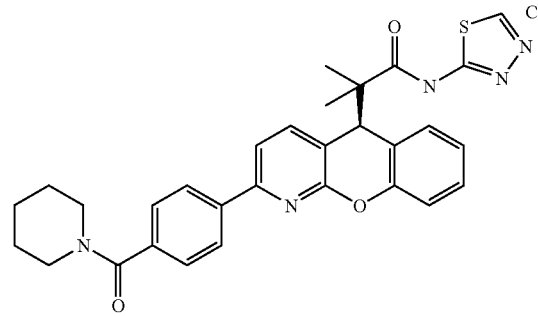
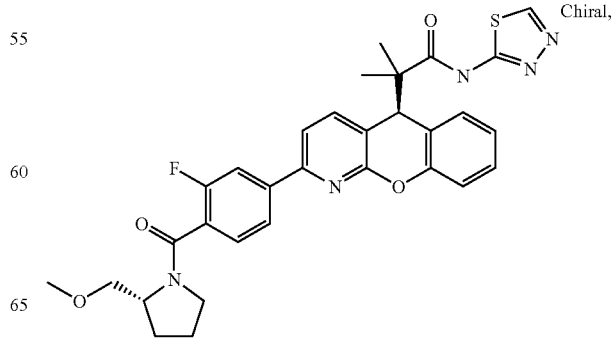

347
-continued
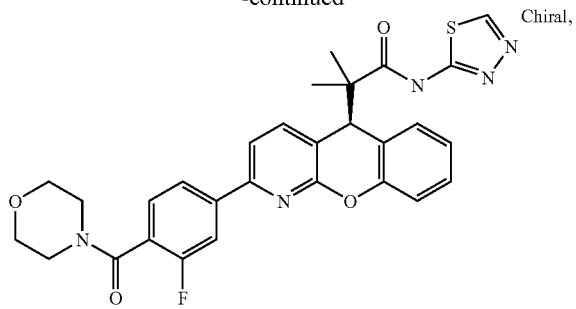
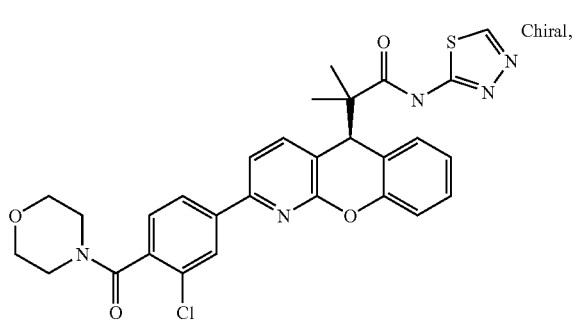
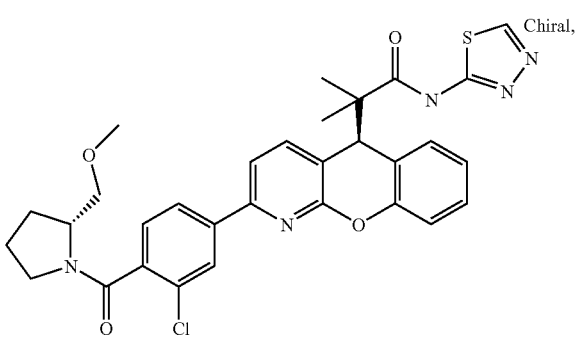
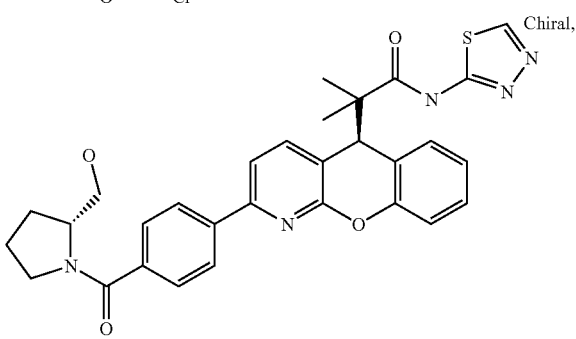
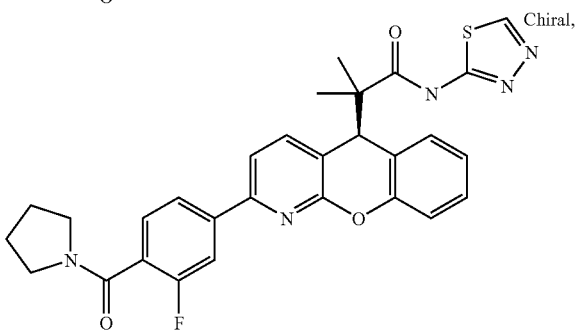
348
-continued
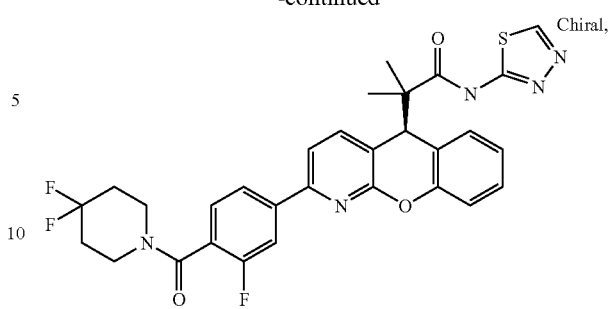
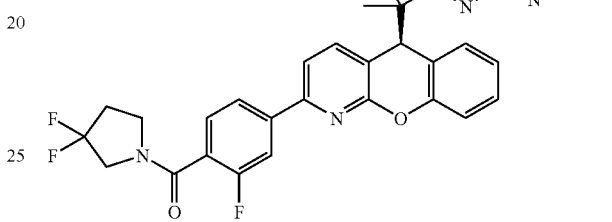
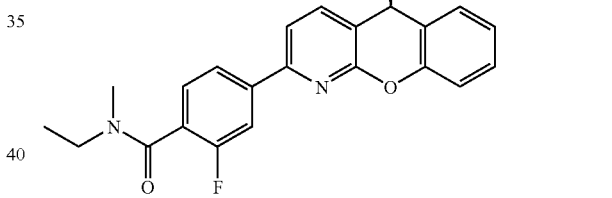
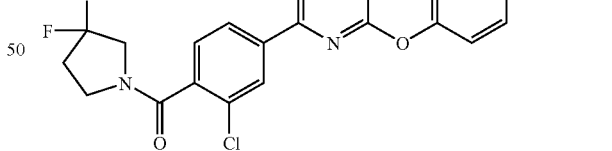
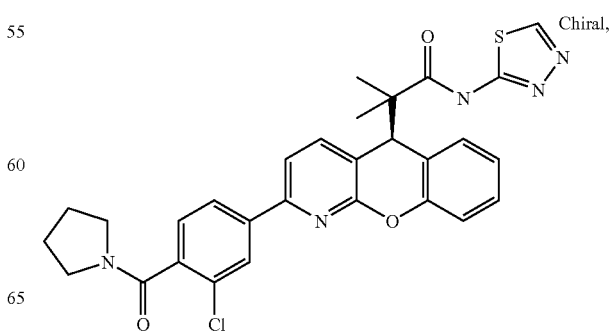

349
-continued
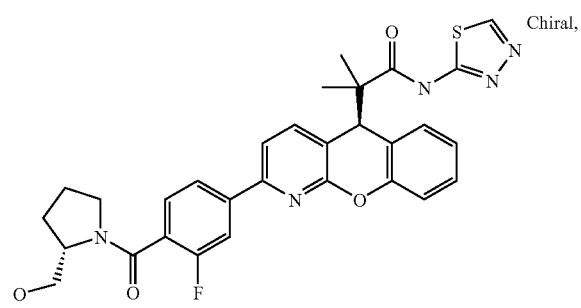
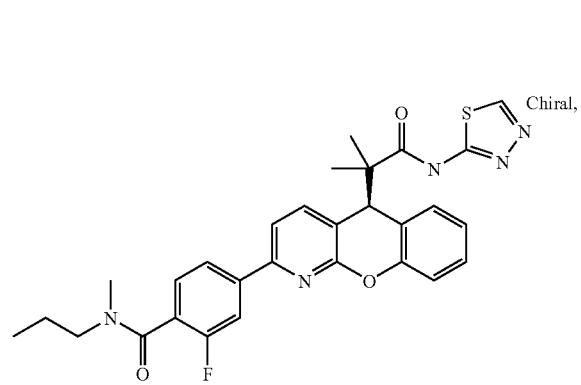
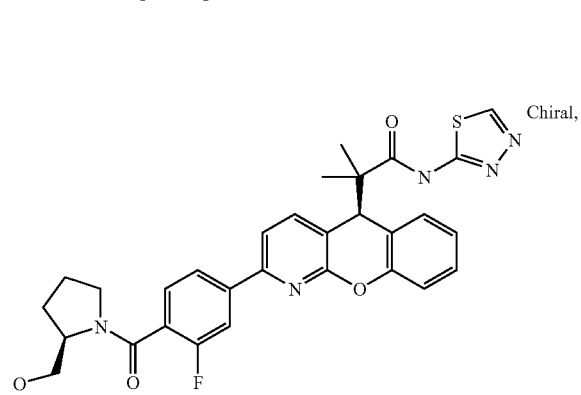
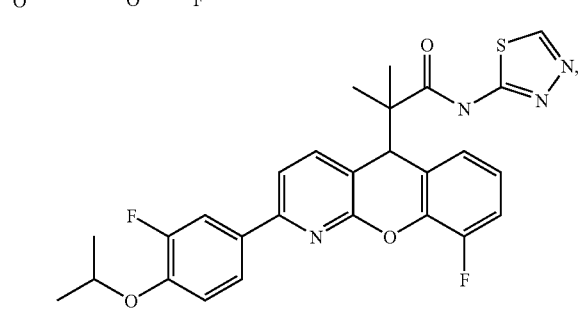
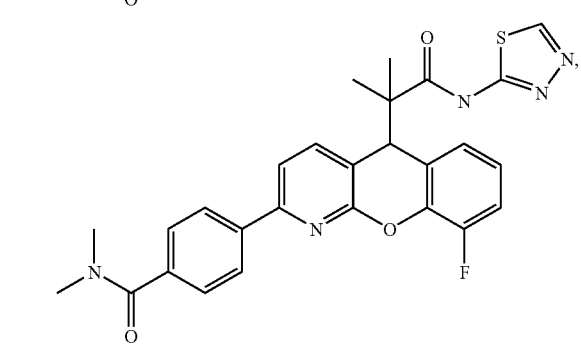
350
-continued
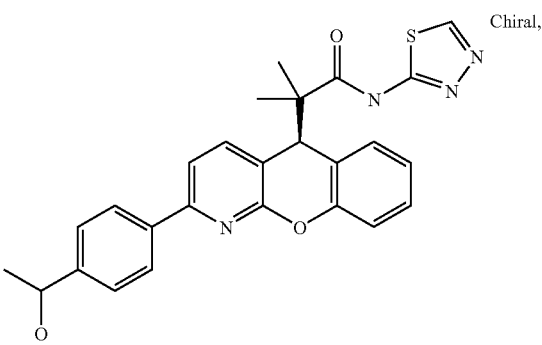
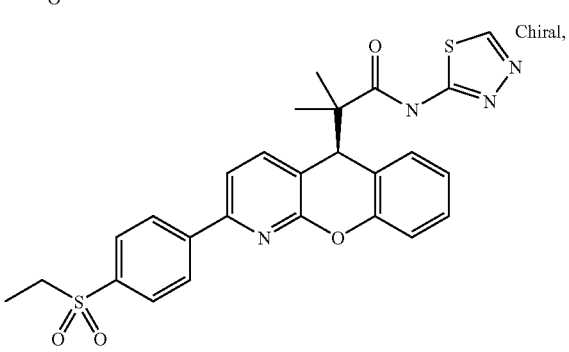
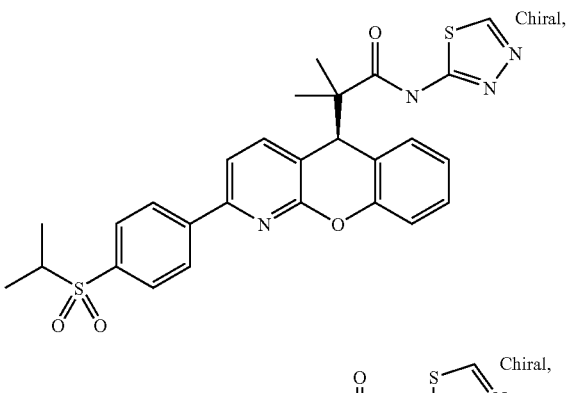
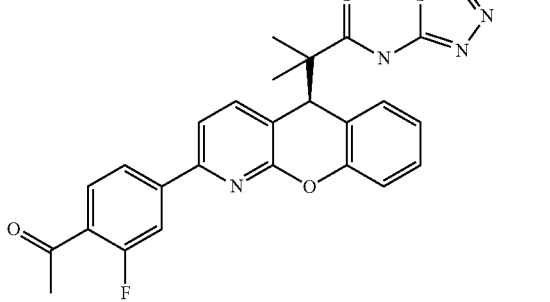
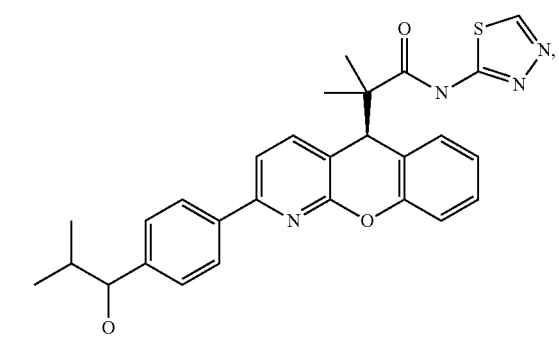

351
-continued
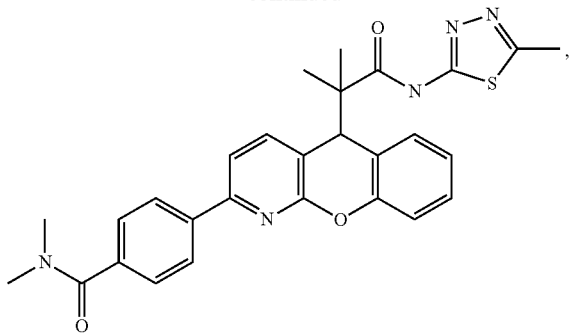
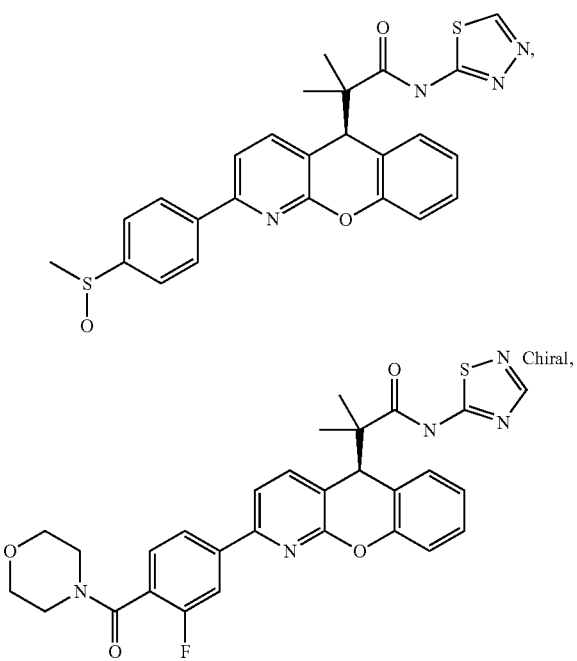
352
-continued
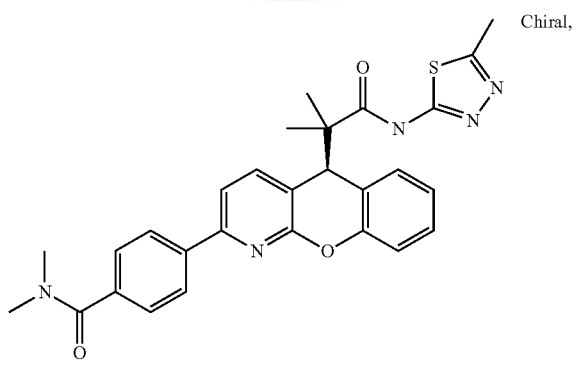
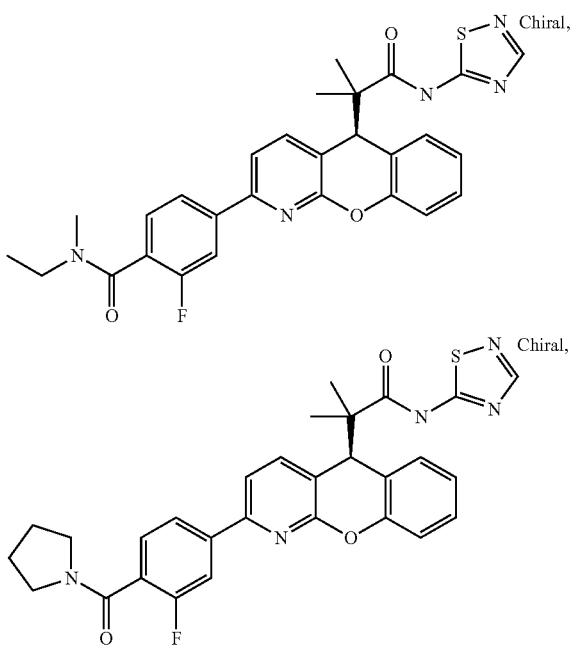
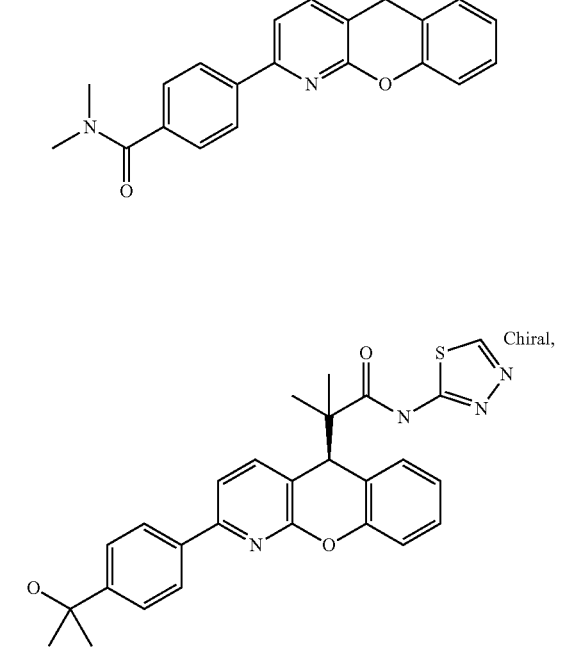

353
-continued
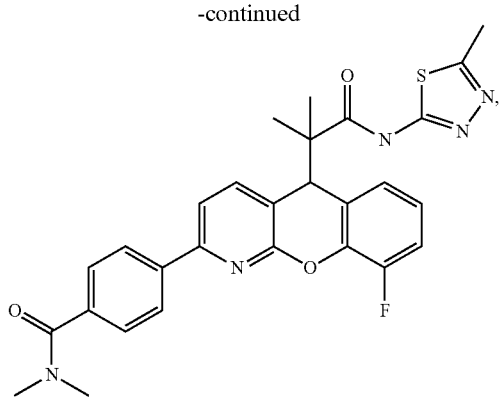
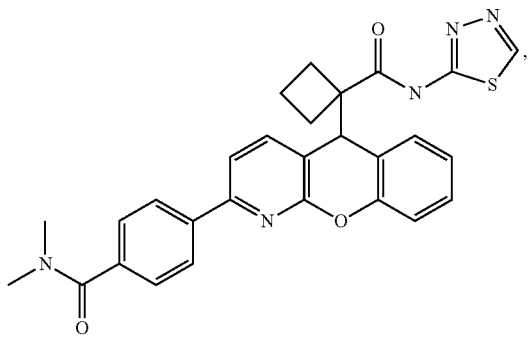
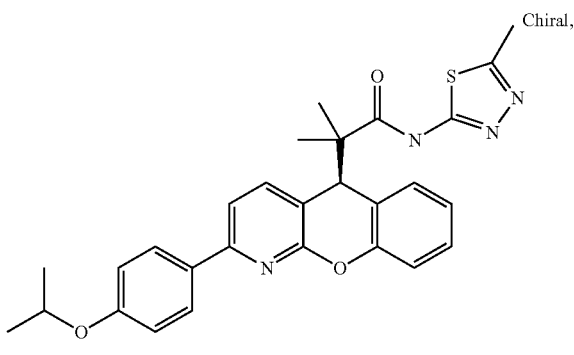
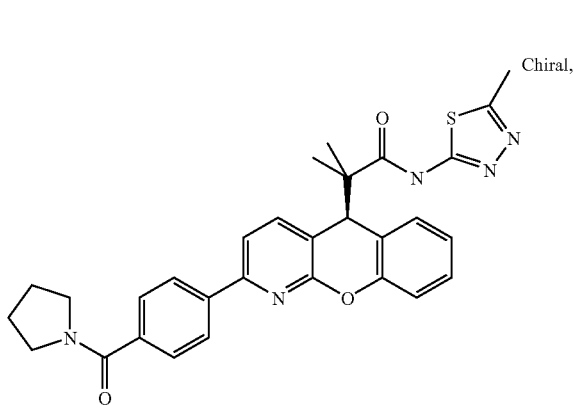
354
-continued
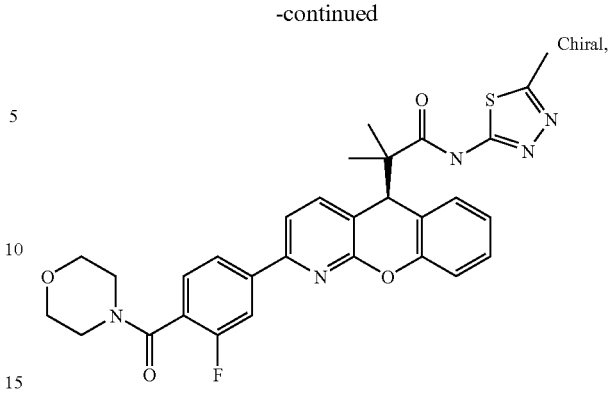
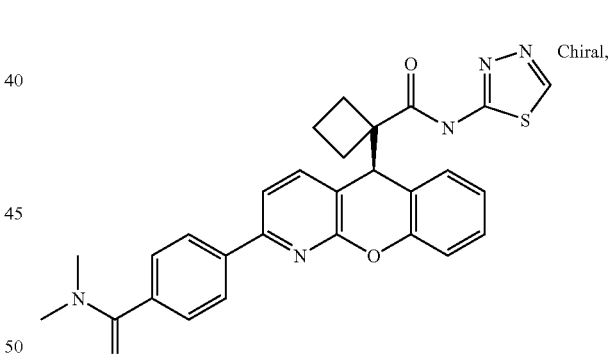
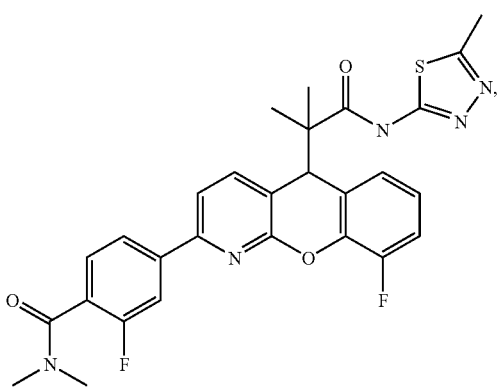

355
-continued
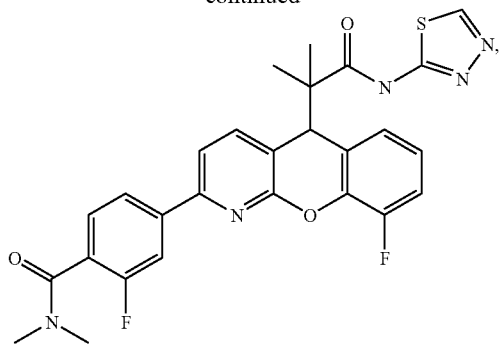
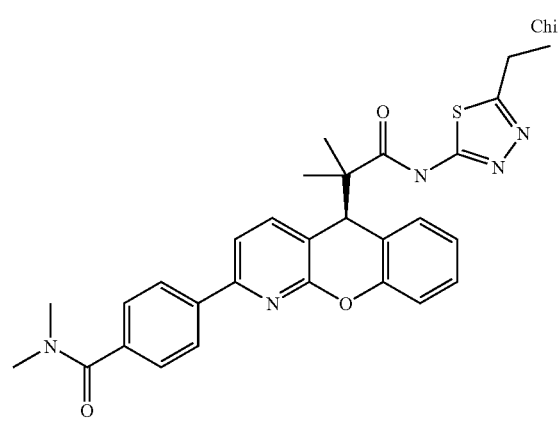
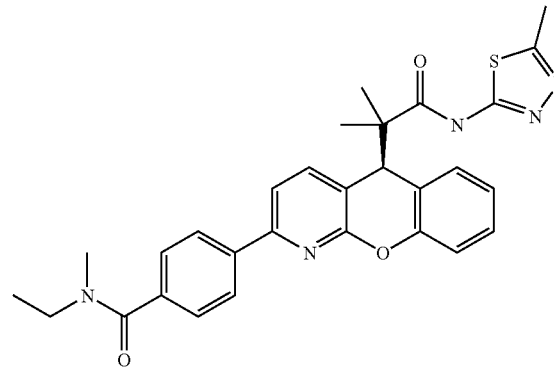
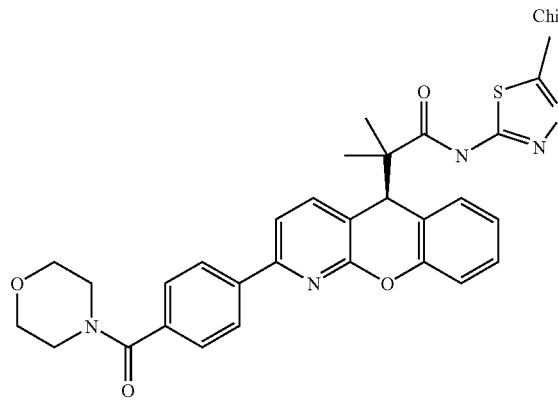
356
-continued
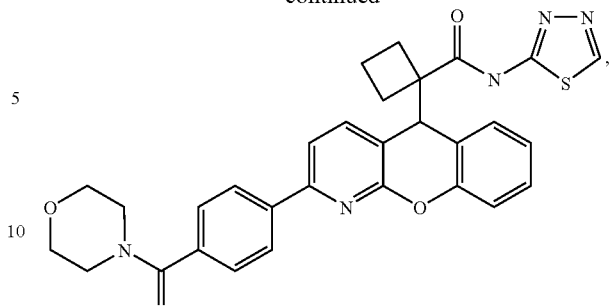
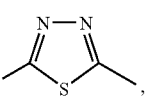
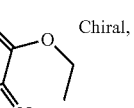
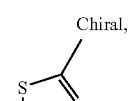
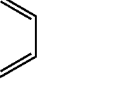

357
-continued
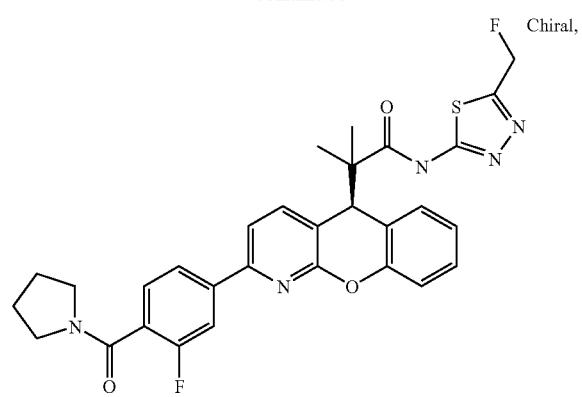
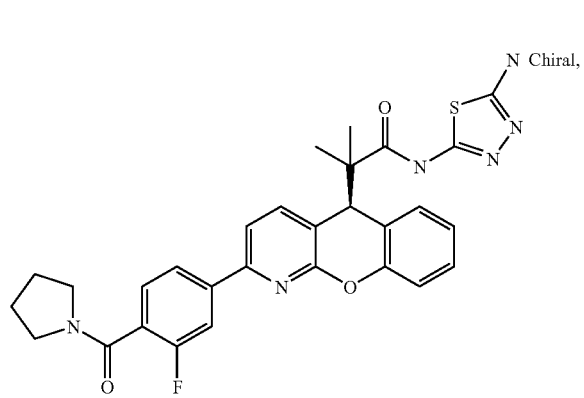
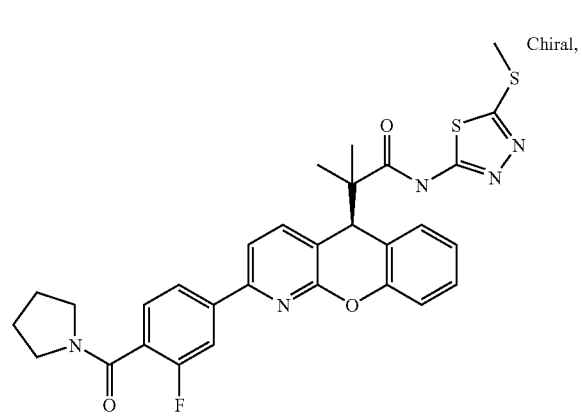
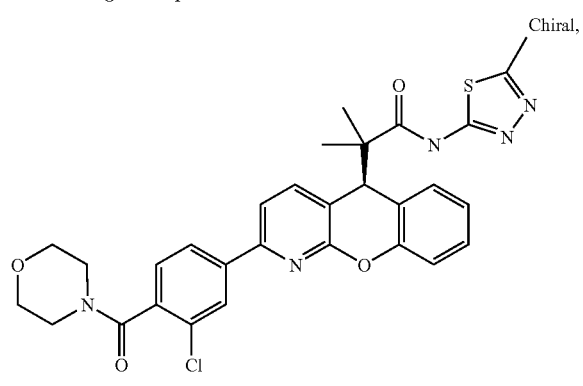
358
-continued
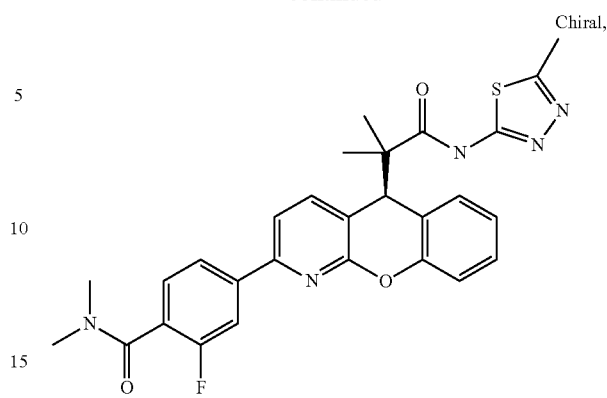
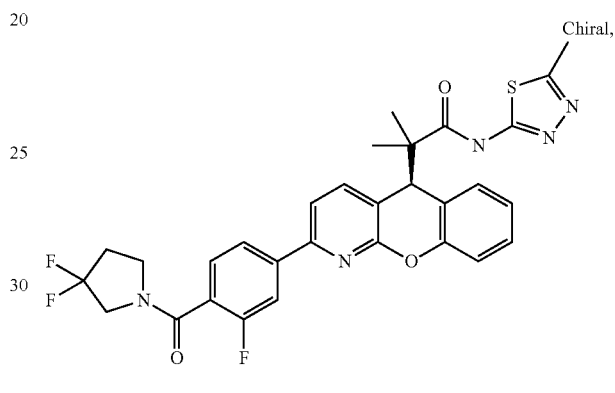
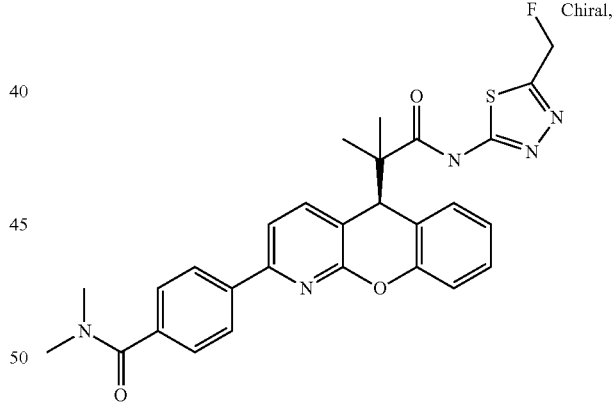
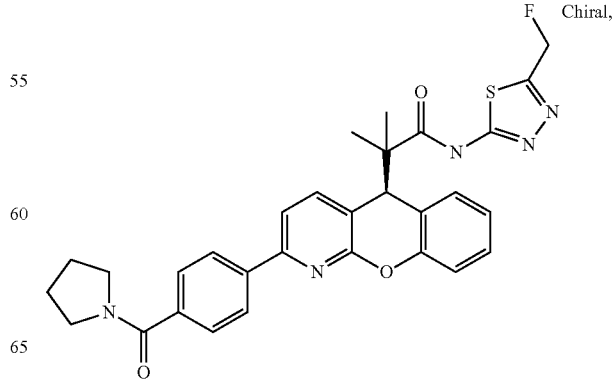

359
-continued
360
-continued
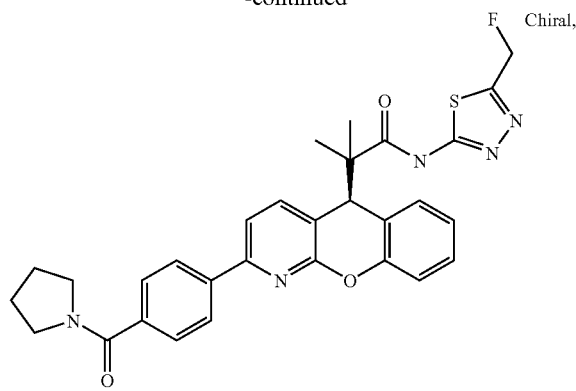
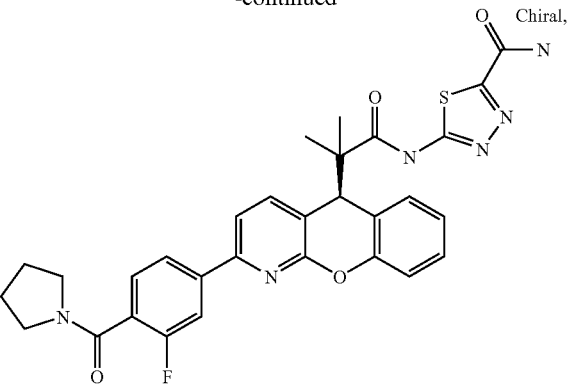
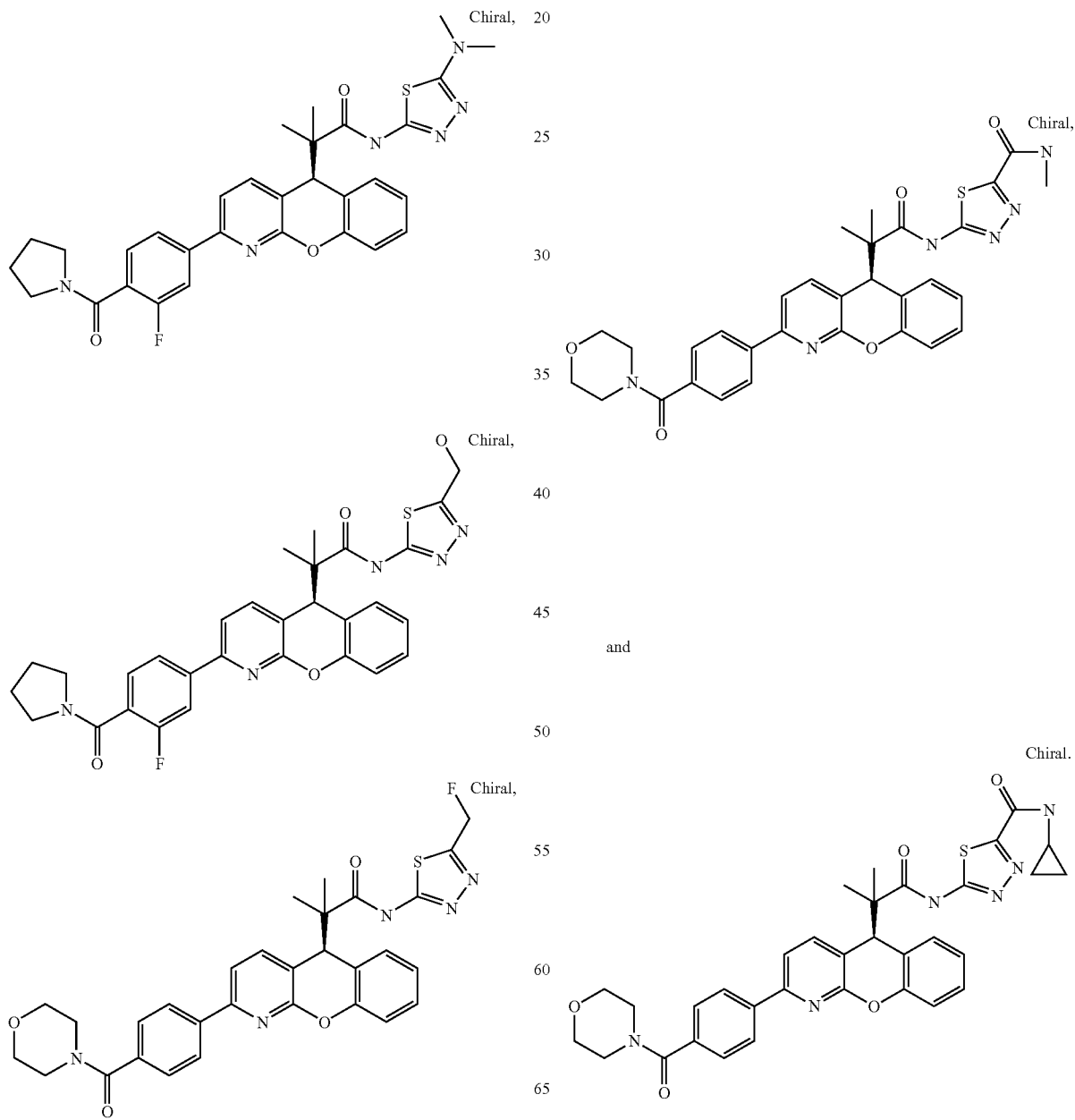
and

361
-continued
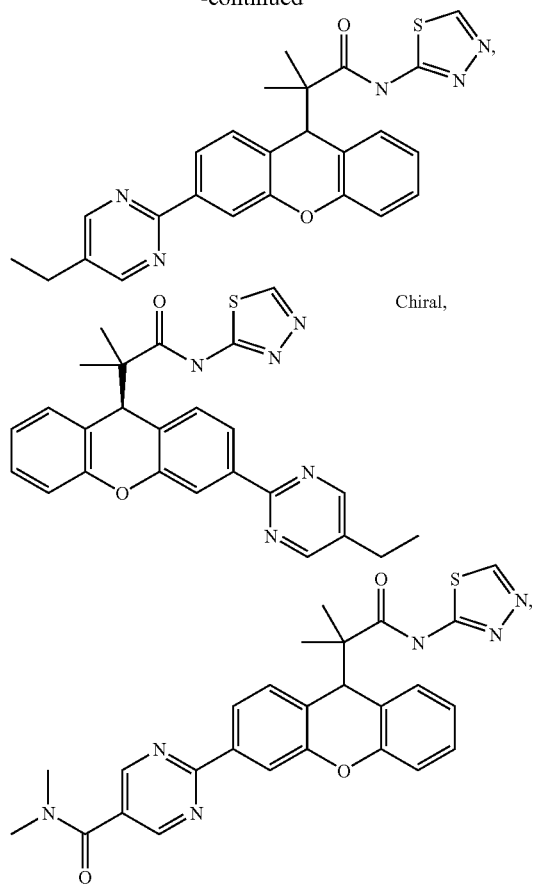
362
-continued
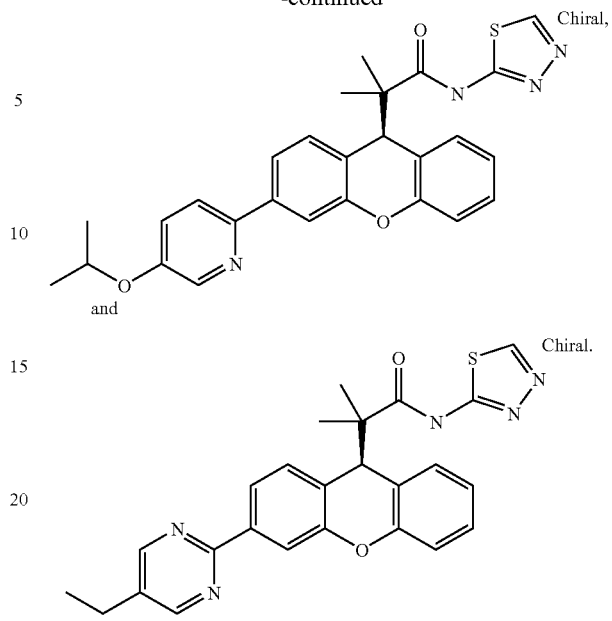
and
10. A pharmaceutical composition comprising a compound as defined in claim 1 and a pharmaceutically acceptable carrier therefor.
11. A pharmaceutical composition comprising a compound as defined in claim 9 and a pharmaceutically acceptable carrier therefor.
* * * * *

UNITED STATES PATENT AND TRADEMARK OFFICE
CERTIFICATE OF CORRECTION

Page 1 of 4

PATENT NO.       : 8,034,940 B2
APPLICATION NO.  : 11/835438
DATED            : October 11, 2011
INVENTOR(S)      : David S. Weinstein et al.

It is certified that error appears in the above-identified patent and that said Letters Patent is hereby corrected as shown below:

On the Title Page:

Item (56), References Cited, under "OTHER PUBLICATIONS":

Column 2, Dorwald, F.A. reference, move "Database Caplus [Online] Chemical Abstracts Service, Columbus, Ohio, US; Jul. 5, 2007, XP002470068 retrieved from STN Database Accession No. 2007:726515 abstract." to next line as a separate paragraph.

In the Claims:

Claim 1:
Column 330, lines 56 to 63, change

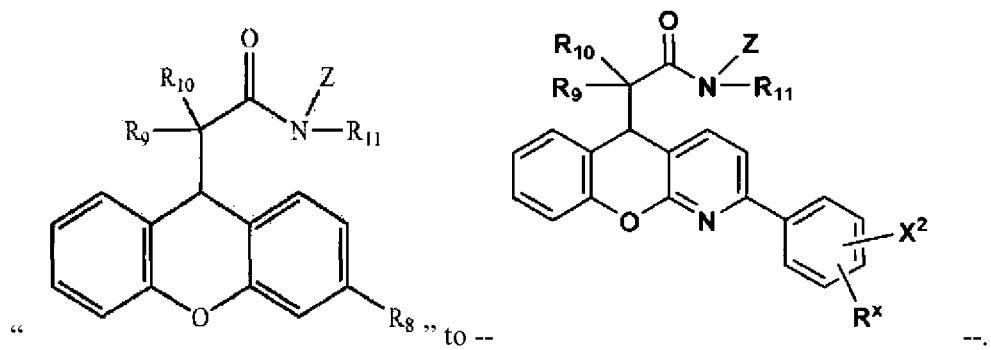

"          " to --          --.

Column 331, line 30, after "alkyl", insert -- ; --.

Signed and Sealed this
Twenty-fourth Day of July, 2012

David J. Kappos
*Director of the United States Patent and Trademark Office*

CERTIFICATE OF CORRECTION (continued)
U.S. Pat. No. 8,034,940 B2

In the Claims:

Claim 2:

Column 333, line 6, after " 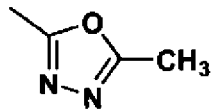 " change ";" to -- . --.

Claim 6:

Column 335, line 1, before "where", delete ",".

Claim 9:

Column 359, lines 1 to 15, delete " 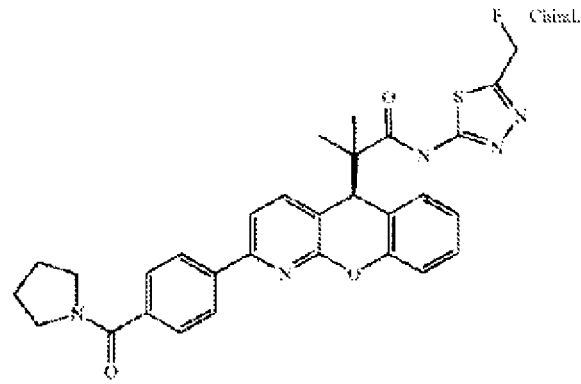 ".

In the Claims:

CERTIFICATE OF CORRECTION (continued)
U.S. Pat. No. 8,034,940 B2

Page 3 of 4

Claim 9 (continued):

Column 361, lines 1 to 34, delete

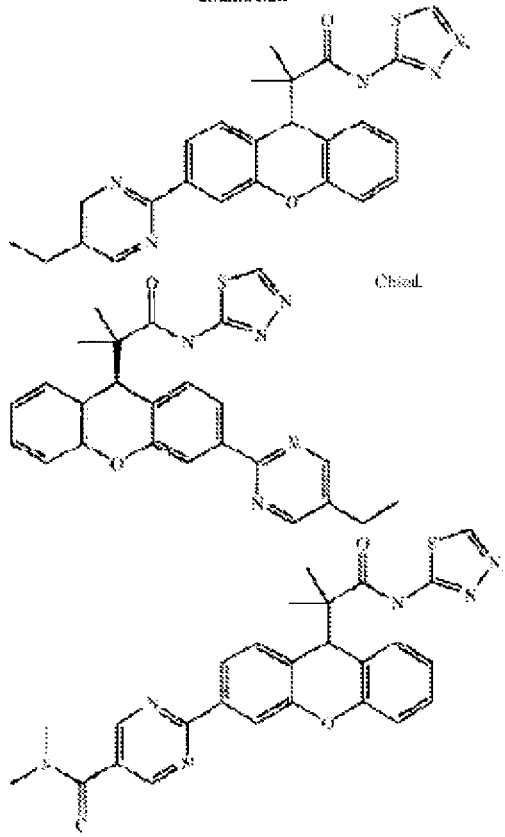

" ".

In the Claims:

CERTIFICATE OF CORRECTION (continued)
U.S. Pat. No. 8,034,940 B2

Claim 9 (continued):

Column 362, lines 1 to 24, delete